United States Patent
Chand et al.

(10) Patent No.: US 11,718,669 B2
(45) Date of Patent: Aug. 8, 2023

(54) ANTI-TIGIT AND ANTI-CD96 ANTIBODIES

(71) Applicant: AGENUS INC., Lexington, MA (US)

(72) Inventors: Dhan Sidhartha Chand, Lexington, MA (US); Zahra Jawad, Lexington, MA (US); Olga Ignatovich, Lexington, MA (US); Nicola Anne Ramsay, Lexington, MA (US); Spencer Campbell, Lexington, MA (US); Beth Wensley, Lexington, MA (US); Emmanuel Cyrille Pascal Briend, Lexington, MA (US); K. Mark Bushell, Lexington, MA (US); Benjamin Maxime Morin, Lexington, MA (US); Veronica Franciszka Ilkow, Lexington, MA (US)

(73) Assignee: AGENUS INC., Lexington, MA (US)

(*) Notice: Subject to any disclaimer, the term of this patent is extended or adjusted under 35 U.S.C. 154(b) by 0 days.

(21) Appl. No.: 17/818,840

(22) Filed: Aug. 10, 2022

(65) Prior Publication Data
US 2023/0014036 A1    Jan. 19, 2023

Related U.S. Application Data

(63) Continuation of application No. 17/662,036, filed on May 4, 2022, now abandoned.
(Continued)

(51) Int. Cl.
*C07K 16/30* (2006.01)
*C07K 16/28* (2006.01)
(Continued)

(52) U.S. Cl.
CPC .......... *C07K 16/2803* (2013.01); *A61P 35/00* (2018.01); *A61K 2039/505* (2013.01);
(Continued)

(58) Field of Classification Search
None
See application file for complete search history.

(56) References Cited

U.S. PATENT DOCUMENTS 9,499,596 B2    11/2016  Clark et al.
9,695,238 B2     7/2017  Gao et al.
(Continued)

FOREIGN PATENT DOCUMENTS

EP           3712170 A1      9/2020
WO     WO-2011109789 A2      9/2011
(Continued)

OTHER PUBLICATIONS

Aguilera et al, "CD96 targeted antibodies need not block CD96-CD155 interactions to promote NK cell anti-metastatic activity," OncoImmunology 2018: e1424677.
(Continued)

*Primary Examiner* — Claire Kaufman
(74) *Attorney, Agent, or Firm* — Dechert LLP; Andrew T. Wilkins; Kayla L. Metzger

(57) ABSTRACT

The instant disclosure provides multispecific molecules that specifically bind to CD96 (e.g., human CD96) and/or TIGIT (e.g., human TIGIT) and isolated antibodies that specifically bind to TIGIT (e.g., human TIGIT). Also provided are pharmaceutical compositions comprising these multispecific molecules and antibodies, nucleic acids encoding these multispecific molecules and antibodies, expression vectors and host cells for making these multispecific molecules and antibodies, and methods of treating a subject using these multispecific molecules and antibodies.

37 Claims, 68 Drawing Sheets
Specification includes a Sequence Listing.

Related U.S. Application Data

(60) Provisional application No. 63/201,537, filed on May 4, 2021.

(51) Int. Cl.
    *A61P 35/00*     (2006.01)
    *A61K 39/00*     (2006.01)

(52) U.S. Cl.
    CPC ...... *C07K 2317/31* (2013.01); *C07K 2317/76* (2013.01); *C07K 2317/92* (2013.01)

(56) References Cited

U.S. PATENT DOCUMENTS

| | | |
|---|---|---|
| 9,713,641 B2 | 7/2017 | Hicklin et al. |
| RE46,534 E | 9/2017 | Baldwin et al. |
| 9,873,740 B2 | 1/2018 | Grogan et al. |
| 10,017,572 B2 | 7/2018 | Grogan et al. |
| 10,112,997 B2 | 10/2018 | Gurney et al. |
| 10,124,061 B2 | 11/2018 | White et al. |
| 10,144,778 B2 | 12/2018 | Eisenbach-Schwartz et al. |
| 10,189,902 B2 | 1/2019 | Maurer et al. |
| 10,329,349 B2 | 6/2019 | Cooper et al. |
| 10,501,737 B2 | 12/2019 | Ishii |
| 10,537,633 B2 | 1/2020 | Tso et al. |
| 10,537,637 B2 | 1/2020 | Sheng et al. |
| 11,021,537 B2 | 6/2021 | Chand et al. |
| 2009/0258013 A1 | 10/2009 | Clark et al. |
| 2013/0287777 A1 | 10/2013 | Duffy et al. |
| 2013/0287797 A1 | 10/2013 | Heider et al. |
| 2016/0108123 A1 | 4/2016 | Freeman et al. |
| 2016/0152720 A1 | 6/2016 | Kim et al. |
| 2016/0193239 A1 | 7/2016 | Baylin et al. |
| 2016/0376371 A1 | 12/2016 | Ravetch et al. |
| 2017/0037127 A1 | 2/2017 | Grogan et al. |
| 2017/0107300 A1 | 4/2017 | Kuchroo et al. |
| 2017/0143825 A1 | 5/2017 | Grogan |
| 2017/0239338 A1 | 8/2017 | Szalay et al. |
| 2017/0260271 A1 | 9/2017 | Igawa et al. |
| 2017/0360932 A1 | 12/2017 | Parry |
| 2018/0066055 A1 | 3/2018 | Williams et al. |
| 2018/0078625 A1 | 3/2018 | Moon et al. |
| 2018/0155422 A1 | 6/2018 | Bhatt et al. |
| 2018/0169239 A1 | 6/2018 | Grogan |
| 2018/0185480 A1 | 7/2018 | Mandelboim et al. |
| 2018/0251548 A1 | 9/2018 | Sabzevari et al. |
| 2018/0355040 A1 | 12/2018 | Chand et al. |
| 2018/0371083 A1 | 12/2018 | Williams et al. |
| 2019/0077869 A1 | 3/2019 | Fiedler et al. |
| 2020/0040082 A1 | 2/2020 | Piasecki et al. |
| 2020/0331999 A1 | 10/2020 | Zhang et al. |
| 2021/0101977 A1 | 4/2021 | Chand et al. |
| 2022/0089732 A1 | 3/2022 | Chand et al. |
| 2022/0389095 A1* | 12/2022 | Ignatovich ......... A61K 47/6803 |

FOREIGN PATENT DOCUMENTS

| | | |
|---|---|---|
| WO | WO-2013184912 A2 | 12/2013 |
| WO | WO-2015024060 A1 | 2/2015 |
| WO | WO-2016004875 A1 | 1/2016 |
| WO | WO-2016011264 A1 | 1/2016 |
| WO | WO-2016180781 A1 | 11/2016 |
| WO | WO-2016191643 A2 | 12/2016 |
| WO | WO-2017023749 A1 | 2/2017 |
| WO | WO-2017030823 A2 | 2/2017 |
| WO | WO-2017040790 A1 | 3/2017 |
| WO | WO-2017048824 A1 | 3/2017 |
| WO | WO-2017059095 A1 | 4/2017 |
| WO | WO-2017062619 A2 | 4/2017 |
| WO | WO-2017062820 A1 | 4/2017 |
| WO | WO-2017123981 A1 | 7/2017 |
| WO | WO-2017223085 A2 | 12/2017 |
| WO | WO-2018053242 A1 | 3/2018 |
| WO | WO-2018102536 A1 | 6/2018 |
| WO | WO-2018183889 A1 | 10/2018 |
| WO | WO-2018-204363 A1 | 11/2018 |
| WO | WO-2018204405 A1 | 11/2018 |
| WO | WO-2018229163 A1 | 12/2018 |
| WO | WO-2018234793 A2 | 12/2018 |
| WO | WO-2019062832 A1 | 4/2019 |
| WO | WO-2019091449 A1 | 5/2019 |
| WO | WO-2019129221 A1 | 7/2019 |
| WO | WO-2019129261 A1 | 7/2019 |
| WO | WO-2019137548 A1 | 7/2019 |
| WO | WO-2019152574 A1 | 8/2019 |
| WO | WO-2019154415 A1 | 8/2019 |
| WO | WO-2019165434 A1 | 8/2019 |
| WO | WO-2019168382 A1 | 9/2019 |
| WO | 2020092554 A1 | 5/2020 |
| WO | 2020185739 A1 | 9/2020 |
| WO | 202063879 A1 | 12/2020 |
| WO | WO-2021042019 A1 | 3/2021 |

OTHER PUBLICATIONS

PCT International Search Report from PCT/US2022/072099 dated Oct. 6, 2022.
AGENUS, "Corporate Presentation", Cantor Fitzgerald Global Healthcare Conference, Sep. 2017, 30 pages.
AGENUS, Integrated Immunotherapy: Enabling Best-in-Class 1-0 Combinations, Non-Confidential Overview, Nov. 2017, 33 pages.
AGENUS; Stein MD, Ph.D., Robert; "Next Generation Immunomodulatory Antibodies: Optimizing Therapeutic Impact", 2017, 16 pages.
Blake et al., "Molecular Pathways: Targeting CD96 and TIGIT for Cancer Immunotherapy", Clin. Cancer Res., 2016, vol. 22, No. 21, pp. 1-6.
Cattaruzza et al., "Pharmacodynamic biomarkers for anti-TIGIT treatment and prevalence of TIGIT expression in multiple solid tumor types", Oncomed Pharmaceuticals, 2017.
Chauvin et al., "TIGIT and PD-1 impair tumor antigen-specific CD8+T cells in melanoma patients" J. Clin. Invest., 2015, 13 pages.
Chew et al., "TIGIT Marks Exhausted T Cells, Correlates with Disease Progression, and Serves as a Target for Immune Restoration in HIV and SIV Infection", PLOS Pathogens, 2016, vol. 12, No. 1, 28 pages.
Dougall et al., "TIGIT and CD96: new checkpoint receptor targets for cancer immunotherapy", Immunological Reviews, 2017, vol. 276, pp. 112-120.
Gur et al., "Binding of the Fap2 Protein of Fusobacterium nucleatum to Human Inhibitory Receptor TIGIT Protects Tumors from Immune Cell Attack", Immunity, 2015, vol. 42, pp. 344-355.
He et al., "CD155T/TIGIT Signaling Regulates CD8b T-cell Metabolism and Promotes Tumor Progression in Human Gastric Cancer", Cancer Research, vol. 77, No. 22, pp. 6375-6388.
Hung et al, "TIGIT and PD-1 dual checkpoint blockade enhances antitumor immunity and survival in GBM", Oncoimmunology, 2018, vol. 7, No. 8,13 pages.
International Search Report and Written Opinion for PCT International Patent Application No. PCT/US2018/030453, dated Sep. 21, 2018,18 pages.
Johnston et al., "The Immunoreceptor TIGIT Regulates Antitumor and Antiviral CD8+ T Cell Effector Function", Cancer Cell, 2014, vol. 26, pp. 923-937.
Joller et al., "Treg Cells Expressing the Coinhibitory Molecule TIGIT Selectively Inhibit Proinflammatory Th1 and Th17 Cell Responses", Immunity, 2014, vol. 40, pp. 569-581.
Kurtulus et al., "TIGIT predominantly regulates the immune response via regulatory T cells", J Clin Invest., 2015, vol. 125, No. 11, pp. 4053-4062.
Lozano et al., "The TIGIT/CD226 Axis Regulates Human T Cell Function", J. Immunol., 2012, vol. 188, pp. 3869-3875.
Manieri et al., "TIGIT: A Key Inhibitor of the Cancer Immunity Cycle", Trends in Immunology, 2016, vol. 38, No. 1, pp. 20-28.
Pauken et al., "TIGIT and CD226: Tipping the Balance between Costimulatory and Coinhibitory Molecules to Augment the Cancer Immunotherapy Toolkit", Cancer Cell, 2014, vol. 26, pp. 785-787.
Samanta et al., "Structural, mutational and biophysical studies reveal a canonical mode of molecular recognition between immune receptor TIGIT andnectin-2", Molecular Immunology, 2017, vol. 81, pp. 151-159.

(56) References Cited

OTHER PUBLICATIONS

Stanietsky et al., "The interaction of TIGIT with PVR and PVRL2 inhibits human NK cell cytotoxicity", PNAS, 2009, vol. 106, No. 42, pp. 17858-17863.

Stengel et al., "Structure of TIGIT immunoreceptor bound to poliovirus receptor reveals a cell-cell adhesion and signaling mechanism that requires cis-trans receptor clustering," PNAS, 2012, vol. 109, No. 14, pp. 5399-5404.

Yu et al., "The surface protein TIGIT suppresses T cell activation by promoting the generation of mature immunoregulatory dendritic cells", Nature Immunology, 2009, vol. 10, No. 1, pp. 48-57.

Zhou et al., "Intrinsic Expression of Immune Checkpoint Molecule TIGIT Could Help Tumor Growth in vivo by Suppressing the Function of NK and CD8+ T Cells", Frontiers in Immunology, 2018, vol. 9, Article 2821, pp. 1-11.

PCT International Search Report and Written Opinion for PCT/US2020/048700 dated Dec. 8, 2020.

\* cited by examiner

ANTI-TIGIT AND ANTI-CD96 ANTIBODIES

1. RELATED APPLICATION

This application is a Continuation of U.S. application Ser. No. 17/662,036, filed on May 4, 2022, which claims benefit to U.S. Provisional Application No. 63/201,537, filed on May 4, 2021, the entirety of which is herein incorporated by reference.

2. SEQUENCE LISTING

The contents of the electronically submitted sequence listing in ASCII .xml file (Name: 404298-AGBW-146USC1 (192959); Size 170966 bytes; Date of Creation: Aug. 9, 2022) is herein incorporated by reference in its entirety.

3. FIELD

The instant disclosure relates to multispecific molecules that specifically bind to CD96 (e.g., human CD96) and/or TIGIT (e.g., human TIGIT), anti-TIGIT antibodies, and methods of using the same.

4. BACKGROUND

CD96 (Cluster of Differentiation 96), also known as TACTILE (T cell-activation, increased late expression), is a type I transmembrane protein in the immunoglobulin (Ig) superfamily. It has a single Ig domain, a type I transmembrane domain, a single intracellular immunoreceptor tyrosine-based inhibitory motif (ITIM), and a single YXXM phosphorylation motif, and is expressed on the surface of T cells and natural killer (NK) cells.

CD96 is believed to play a role in the regulation of immune cells (e.g., NK cells and T cells) and tumor metastasis. In particular, it has been shown that blockade of CD96 function suppressed primary tumor growth in several mouse tumor models in a CD8+ T cell-dependent manner.

The protein T-cell immunoreceptor with Ig and ITIM domains (TIGIT), also known as VSIG9 or VSTM3, is a type I transmembrane protein in the immunoglobulin (Ig) superfamily. It has a single Ig domain, a type I transmembrane domain, a single intracellular immunoreceptor tyrosine-based inhibitory motif (ITIM) and a single immunoglobulin tail tyrosine (ITT)-like phosphorylation motif and is expressed on activated CD4-positive/CD25-positive regulatory T cells (Tregs), memory CD45RO-positive T cells, and natural killer (NK) cells, but not naïve T cells.

CD155 (also known as poliovirus receptor (PVR)) is highly expressed on monocytes and dendritic cells, and is capable of activating effector T cells and NK cells, as well as attenuating the activity of Tregs, through binding to its two receptors CD226 and CD96. TIGIT binds to CD155 and has been shown to antagonize the interaction of CD155 with CD226 and CD96, thereby suppressing T cell- and NK cell-mediated immune activity.

Given the role of human CD96 and human TIGIT in modulating immune responses, therapeutic agents designed to block CD96 ligand interactions and/or TIGIT ligand interactions hold great promise for the treatment of diseases that involve immune suppression.

5. SUMMARY

The instant disclosure provides multispecific molecules that specifically bind to CD96 (e.g., human CD96) and/or TIGIT (e.g., human TIGIT) and antibodies that specifically bind to TIGIT (e.g., human TIGIT). Also provided are pharmaceutical compositions comprising these multispecific molecules and antibodies, nucleic acids encoding these multispecific molecules and antibodies, expression vectors and host cells for making these multispecific molecules and antibodies, and methods of treating a subject using these multispecific molecules and antibodies.

In one aspect, the instant disclosure provides a multispecific molecule comprising:

(a) a first antigen-binding region that specifically binds to human CD96, the first antigen-binding region comprising a first VH comprising CDRs CDRH1, CDRH2, and CDRH3, and a first VL comprising CDRs CDRL1, CDRL2, and CDRL3, wherein
  (i) the first VH comprises the CDRH1, CDRH2, and CDRH3 amino acid sequences of the VH amino acid sequence of SEQ ID NO: 34; and the first VL comprises the CDRL1, CDRL2, and CDRL3 amino acid sequences of the VL amino acid sequence of SEQ ID NO: 35,
  (ii) the first VH comprises the CDRH1, CDRH2, and CDRH3 amino acid sequences of the VH amino acid sequence of SEQ ID NO: 36; and the first VL comprises the CDRL1, CDRL2, and CDRL3 amino acid sequences of the VL amino acid sequence of SEQ ID NO: 37, or
  (iii) the first VH comprises the CDRH1, CDRH2, and CDRH3 amino acid sequences of the VH amino acid sequence of SEQ ID NO: 38; and the first VL comprises the CDRL1, CDRL2, and CDRL3 amino acid sequences of the VL amino acid sequence of SEQ ID NO: 39; and (b) a second antigen-binding region that specifically binds to an antigen other than human CD96, the second antigen-binding region comprising a second VH comprising CDRs CDRH1, CDRH2, and CDRH3, and a second VL comprising CDRs CDRL1, CDRL2, and CDRL3.

In certain embodiments, the CDRH1, CDRH2, CDRH3, CDRL1, CDRL2, and CDRL3 of the first antigen-binding region comprise the amino acid sequences of SEQ ID NOs: 10, 11, 12, 13, 14, and 15; 16, 17, 18, 19, 20, and 21; or 22, 23, 24, 25, 26, and 27, respectively.

In certain embodiments, the second antigen-binding region specifically binds to human TIGIT. In a specific embodiment, the second VH comprises the CDRH1, CDRH2, and CDRH3 amino acid sequences of the VH amino acid sequence of SEQ ID NO: 40; and the second VL comprises the CDRL1, CDRL2, and CDRL3 amino acid sequences of the VL amino acid sequence of SEQ ID NO: 41. In another embodiment, the CDRH1, CDRH2, CDRH3, CDRL1, CDRL2, and CDRL3 of the second antigen-binding region comprise the amino acid sequences of SEQ ID NOs: 28, 29, 30, 31, 32, and 33, respectively.

In another aspect, the instant disclosure provides a multispecific molecule comprising:

(a) a first antigen-binding region that specifically binds to an antigen other than human TIGIT, the first antigen-binding region comprising a first VH comprising CDRs CDRH1, CDRH2, and CDRH3, and a first VL comprising CDRs CDRL1, CDRL2, and CDRL3; and (b) a second antigen-binding region that specifically binds to human TIGIT, the second antigen-binding region comprising a second VH comprising the CDRH1, CDRH2, and CDRH3 amino acid sequences of the VH amino acid sequence of SEQ ID NO: 40; and a second VL comprising the CDRL1, CDRL2, and CDRL3 amino acid sequences of the VL amino acid sequence of SEQ ID NO: 41.

In certain embodiments, the CDRH1, CDRH2, CDRH3, CDRL1, CDRL2, and CDRL3 of the second antigen-binding region comprise the amino acid sequences of SEQ ID NOs: 28, 29, 30, 31, 32, and 33, respectively.

In certain embodiments, the first antigen-binding region specifically binds to human CD96. In a specific embodiment, the first VH comprises an amino acid sequence that is at least 75%, 80%, 85%, 90%, 95%, 99%, or 100% identical to the amino acid sequence of SEQ ID NO: 34, 36, or 38. In another embodiment, the amino acid sequence of the first VH consists of the amino acid sequence of SEQ ID NO: 34, 36, or 38. In another embodiment, the first VL comprises an amino acid sequence that is at least 75%, 80%, 85%, 90%, 95%, 99%, or 100% identical to the amino acid sequence of SEQ ID NO: 35, 37, or 39. In another embodiment, the amino acid sequence of the first VL consists of the amino acid sequence of SEQ ID NO: 35, 37, or 39.

In certain embodiments, the second VH comprises an amino acid sequence that is at least 75%, 80%, 85%, 90%, 95%, 99%, or 100% identical to the amino acid sequence of SEQ ID NO: 40. In a specific embodiment, the amino acid sequence of the second VH consists of the amino acid sequence of SEQ ID NO: 40.

In certain embodiments, the second VL comprises an amino acid sequence that is at least 75%, 80%, 85%, 90%, 95%, 99%, or 100% identical to the amino acid sequence of SEQ ID NO: 41. In a specific embodiment, the amino acid sequence of the second VL consists of the amino acid sequence of SEQ ID NO: 41.

In another aspect, the instant disclosure provides a multispecific molecule comprising:

(a) a first antigen-binding region that specifically binds to human CD96, the antigen-binding region comprising a first VH and a first VL, wherein the first VH comprises the amino acid sequence of SEQ ID NO: 34, 36, or 38; and/or the first VL comprises the amino acid sequence of SEQ ID NO: 35, 37, or 39; and (b) a second antigen-binding region that specifically binds to an antigen other than human CD96, the second antigen-binding region comprising a second VH and a second VL.

In certain embodiments, the second antigen-binding region specifically binds to human TIGIT.

In another aspect, the instant disclosure provides a multispecific molecule comprising:

(a) a first antigen-binding region that specifically binds to an antigen other than human TIGIT, the first antigen-binding region comprising a first VH and first VL; and (b) a second antigen-binding region that specifically binds to human TIGIT, the antigen-binding region comprising a second VH and a second VL, wherein the second VH comprises the amino acid sequence of SEQ ID NO: 40; and/or the second VL comprises the amino acid sequence of SEQ ID NO: 41.

In certain embodiments, the first antigen-binding region specifically binds to human CD96. In a specific embodiment, the first VH comprises the amino acid sequence of SEQ ID NO: 34, 36, or 38 and the first VL comprises the amino acid sequence of SEQ ID NO: 35, 37, or 39. In another embodiment, the amino acid sequence of the first VH consists of SEQ ID NO: 34, 36, or 38 and the amino acid sequence of the first VL consists of SEQ ID NO: 35, 37, or 39. In another embodiment, the first VH and the first VL comprise the amino acid sequences of SEQ ID NOs: 34 and 35; 36 and 37; or 38 and 39, respectively. In another embodiment, the amino acid sequences of the first VH and the first VL consist of the amino acid sequences of SEQ ID NOs: 34 and 35; 36 and 37; or 38 and 39, respectively. In another embodiment, the second VH comprises the amino acid sequence of SEQ ID NO: 40 and the second VL comprises the amino acid sequence of SEQ ID NO: 41. In another embodiment, the amino acid sequences of the second VH and the second VL consist of the amino acid sequences of SEQ ID NOs: 40 and 41, respectively. In another embodiment, the first VH and the first VL comprise the amino acid sequences of SEQ ID NOs: 34 and 35; 36 and 37; or 38 and 39, respectively; and the second VH and the second VL comprise the amino acid sequences of SEQ ID NOs: 40 and 41, respectively. In another embodiment, the amino acid sequences of the first VH and the first VL consist of the amino acid sequences of SEQ ID NOs: 34 and 35; 36 and 37; or 38 and 39, respectively; and the amino acid sequences of the second VH and the second VL consist of the amino acid sequences of SEQ ID NOs: 40 and 41, respectively.

In certain embodiments, the first and/or second antigen-binding region comprises a heavy chain constant region selected from the group consisting of human $IgG_1$, $IgG_2$, $IgG_3$, $IgG_4$, $IgA_1$, and $IgA_2$. In a specific embodiment, the heavy chain constant region is an $IgG_1$ heavy chain constant region. In another embodiment, the heavy chain constant region comprises the amino acid sequence of any one of SEQ ID NO: 49-60.

In certain embodiments, the amino acid sequence of the $IgG_1$ heavy chain constant region comprises an N297A mutation, numbered according to the EU numbering system.

In certain embodiments, the first and/or second antigen-binding region comprises a heavy chain constant region that is a variant of a wild type heavy chain constant region, wherein the variant heavy chain constant region binds to an FcγR with higher affinity than the wild type heavy chain constant region binds to the FcγR. In a specific embodiment, the FcγR is FcγRIIB or FcγRIIIA.

In certain embodiments, the amino acid sequence of the $IgG_1$ heavy chain constant region comprises S267E and L328F mutations, numbered according to the EU numbering system.

In certain embodiments, the amino acid sequence of the $IgG_1$ heavy chain constant region comprises at least one mutation selected from the group consisting of S239D, A330L, and I332E, numbered according to the EU numbering system.

In certain embodiments, the first antigen-binding region comprises a first heavy chain constant region comprising aspartate at amino acid position 239; aspartate and glutamate at amino acid positions 239 and 332, respectively; or aspartate, leucine, and glutamate at amino acid positions 239, 330, and 332, respectively; and the second antigen-binding region comprises a second heavy chain constant region that does not comprise aspartate, leucine, and glutamate at amino acid positions 239, 330, and 332, respectively, wherein the amino acid positions are numbered according to the EU numbering system.

In a specific embodiment, the first heavy chain constant region and the second heavy chain constant region comprise SEQ ID NOs: 58 and 57; 59 and 57; or 60 and 57, respectively.

In certain embodiments, the first antigen-binding region comprises a first heavy chain constant region comprising aspartate and glutamate at amino acid positions 239 and 332, respectively; or aspartate, leucine, and glutamate at amino acid positions 239, 330, and 332, respectively; and the second antigen-binding region comprises a second heavy chain constant region comprising aspartate at amino acid positions 239, wherein the amino acid positions are numbered according to the EU numbering system.

In a specific embodiment, the first heavy chain constant region and the second heavy chain and constant region comprise SEQ ID NOs: 59 and 58; or 60 and 58, respectively.

In certain embodiments, the first heavy chain constant region comprises aspartate, leucine, and glutamate at amino acid positions 239, 330, and 332, respectively; and the second heavy chain constant region further comprises glutamate at amino acid position 332, wherein the amino acid positions are numbered according to the EU numbering system.

In a specific embodiment, the first heavy chain constant region and the second heavy chain constant region comprise SEQ ID NOs: 60 and 59, respectively.

In certain embodiments, the first antigen-binding region comprises a first heavy chain constant region that does not comprise aspartate, leucine, and glutamate at amino acid positions 239, 330, and 332, respectively; and the second antigen-binding region comprises a second heavy chain constant region comprising aspartate at amino acid position 239; aspartate and glutamate at amino acid positions 239 and 332, respectively; or aspartate, leucine, and glutamate at amino acid positions 239, 330, and 332, respectively, wherein the amino acid positions are numbered according to the EU numbering system.

In a specific embodiment, the first heavy chain constant region and the second heavy chain constant region comprise SEQ ID NOs: 57 and 60; 57 and 59; or 57 and 58, respectively.

In certain embodiments, the first antigen-binding region comprises a first heavy chain constant region comprising aspartate at amino acid positions 239; and the second antigen-binding region comprises a second heavy chain constant region comprising aspartate and glutamate at amino acid positions 239 and 332, respectively; or aspartate, leucine, and glutamate at amino acid positions 239, 330, and 332, respectively, wherein the amino acid positions are numbered according to the EU numbering system.

In a specific embodiment, the first heavy chain constant region and the second heavy chain constant region comprise SEQ ID NOs: 58 and 60; or 58 and 59, respectively.

In certain embodiments, the first heavy chain constant region further comprises glutamate at amino acid position 332; and the second heavy chain constant region comprises aspartate, leucine, and glutamate at amino acid positions 239, 330, and 332, respectively, wherein the amino acid positions are numbered according to the EU numbering system.

In a specific embodiment, the first heavy chain constant region and the second heavy chain constant region comprise SEQ ID NOs: 59 and 60, respectively.

In certain embodiments, the first antigen-binding region comprises a first heavy chain constant region comprising tryptophan at amino acid position 366; and the second antigen-binding region comprises a second heavy chain constant region comprising serine, alanine, and valine at amino acid positions 366, 368, and 407, respectively, wherein the amino acid positions are numbered according to the EU numbering system.

In a specific embodiment, the first heavy chain constant region comprises SEQ ID NO: 53, 54, 55, or 56; and the second heavy chain constant region comprises SEQ ID NO: 49, 50, 51, or 52.

In certain embodiments, the first antigen-binding region comprises a first heavy chain constant region comprising serine, alanine, and valine at amino acid positions 366, 368, and 407, respectively; and the second antigen-binding region comprises a second heavy chain constant region comprising tryptophan at amino acid position 366, wherein the amino acid positions are numbered according to the EU numbering system.

In a specific embodiment, the first heavy chain constant region comprises SEQ ID NO: 49, 50, 51, or 52; and the second heavy chain constant region comprises SEQ ID NO: 53, 54, 55, or 56.

In certain embodiments, the first antigen-binding region comprises a first heavy chain comprising the amino acid sequence of SEQ ID NO: 1, 3, 5, or 67-99. In a specific embodiment, the first heavy chain consists of the amino acid sequence of SEQ ID NO: 1, 3, 5, or 67-99. In certain embodiments, the second antigen-binding region comprises a second heavy chain comprising the amino acid sequence of SEQ ID NO: 7 or 100-110. In a specific embodiment, the amino acid sequence of the second heavy chain consists of the amino acid sequence of SEQ ID NO: 7 or 100-110.

In certain embodiments, the multispecific molecule comprises a light chain constant region comprising the amino acid sequence of SEQ ID NO: 42, 43, or 44. In a specific embodiment, the first antigen-binding region comprises a first light chain comprising the amino acid sequence of SEQ ID NO: 2, 4, or 6. In another embodiment, the first light chain consists of the amino acid sequence of SEQ ID NO: 2, 4, or 6. In a specific embodiment, the second antigen-binding region comprises a second light chain comprising the amino acid sequence of SEQ ID NO: 8 or 9. In another embodiment, the amino acid sequence of the second light chain consists of the amino acid sequence of SEQ ID NO: 8 or 9.

In another aspect, the instant disclosure provides a multispecific molecule comprising:

(a) a first antigen-binding region that specifically binds to human CD96, the first antigen-binding region comprising a first heavy chain comprising the amino acid sequence of SEQ ID NO: 1, 3, 5, or 67-99; and/or a first light chain comprising the amino acid sequence of SEQ ID NO: 2, 4, or 6; and (b) a second antigen-binding region that specifically binds to an antigen other than human CD96, the second antigen-binding region comprising a second heavy chain and a second light chain.

In certain embodiments, the second antigen-binding region specifically binds to human TIGIT.

In another aspect, the instant disclosure provides a multispecific molecule comprising:

(a) a first antigen-binding region that specifically binds to an antigen other than human TIGIT, the first antigen-binding region comprising a first heavy chain and a first light chain; and (b) a second antigen-binding region that specifically binds to human TIGIT, the second antigen-binding region comprising a second heavy chain comprising the amino acid sequence of SEQ ID NO: 7 or 100-110; and/or a second light chain comprising the amino acid sequence of SEQ ID NO: 8 or 9.

In certain embodiments, the first antigen-binding region specifically binds to human CD96. In a specific embodiment, the first heavy chain comprises the amino acid sequence of SEQ ID NO: 1, 3, 5, or 67-99; and/or the first light chain comprises the amino acid sequence of SEQ ID NO: 2, 4, or 6. In another embodiment, the first heavy chain comprises the amino acid sequence of SEQ ID NO: 1, 3, 5, or 67-99; and the first light chain comprises the amino acid sequence of SEQ ID NO: 2, 4, or 6. In another embodiment, the amino acid sequence of the first heavy chain consists of SEQ ID NO: 1, 3, 5, or 67-99; and the amino acid sequence of the first light chain consists of the amino acid sequence of SEQ ID NO: 2, 4, or 6.

In certain embodiments, the second heavy chain comprises the amino acid sequence of SEQ ID NO: 7 or 100-110; and/or the second light chain comprises the amino acid sequence of SEQ ID NO: 8 or 9. In a specific embodiment, the second heavy chain comprises the amino acid sequence of SEQ ID NO: 7 or 100-110; and the second light chain comprises the amino acid sequence of SEQ ID NO: 8 or 9. In another embodiment, the amino acid sequence of the second heavy chain consists of SEQ ID NO: 7; and the amino acid sequence of the second light chain consists of the amino acid sequence of SEQ ID NO: 8 or 9.

In certain embodiments, the first heavy chain and the first light chain comprise the amino acid sequences of SEQ ID NOs: 1 and 2; 3 and 4; or 5 and 6, respectively; and/or the second heavy chain and second light chain comprise the amino acid sequences of SEQ ID NOs: 7 and 8; or 7 and 9, respectively. In a specific embodiment, the first heavy chain and the first light chain comprise the amino acid sequences of SEQ ID NOs: 1 and 2; 3 and 4; or 5 and 6, respectively; and the second heavy chain and second light chain comprise the amino acid sequences of SEQ ID NOs: 7 and 8; or 7 and 9, respectively. In another embodiment, the amino acid sequences of the first heavy chain and the first light chain consist of SEQ ID NOs: 1 and 2; 3 and 4; or 5 and 6, respectively; and the amino acid sequences of the second heavy chain and the second light chain consist of the amino acid sequences of SEQ ID NOs: 7 and 8; or 7 and 9, respectively.

In another aspect, the instant disclosure provides a multispecific molecule comprising a first antigen-binding region that specifically binds to human CD96; and a second antigen-binding region that specifically binds to human TIGIT, wherein:

(a) the first antigen-binding region comprises aspartate, leucine, glutamate, and tryptophan at amino acid positions 239, 330, 332, and 366, respectively; and (b) the second antigen-binding region comprises serine, alanine, and valine at amino acid positions 366, 368, and 407, respectively, but does not comprise aspartate, leucine, and glutamate at amino acid positions 239, 330, and 332, respectively, wherein the amino acid positions are numbered according to the EU numbering system.

In some embodiments, the first antigen-binding region comprises SEQ ID NO: 73, 84, 95, or 56; and the second antigen-binding region comprises SEQ ID NO: 103 or 49.

In another aspect, the instant disclosure provides a multispecific molecule comprising a first antigen-binding region that specifically binds to human CD96; and a second antigen-binding region that specifically binds to human TIGIT, wherein:

(a) the first antigen-binding region comprises aspartate, leucine, glutamate, and tryptophan at amino acid positions 239, 330, 332, and 366, respectively; and (b) the second antigen-binding region comprises aspartate, serine, alanine, and valine at amino acid positions 239, 366, 368, and 407, respectively, wherein the amino acid positions are numbered according to the EU numbering system.

In certain embodiments, the first antigen-binding region comprises SEQ ID NO: 73, 84, 95, or 56; and the second antigen-binding region comprises SEQ ID NO: 104 or 50.

In another aspect, the instant disclosure provides a multispecific molecule comprising a first antigen-binding region that specifically binds to human CD96; and a second antigen-binding region that specifically binds to human TIGIT, wherein:

(a) the first antigen-binding region comprises serine, alanine, and valine at amino acid positions 366, 368, and 407, respectively, but does not comprise aspartate, leucine, and glutamate at amino acid positions 239, 330, and 332, respectively; and (b) the second antigen-binding region comprises aspartate, leucine, glutamate, and tryptophan at amino acid positions 239, 330, 332, and 366, respectively, wherein the amino acid positions are numbered according to the EU numbering system.

In certain embodiments, the first antigen-binding region comprises SEQ ID NO: 67, 78, 89, or 49; and the second antigen-binding region comprises SEQ ID NO: 7 or 56.

In another aspect, the instant disclosure provides a multispecific molecule comprising a first antigen-binding region that specifically binds to human CD96; and a second antigen-binding region that specifically binds to human TIGIT, wherein:

(a) the first antigen-binding region aspartate, serine, alanine, and valine at amino acid positions 239, 366, 368, and 407, respectively; and (b) the second antigen-binding region comprises aspartate, leucine, glutamate, and tryptophan at amino acid positions 239, 330, 332, and 366, respectively, wherein the amino acid positions are numbered according to the EU numbering system.

In certain embodiments, the first antigen-binding region comprises SEQ ID NO: 1, 3, 5, or 50; and the second antigen-binding region comprises SEQ ID NO: 7 or 56.

In another aspect, the instant disclosure provides a multispecific molecule comprising a first antigen-binding region that specifically binds to human CD96; and a second antigen-binding region that specifically binds to human TIGIT, wherein:

(a) the first antigen-binding region comprises aspartate, glutamate, and tryptophan at amino acid positions 239, 332, and 366, respectively; and (b) the second antigen-binding region comprises serine, alanine, and valine at amino acid positions 366, 368, and 407, respectively, but does not comprise aspartate, leucine, and glutamate at amino acid positions 239, 330, and 332, respectively, wherein the amino acid positions are numbered according to the EU numbering system.

In certain embodiments, the first antigen-binding region comprises SEQ ID NO: 72, 83, 94, or 55; and the second antigen-binding region comprises SEQ ID NO: 103 or 49.

In another aspect, the instant disclosure provides a multispecific molecule comprising a first antigen-binding region that specifically binds to human CD96; and a second antigen-binding region that specifically binds to human TIGIT, wherein:

(a) the first antigen-binding region comprises serine, alanine, and valine at amino acid positions 366, 368, and 407, respectively, but does not comprise aspartate, leucine, and glutamate at amino acid positions 239, 330, and 332, respectively; and (b) the second antigen-binding region comprises aspartate, glutamate, and tryptophan at amino acid positions 239, 332, and 366, respectively, wherein the amino acid positions are numbered according to the EU numbering system.

In certain embodiments, the first antigen-binding region comprises SEQ ID NO: 67, 78, 89, or 49; and the second antigen-binding region comprises SEQ ID NO: 102 or 55.

In another aspect, the instant disclosure provides an isolated antibody that specifically binds to human TIGIT, the antibody comprising: a VH comprising the CDRH1, CDRH2, and CDRH3 amino acid sequences of the VH amino acid sequence of SEQ ID NO: 40; and a VL comprising the CDRL1, CDRL2, and CDRL3 amino acid sequences of the VL amino acid sequence of SEQ ID NO: 41. In certain embodiments, the antibody comprises the CDRH1, CDRH2, CDRH3, CDRL1, CDRL2, and CDRL3 amino acid sequences of SEQ ID NOs: 28, 29, 30, 31, 32, and 33, respectively. In a specific embodiment, the antibody comprises the VH amino acid sequence of SEQ ID NO: 40. In another embodiment, the VH consists of the amino acid sequence of SEQ ID NO: 40. In another embodiment, the antibody comprises the VL amino acid sequence of SEQ ID NO: 41. In another embodiment, the amino acid sequence of the VL consists of the amino acid sequence of SEQ ID NO: 41.

In another aspect, the instant disclosure provides an isolated antibody that specifically binds to human TIGIT, the antibody comprising a VH and a VL comprising the amino acid sequences of SEQ ID NOs: 40 and 41, respectively. In certain embodiments, the VH and the VL consist of the amino acid sequences of SEQ ID NOs: 40 and 41, respectively.

In some embodiments, the antibody comprises a heavy chain constant region selected from the group consisting of human $IgG_1$, $IgG_2$, $IgG_3$, $IgG_4$, $IgA_1$, and $IgA_2$. In a specific embodiment, the antibody comprises an $IgG_1$ heavy chain constant region. In another embodiment, the antibody comprises a heavy chain constant region comprising the amino acid sequence of SEQ ID NO: 57, 58, 59, or 60.

In certain embodiments, the amino acid sequence of the $IgG_1$ heavy chain constant region comprises an N297A mutation, numbered according to the EU numbering system.

In certain embodiments, the antibody comprises a heavy chain constant region that is a variant of a wild type heavy chain constant region, wherein the variant heavy chain constant region binds to an FcγR with higher affinity than the wild type heavy chain constant region binds to the FcγR. In a specific embodiment, the FcγR is FcγRIIB or FcγRIIIA.

In certain embodiments, the amino acid sequence of the $IgG_1$ heavy chain constant region comprises S267E and L328F mutations, numbered according to the EU numbering system.

In certain embodiments, the $IgG_1$ heavy chain constant region comprises at least one mutation selected from the group consisting of S239D, A330L, and I332E mutations, numbered according to the EU numbering system.

In certain embodiments, the antibody comprises a heavy chain comprising the amino acid sequence of SEQ ID NO: 7. In a specific embodiment, the amino acid sequence of the heavy chain consists of the amino acid sequence of SEQ ID NO: 7.

In certain embodiments, the antibody comprises a light chain constant region comprising the amino acid sequence of SEQ ID NO: 43 or 44. In a specific embodiment, the antibody comprises a light chain comprising the amino acid sequence of SEQ ID NO: 8 or 9. In another embodiment, the amino acid sequence of the light chain consists of the amino acid sequence of SEQ ID NO: 8 or 9.

In another aspect, the instant disclosure provides an isolated antibody that specifically binds to human TIGIT, the antibody comprising a heavy chain comprising the amino acid sequence of SEQ ID NO: 107, 108, 109, or 110; and a light chain comprising the amino acid sequence of SEQ ID NO: 8 or 9. In a specific embodiment, the amino acid sequence of the heavy chain consists of the amino acid sequence of SEQ ID NO: 107, 108, 109, or 110; and the amino acid sequence of the light chain consists of the amino acid sequence of SEQ ID NO: 8 or 9. In another embodiment, the heavy chain and light chain comprise the amino acid sequences of SEQ ID NOs: 107 and 8; 107, and 9; 108 and 8; 108 and 9; 109 and 8; 109 and 9; 110 and 8; or 110 and 9, respectively. In another embodiment, the amino acid sequences of the heavy chain and the light chain consist of the amino acid sequences of SEQ ID NOs: 107 and 8; 107, and 9; 108 and 8; 108 and 9; 109 and 8; 109 and 9; 110 and 8; or 110 and 9, respectively.

In certain embodiments, the antibody is multispecific.

In certain embodiments, the multispecific molecule or isolated antibody is conjugated to a cytotoxic agent, cytostatic agent, toxin, radionuclide, or detectable label. In certain embodiments, the multispecific molecule or isolated antibody is conjugated to an antibody.

In another aspect, the instant disclosure provides an isolated polynucleotide encoding:

(a) a VH, VL, heavy chain, and/or light chain of a multispecific molecule disclosed herein;

(b) the first VH and the first VL of a multispecific molecule disclosed herein;

(c) the second VH and the second VL of a multispecific molecule disclosed herein;

(d) the first heavy chain and the first light chain of a multispecific molecule disclosed herein; or (e) the second heavy chain and the second light chain of a multispecific molecule disclosed herein.

In another aspect, the instant disclosure provides an isolated polynucleotide encoding the VH and/or the VL, or the heavy chain and/or the light chain, of an isolated antibody disclosed herein.

In another aspect, the instant disclosure provides, a vector comprising a polynucleotide disclosed herein.

In another aspect, the instant disclosure provides a recombinant host cell comprising:

(a) a polynucleotide disclosed herein;

(b) a vector disclosed herein;

(c) a first polynucleotide encoding the VH and VL of a first antigen-binding region disclosed herein, and a second polynucleotide encoding the VH and VL of a second antigen-binding region disclosed herein;

(d) a first vector comprising a first polynucleotide encoding the VH and VL of a first antigen-binding region disclosed herein, and a second vector comprising a second polynucleotide encoding the VH and VL of a second antigen-binding region disclosed herein;

(e) a first polynucleotide encoding the VH of a first antigen-binding region disclosed herein, a second polynucleotide encoding the VL of a first antigen-binding region disclosed herein, a third polynucleotide encoding the VH of a second antigen-binding region disclosed herein, and a fourth polynucleotide encoding the VL of a second antigen-binding region disclosed herein;

(f) a first vector comprising a first polynucleotide encoding the VH of a first antigen-binding region disclosed herein, a second vector comprising a second polynucleotide encoding the VL of a first antigen-binding region disclosed herein, a third vector comprising a third polynucleotide encoding the VH of a second antigen-binding region disclosed herein, and a fourth vector comprising a fourth polynucleotide encoding the VL of a second antigen-binding region disclosed herein;

(g) a first polynucleotide encoding the heavy chain and light chain of a first antigen-binding region disclosed herein, and a second polynucleotide encoding the heavy chain and light chain of a second antigen-binding region disclosed herein;

(h) a first vector comprising a first polynucleotide encoding the heavy chain and light chain of a first antigen-binding region disclosed herein, and a second vector comprising a second polynucleotide encoding the heavy chain and light chain of a second antigen-binding region disclosed herein;

(i) a first polynucleotide encoding the heavy chain of a first antigen-binding region of disclosed herein, a second polynucleotide encoding the light chain of a first antigen-binding region disclosed herein, a third polynucleotide encoding the heavy chain of a second antigen-binding region disclosed herein, and a fourth polynucleotide encoding the VL of a second antigen-binding region disclosed herein; or (j) a first vector comprising a first polynucleotide encoding the heavy chain of a first antigen-binding region disclosed herein, a second vector comprising a second polynucleotide encoding the light chain of a first antigen-binding region disclosed herein, a third vector comprising a third polynucleotide encoding the heavy chain of a second antigen-binding region disclosed herein, and a fourth vector comprising a fourth polynucleotide encoding the light chain of a second antigen-binding region disclosed herein.

In another aspect, the instant disclosure provides a recombinant host cell comprising:

(a) a polynucleotide disclosed herein;

(b) a vector disclosed herein;

(c) a polynucleotide encoding the VH and VL of an isolated antibody disclosed herein;

(d) a first vector comprising a polynucleotide encoding the VH and VL of an isolated antibody disclosed herein;

(e) a first polynucleotide encoding the VH of an isolated antibody disclosed herein, and a second polynucleotide encoding the VL of an isolated antibody disclosed herein; or (f) a first vector comprising a first polynucleotide encoding the VH of an isolated antibody disclosed herein, and a second vector comprising a second polynucleotide encoding the VL of an isolated antibody disclosed herein.

In another aspect, the instant disclosure provides a pharmaceutical composition comprising a multispecific molecule disclosed herein, an isolated antibody disclosed herein, a polynucleotide disclosed herein, a vector disclosed herein, or a host cell disclosed herein; and a pharmaceutically acceptable carrier or excipient.

In another aspect, the instant disclosure provides a method of producing a multispecific molecule or isolated antibody, the method comprising culturing a host cell disclosed herein under suitable conditions so that the polynucleotide is expressed and the multispecific molecule or isolated antibody is produced.

In another aspect, the instant disclosure provides a method of producing a multispecific molecule, the method comprising expressing in a cell:

(a) a first polynucleotide encoding the VH and VL of a first antigen-binding region disclosed herein; and a second polynucleotide encoding the VH and VL of a second antigen-binding region disclosed herein; or (b) a first polynucleotide encoding the heavy chain and light chain of a first antigen-binding region disclosed herein; and a second polynucleotide encoding the heavy chain and light chain of a second antigen-binding region disclosed herein, under suitable conditions so that the polynucleotides are expressed and the multispecific molecule is produced.

In another aspect, the instant disclosure provides a method of producing a multispecific molecule, the method comprising expressing in a cell:

(a) a first polynucleotide encoding the VH of a first antigen-binding region disclosed herein, a second polynucleotide encoding the VL of a first antigen-binding region disclosed herein, a third polynucleotide encoding the VH of a second antigen-binding disclosed herein, and a fourth polynucleotide encoding the VL of a second antigen-binding region disclosed herein; or (b) a first polynucleotide encoding the heavy chain of a first antigen-binding region disclosed herein, a second polynucleotide encoding the light chain of a first antigen-binding region disclosed herein, a third polynucleotide encoding the heavy chain of a second antigen-binding region disclosed herein, and a fourth polynucleotide encoding the light chain of a second antigen-binding region disclosed herein, under suitable conditions so that the polynucleotides are expressed and the multispecific molecule is produced.

In another aspect, the instant disclosure provides a method of producing a multispecific molecule, the method comprising:

(a) expressing in a first cell a first polynucleotide encoding the VH and VL of a first antigen-binding region disclosed herein, under conditions whereby the first antigen-binding region is produced;

(b) expressing in a second cell a second polynucleotide encoding the VH and VL of a second antigen-binding region disclosed herein, under conditions whereby the second antigen-binding region is produced; and (c) contacting the first and the second antigen-binding regions produced in steps (a) and (b), under suitable conditions so that the multispecific molecule is produced.

In another aspect, the instant disclosure provides a method of producing a multispecific molecule, the method comprising:

(a) expressing in a first cell a first polynucleotide encoding the VH of a first antigen-binding region disclosed herein and second polynucleotide encoding the VL of a first antigen-binding region disclosed herein, under conditions whereby the first antigen-binding region is produced;

(b) expressing in a second cell a third polynucleotide encoding the VH of a second antigen-binding region disclosed herein and fourth polynucleotide encoding the VL of a second antigen-binding region disclosed herein, under conditions whereby the second antigen-binding region is produced; and (c) contacting the first and the second antigen-binding regions produced in steps (a) and (b), under conditions so that the multispecific molecule is produced.

In another aspect, the instant disclosure provides a method of producing a multispecific molecule, the method comprising contacting a first antigen-binding region and a second antigen-binding region disclosed herein under conditions so that the multispecific molecule is produced.

In another aspect, the instant disclosure provides a method of producing an isolated antibody, the method comprising expressing in a cell:

(a) a polynucleotide encoding the VH and VL of an antibody disclosed herein; or (b) a polynucleotide encoding the heavy chain and light chain of an antibody disclosed herein, under suitable conditions so that the polynucleotides are expressed and the antibody is produced.

In another aspect, the instant disclosure provides a method of producing an isolated antibody, the method comprising expressing in a cell:

(a) a first polynucleotide encoding the VH of an antibody disclosed herein; and a second polynucleotide encoding the VL an antibody disclosed herein; or (b) a first polynucleotide encoding the heavy chain of an antibody disclosed herein; and a second polynucleotide encoding the light chain of the light chain of an antibody disclosed herein, under suitable conditions so that the polynucleotides are expressed and the antibody is produced.

In another aspect, the instant disclosure provides a method of enhancing an immune response in a subject, the method comprising administering to the subject an effective amount of a multispecific molecule disclosed herein, an isolated antibody disclosed herein, a polynucleotide disclosed herein, a vector disclosed herein, a host cell disclosed herein, or a pharmaceutical composition disclosed herein.

In another aspect, the instant disclosure provides, a method of treating cancer in a subject, the method comprising administering to the subject an effective amount of a multispecific molecule disclosed herein, an isolated antibody disclosed herein, a polynucleotide disclosed herein, a vector disclosed herein, a host cell disclosed herein, or a pharmaceutical composition disclosed herein.

In certain embodiments, the multispecific molecule, isolated antibody, polynucleotide, vector, host cell, or pharmaceutical composition is administered, systemically, intravenously, subcutaneously, intratumorally, or is delivered to a tumor draining lymph node.

In certain embodiments, the method further comprises administering an additional therapeutic agent to the subject. In a specific embodiment, the additional therapeutic agent is a chemotherapeutic agent. In a specific embodiment, the additional therapeutic agent is a checkpoint targeting agent. In another embodiment, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-VISTA antibody, an antagonist anti-TIGIT antibody, an antagonist anti-CEACAM1 antibody, an antagonist anti-CD96 antibody, an agonist anti-GITR antibody, and an agonist anti-OX40 antibody. In another embodiment, the additional therapeutic agent is an anti-PD-1 antibody, optionally wherein the anti-PD-1 antibody is pembrolizumab or nivolumab. In a specific embodiment, the additional therapeutic agent is an inhibitor of indoleamine-2,3-dioxygenase (IDO). In another embodiment, the inhibitor is selected from the group consisting of epacadostat, F001287, indoximod, and NLG919. In a specific embodiment, the additional therapeutic agent is a vaccine. In another embodiment, the vaccine comprises a heat shock protein peptide complex (HSPPC) comprising a heat shock protein complexed with an antigenic peptide. In another embodiment, the heat shock protein is hsc70 and is complexed with a tumor-associated antigenic peptide. In another embodiment, the heat shock protein is gp96 protein and is complexed with a tumor-associated antigenic peptide, optionally wherein the HSPPC is derived from a tumor obtained from a subject.

In another aspect, the instant disclosure provides a method of treating an infectious disease in a subject, the method comprising administering to the subject an effective amount of a multispecific molecule disclosed herein, an isolated antibody disclosed herein, a polynucleotide disclosed herein, a vector disclosed herein, a host cell disclosed herein, or a pharmaceutical composition disclosed herein.

6. BRIEF DESCRIPTION OF THE DRAWINGS

FIG. 1A-FIG. 1C are a series of sensorgrams showing simultaneous binding of the extracellular domains of human TIGIT and human CD96 to multispecific molecules BA123 (FIG. 1A), BA125 (FIG. 1B), and BA127 (FIG. 1C).

FIG. 2A-FIG. 2B are graphs showing simultaneous binding of the anti-TIGIT×CD96 multispecific molecule BA127 to CHO cells engineered to express human TIGIT or human CD96 as compared control multispecific molecules BA128, BA131, and BA133. Dual binding of cell-expressed human TIGIT and soluble His-tagged human CD96 (FIG. 2A) or cell-expressed human CD96 and soluble His-tagged human TIGIT (FIG. 2B) was detected by flow cytometry using fluorochrome-conjugated (Alex Fluor 488) anti-His antibody.

FIG. 3A-FIG. 3I are a series of graphs showing the binding of the anti-TIGIT×CD96 multispecific molecules BA123 (FIG. 3A), BA125 (FIG. 3B), or BA127 (FIG. 3C), or control multispecific molecules BA129 (FIG. 3D), BA130 (FIG. 3E), BA131 (FIG. 3F), BA133 (FIG. 3G), BA134 (FIG. 3H), or BA136 (FIG. 3I), to CHO cells engineered to express high levels of cell surface isoform 2 of human CD96, compared to an isotype control multispecific molecule (BA128). The levels of binding, as assessed by median fluorescence intensity (MFI), in each case in comparison with CHO cell binding of BA128, were plotted against the concentrations of the respective antibody incubated with the cells.

FIG. 4A-FIG. 4I are a series of graphs showing the binding of the anti-TIGIT×CD96 multispecific molecules BA123 (FIG. 4A), BA127 (FIG. 4B), or BA125 (FIG. 4C), or control multispecific molecules BA129 (FIG. 4D), BA130 (FIG. 4E), BA131 (FIG. 4F), BA133 (FIG. 4G), BA134 (FIG. 4H), or BA136 (FIG. 4I), to CHO cells engineered to express high levels of cell surface isoform 1 of human CD96, compared to an isotype control multispecific molecule (BA128). The levels of binding, as assessed by median fluorescence intensity (MFI), in each case in comparison with CHO cell binding of BA128, were plotted against the concentrations of the respective antibody incubated with the cells.

FIG. 5A-FIG. 5I are a series of graphs showing the binding of the anti-TIGIT×CD96 multispecific molecules BA123 (FIG. 5A), BA125 (FIG. 5B), or BA127 (FIG. 5C), or control multispecific molecules BA129 (FIG. 5D), BA130 (FIG. 5E), BA131 (FIG. 5F), BA133 (FIG. 5G), BA134 (FIG. 5H), or BA136 (FIG. 5I), to CHO cells engineered to express high levels of cell surface isoform 2 of cynomolgus monkey CD96, compared to an isotype control multispecific molecule (BA128). The levels of binding, as assessed by median fluorescence intensity (MFI), in each case in comparison with CHO cell binding of BA128, are plotted against the concentrations of the respective antibody incubated with the cells.

FIG. 6A-FIG. 6I are a series of graphs showing the blockade of human CD155-Fc binding to CHO cells, engineered to express high levels of cell surface isoform 2 of human CD96, by the anti-TIGIT×CD96 multispecific molecules BA123 (FIG. 6A), BA125 (FIG. 6B), or BA127 (FIG. 6C), or control multispecific molecules BA129 (FIG. 6D), BA130 (FIG. 6E), BA131 (FIG. 6F), BA133 (FIG. 6G), BA134 (FIG. 6H), or BA136 (FIG. 6I). The levels of binding of CD155-Fc, as assessed by median fluorescence intensity (MFI), in each case in comparison with blockade by an isotype control multispecific molecule (BA128), were plotted as percent maximal response against the concentrations of the respective antibody incubated with the cells.

FIG. 7A-FIG. 7I are a series of graphs showing the blockade of human CD155-Fc binding to CHO cells, engineered to express high levels of cell surface isoform 2 of cynomolgus monkey CD96, by the anti-TIGIT×CD96 multispecific molecules BA123 (FIG. 7A), BA125 (FIG. 7B), or BA127 (FIG. 7C), or control multispecific molecules BA129 (FIG. 7D), BA130 (FIG. 7E), BA131 (FIG. 7F), BA133 (FIG. 7G), BA134 (FIG. 7H), or BA136 (FIG. 7I). The levels of binding of CD155-Fc, as assessed by median fluorescence intensity (MFI), in each case in comparison with blockade by an isotype control multispecific molecule (BA128), were plotted as percent maximal response against the concentrations of the respective multispecific molecule incubated with the cells.

FIG. 8A-FIG. 8I are a series of graphs showing the binding of the anti-TIGIT×CD96 multispecific molecules BA123 (FIG. 8A), BA125 (FIG. 8B), or BA127 (FIG. 8C), or control multispecific molecules BA129 (FIG. 8D), BA130 (FIG. 8E), BA131 (FIG. 8F), BA133 (FIG. 8G), BA134 (FIG. 8H), or BA136 (FIG. 8I), to CHO cells engineered to express high levels of cell surface human TIGIT. The levels of binding, as assessed by median fluorescence intensity (MFI), in each case in comparison with CHO cell binding of an isotype control multispecific molecule (BA128), were plotted against the concentrations of the respective antibody incubated with the cells.

FIG. 9A-FIG. 9I are a series of graphs showing the binding of the anti-TIGIT×CD96 multispecific molecules BA123 (FIG. 9A), BA125 (FIG. 9B), or BA127 (FIG. 9C), or control multispecific molecules BA129 (FIG. 9D), BA130 (FIG. 9E), BA131 (FIG. 9F), BA133 (FIG. 9G), BA134 (FIG. 9H), or BA136 (FIG. 9I), to CHO cells engineered to express high levels of cell surface cynomolgus monkey TIGIT. The levels of binding, as assessed by median fluorescence intensity (MFI), in each case compared to binding of an isotype control multispecific molecule (BA128), were plotted against the concentrations of the respective antibody incubated with the cells.

FIG. 10A-FIG. 10I are a series of graphs showing the blockade of human CD155-Fc binding to CHO cells, engineered to express high levels of cell surface human TIGIT, by the anti-TIGIT×CD96 multispecific molecules BA123 (FIG. 10A), BA125 (FIG. 10B), or BA127 (FIG. 10C), or control multispecific molecules BA129 (FIG. 10D), BA134 (FIG. 10E), BA131 (FIG. 10F), BA133 (FIG. 10G), BA130 (FIG. 10H), or BA136 (FIG. 10I). The levels of binding of CD155-Fc, as assessed by median fluorescence intensity (MFI), in each case compared to blockade by isotype control multispecific molecule (BA128), were plotted as percent maximal response against the concentrations of the respective antibody incubated with the cells.

FIG. 11A-FIG. 11I are a series of graphs showing the blockade of human CD155-Fc binding to CHO cells, engineered to express high levels of cell surface cynomolgus monkey TIGIT, by the anti-TIGIT×CD96 multispecific molecules BA123 (FIG. 11A), BA125 (FIG. 11B), or BA127 (FIG. 11C), or control multispecific molecules BA129 (FIG. 11D), BA130 (FIG. 11E), BA131 (FIG. 11F), BA133 (FIG. 11G), BA134 (FIG. 11H), or BA136 (FIG. 11I). The levels of binding of CD155-Fc, as assessed by median fluorescence intensity (MFI), in each case compared to blockade by an isotype control multispecific molecule (BA128), were plotted as percent maximal response against the concentrations of the respective antibody incubated with the cells.

FIG. 12A-FIG. 12I are a series of graphs showing the binding of the anti-TIGIT×CD96 multispecific molecules BA123 (FIG. 12A), BA125 (FIG. 12B), or BA127 (FIG. 12C), or control multispecific molecules BA129 (FIG. 12D), BA130 (FIG. 12E), BA131 (FIG. 12F), BA133 (FIG. 12G), BA134 (FIG. 12H), or BA136 (FIG. 12I), to CHO cells engineered to co-express high levels of cell surface human TIGIT and isoform 2 of human CD96. The levels of binding, as assessed by median fluorescence intensity (MFI), in each case compared to binding of an isotype control multispecific molecule (BA128), were plotted against the concentrations of the respective antibody incubated with the cells.

FIG. 13A-FIG. 13I are a series of graphs showing the blockade of human CD155-Fc binding to CHO cells, engineered to co-express high levels of cell surface human TIGIT and isoform 2 of human CD96, by the anti-TIGIT×CD96 multispecific molecules BA123 (FIG. 13A), BA125 (FIG. 13B), or BA127 (FIG. 13C), or control multispecific molecules BA129 (FIG. 13D), BA130 (FIG. 13E), BA131 (FIG. 13F), BA133 (FIG. 13G), BA134 (FIG. 13H), or BA136 (FIG. 13I). The levels of binding of CD155-Fc, as assessed by median fluorescence intensity (MFI), in each case compared to blockade by an isotype control multispecific molecule (BA128), were plotted as percent maximal response against the concentrations of the respective antibody incubated with the cells.

FIG. 14A-FIG. 14F are a series of graphs showing the binding of the anti-TIGIT×CD96 multispecific molecules BA123 (FIG. 14A), BA125 (FIG. 14B), or BA127 (FIG. 14C), or control multispecific molecules BA129 (FIG. 14D), BA130 (FIG. 14E), and BA131 (FIG. 14F) to CHO cells engineered to express high levels of cell surface variant V/V of human FcγRIIIa. The levels of binding, as assessed by median fluorescence intensity (MFI) were plotted against the concentrations of the respective antibody incubated with the cells.

FIG. 15A-FIG. 15F are a series of graphs showing the binding of the anti-TIGIT×CD96 multispecific molecules BA123 (FIG. 15A), BA125 (FIG. 15B), or BA127 (FIG. 15C), or control multispecific molecules BA129 (FIG. 15D), BA130 (FIG. 15E) and BA131 (FIG. 15F) to CHO cells engineered to express high levels of cell surface variant F/F of human FcγRIIIa. The levels of binding, as assessed by median fluorescence intensity (MFI) were plotted against the concentrations of the respective antibody incubated with the cells.

FIG. 16A-FIG. 16C are a series of graphs showing the binding of the anti-CD96 antibodies BA143 (FIG. 16A), BA144 (FIG. 16B), BA145 (FIG. 16C), compared to an isotype control antibody (BA146), to CHO cells engineered to express high levels of cell surface isoform 2 of human CD96. The levels of binding, as assessed by median fluorescence intensity (MFI), in each case in comparison with CHO cell binding of BA146 were plotted against the concentrations of the respective antibody incubated with the cells.

FIG. 17A-FIG. 17C are a series of graphs showing the binding of the anti-CD96 antibodies BA143 (FIG. 17A), BA144 (FIG. 17B), BA145 (FIG. 17C), compared to an isotype control antibody (BA146), to CHO cells engineered to express high levels of cell surface isoform 2 of cynomolgus monkey CD96. The levels of binding, as assessed by median fluorescence intensity (MFI), in each case in comparison with CHO cell binding of BA146, were plotted against the concentrations of the respective antibody incubated with the cells.

FIG. 18A-FIG. 18C are a series of graphs showing the blockade of human CD155-Fc binding to CHO cells, engineered to express high levels of cell surface isoform 2 of human CD96, by the anti-CD96 antibodies BA143 (FIG. 18A), BA144 (FIG. 18B), and BA145 (FIG. 18C). The levels of binding of CD155-Fc, as assessed by median fluorescence intensity (MFI), in each case compared to blockade by an isotype control antibody (BA146), were plotted as percent maximal response against the concentrations of the respective antibody incubated with the cells.

FIG. 19A-FIG. 19C are a series of graphs showing the blockade of human CD155-Fc binding to CHO cells, engineered to express high levels of cell surface isoform 2 of cynomolgus monkey CD96, by the anti-CD96 antibodies BA143 (FIG. 19A), BA144 (FIG. 19B), and BA145 (FIG. 19C). The levels of binding of CD155-Fc, as assessed by median fluorescence intensity (MFI), in each case compared to blockade by an isotype control antibody (BA146), were plotted as percent maximal response against the concentrations of the respective antibody incubated with the cells.

FIG. 20 is a graph showing the binding of the anti-TIGIT IgG$_1$ antibody BA148, compared to an isotype control antibody (BA149), to CHO cells engineered to express high levels of cell surface human TIGIT. The levels of binding, as assessed by median fluorescence intensity (MFI), in each case in comparison with CHO cell binding of BA149, were plotted against the concentrations of the respective antibody incubated with the cells.

FIG. 21 is a graph showing the binding of the anti-TIGIT antibody BA148, compared to an isotype control antibody (BA149), to CHO cells engineered to express high levels of cell surface cynomolgus monkey TIGIT. The levels of binding, as assessed by median fluorescence intensity (MFI), in each case in comparison with CHO cell binding of BA149 were plotted against the concentrations of the respective antibody incubated with the cells.

FIG. 22 is a graph showing the blockade of human CD155-Fc binding to CHO cells, engineered to express high levels of human TIGIT, by the anti-TIGIT antibody BA148. The levels of binding of CD155-Fc, as assessed by median fluorescence intensity (MFI), compared to blockade by an isotype control antibody (BA149), was plotted as percent maximal response against the concentrations of the respective antibody incubated with the cells.

FIG. 23 is a graph showing the blockade of human CD155-Fc binding to CHO cells, engineered to express high levels of cynomolgus monkey TIGIT, by the anti-TIGIT antibody BA148. The levels of binding of CD155-Fc, as assessed by median fluorescence intensity (MFI), compared to blockade by an isotype control antibody (BA149), was plotted as percent maximal response against the concentrations of the respective antibody incubated with the cells.

FIG. 24A-FIG. 24D are a series of graphs showing the binding of the anti-TIGIT antibody BA148, and anti-CD96 antibodies BA143, BA144, and BA145 to CHO cells engineered to express high levels of cell surface of variant V/V of human FcγRIIIa. The levels of binding of BA143 (FIG. 24A), BA144 (FIG. 24B), BA145 (FIG. 24C), and BA148 (FIG. 24D), as assessed by median fluorescence intensity (MFI), were plotted against the concentrations of the respective antibody incubated with the cells.

FIG. 25A-FIG. 25D are a series of graphs showing the binding of the anti-TIGIT IgG$_1$ antibody BA148, and anti-CD96 IgG$_1$ WT antibodies BA143, BA144, and BA145 to CHO cells engineered to express high levels of cell surface of variant F/F of human FcγRIIIa. The levels of binding of BA143 (FIG. 25A), BA144 (FIG. 25B), BA145 (FIG. 25C), and BA148 (FIG. 25D), as assessed by median fluorescence intensity (MFI), were plotted against the concentrations of the respective antibody incubated with the cells.

FIG. 26A-FIG. 26F are a series of graphs showing the ability of BA127, BA143, BA148, or BA128 to bind to activated human T cells in three different donors. Binding to CD4+ T cells (FIG. 26A, FIG. 26B, and FIG. 26C) and CD8+ T cells (FIG. 26D, FIG. 26E, and FIG. 26F), as assessed by median fluorescence intensity (MFI), was plotted against the concentrations of the respective antibody incubated with the cells.

Figure 31A:
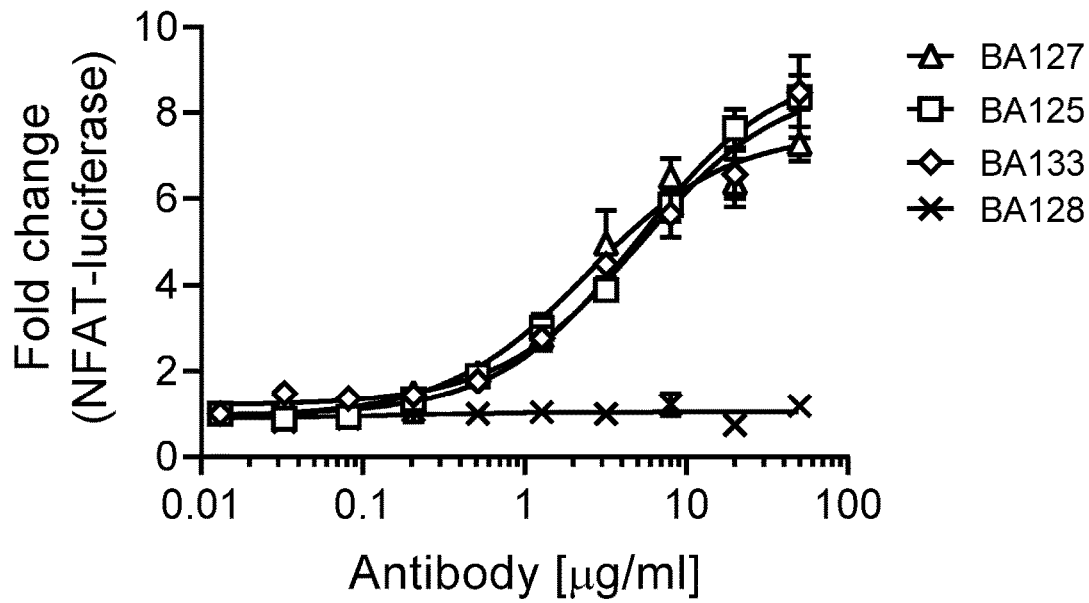
Figure 31B:
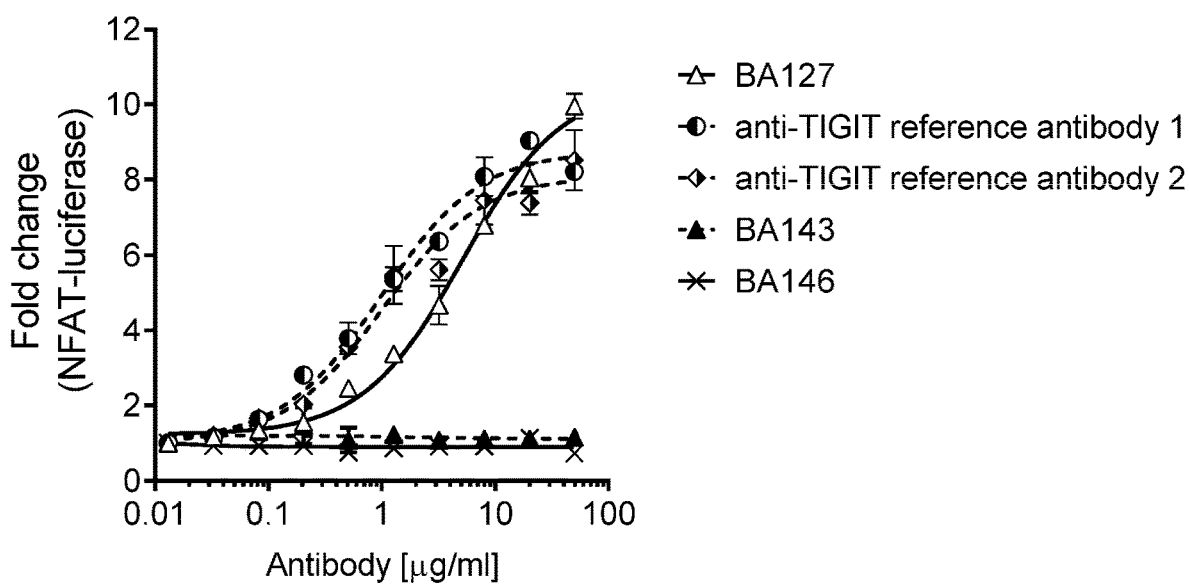
Figure 31C:
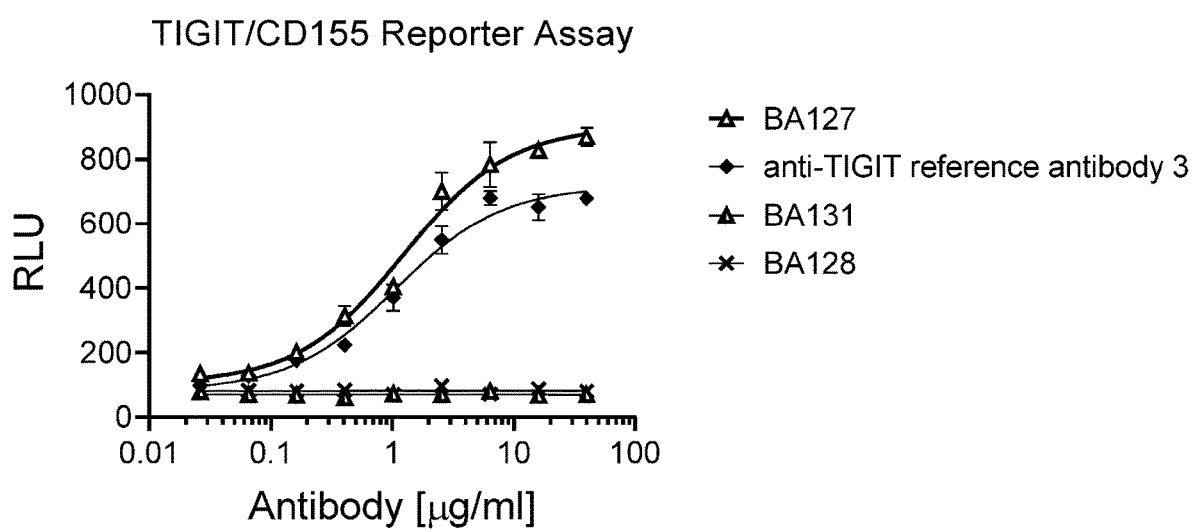

FIG. 31A-FIG. 31B are graphs showing the ability of BA125, BA127, BA128, and BA133 (FIG. 31A) and BA127, BA143, BA146, anti-TIGIT monospecific reference antibody 1, and anti-TIGIT monospecific reference antibody 2 (FIG. 31B), to block binding of TIGIT expressed on Jurkat cells to CD155 expressed on CHO cells. FIG. 31C is a graph showing the ability of BA127, BA131, BA128, and anti-TIGIT reference antibody 3 to block binding of TIGIT expressed on Jurkat cells to CD155 expressed on CHO cells. Blocking is expressed as fold change in NFAT-luciferase signal over a range of antibody concentrations.

Figure 32A:
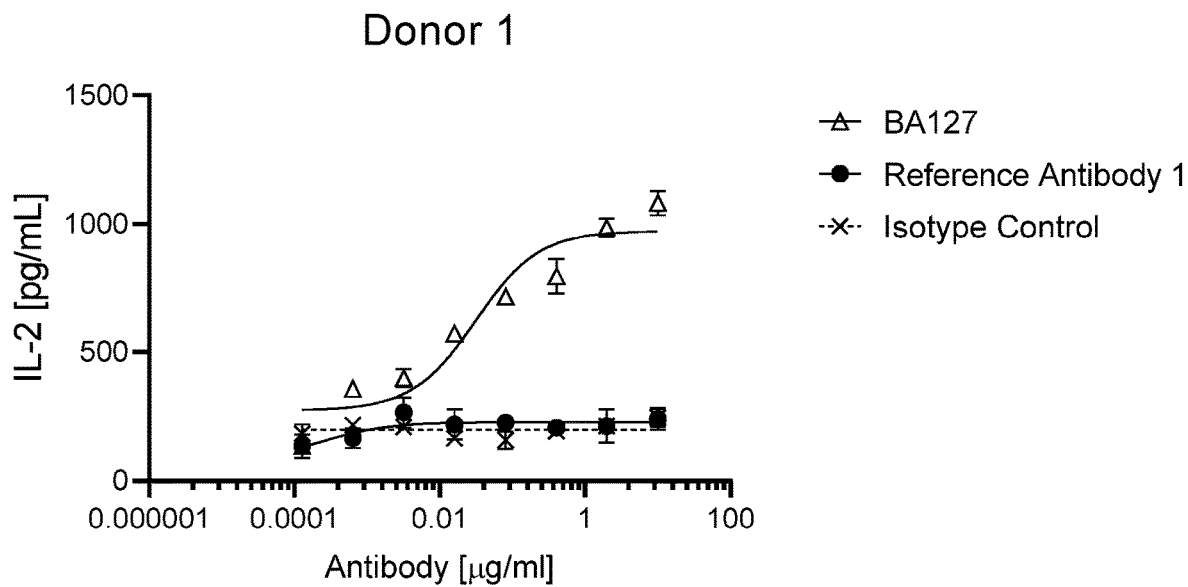
Figure 32B:
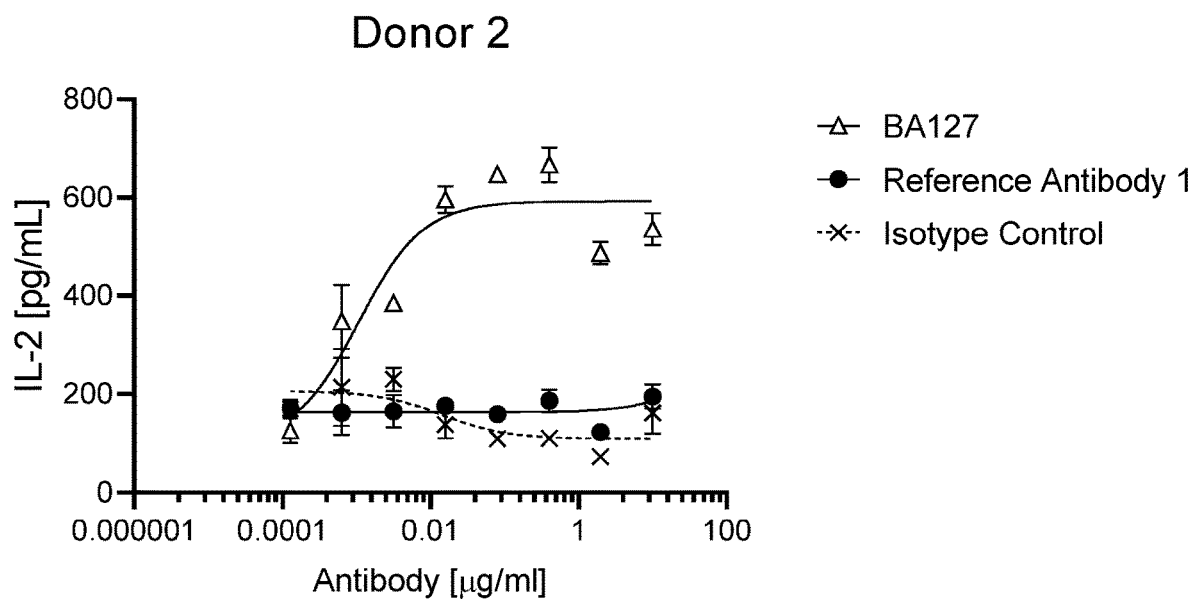

FIG. 32A-FIG. 32B are graphs showing the ability of the anti-TIGIT×CD96 multispecific molecule BA127, a reference anti-TIGIT antibody, and an isotype control antibody, to elicit IL-2 cytokine secretion in primary healthy donor human PBMCs stimulated with a sub-optimal concentration of the SEA superantigen from two donors over a range of concentrations.

Figures 33A, 33B, 33C:
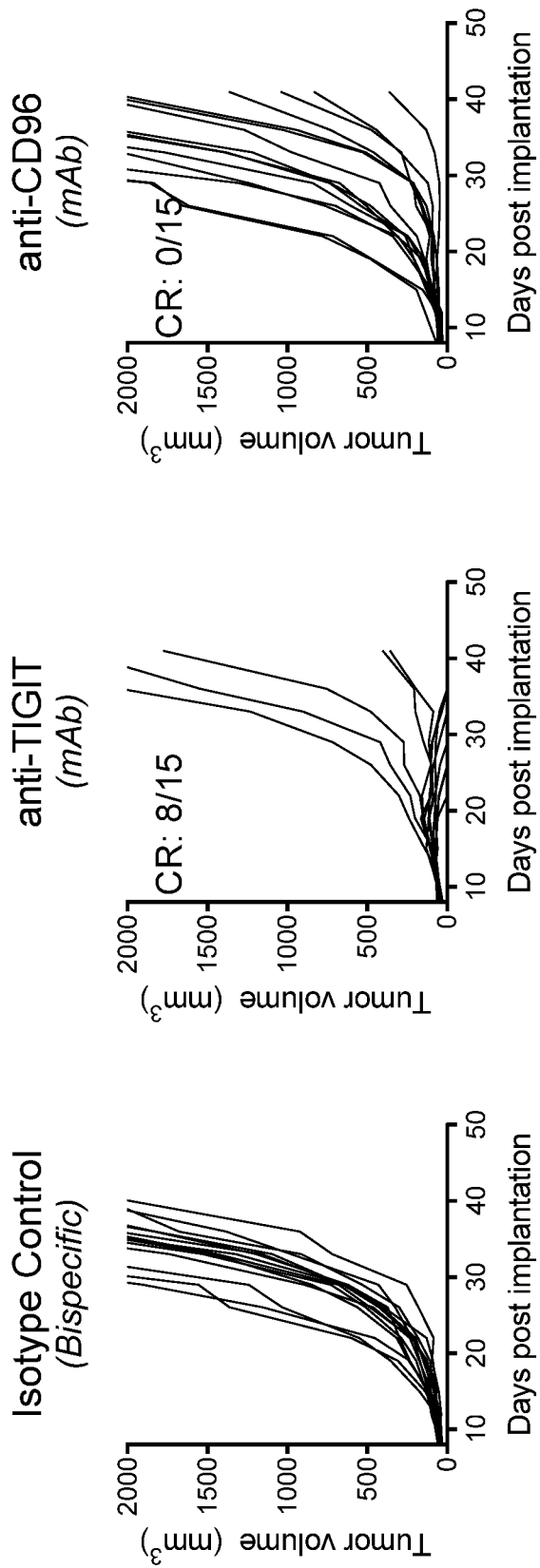
Figures 33D, 33E:
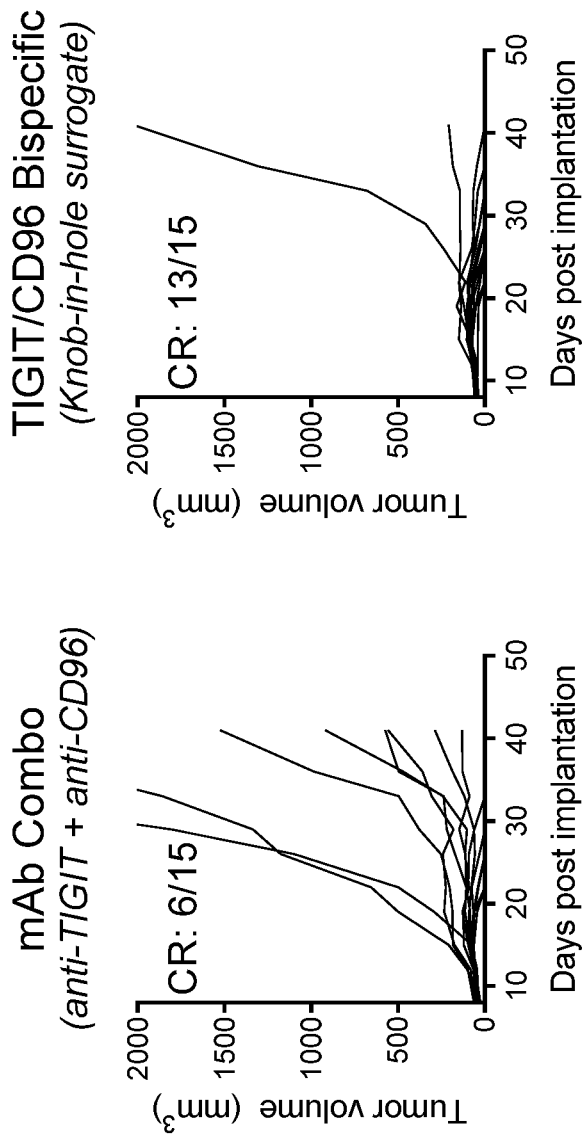

FIG. 33A-FIG. 33E are a series of graphs showing tumor volume over time in a mouse colorectal carcinoma model where mice were administered a bispecific isotype control (FIG. 33A), an anti-TIGIT mouse surrogate monospecific antibody (FIG. 33B), an anti-CD96 mouse surrogate monospecific (FIG. 33C), both anti-TIGIT and anti-CD96 mouse surrogate monospecific antibodies (FIG. 33D), or an anti-TIGIT×CD96 mouse surrogate multispecific molecule (FIG. 33E).

Figure 34A:
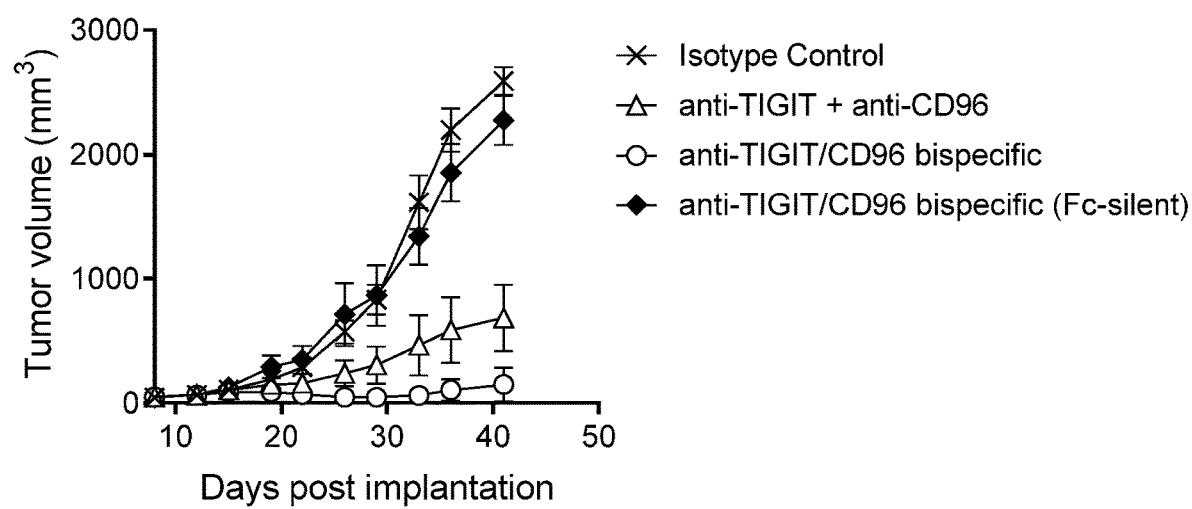
Figure 34B:
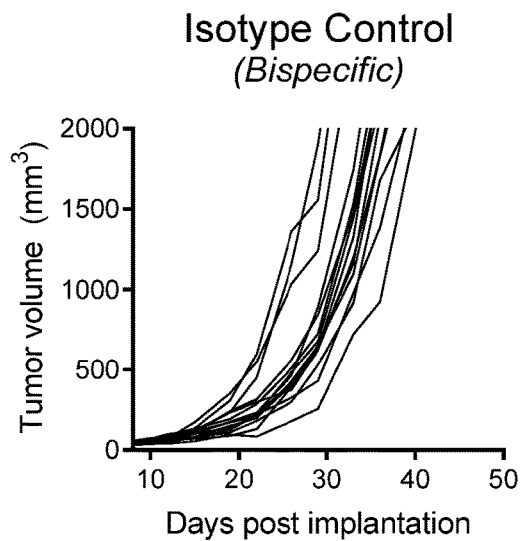
Figure 34C:
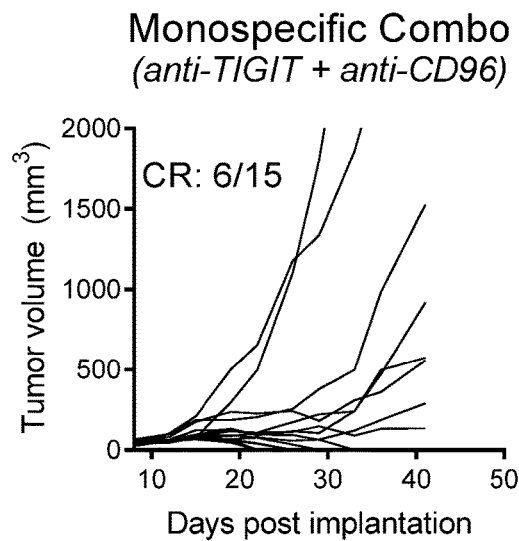
Figure 34D:
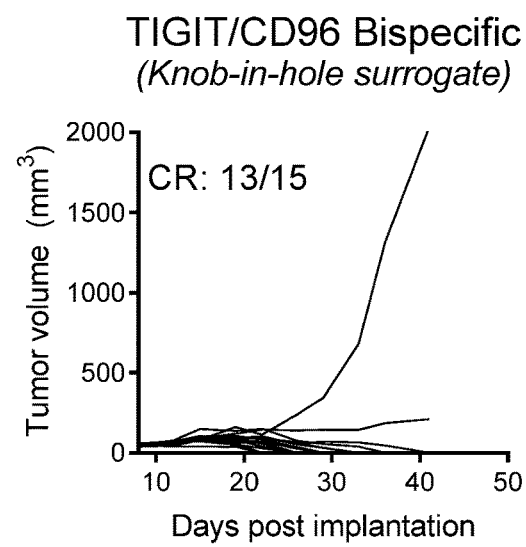
Figure 34E:
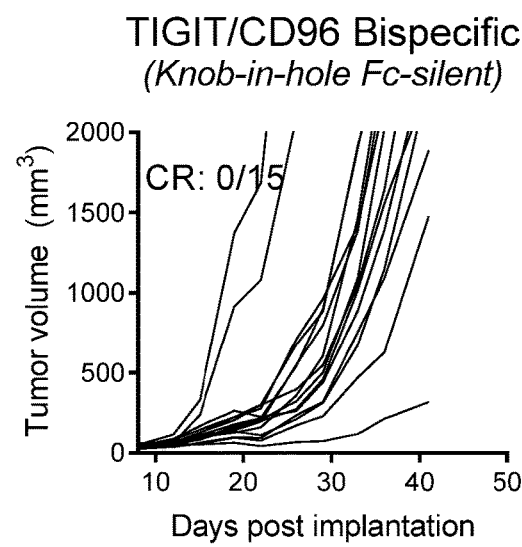

FIG. 34A is a graph showing average tumor volume over time in a mouse colorectal carcinoma model where mice were administered both anti-TIGIT and anti-CD96 mouse surrogate monospecific antibodies, an anti-TIGIT×CD96 mouse surrogate multispecific molecule, an Fc silent anti-TIGIT×CD96 mouse surrogate multispecific molecule, or an isotype control. FIG. 34B-FIG. 34E are a series of graphs showing individual tumor volumes over time for each individual mouse administered both anti-TIGIT and anti-CD96 mouse surrogate monospecific antibodies (FIG. 34C), an anti-TIGIT×CD96 mouse surrogate multispecific molecule (FIG. 34D), an Fc-silent anti-TIGIT×CD96 mouse surrogate multispecific molecule (FIG. 34E), or an isotype control (FIG. 34B).

7. DETAILED DESCRIPTION

The instant disclosure provides multispecific molecules that specifically bind to CD96 (e.g., human CD96 or cynomolgus CD96) and/or TIGIT (e.g., human TIGIT or cynomolgus TIGIT) and isolated anti-TIGIT antibodies. Also provided are pharmaceutical compositions comprising these multispecific molecules and antibodies, nucleic acids encoding these multispecific molecules and antibodies, expression vectors and host cells for making these multispecific molecules and antibodies, and methods of treating a subject using these multispecific molecules and antibodies. The multispecific molecules and antibodies disclosed herein are particularly useful for increasing immune cell activation, and hence, are useful for treating cancer in a subject or treating or preventing an infectious disease in a subject.

7.1 Definitions

As used herein, the term "CD96" refers to Cluster of Differentiation 96, also known as TACTILE (T cell-activation, increased late expression), that in humans is encoded by the CD96 gene. As used herein, the term "human CD96" refers to a CD96 protein encoded by a wild-type human CD96 gene (e.g., GenBank™ accession number NM_005816.5), a fragment, or a variant thereof. Exemplary extracellular portions of human CD96 are provided herein as SEQ ID NOs 61-65. Exemplary extracellular portions of cynomolgus CD96 are provided herein as SEQ ID NOs: 66, 111, and 112.

As used herein, the term "TIGIT" refers to T-cell immunoreceptor with Ig and ITIM domains (also known as VSIG9 or VSTM3) that in humans is encoded by the TIGIT gene. As used herein, the term "human TIGIT" refers to a TIGIT protein encoded by a wild-type human TIGIT gene (e.g., GenBank™ accession number NM_173799.3) or an extracellular domain of such a protein. Exemplary amino acid sequences of an extracellular domain of a mature human TIGIT protein and cynomolgus TIGIT protein are provided as SEQ ID NOs: 113 and 114, respectively.

As used herein, "multispecific molecules" are molecules that comprise two or more antigen-binding regions that specifically bind to different antigens.

As used herein, "antigen-binding region" refers to the portion of a multispecific molecule or an antibody which comprises the amino acid residues that confer on the multispecific molecule or antibody its specificity for an antigen. Examples of antigen-binding regions include antibody complementarity determining regions (CDR), heavy chain variable regions, light chain variable regions, heavy chains, light chains, and any fragment thereof. The antigen-binding region can be derived from any animal species, such as rodents (e.g., mouse, rat, or hamster) and humans.

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affibodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

"Multispecific antibodies" are antibodies (e.g., bispecific antibodies) that specifically bind to two or more different antigens or two or more different regions of the same antigen. Multispecific antibodies include bispecific antibodies that contain two different antigen-binding sites (exclusive of the Fc region). Multispecific antibodies can include, for example, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, heteroconjugate antibodies, linked single chain antibodies or linked-single-chain Fvs (scFv), camelized antibodies, affybodies, linked Fab fragments, F(ab')$_2$ fragments, chemically-linked Fvs, and disulfide-linked Fvs (sdFv). Multispecific antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, multispecific antibodies described herein are IgG antibodies, or a class (e.g., human IgG$_1$, IgG$_2$, or IgG$_4$) or subclass thereof.

As used herein, the term "CDR" or "complementarity determining region" means the noncontiguous antigen combining sites found within the variable regions of heavy and light chain polypeptides. These particular regions have been described by, for example, Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol.

Biol. 262:732-745 (1996), all of which are herein incorporated by reference in their entireties, where the definitions include overlapping or subsets of amino acid residues when compared against each other. CDRH1, CDRH2, and CDRH3 denote the heavy chain CDRs, and CDRL1, CDRL2, and CDRL3 denote the light chain CDRs.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable region are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In certain embodiments, the variable region is a primate (e.g., non-human primate) variable region. In certain embodiments, the variable region comprises rodent or murine CDRs and primate (e.g., non-human primate) framework regions (FRs).

As used herein, the terms "VH" and "VL" refer to antibody heavy and light chain variable regions, respectively, as described in Kabat et al., (1991) Sequences of Proteins of Immunological Interest (NIH Publication No. 91-3242, Bethesda), which is herein incorporated by reference in its entirety.

As used herein, the term "constant region" is common in the art. The constant region is an antibody portion, e.g., a carboxyl terminal portion of a light and/or heavy chain, which is not directly involved in binding of an antibody to antigen but which can exhibit various effector functions, such as interaction with an Fc receptor (e.g., Fc gamma receptor).

As used herein, the term "heavy chain" when used in reference to an antibody can refer to any distinct type, e.g., alpha (α), delta (δ), epsilon (ε), gamma (γ), and mu (μ), based on the amino acid sequence of the constant region, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (χ) or lambda (λ), based on the amino acid sequence of the constant region. Light chain amino acid sequences are well known in the art. In specific embodiments, the light chain is a human light chain.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs (e.g., factors of 10), 2.5 logs, 3 logs, 4 logs, or greater than the $K_A$ when the molecules bind non-specifically to another antigen.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In certain embodiments, the subject is a human or non-human mammal. In certain embodiments, the subject is a human.

As used herein with respect to an antibody or polynucleotide, the term "isolated" refers to an antibody or polynucleotide that is separated from one or more contaminants (e.g., polypeptides, polynucleotides, lipids, or carbohydrates, etc.) which are present in a natural source of the antibody or polynucleotide. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and)(BLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the)(BLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

7.2 Multispecific Molecules that Bind to CD96 and/or TIGIT and Anti-TIGIT Antibodies In one aspect, the instant disclosure provides multispecific molecules that specifically bind to CD96 (e.g., human CD96 or cynomolgus CD96) and/or TIGIT (e.g., human TIGIT or cynomolgus TIGIT). For example, a multispecific molecule provided herein can comprise a first antigen-binding region that binds to CD96 and a second antigen-binding region that binds to an antigen other than CD96. A multispecific molecule provided herein can also comprise a first antigen-binding region that binds to an antigen other than TIGIT and a second antigen-binding region that binds to TIGIT. Also provided herein are multispecific molecules that comprise a first antigen-binding region that binds to CD96 and a second antigen-binding region that binds to TIGIT. The amino acid sequences of exemplary anti-CD96 antigen-binding regions and anti-TIGIT antigen-binding regions are set forth in Table 1 and Table 2, respectively.

In another aspect, the instant disclosure provides antibodies that specifically bind to TIGIT (e.g., human TIGIT or cynomolgus TIGIT). The amino acid sequences of exemplary antibodies are set forth in Table 2.

TABLE 1

Amino acid sequences of exemplary anti-CD96 antigen-binding regions.

| Description | Amino Acid Sequence | SEQ ID NO |
|---|---|---|
| BA137 heavy chain | QVQLVQSGAEVRRPGASVRVSCRASGYTFTSYGISWVRQAPG QGLEWMGWISAYNANTNYAQKLQGRVTMTTDTSTSTAYMELR SLRSDDTAVYYCARSAGVLGGMDVWGRGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TRVDRRVEPRSCDRTHTCPPCPAPELLGGPDVFLFPPRPRDT LMISRTPEVTCVVVDVSHEDPEVRFNWYVDGVEVHNARTRPR EEQYNSTYRVVSVLTVLHQDWLNGKEYKCKVSNKALPAPIEK TISRARGQPREPQVYTLPPSREEMTRNQVSLSCAVRGFYPSD IAVEWESNGQPENNYRTTPPVLDSDGSFFLVSRLTVDRSRWQ QGNVFSCSVMHEALHNHYTQRSLSLSPG | 1 |
| BA137 BA145 light chain | EIVMTQSPATLSVSPGERATLSCRASQSVNAYLAWYQQRPGQ APRLLIYGASTRATGIPARFSGSGSGTEFTLTISSLQSEDFA VYYCQQYNNWPSFGQGTRLEIRRTVAAPSVFIFPPSDEQLRS GTASVVCLLNNFYPREAKVQWKVDNALQSGNSQESVTEQDSK DSTYSLSSTLTLSRADYERHRVYACEVTHQGLSSPVTRSFNR GEC | 2 |
| BA138 heavy chain | QVQLVQSGAEVRRPGASVRVSCRASGYTFTNYAVHWVRQAPG QRLEWMGWINTGNANTRYSQRFQGRVTITRDTSASTAYMELS SLRSEDTAVYYCARSLGVYYGMDVWGQGTTVTVSSASTRGPS VFPLAPSSRSTSGGTAALGCLVRDYFPEPVTVSWNSGALTSG VHTFPAVLQSSGLYSLSSVVTVPSSSLGTQTYICNVNHKPSN TRVDRRVEPRSCDRTHTCPPCPAPELLGGPDVFLFPPRPRDT LMISRTPEVTCVVVDVSHEDPEVRFNWYVDGVEVHNARTRPR EEQYNSTYRVVSVLTVLHQDWLNGREYRCRVSNRALPAPIER TISRARGQPREPQVYTLPPSREEMTRNQVSLSCAVRGFYPSD IAVEWESNGQPENNYRTTPPVLDSDGSFFLVSRLTVDRSRWQ QGNVFSCSVMHEALHNHYTQRSLSLSPG | 3 |
| BA138 BA144 light chain | DIQMTQSPSSLSASVGDRVTITCRASQSVSTFLNWYQQRPGR APRLLIYAASSLQSGVPSRFSGSGSGTDFTLTISSLQPEDFA TYYCLQTYSIPYTFGQGTRLEIRRTVAAPSVFIFPPSDEQLR SGTASVVCLLNNFYPREARVQWRVDNALQSGNSQESVTEQDS RDSTYSLSSTLTLSRADYERHRVYACEVTHQGLSSPVTRSFN RGEC | 4 |

TABLE 1-continued

Amino acid sequences of exemplary anti-CD96 antigen-binding regions.

| Description | Amino Acid Sequence | SEQ ID NO |
|---|---|---|
| BA139 heavy chain | QVQLVQSGAEVRRPGASVRVSCRASGYTFTTYALHWVRQAPG QRLEWMGWINTGSGDTRYSQRFQGRVTITRDTSASTAYMELS SLRSEDTAVYYCARSLGVYYGMDVWGQGTLVTVSSASTRGPS VFPLAPSSRSTSGGTAALGCLVRDYFPEPVTVSWNSGALTSG VHTFPAVLQSSGLYSLSSVVTVPSSSLGTQTYICNVNHRPSN TKVDKRVEPRSCDKTHTCPPCPAPELLGGPDVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLSCAVKGFYPSD IAVEWESNGQPENNYKTTPPVLDSDGSFFLVSKLTVDKSRWQ QGNVFSCSVMHEALHNHYTQKSLSLSPG | 5 |
| BA139 BA143 light chain | DIQMTQSPSSLSASVGDRVTITCRASQSISSYLNWYQQKPGK APKLLIYAASSLQSGVPSRFSGSGSGTDFTLTISSLQPEDFA TYYCQQSYSTPKITFGQGTKLEIKRTVAAPSVFIFPPSDEQL KSGTASVVCLLNNFYPREAKVQWKVDNALQSGNSQESVTEQD SKDSTYSLSSTLTLSKADYEKHKVYACEVTHQGLSSPVTKSF NRGEC | 6 |
| BA137 BA145 HCDR1 | SYGIS | 10 |
| BA137 BA145 HCDR2 | WISAYNANTNYAQKLQG | 11 |
| BA137 BA145 HCDR3 | SAGVLGGMDV | 12 |
| BA137 BA145 LCDR1 | RASQSVNAYLA | 13 |
| BA137 BA145 LCDR2 | GASTRAT | 14 |
| BA137 BA145 LCDR3 | QQYNNWPS | 15 |
| BA138 BA144 HCDR1 | NYAVH | 16 |
| BA138 BA144 HCDR2 | WINTGNANTKYSQKFQG | 17 |
| BA138 BA144 HCDR3 | SLGVYYGMDV | 18 |
| BA138 BA144 LCDR1 | RASQSVSTFLN | 19 |
| BA138 BA144 LCDR2 | AASSLQS | 20 |
| BA138 BA144 LCDR3 | LQTYSIPYT | 21 |
| BA139 BA143 HCDR1 | TYALH | 22 |

TABLE 1-continued

Amino acid sequences of exemplary anti-CD96 antigen-binding regions.

| Description | Amino Acid Sequence | SEQ ID NO |
|---|---|---|
| BA139 BA143 HCDR2 | WINTGSGDTKYSQKFQG | 23 |
| BA139 BA143 HCDR3 | SLGVYYGMDV | 24 |
| BA139 BA143 LCDR1 | RASQSISSYLN | 25 |
| BA139 BA143 LCDR2 | AASSLQS | 26 |
| BA139 BA143 LCDR3 | QQSYSTPKIT | 27 |
| BA137 BA145 VH | QVQLVQSGAEVRRPGASVRVSCRASGYTFTSYGISWVRQAPG QGLEWMGWISAYNANTNYAQKLQGRVTMTTDTSTSTAYMELR SLRSDDTAVYYCARSAGVLGGMDVWGRGTLVTVSS | 34 |
| BA137 BA145 VL | EIVMTQSPATLSVSPGERATLSCRASQSVNAYLAWYQQRPGQ APRLLIYGASTRATGIPARFSGSGSGTEFTLTISSLQSEDFA VYYCQQYNNWPSFGQGTKLEIK | 35 |
| BA138 BA144 VH | QVQLVQSGAEVRRPGASVRVSCRASGYTFTNYAVHWVRQAPG QRLEWMGWINTGNANTKYSQKFQGRVTITRDTSASTAYMELS SLRSEDTAVYYCARSLGVYYGMDVWGQGTTVTVSS | 36 |
| BA138 BA144 VL | DIQMTQSPSSLSASVGDRVTITCRASQSVSTFLNWYQQRPGR APKLLIYAASSLQSGVPSRFSGSGSGTDFTLTISSLQPEDFA TYYCLQTYSIPYTFGQGTKLEIK | 37 |
| BA139 BA143 VH | QVQLVQSGAEVRRPGASVRVSCRASGYTFTTYALHWVRQAPG QRLEWMGWINTGSGDTKYSQKFQGRVTITRDTSASTAYMELS SLRSEDTAVYYCARSLGVYYGMDVWGQGTLVTVSS | 38 |
| BA139 BA143 VL | DIQMTQSPSSLSASVGDRVTITCRASQSISSYLNWYQQRPGR APKLLIYAASSLQSGVPSRFSGSGSGTDFTLTISSLQPEDFA TYYCQQSYSTPKITFGQGTKLEIK | 39 |
| BA137 BA138 BA139 BA143 BA144 BA145 light chain constant region | RTVAAPSVFIFPPSDEQLKSGTASVVCLLNNFYPREAKVQWK VDNALQSGNSQESVTEQDSRDSTYSLSSTLTLSRADYERHRV YACEVTHQGLSSPVTRSFNRGEC | 42 |
| BA137a heavy chain | QVQLVQSGAEVRRPGASVRVSCRASGYTFTSYGISWVRQAPG QGLEWMGWISAYNANTNYAQKLQGRVTMTTDTSTSTAYMELR SLRSDDTAVYYCARSAGVLGGMDVWGRGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPRSCDKTHTCPPCPAPELLGGPSVFLFPPKPKDT LMISRTPEVTCVVVDVSHEDPEVRFNWYVDGVEVHNARTRPR EEQYNSTYRVVSVLTVLHQDWLNGKEYKCKVSNKALPAPIEK TISRARGQPREPQVYTLPPSREEMTRNQVSLSCAVRGFYPSD IAVEWESNGQPENNYRTTPPVLDSDGSFFLVSRLTVDRSRWQ QGNVFSCSVMHEALHNHYTQKSLSLSPG | 67 |
| BA137b heavy chain | QVQLVQSGAEVKKPGASVKVSCKASGYTFTSYGISWVRQAPG QGLEWMGWISAYNANTNYAQKLQGRVTMTTDTSTSTAYMELR SLRSDDTAVYYCARSAGVLGGMDVWGRGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPDVFLFPPKPKDT | 68 |

TABLE 1-continued

Amino acid sequences of exemplary anti-CD96 antigen-binding regions.

| Description | Amino Acid Sequence | SEQ ID NO |
|---|---|---|
| | LMISRTPEVTCVVVDVSHEDPEVKFNWYVDGVEVHNAKTKPR<br>EEQYNSTYRVVSVLTVLHQDWLNGKEYKCKVSNKALPAPEEK<br>TISKAKGQPREPQVYTLPPSREEMTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | |
| BA137c heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | 69 |
| BA137d heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 70 |
| BA137e heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 71 |
| BA137f heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 72 |
| BA137g heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 73 |
| BA137h heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR | 74 |

TABLE 1-continued

Amino acid sequences of exemplary anti-CD96 antigen-binding regions.

| Description | Amino Acid Sequence | SEQ ID NO |
|---|---|---|
| | EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | |
| BA137i heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 75 |
| BA137j heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 76 |
| BA137k heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 77 |
| BA145 heavy chain | QVQLVQSGAEVKKPGASVKVSCKASGYTFTSYGISWVRQAPG<br>QGLEWMGWISAYNANTNYAQKLQGRVTMTTDTSTSTAYMELR<br>SLRSDDTAVYYCARSAGVLGGMDVWGRGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGK | 45 |
| BA138a heavy chain | QVQLVQSGAEVKKPGASVKVSCKASGYTFTNYAVHWVRQAPG<br>QRLEWMGWINTGNANTKYSQKFQGRVTITRDTSASTAYMELS<br>SLRSEDTAVYYCARSLGVYYGMDVWGQTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | 78 |
| BA138b heavy chain | QVQLVQSGAEVKKPGASVKVSCKASGYTFTNYAVHWVRQAPG<br>QRLEWMGWINTGNANTKYSQKFQGRVTITRDTSASTAYMELS<br>SLRSEDTAVYYCARSLGVYYGMDVWGQTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK | 79 |

TABLE 1-continued

Amino acid sequences of exemplary anti-CD96 antigen-binding regions.

| Description | Amino Acid Sequence | SEQ ID NO |
|---|---|---|
| | TISKAKGQPREPQVYTLPPSREEMTKNQVSLSCAVKGFYPSD IAVEWESNGQPENNYKTTPPVLDSDGSFFLVSKLTVDKSRWQ QGNVFSCSVMHEALHNHYTQKSLSLSPG | |
| BA138c heavy chain | QVQLVQSGAEVKKPGASVKVSCKASGYTFTNYAVHWVRQAPG QRLEWMGWINTGNANTKYSQKFQGRVTITRDTSASTAYMELS SLRSEDTAVYYCARSLGVYYGMDVWGQGTTVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPDVFLFPPKPKDT LMISRTPEVTCVVVDVSHEDPEVKFNWYVDGVEVHNAKTKPR EEQYNSTYRVVSVLTVLHQDWLNGKEYKCKVSNKALPLPEEK TISKAKGQPREPQVYTLPPSREEMTKNQVSLSCAVKGFYPSD IAVEWESNGQPENNYKTTPPVLDSDGSFFLVSKLTVDKSRWQ QGNVFSCSVMHEALHNHYTQKSLSLSPG | 80 |
| BA138d heavy chain | QVQLVQSGAEVKKPGASVKVSCKASGYTFTNYAVHWVRQAPG QRLEWMGWINTGNANTKYSQKFQGRVTITRDTSASTAYMELS SLRSEDTAVYYCARSLGVYYGMDVWGQGTTVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLWCLVKGFYPSD IAVEWESNGQPENNYKTTPPVLDSDGSFFLYSKLTVDKSRWQ QGNVFSCSVMHEALHNHYTQKSLSLSPG | 81 |
| BA138e heavy chain | QVQLVQSGAEVKKPGASVKVSCKASGYTFTNYAVHWVRQAPG QRLEWMGWINTGNANTKYSQKFQGRVTITRDTSASTAYMELS SLRSEDTAVYYCARSLGVYYGMDVWGQGTTVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPDVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLWCLVKGFYPSD IAVEWESNGQPENNYKTTPPVLDSDGSFFLYSKLTVDKSRWQ QGNVFSCSVMHEALHNHYTQKSLSLSPG | 82 |
| BA138f heavy chain | QVQLVQSGAEVKKPGASVKVSCKASGYTFTNYAVHWVRQAPG QRLEWMGWINTGNANTKYSQKFQGRVTITRDTSASTAYMELS SLRSEDTAVYYCARSLGVYYGMDVWGQGTTVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPDVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPEEK TISKAKGQPREPQVYTLPPSREEMTKNQVSLWCLVKGFYPSD IAVEWESNGQPENNYKTTPPVLDSDGSFFLYSKLTVDKSRWQ QGNVFSCSVMHEALHNHYTQKSLSLSPG | 83 |
| BA138g heavy chain | QVQLVQSGAEVKKPGASVKVSCKASGYTFTNYAVHWVRQAPG QRLEWMGWINTGNANTKYSQKFQGRVTITRDTSASTAYMELS SLRSEDTAVYYCARSLGVYYGMDVWGQGTTVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPDVFLFPPKPKDT LMISRTPEVTCVVVDVSHEDPEVKFNWYVDGVEVHNAKTKPR EEQYNSTYRVVSVLTVLHQDWLNGKEYKCKVSNKALPLPEEK TISKAKGQPREPQVYTLPPSREEMTKNQVSLWCLVKGFYPSD IAVEWESNGQPENNYKTTPPVLDSDGSFFLYSKLTVDKSRWQ QGNVFSCSVMHEALHNHYTQKSLSLSPG | 84 |
| BA138h heavy chain | QVQLVQSGAEVKKPGASVKVSCKASGYTFTNYAVHWVRQAPG QRLEWMGWINTGNANTKYSQKFQGRVTITRDTSASTAYMELS SLRSEDTAVYYCARSLGVYYGMDVWGQGTTVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSD | 85 |

TABLE 1-continued

Amino acid sequences of exemplary anti-CD96 antigen-binding regions.

| Description | Amino Acid Sequence | SEQ ID NO |
|---|---|---|
| | IAVEWESNGQPENNYKTTPPVLDSDGSFFLYSKLTVDKSRWQ<br>QGNVFSCSVMHEALHNHYTQKSLSLSPG | |
| BA138i heavy chain | QVQLVQSGAEVKKPGASVKVSCKASGYTFTNYAVHWVRQAPG<br>QRLEWMGWINTGNANTKYSQKFQGRVTITRDTSASTAYMELS<br>SLRSEDTAVYYCARSLGVYYGMDVWGQGTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 86 |
| BA138j heavy chain | QVQLVQSGAEVKKPGASVKVSCKASGYTFTNYAVHWVRQAPG<br>QRLEWMGWINTGNANTKYSQKFQGRVTITRDTSASTAYMELS<br>SLRSEDTAVYYCARSLGVYYGMDVWGQGTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 87 |
| BA138k heavy chain | QVQLVQSGAEVKKPGASVKVSCKASGYTFTNYAVHWVRQAPG<br>QRLEWMGWINTGNANTKYSQKFQGRVTITRDTSASTAYMELS<br>SLRSEDTAVYYCARSLGVYYGMDVWGQGTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 88 |
| BA144 heavy chain | QVQLVQSGAEVKKPGASVKVSCKASGYTFTNYAVHWVRQAPG<br>QRLEWMGWINTGNANTKYSQKFQGRVTITRDTSASTAYMELS<br>SLRSEDTAVYYCARSLGVYYGMDVWGQGTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGK | 46 |
| BA139a heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | 89 |
| BA139b heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTTVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK | 90 |

TABLE 1-continued

Amino acid sequences of exemplary anti-CD96 antigen-binding regions.

| Description | Amino Acid Sequence | SEQ ID NO |
|---|---|---|
| | TISKAKGQPREPQVYTLPPSREEMTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | |
| BA139c heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | 91 |
| BA139d heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 92 |
| BA139e heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 93 |
| BA139f heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 94 |
| BA139g heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLWCLVKGFYPSD<br>IAVEWESNGQPENNYKTTPPVLDSDGSFFLYSKLTVDKSRWQ<br>QGNVFSCSVMHEALHNHYTQKSLSLSPG | 95 |
| BA139h heavy chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD | 96 |

TABLE 1-continued

Amino acid sequences of exemplary anti-CD96 antigen-binding regions.

| Description | Amino Acid Sequence | SEQ ID NO |
|---|---|---|
| | IAVEWESNGQPENNYKTTPPVLDSDGSFFLYSKLTVDKSRWQ<br>QGNVFSCSVMHEALHNHYTQKSLSLSPG | |
| BA139i<br>heavy<br>chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 97 |
| BA139j<br>heavy<br>chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPEEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 98 |
| BA139k<br>heavy<br>chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPDVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPLPEEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 99 |
| BA143<br>heavy<br>chain | QVQLVQSGAEVKKPGASVKVSCKASGYTFTTYALHWVRQAPG<br>QRLEWMGWINTGSGDTKYSQKFQGRVTITRDTSASTAYMELS<br>SLRSEDTAVYYCARSLGVYYGMDVWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGK | 47 |
| BA137a<br>BA138a<br>BA139a<br>heavy<br>chain<br>constant<br>region | ASTKGPSVFPLAPSSKSTSGGTAALGCLVKDYFPEPVTVSWN<br>SGALTSGVHTFPAVLQSSGLYSLSSVVTVPSSSLGTQTYICN<br>VNHKPSNTKVDKRVEPKSCDKTHTCPPCPAPELLGGPSVFLF<br>PPKPKDTLMISRTPEVTCVVVDVSHEDPEVKFNWYVDGVEVH<br>NAKTKPREEQYNSTYRVVSVLTVLHQDWLNGKEYKCKVSNKA<br>LPAPIEKTISKAKGQPREPQVYTLPPSREEMTKNQVSLSCAV<br>KGFYPSDIAVEWESNGQPENNYKTTPPVLDSDGSFFLVSKLT<br>VDKSRWQQGNVFSCSVMHEALHNHYTQKSLSLSPG | 49 |
| BA137<br>BA138<br>BA139<br>heavy<br>chain<br>constant<br>region | ASTKGPSVFPLAPSSKSTSGGTAALGCLVKDYFPEPVTVSWN<br>SGALTSGVHTFPAVLQSSGLYSLSSVVTVPSSSLGTQTYICN<br>VNHKPSNTKVDKRVEPKSCDKTHTCPPCPAPELLGGPDVFLF<br>PPKPKDTLMISRTPEVTCVVVDVSHEDPEVKFNWYVDGVEVH<br>NAKTKPREEQYNSTYRVVSVLTVLHQDWLNGKEYKCKVSNKA<br>LPAPIEKTISKAKGQPREPQVYTLPPSREEMTKNQVSLSCAV<br>KGFYPSDIAVEWESNGQPENNYKTTPPVLDSDGSFFLVSKLT<br>VDKSRWQQGNVFSCSVMHEALHNHYTQKSLSLSPG | 50 |
| BA137b<br>BA138b<br>BA139b<br>heavy | ASTKGPSVFPLAPSSKSTSGGTAALGCLVKDYFPEPVTVSWN<br>SGALTSGVHTFPAVLQSSGLYSLSSVVTVPSSSLGTQTYICN<br>VNHKPSNTKVDKRVEPKSCDKTHTCPPCPAPELLGGPDVFLF<br>PPKPKDTLMISRTPEVTCVVVDVSHEDPEVKFNWYVDGVEVH | 51 |

TABLE 1-continued

Amino acid sequences of exemplary anti-CD96 antigen-binding regions.

| Description | Amino Acid Sequence | SEQ ID NO |
|---|---|---|
| chain constant region | NAKTKPREEQYNSTYRVVSVLTVLHQDWLNGKEYKCKVSNKA LPAPEEKTISKAKGQPREPQVYTLPPSREEMTKNQVSLSCAV KGFYPSDIAVEWESNGQPENNYKTTPPVLDSDGSFFLVSKLT VDKSRWQQGNVFSCSVMHEALHNHYTQKSLSLSPG | |
| BA137c BA138c BA139c heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA LPLPEEKTISKAKGQPREPQVYTLPPSREEMTKNQVSLSCAV KGFYPSDIAVEWESNGQPENNYKTTPPVLDSDGSFFLVSKLT VDKSRWQQGNVFSCSVMHEALHNHYTQKSLSLSPG | 52 |
| BA137d BA138d BA139d heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPSVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPIEKTISKAKGQPREPQVYTLPPSREEMTKNQVSLWCLV KGFYPSDIAVEWESNGQPENNYKTTPPVLDSDGSFFLYSKLT VDKSRWQQGNVFSCSVMHEALHNHYTQKSLSLSPG | 53 |
| BA137e BA138e BA139e heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPIEKTISKAKGQPREPQVYTLPPSREEMTKNQVSLWCLV KGFYPSDIAVEWESNGQPENNYKTTPPVLDSDGSFFLYSKLT VDKSRWQQGNVFSCSVMHEALHNHYTQKSLSLSPG | 54 |
| BA137f BA138f BA139f heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPEEKTISKAKGQPREPQVYTLPPSREEMTKNQVSLWCLV KGFYPSDIAVEWESNGQPENNYKTTPPVLDSDGSFFLYSKLT VDKSRWQQGNVFSCSVMHEALHNHYTQKSLSLSPG | 55 |
| BA137g BA138g BA139g heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA LPLPEEKTISKAKGQPREPQVYTLPPSREEMTKNQVSLWCLV KGFYPSDIAVEWESNGQPENNYKTTPPVLDSDGSFFLYSKLT VDKSRWQQGNVFSCSVMHEALHNHYTQKSLSLSPG | 56 |
| BA137h BA138h BA139h heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPSVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPIEKTISKAKGQPREPQVYTLPPSREEMTKNQVSLTCLV KGFYPSDIAVEWESNGQPENNYKTTPPVLDSDGSFFLYSKLT VDKSRWQQGNVFSCSVMHEALHNHYTQKSLSLSPG | 57 |
| BA137i BA138i BA139i heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPIEKTISKAKGQPREPQVYTLPPSREEMTKNQVSLTCLV KGFYPSDIAVEWESNGQPENNYKTTPPVLDSDGSFFLYSKLT VDKSRWQQGNVFSCSVMHEALHNHYTQKSLSLSPG | 58 |
| BA137j BA138j BA139j heavy chain | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA | 59 |

TABLE 1-continued

Amino acid sequences of exemplary anti-CD96 antigen-binding regions.

| Description | Amino Acid Sequence | SEQ ID NO |
|---|---|---|
| constant region | LPAPEEKTISKAKGQPREPQVYTLPPSREEMTKNQVSLTCLV KGFYPSDIAVEWESNGQPENNYKTTPPVLDSDGSFFLYSKLT VDKSRWQQGNVFSCSVMHEALHNHYTQKSLSLSPG | |
| BA137k BA138k BA139k heavy chain constant region | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPDVFLF PPKPKDTLMISRTPEVTCVVVDVSHEDPEVKFNWYVDGVEVH NAKTKPREEQYNSTYRVVSVLTVLHQDWLNGKEYKCKVSNKA LPLPEEKTISKAKGQPREPQVYTLPPSREEMTKNQVSLTCLV KGFYPSDIAVEWESNGQPENNYKTTPPVLDSDGSFFLYSKLT VDKSRWQQGNVFSCSVMHEALHNHYTQKSLSLSPG | 60 |

TABLE 2

Amino acid sequences of exemplary anti-TIGIT antigen-binding regions and anti-TIGIT antibodies.

| Description | Amino Acid Sequence | SEQ ID NO |
|---|---|---|
| BA142 BA150 heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPDVFLFPPKPKDTLMIS RTPEVTCVVVDVSHEDPEVKFNWYVDGVEVHNAKTKP REEQYNSTYRVVSVLTVLHQDWLNGKEYKCKVSNKAL PLPEEKTISKAKGQPREPQVYTLPPSREEMTKNQVSL WCLVKGFYPSDIAVEWESNGQPENNYKTTPPVLDSDG SFFLYSKLTVDKSRWQQGNVFSCSVMHEALHNHYTQK SLSLSPG | 7 |
| BA142 light chain | QSALTQPRSVSGSPGQSVTISCTGTSPDVGSHAYRSW YQQHPGKAPKLMIYEVSYRPSGVSNRFSGSKSGNTAS LTISGLQAEDEADYYCSSYPPSSATVFGAGTKLTVLG QPKAAPSVTLFPPSSEELQANKATLVCLISDFYPGAV TVAWKADSSPVKAGVETTTPSKQSNNKYAASSYLSLT PEQWKSHRSYSCQVTHEGSTVEKTVAPTECS | 8 |
| BA150 BA148 light chain | QSALTQPRSVSGSPGQSVTISCTGTSPDVGSHAYRSW YQQHPGKAPKLMIYEVSYRPSGVSNRFSGSKSGNTAS LTISGLQAEDEADYYCSSYPPSSATVFGAGTKLTVLG QPKAAPSVTLFPPSSEELQANKATLVCLISDFYPGAV TVAWKADSSPVKAGVETTTPSKQSNNKYAASSYLSLT PEQWKSHRSYSCQVTHEGSTVEKTVAPTEC | 9 |
| BA142 BA150 BA148 HCDR1 | SYGIS | 28 |
| BA142 BA150 BA148 HCDR2 | GITPFFNRVDVAEKFQG | 29 |
| BA142 BA150 BA148 HCDR3 | DLRRGGVGDAFDI | 30 |
| BA142 BA150 BA148 LCDR1 | TGTSPDVGSHAYRS | 31 |

TABLE 2-continued

Amino acid sequences of exemplary anti-TIGIT antigen-binding regions and anti-TIGIT antibodies.

| Description | Amino Acid Sequence | SEQ ID NO |
|---|---|---|
| BA142 BA150 BA148 LCDR2 | EVSYRPS | 32 |
| BA142 BA150 BA148 LCDR3 | SSYPPSSATV | 33 |
| BA142 BA150 BA148 VH | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSS | 40 |
| BA142 BA150 BA148 VL | QSALTQPRSVSGSPGQSVTISCTGTSPDVGSHAYRSW YQQHPGKAPKLMIYEVSYRPSGVSNRFSGSKSGNTAS LTISGLQAEDEADYYCSSYPPSSATVFGAGTKLTVL | 41 |
| BA142 light chain constant region | GQPKAAPSVTLFPPSSEELQANKATLVCLISDFYPGA VTVAWKADSSPVKAGVETTTPSKQSNNKYAASSYLSL TPEQWKSHRSYSCQVTHEGSTVEKTVAPTECS | 43 |
| BA150 BA148 light chain constant region | GQPKAAPSVTLFPPSSEELQANKATLVCLISDFYPGA VTVAWKADSSPVKAGVETTTPSKQSNNKYAASSYLSL TPEQWKSHRSYSCQVTHEGSTVEKTVAPTEC | 44 |
| BA142d BA150d heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPSVFLFPPKPKDTLMIS RTPEVTCVVVDVSHEDPEVKFNWYVDGVEVHNAKTKP REEQYNSTYRVVSVLTVLHQDWLNGKEYKCKVSNKAL PAPIEKTISKAKGQPREPQVYTLPPSREEMTKNQVSL WCLVKGFYPSDIAVEWESNGQPENNYKTTPPVLDSDG SFFLYSKLTVDKSRWQQGNVFSCSVMHEALHNHYTQK SLSLSPG | 100 |
| BA142e BA150e heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPDVFLFPPKPKDTLMIS RTPEVTCVVVDVSHEDPEVKFNWYVDGVEVHNAKTKP REEQYNSTYRVVSVLTVLHQDWLNGKEYKCKVSNKAL PAPIEKTISKAKGQPREPQVYTLPPSREEMTKNQVSL WCLVKGFYPSDIAVEWESNGQPENNYKTTPPVLDSDG SFFLYSKLTVDKSRWQQGNVFSCSVMHEALHNHYTQK SLSLSPG | 101 |
| BA142f BA150f heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPDVFLFPPKPKDTLMIS RTPEVTCVVVDVSHEDPEVKFNWYVDGVEVHNAKTKP REEQYNSTYRVVSVLTVLHQDWLNGKEYKCKVSNKAL PAPEEKTISKAKGQPREPQVYTLPPSREEMTKNQVSL WCLVKGFYPSDIAVEWESNGQPENNYKTTPPVLDSDG SFFLYSKLTVDKSRWQQGNVFSCSVMHEALHNHYTQK SLSLSPG | 102 |
| BA142a BA150a heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI | 103 |

TABLE 2-continued

Amino acid sequences of exemplary anti-TIGIT antigen-binding regions and anti-TIGIT antibodies.

| Description | Amino Acid Sequence | SEQ ID NO |
|---|---|---|
| | WGRGTLVTVSSASTKGPSVFPLAPSSKSTSGGTAALG<br>CLVKDYFPEPVTVSWNSGALTSGVHTFPAVLQSSGLY<br>SLSSVVTVPSSSLGTQTYICNVNHKPSNTKVDKRVEP<br>KSCDKTHTCPPCPAPELLGGPSVFLFPPKPKDTLMIS<br>RTPEVTCVVVDVSHEDPEVKFNWYVDGVEVHNAKTKP<br>REEQYNSTYRVVSVLTVLHQDWLNGKEYKCKVSNKAL<br>PAPIEKTISKAKGQPREPQVYTLPPSREEMTKNQVSL<br>SCAVKGFYPSDIAVEWESNGQPENNYKTTPPVLDSDG<br>SFFLVSKLTVDKSRWQQGNVFSCSVMHEALHNHYTQK<br>SLSLSPG | |
| BA142g<br>BA150g<br>heavy chain | EVQLVQSGAEVKKPGSSVKVSCKASGYTFASYGISWV<br>RQAPGQGLEWMGGITPFFNRVDVAEKFQGRVTITADK<br>STSTAYIELSSLRSEDTAVYYCARDLRRGGVGDAFDI<br>WGRGTLVTVSSASTKGPSVFPLAPSSKSTSGGTAALG<br>CLVKDYFPEPVTVSWNSGALTSGVHTFPAVLQSSGLY<br>SLSSVVTVPSSSLGTQTYICNVNHKPSNTKVDKRVEP<br>KSCDKTHTCPPCPAPELLGGPDVFLFPPKPKDTLMIS<br>RTPEVTCVVVDVSHEDPEVKFNWYVDGVEVHNAKTKP<br>REEQYNSTYRVVSVLTVLHQDWLNGKEYKCKVSNKAL<br>PAPIEKTISKAKGQPREPQVYTLPPSREEMTKNQVSL<br>SCAVKGFYPSDIAVEWESNGQPENNYKTTPPVLDSDG<br>SFFLVSKLTVDKSRWQQGNVFSCSVMHEALHNHYTQK<br>SLSLSPG | 104 |
| BA142b<br>BA150b<br>heavy chain | EVQLVQSGAEVKKPGSSVKVSCKASGYTFASYGISWV<br>RQAPGQGLEWMGGITPFFNRVDVAEKFQGRVTITADK<br>STSTAYIELSSLRSEDTAVYYCARDLRRGGVGDAFDI<br>WGRGTLVTVSSASTKGPSVFPLAPSSKSTSGGTAALG<br>CLVKDYFPEPVTVSWNSGALTSGVHTFPAVLQSSGLY<br>SLSSVVTVPSSSLGTQTYICNVNHKPSNTKVDKRVEP<br>KSCDKTHTCPPCPAPELLGGPDVFLFPPKPKDTLMIS<br>RTPEVTCVVVDVSHEDPEVKFNWYVDGVEVHNAKTKP<br>REEQYNSTYRVVSVLTVLHQDWLNGKEYKCKVSNKAL<br>PAPEEKTISKAKGQPREPQVYTLPPSREEMTKNQVSL<br>SCAVKGFYPSDIAVEWESNGQPENNYKTTPPVLDSDG<br>SFFLVSKLTVDKSRWQQGNVFSCSVMHEALHNHYTQK<br>SLSLSPG | 105 |
| BA142c<br>BA150c<br>heavy chain | EVQLVQSGAEVKKPGSSVKVSCKASGYTFASYGISWV<br>RQAPGQGLEWMGGITPFFNRVDVAEKFQGRVTITADK<br>STSTAYIELSSLRSEDTAVYYCARDLRRGGVGDAFDI<br>WGRGTLVTVSSASTKGPSVFPLAPSSKSTSGGTAALG<br>CLVKDYFPEPVTVSWNSGALTSGVHTFPAVLQSSGLY<br>SLSSVVTVPSSSLGTQTYICNVNHKPSNTKVDKRVEP<br>KSCDKTHTCPPCPAPELLGGPDVFLFPPKPKDTLMIS<br>RTPEVTCVVVDVSHEDPEVKFNWYVDGVEVHNAKTKP<br>REEQYNSTYRVVSVLTVLHQDWLNGKEYKCKVSNKAL<br>PLPEEKTISKAKGQPREPQVYTLPPSREEMTKNQVSL<br>SCAVKGFYPSDIAVEWESNGQPENNYKTTPPVLDSDG<br>SFFLVSKLTVDKSRWQQGNVFSCSVMHEALHNHYTQK<br>SLSLSPG | 106 |
| BA142h<br>BA150h<br>heavy chain | EVQLVQSGAEVKKPGSSVKVSCKASGYTFASYGISWV<br>RQAPGQGLEWMGGITPFFNRVDVAEKFQGRVTITADK<br>STSTAYIELSSLRSEDTAVYYCARDLRRGGVGDAFDI<br>WGRGTLVTVSSASTKGPSVFPLAPSSKSTSGGTAALG<br>CLVKDYFPEPVTVSWNSGALTSGVHTFPAVLQSSGLY<br>SLSSVVTVPSSSLGTQTYICNVNHKPSNTKVDKRVEP<br>KSCDKTHTCPPCPAPELLGGPSVFLFPPKPKDTLMIS<br>RTPEVTCVVVDVSHEDPEVKFNWYVDGVEVHNAKTKP<br>REEQYNSTYRVVSVLTVLHQDWLNGKEYKCKVSNKAL<br>PAPIEKTISKAKGQPREPQVYTLPPSREEMTKNQVSL<br>TCLVKGFYPSDIAVEWESNGQPENNYKTTPPVLDSDG<br>SFFLYSKLTVDKSRWQQGNVFSCSVMHEALHNHYTQK<br>SLSLSPG | 107 |
| BA142i<br>BA150i<br>heavy chain | EVQLVQSGAEVKKPGSSVKVSCKASGYTFASYGISWV<br>RQAPGQGLEWMGGITPFFNRVDVAEKFQGRVTITADK<br>STSTAYIELSSLRSEDTAVYYCARDLRRGGVGDAFDI<br>WGRGTLVTVSSASTKGPSVFPLAPSSKSTSGGTAALG<br>CLVKDYFPEPVTVSWNSGALTSGVHTFPAVLQSSGLY<br>SLSSVVTVPSSSLGTQTYICNVNHKPSNTKVDKRVEP<br>KSCDKTHTCPPCPAPELLGGPDVFLFPPKPKDTLMIS | 108 |

TABLE 2-continued

Amino acid sequences of exemplary anti-TIGIT antigen-binding regions and anti-TIGIT antibodies.

| Description | Amino Acid Sequence | SEQ ID NO |
|---|---|---|
| | RTPEVTCVVVDVSHEDPEVKFNWYVDGVEVHNAKTKP REEQYNSTYRVVSVLTVLHQDWLNGKEYKCKVSNKAL PAPIEKTISKAKGQPREPQVYTLPPSREEMTKNQVSL TCLVKGFYPSDIAVEWESNGQPENNYKTTPPVLDSDG SFFLYSKLTVDKSRWQQGNVFSCSVMHEALHNHYTQK SLSLSPG | |
| BA142j BA150j heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPDVFLFPPKPKDTLMIS RTPEVTCVVVDVSHEDPEVKFNWYVDGVEVHNAKTKP REEQYNSTYRVVSVLTVLHQDWLNGKEYKCKVSNKAL PAPEEKTISKAKGQPREPQVYTLPPSREEMTKNQVSL TCLVKGFYPSDIAVEWESNGQPENNYKTTPPVLDSDG SFFLYSKLTVDKSRWQQGNVFSCSVMHEALHNHYTQK SLSLSPG | 109 |
| BA142k BA150k heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPDVFLFPPKPKDTLMIS RTPEVTCVVVDVSHEDPEVKFNWYVDGVEVHNAKTKP REEQYNSTYRVVSVLTVLHQDWLNGKEYKCKVSNKAL PLPEEKTISKAKGQPREPQVYTLPPSREEMTKNQVSL TCLVKGFYPSDIAVEWESNGQPENNYKTTPPVLDSDG SFFLYSKLTVDKSRWQQGNVFSCSVMHEALHNHYTQK SLSLSPG | 110 |
| BA148 heavy chain | EVQLVQSGAEVKKPGSSVKVSCKASGYTFASYGISWV RQAPGQGLEWMGGITPFFNRVDVAEKFQGRVTITADK STSTAYIELSSLRSEDTAVYYCARDLRRGGVGDAFDI WGRGTLVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPDVFLFPPKPKDTLMIS RTPEVTCVVVDVSHEDPEVKFNWYVDGVEVHNAKTKP REEQYNSTYRVVSVLTVLHQDWLNGKEYKCKVSNKAL PLPEEKTISKAKGQPREPQVYTLPPSREEMTKNQVSL TCLVKGFYPSDIAVEWESNGQPENNYKTTPPVLDSDG SFFLYSKLTVDKSRWQQGNVFSCSVMHEALHNHYTQK SLSLSPGK | 48 |
| BA142a BA150a heavy chain constant region | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLSCAVKGFYPSD IAVEWESNGQPENNYKTTPPVLDSDGSFFLVSKLTVD KSRWQQGNVFSCSVMHEALHNHYTQKSLSLSPG | 49 |
| BA142g BA150g heavy chain constant region | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPDVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLSCAVKGFYPSD IAVEWESNGQPENNYKTTPPVLDSDGSFFLVSKLTVD KSRWQQGNVFSCSVMHEALHNHYTQKSLSLSPG | 50 |
| BA142b BA150b heavy chain constant region | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPDVFLFPPKPKDTLMISRTPEVTCVVVD VSHEDPEVKFNWYVDGVEVHNAKTKPREEQYNSTYRV | 51 |

TABLE 2-continued

Amino acid sequences of exemplary anti-TIGIT antigen-binding regions and anti-TIGIT antibodies.

| Description | Amino Acid Sequence | SEQ ID NO |
|---|---|---|
| | VSVLTVLHQDWLNGKEYKCKVSNKALPAPEEKTISKA<br>KGQPREPQVYTLPPSREEMTKNQVSLSCAVKGFYPSD<br>IAVEWESNGQPENNYKTTPPVLDSDGSFFLVSKLTVD<br>KSRWQQGNVFSCSVMHEALHNHYTQKSLSLSPG | |
| BA142c<br>BA150c<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPLPEEKTISKA<br>KGQPREPQVYTLPPSREEMTKNQVSLSCAVKGFYPSD<br>IAVEWESNGQPENNYKTTPPVLDSDGSFFLVSKLTVD<br>KSRWQQGNVFSCSVMHEALHNHYTQKSLSLSPG | 52 |
| BA142d<br>BA150d<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKA<br>KGQPREPQVYTLPPSREEMTKNQVSLWCLVKGFYPSD<br>IAVEWESNGQPENNYKTTPPVLDSDGSFFLYSKLTVD<br>KSRWQQGNVFSCSVMHEALHNHYTQKSLSLSPG | 53 |
| BA142e<br>BA150e<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKA<br>KGQPREPQVYTLPPSREEMTKNQVSLWCLVKGFYPSD<br>IAVEWESNGQPENNYKTTPPVLDSDGSFFLYSKLTVD<br>KSRWQQGNVFSCSVMHEALHNHYTQKSLSLSPG | 54 |
| BA142f<br>BA150f<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPEEKTISKA<br>KGQPREPQVYTLPPSREEMTKNQVSLWCLVKGFYPSD<br>IAVEWESNGQPENNYKTTPPVLDSDGSFFLYSKLTVD<br>KSRWQQGNVFSCSVMHEALHNHYTQKSLSLSPG | 55 |
| BA142<br>BA150<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPLPEEKTISKA<br>KGQPREPQVYTLPPSREEMTKNQVSLWCLVKGFYPSD<br>IAVEWESNGQPENNYKTTPPVLDSDGSFFLYSKLTVD<br>KSRWQQGNVFSCSVMHEALHNHYTQKSLSLSPG | 56 |
| BA142h<br>BA150h<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPG | 57 |
| BA142i<br>BA150i<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPG | 58 |

TABLE 2-continued

Amino acid sequences of exemplary anti-TIGIT antigen-binding regions and anti-TIGIT antibodies.

| Description | Amino Acid Sequence | SEQ ID NO |
|---|---|---|
| BA142j<br>BA150j<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPEEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPG | 59 |
| BA142k<br>BA150k<br>heavy chain constant region | ASTKGPSVFPLAPSSKSTSGGTAALGCLVKDYFPEPV<br>TVSWNSGALTSGVHTFPAVLQSSGLYSLSSVVTVPSS<br>SLGTQTYICNVNHKPSNTKVDKRVEPKSCDKTHTCPP<br>CPAPELLGGPDVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPLPEEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPG | 60 |

TABLE 3

Exemplary CD96 sequences.

| Description | Amino Acid Sequence | SEQ ID NO |
|---|---|---|
| Exemplary Human CD96 extracellular domain isoform 1 sequence[1] | VWEKTVNTEENVYATLGSDVNLTCQTQTVGFFVQMQWSKVT<br>NKIDLIAVYHPQYGFYCAYGRPCESLVTFTETPENGSKWTL<br>HLRNMSCSVSGRYECMLVLYPEGIQTKIYNLLIQTHVTADE<br>WNSNHTIEIEINQTLEIPCFQNSSSKISSEFTYAWSVENSS<br>TDSWVLLSKGIKEDNGTQETLISQNHLISNSTLLKDRVKLG<br>TDYRLHLSPVQIFDDGRKFSCHIRVGPNKILRSSTTVKVFA<br>KPEIPVIVENNSTDVLVERRFTCLLKNVFPKANITWFIDGS<br>FLHDEKEGIYITNEERKGKDGFLELKSVLTRVHSNKPAQSD<br>NLTIWCMALSPVPGNKVWNISSEKITFLLGSEISSTDPPLS<br>VTESTLDTQPSPASSVSPARYPATSSVTLVDVSALRPNTTP<br>QPSNSSMTTRGFNYPWTSSGTDTKKSVSRIPSETYSSSPSG<br>AGSTLHDNVFTSTARAFSEVPTTANGSTKTNHVHITGIVVN<br>KPKDGM | 61 |
| Exemplary Human CD96 extracellular domain isoform 2 sequence[1] | VWEKTVNTEENVYATLGSDVNLTCQTQTVGFFVQMQWSKVT<br>NKIDLIAVYHPQYGFYCAYGRPCESLVTFTETPENGSKWTL<br>HLRNMSCSVSGRYECMLVLYPEGIQTKIYNLLIQTHVTADE<br>WNSNHTIEIEINQTLEIPCFQNSSSKISSEFTYAWSVEDNG<br>TQETLISQNHLISNSTLLKDRVKLGTDYRLHLSPVQIFDDG<br>RKFSCHIRVGPNKILRSSTTVKVFAKPEIPVIVENNSTDVL<br>VERRFTCLLKNVFPKANITWFIDGSFLHDEKEGIYITNEER<br>KGKDGFLELKSVLTRVHSNKPAQSDNLTIWCMALSPVPGNK<br>VWNISSEKITFLLGSEISSTDPPLSVTESTLDTQPSPASSV<br>SPARYPATSSVTLVDVSALRPNTTPQPSNSSMTTRGFNYPW<br>TSSGTDTKKSVSRIPSETYSSSPSGAGSTLHDNVFTSTARA<br>FSEVPTTANGSTKTNHVHITGIVVNKPKDGM | 62 |
| Exemplary Human CD96 extracellular domain isoform 2 C89S[1] | VWEKTVNTEENVYATLGSDVNLTCQTQTVGFFVQMQWSKVT<br>NKIDLIAVYHPQYGFYCAYGRPCESLVTFTETPENGSKWTL<br>HLRNMSSSVSGRYECMLVLYPEGIQTKIYNLLIQTHVTADE<br>WNSNHTIEIEINQTLEIPCFQNSSSKISSEFTYAWSVEDNG<br>TQETLISQNHLISNSTLLKDRVKLGTDYRLHLSPVQIFDDG<br>RKFSCHIRVGPNKILRSSTTVKVFAKPEIPVIVENNSTDVL<br>VERRFTCLLKNVFPKANITWFIDGSFLHDEKEGIYITNEER<br>KGKDGFLELKSVLTRVHSNKPAQSDNLTIWCMALSPVPGNK<br>VWNISSEKITFLLGSEISSTDPPLSVTESTLDTQPSPASSV<br>SPARYPATSSVTLVDVSALRPNTTPQPSNSSMTTRGFNYPW<br>TSSGTDTKKSVSRIPSETYSSSPSGAGSTLHDNVFTSTARA<br>FSEVPTTANGSTKTNHVHITGIVVNKPKDGMENLYFQGLEH<br>HHHHHHHHGGSGGLPETGGDR | 63 |
| Exemplary Human | VWEKTVNTEENVYATLGSDVNLTCQTQTVGFFVQMQWSKVT<br>NKIDLIAVYHPQYGFYCAYGRPCESLVTFTETPENGSKWTL | 64 |

TABLE 3-continued

Exemplary CD96 sequences.

| Description | Amino Acid Sequence | SEQ ID NO |
|---|---|---|
| CD96 domain 1[1] | HLRNMSCSVSGRYECMLVLYPEGIQTKIYNLLIQTHV | |
| Exemplary Human CD96 domain 1 C89S[1] | VWEKTVNTEENVYATLGSDVNLTCQTQTVGFFVQMQWSKVT NKIDLIAVYHPQYGFYCAYGRPCESLVTFTETPENGSKWTL HLRNMSSSVSGRYECMLVLYPEGIQTKIYNLLIQTHV | 65 |
| Exemplary Cyno CD96 extracellular domain isoform 1[2] | VWGKPFNTEENIYATLGSDVNLTCQTQAKGFLVQMQWSKVT DKADLIALYHPQYGFHCAYGSPCESLVTFTQTPENGSKWTL HLRNMSSSVSGRYECMLTLYPEGMQTKIYNLLIQTHVTPDE WKSNHTIEIEINQTLEIPCFQNSSSEISSEFTYAWLWKNS STDSWVLLSKGKRYDNGTQQTLISQDHLISSSTLLKDRVKV GIDYRLHLSPVQIFDDGRKFSCHIRVGPDKILRSSTTIKVF AKPEIPMIVENNSTDVLVERTFTCLLKNVFPKANIIWFIDG SFLHDEKEGIYITNEERKGKDGFLELKSVLTRVHSDKPAQS DNLTIWCMALSPVPGNKVWNISSEKITFLLGSEMSTTDLPP SVTESTLDTQPSPASSVSPTRYPATSSVTLADVSALRPNTT PQSSSSSVTTQDFNYPWTSSGTDAKKSFSQIPSETYSSSPS GAGSTLHDNVFTSTTRALSEVPTTANGSTKTNHVHITGIVV SKPKDGM | 66 |
| Exemplary Cyno CD96 extracellular domain sequence isoform 2[2] | VWGKPFNTEENIYATLGSDVNLTCQTQAKGFLVQMQWSKVT DKADLIALYHPQYGFHCAYGSPCESLVTFTQTPENGSKWTL HLRNMSSSVSGRYECMLTLYPEGMQTKIYNLLIQTHVTPDE WKSNHTIEIEINQTLEIPCFQNSSSEISSEFTYAWLVEDNG TQQTLISQDHLISSSTLLKDRVKVGIDYRLHLSPVQIFDDG RKFSCHIRVGPDKILRSSTTIKVFAKPEIPMIVENNSTDVL VERTFTCLLKNVFPKANIIWFIDGSFLHDEKEGIYITNEER KGKDGFLELKSVLTRVHSDKPAQSDNLTIWCMALSPVPGNK VWNISSEKITFLLGSEMSTTDLPPSVTESTLDTQPSPASSV SPTRYPATSSVTLADVSALRPNTTPQSSSSSVTTQDFNYPW TSSGTDAKKSFSQIPSETYSSSPSGAGSTLHDNVFTSTTRA LSEVPTTANGSTKTNHVHITGIVVSKPKDGMENLYFQGLEH HHHHHHHHHGGSGGLPETGGDR | 111 |
| Exemplary Cyno CD96 domain 1[2] | VWGKPFNTEENIYATLGSDVNLTCQTQAKGFLVQMQWSKVT DKADLIALYHPQYGFHCAYGSPCESLVTFTQTPENGSKWTL HLRNMSSSVSGRYECMLTLYPEGMQTKIYNLLIQTHV | 112 |

[1]Domains assigned based on UniProt description of domains for hCD96.
[2]For cyCD96 sequence homology between the hCD96 sequence & the cyCD96 sequence was used to define domain 1, domain 2, or domain 3.

TABLE 4

Exemplary TIGIT sequences.

| Description | Amino Acid Sequence | SEQ ID NO |
|---|---|---|
| Exemplary Human TIGIT extracellular domain | MMTGTIETTGNISAEKGGSII LQCHLSSTTAQVTQVNWEQQD QLLAICNADLGWHISPSFKDR VAPGPGLGLTLQSLTVNDTGE YFCIYHTYPDGTYTGRIFLEV LESSVAEHGARFQENLYFQGL EHHHHHHHHHHGGSGGLPETG GDR | 113 |
| Exemplary Cyno TIGIT extracellular domain | MMTGTIETTGNISAKKGGSVI LQCHLSSTMAQVTQVNWEQHD HSLLAIRNAELGWHIYPAFKD RVAPGPGLGLTLQSLTMNDTG EYFCTYHTYPDGTYRGRIFLE VLESSVAEHSARFQENLYFQG LEHHHHHHHHHHGGSGGLPET GGDR | 114 |

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, the first antigen-binding region comprising a VH comprising one, two, or all three of the CDRs of a VH set forth in Table 1. In certain embodiments, the first antigen-binding region comprises the CDRH1 of a VH set forth in Table 1. In certain embodiments, the first antigen-binding region comprises the CDRH2 of a VH set forth in Table 1. In certain embodiments, the first antigen-binding region comprises the CDRH3 of a VH set forth in Table 1.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, the first antigen-binding region comprising a VL comprising one, two, or all three of the CDRs of a VL disclosed in Table 1. In certain embodiments, the first antigen-binding region comprises the CDRL1 of a VL set forth in Table 1. In certain embodiments, the first antigen-binding region comprises the CDRL2 of a VL set forth in Table 1. In certain embodiments, the first antigen-binding region comprises the CDRL3 of a VL set forth in Table 1.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), the second antigen-binding region comprising a VH comprising one, two, or all three of the CDRs of a VH set forth in Table 2. In certain embodiments, the second antigen-binding region comprises the CDRH1 of a VH set forth in Table 2. In certain embodiments, the second antigen-binding region comprises the CDRH2 of a VH set forth in Table 2. In certain embodiments, the second antigen-binding region comprises the CDRH3 of a VH set forth in Table 2.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), the second antigen-binding region comprising a VL comprising one, two, or all three of the CDRs of a VL set forth in Table 2. In certain embodiments, the second antigen-binding region comprises the CDRH1 of a VL set forth in Table 2. In certain embodiments, the second antigen-binding region comprises the CDRH2 of a VL set forth in Table 2. In certain embodiments, the second antigen-binding region comprises the CDRH3 of a VL set forth in Table 2.

In certain embodiments, the instant disclosure provides a multispecific molecule comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), the first antigen-binding region comprising a VH comprising one, two, or all three of the CDRs of a VH set forth in Table 1, and the second antigen-binding region comprising a VH comprising one, two, or all three of the CDRs of a VH set forth in Table 2. In certain embodiments, the first antigen-binding region comprises the CDRH1 of a VH set forth in Table 1, and the second antigen-binding region comprises the CDRH1 of a VH set forth in Table 2. In certain embodiments, the first antigen-binding region comprises the CDRH2 of a VH set forth in Table 1, and the second antigen-binding region comprises the CDRH2 of a VH set forth in Table 2. In certain embodiments, the first antigen-binding region comprises the CDRH3 of a VH set forth in Table 1, and the second antigen-binding region comprises the CDRH3 of a VH set forth in Table 2.

In certain embodiments, the instant disclosure provides a multispecific molecule comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), the first antigen-binding region comprising a VL comprising one, two, or all three of the CDRs of a VL set forth in Table 1, and the second antigen-binding region comprising a VL comprising one, two, or all three of the CDRs of a VL set forth in Table 2. In certain embodiments, the first antigen-binding region comprises the CDRH1 of a VL set forth in Table 1, and the second antigen-binding region comprises the CDRH1 of a VL set forth in Table 2. In certain embodiments, the first antigen-binding region comprises the CDRH2 of a VL set forth in Table 1, and the second antigen-binding region comprises the CDRH2 of a VL set forth in Table 2. In certain embodiments, the first antigen-binding region comprises the CDRH3 of a VL set forth in Table 1, and the second antigen-binding region comprises the CDRH3 of a VL set forth in Table 2.

In certain embodiments, the instant disclosure provides an isolated antibody that specifically binds to TIGIT (e.g., human TIGIT or cynomolgus TIGIT), the antibody comprising a VH domain comprising one, two, or all three of the CDRs of a VH domain set forth in Table 2. In certain embodiments, the antibody comprises the CDRH1 of a VH domain set forth in Table 2. In certain embodiments, the antibody comprises the CDRH2 of a VH domain set forth in Table 2. In certain embodiments, the antibody comprises the CDRH3 of a VH domain set forth in Table 2.

In certain embodiments, the instant disclosure provides an isolated antibody that specifically binds to TIGIT (e.g., human TIGIT or cynomolgus TIGIT), the antibody comprising a VL domain comprising one, two, or all three of the CDRs of a VL domain disclosed in Table 2. In certain embodiments, the antibody comprises the CDRL1 of a VL domain set forth in Table 2. In certain embodiments, the antibody comprises the CDRL2 of a VL domain set forth in Table 2. In certain embodiments, the antibody comprises the CDRL3 of a VL domain set forth in Table 2.

The individual CDRs of a multispecific molecule or an antibody disclosed herein can be determined according to any CDR numbering scheme known in the art.

In certain embodiments, one or more of the CDRs of a multispecific molecule or an antibody disclosed herein can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the instant disclosure provides multispecific molecules comprising a first antigen-binding region that specifically binds to CD96 (e.g., human CD96 or cynomolgus CD96) and a second antigen-binding region that specifically binds to an antigen other than CD96, wherein the first antigen-binding region comprises CDRs of an antigen-binding region disclosed in Table 1 herein, as determined by the Kabat numbering scheme.

In certain embodiments, the instant disclosure provides multispecific molecules comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the CDRs of an antigen-binding region disclosed in Table 2 herein, as determined by the Kabat numbering scheme.

In certain embodiments, the instant disclosure provides multispecific molecules comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding region comprises CDRs of an antigen-binding region disclosed in Table 1 herein, and the second antigen-binding region comprises CDRs of an antigen-binding region disclosed in Table 2 herein, as determined by the Kabat numbering scheme.

In certain embodiments, the instant disclosure provides antibodies that specifically bind to TIGIT (e.g., human TIGIT or cynomolgus TIGIT) and comprise CDRs of an antibody disclosed in Table 2 herein as determined by the Kabat numbering scheme.

In certain embodiments, one or more of the CDRs of a multispecific molecule or an antibody disclosed herein can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273:

927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties).

In certain embodiments, the instant disclosure provides multispecific molecules comprising a first antigen-binding region that specifically binds to CD96 (e.g., human CD96 or cynomolgus CD96) and a second antigen-binding region that specifically binds to an antigen other than CD96, wherein the first antigen-binding region comprises CDRs of an antigen-binding region disclosed in Table 1 herein, as determined by the Chothia numbering system.

In certain embodiments, the instant disclosure provides multispecific molecules comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the CDRs of an antigen-binding region disclosed in Table 2 herein, as determined by the Chothia numbering system.

In certain embodiments, the instant disclosure provides multispecific molecules comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding region comprises CDRs of an antigen-binding region disclosed in Table 1 herein, and the second antigen-binding region comprises CDRs of an antigen-binding region disclosed in Table 2 herein, as determined by the Chothia numbering system.

In certain embodiments, the instant disclosure provides antibodies that specifically bind to TIGIT (e.g., human TIGIT or cynomolgus TIGIT) and comprise CDRs of an antibody disclosed in Table 2 herein, as determined by the Chothia numbering system.

In certain embodiments, one or more of the CDRs of a multispecific molecule or an antibody disclosed herein can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the instant disclosure provides multispecific molecules comprising a first antigen-binding region that specifically binds to CD96 (e.g., human CD96 or cynomolgus CD96) and a second antigen-binding region that specifically binds to an antigen other than CD96, wherein the first antigen-binding region comprises CDRs of an antigen-binding region disclosed in Table 1 herein, as determined by the MacCallum numbering system.

In certain embodiments, the instant disclosure provides multispecific molecules comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the CDRs of an antigen-binding region disclosed in Table 2 herein, as determined by the MacCallum numbering system.

In certain embodiments, the instant disclosure provides multispecific molecules comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding region comprises CDRs of an antigen-binding region disclosed in Table 1 herein, and the second antigen-binding region comprises CDRs of an antigen-binding region disclosed in Table 2 herein, as determined by the MacCallum numbering system.

In certain embodiments, the instant disclosure provides antibodies that specifically bind to TIGIT (e.g., human TIGIT or cynomolgus TIGIT) and comprise CDRs of an antibody disclosed in Table 2 herein, as determined by the MacCallum numbering system.

In certain embodiments, the CDRs of a multispecific molecule or an antibody disclosed herein can be determined according to the IMGT numbering system as described in: Lefranc M-P, (1999) The Immunologist 7: 132-136; Lefranc M-P et al., (1999) Nucleic Acids Res 27: 209-212, each of which is herein incorporated by reference in its entirety; and Lefranc M-P et al., (2009) Nucleic Acids Res 37: D1006-D1012.

In certain embodiments, the instant disclosure provides multispecific molecules comprising a first antigen-binding region that specifically binds to CD96 (e.g., human CD96 or cynomolgus CD96) and a second antigen-binding region that specifically binds to an antigen other than CD96, wherein the first antigen-binding region comprises CDRs of an antigen-binding region disclosed in Table 1 herein, as determined by the IMGT numbering system.

In certain embodiments, the instant disclosure provides multispecific molecules comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the CDRs of an antigen-binding region disclosed in Table 2 herein, as determined by the IMGT numbering system.

In certain embodiments, the instant disclosure provides multispecific molecules comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding region comprises CDRs of an antigen-binding region disclosed in Table 1 herein, and the second antigen-binding region comprises CDRs of an antigen-binding region disclosed in Table 2 herein, as determined by the IMGT numbering system.

In certain embodiments, the instant disclosure provides antibodies that specifically bind to TIGIT (e.g., human TIGIT or cynomolgus TIGIT) and comprise CDRs of an antibody disclosed in Table 2 herein, as determined by the IMGT numbering system.

In certain embodiments, the CDRs of a multispecific molecule or an antibody disclosed herein can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

In certain embodiments, the instant disclosure provides multispecific molecules comprising a first antigen-binding region that specifically binds to CD96 (e.g., human CD96 or cynomolgus CD96) and a second antigen-binding region that specifically binds to an antigen other than CD96, wherein the first antigen-binding region comprises CDRs of an antigen-binding region disclosed in Table 1 herein, as determined by the AbM numbering scheme.

In certain embodiments, the instant disclosure provides multispecific molecules comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the CDRs of an antigen-binding region disclosed in Table 2 herein, as determined by the AbM numbering scheme.

In certain embodiments, the instant disclosure provides multispecific molecules comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding region comprises CDRs of an antigen-binding region disclosed in Table 1 herein, and the second antigen-binding region comprises CDRs of an antigen-binding region disclosed in Table 2 herein, as determined by the AbM numbering scheme.

In certain embodiments, the instant disclosure provides antibodies that specifically bind to TIGIT (e.g., human TIGIT or cynomolgus TIGIT) and comprise CDRs of an antibody disclosed in Table 2 herein as determined by the AbM numbering scheme.

In certain embodiments, the CDRs of an antibody disclosed herein can be determined according to the AHo numbering system, as described in Honegger and Plücktthun, J. Mol. Biol. 309:657-670 (2001), herein incorporated by reference in its entirety.

In certain embodiments, the instant disclosure provides multispecific molecules comprising a first antigen-binding region that specifically binds to CD96 (e.g., human CD96 or cynomolgus CD96) and a second antigen-binding region that specifically binds to an antigen other than CD96, wherein the first antigen-binding region comprises CDRs of an antigen-binding region disclosed in Table 1 herein, as determined by the AHo numbering system.

In certain embodiments, the instant disclosure provides multispecific molecules comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the CDRs of an antigen-binding region disclosed in Table 2 herein, as determined by the AHo numbering system.

In certain embodiments, the instant disclosure provides multispecific molecules comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding region comprises CDRs of an antigen-binding region disclosed in Table 1 herein, and the second antigen-binding region comprises CDRs of an antigen-binding region disclosed in Table 2 herein, as determined by the AHo numbering system.

In certain embodiments, the instant disclosure provides antibodies that specifically bind to TIGIT (e.g., human TIGIT or cynomolgus TIGIT) and comprise CDRs of an antibody disclosed in Table 2 herein, as determined by the AHo numbering system.

In certain embodiments, the individual CDRs of a multispecific molecule or an antibody disclosed herein are each independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of CD96 or TIGIT.

In certain embodiments, the instant disclosure provides a multispecific molecule comprising a first antigen-binding region that specifically binds to CD96 (e.g., human CD96 or cynomolgus CD96) and a second antigen-binding region that specifically binds to an antigen other than CD96, wherein the first antigen-binding region comprises a VH comprising the CDRH1, CDRH2, and CDRH3 region amino acid sequences of a VH set forth in SEQ ID NO: 34, 36, or 38, and a VL comprising the CDRL1, CDRL2, and CDRL3 region amino acid sequences of a VL set forth in SEQ ID NO: 35, 37, or 39, wherein each CDR is independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of CD96 (e.g., human CD96 or cynomolgus CD96).

In certain embodiments, the instant disclosure provides a multispecific molecule comprising a first antigen-binding region that specifically binds to an antigen other than TIGIT and a second antigen-binding region that specifically binds to TIGIT (e.g., human TIGIT or cynomolgus TIGIT), wherein the second antigen-binding region comprises a VH comprising the CDRH1, CDRH2, and CDRH3 region amino acid sequences of a VH set forth in SEQ ID NO: 40, and a VL comprising the CDRL1, CDRL2, and CDRL3 region amino acid sequences of a VL set forth in SEQ ID NO: 41, wherein each CDR is independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of TIGIT (e.g., human TIGIT or cynomolgus TIGIT).

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a VH comprising the CDRH1, CDRH2, and CDRH3 region amino acid sequences of a VH set forth in SEQ ID NO: 34, 36, or 38, and a VL comprising the CDRL1, CDRL2, and CDRL3 region amino acid sequences of a VL set forth in SEQ ID NO: 35, 37, or 39, and the second antigen-binding region comprises a VH comprising the CDRH1, CDRH2, and CDRH3 region amino acid sequences of a VH set forth in SEQ ID NO: 40, and a VL comprising the CDRL1, CDRL2, and CDRL3 region amino acid sequences of a VL set forth in SEQ ID NO: 41, wherein each CDR is independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of CD96 (e.g., human CD96 or cynomolgus CD96) and TIGIT (e.g., human TIGIT or cynomolgus TIGIT), respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising the CDRH1, CDRH2, and CDRH3 amino acid sequences set forth in SEQ ID NOs: 10, 11, and 12; 16, 17, and 18; or 22, 23, and 24, respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VL comprising the CDRL1, CDRL2, and CDRL3 amino acid sequences set forth in SEQ ID NOs: 13, 14, and 15; 19, 20, and 21; or 25, 26, and 27, respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 10, 11, 12, 13, 14, and 15; 16, 17, 18, 19, 20, and 21; or 22, 23, 24, 25, 26, and 27, respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 34, 36, or 38. In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising an amino acid sequence set forth in SEQ ID NO: 34, 36, or 38. In certain embodiments, the amino acid sequence of the VH consists of the amino acid sequence selected from the group consisting of SEQ ID NO: 34, 36, and 38.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 35, 37, or 39. In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VL comprising an amino acid sequence set forth in SEQ ID NO: 35, 37, or 39. In certain embodiments, the amino acid sequence of the VL consists of the amino acid sequence selected from the group consisting of SEQ ID NO: 35, 37, and 39.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 34, 36, or 38, and a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 35, 37, or 39. In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising an amino acid sequence of SEQ ID NO: 34, and a VL comprising an amino acid sequence of SEQ ID NO: 35. In certain embodiments, the amino acid sequence of the VH consists of the amino acid sequence set forth in SEQ ID NO: 34; and the amino acid sequence of the VL consists of the amino acid sequence set forth in SEQ ID NO: 35. In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising an amino acid sequence of SEQ ID NO: 36, and a VL comprising an amino acid sequence of SEQ ID NO: 37. In certain embodiments, the amino acid sequence of the VH consists of the amino acid sequence set forth in SEQ ID NO: 36; and the amino acid sequence of the VL consists of the amino acid sequence set forth in SEQ ID NO: 37. In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises a VH comprising an amino acid sequence of SEQ ID NO: 38, and a VL comprising an amino acid sequence of SEQ ID NO: 39. In certain embodiments, the amino acid sequence of the VH consists of the amino acid sequence set forth in SEQ ID NO: 38; and the amino acid sequence of the VL consists of the amino acid sequence set forth in SEQ ID NO: 39.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96, wherein the first antigen-binding region comprises the VH and VL amino acid sequences set forth in SEQ ID NOs: 34 and 35; 36 and 37; or 38 and 39, respectively. In certain embodiments, the amino acid sequences of the VH and VL consists of amino acid sequence selected from the groups consisting of SEQ ID NOs: 34 and 35; 36 and 37; and 38 and 39, respectively.

In certain embodiments, the instant disclosure provides a multispecific molecule that cross-competes for binding to CD96 (e.g., human CD96 or cynomolgus CD96) with a multispecific molecule comprising the VH and VL amino acid sequences set forth in SEQ ID NOs: 34 and 35; 36 and 37; or 38 and 39, respectively.

In certain embodiments, the instant disclosure provides a multispecific molecule that binds to the same or an overlapping epitope of CD96 (e.g., an epitope of human CD96 or an epitope of cynomolgus CD96) as a multispecific molecule described herein, e.g., a multispecific molecule comprising the VH and VL amino acid sequences set forth in SEQ ID NOs: 34 and 35; 36 and 37; or 38 and 39, respectively.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VH comprising the CDRH1, CDRH2, and CDRH3 amino acid sequences set forth in SEQ ID NOs: 28, 29, and 30, respectively.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VL comprising the CDRL1, CDRL2, and CDRL3 amino acid sequences set forth in SEQ ID NOs: 31, 32, and 33, respectively.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 28, 29, 30, 31, 32, and 33, respectively.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 40. In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VH comprising an amino acid sequence set forth in SEQ ID NO: 40. In certain embodiments, the amino acid sequence of the VH consists of the amino acid sequence set forth in SEQ ID NO: 40.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 41. In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VL comprising an amino acid sequence set forth in SEQ ID NO: 41. In certain embodiments, the amino acid sequence of the VL consists of the amino acid sequence set forth in SEQ ID NO: 41.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 40, and a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 41. In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises a VH comprising an amino acid sequence of SEQ ID NO: 40, and a VL comprising an amino acid sequence of SEQ ID NO: 41. In certain embodiments, the amino acid sequence of the VH consists of the amino acid sequence set forth in SEQ ID NO: 40; and the amino acid sequence of the VL consists of the amino acid sequence set forth in SEQ ID NO: 41.

In certain embodiments, the instant disclosure provides a multispecific molecule comprising a first antigen-binding region that specifically binds to an antigen other than TIGIT, and a second antigen-binding region that specifically binds to TIGIT (e.g., human TIGIT or cynomolgus TIGIT), wherein the second antigen-binding region comprises the VH and VL amino acid sequences set forth in SEQ ID NOs: 40 and 41, respectively. In certain embodiments, the amino acid sequences of VH and VL consist of the amino acid sequences set forth in SEQ ID NOs: 40 and 41, respectively.

In certain embodiments, the instant disclosure provides a multispecific molecule that cross-competes for binding to TIGIT (e.g., human TIGIT or cynomolgus TIGIT) with a multispecific molecule comprising the VH and VL amino acid sequences set forth in SEQ ID NOs: 40 and 41, respectively.

In certain embodiments, the instant disclosure provides a multispecific molecule that binds to the same or an overlapping epitope of TIGIT (e.g., an epitope of human TIGIT or an epitope of cynomolgus TIGIT) as a multispecific molecule described herein, e.g., a multispecific molecule comprising the VH and VL amino acid sequences set forth in SEQ ID NOs: 40 and 41, respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding molecule comprises a first VH comprising the CDRH1, CDRH2, and CDRH3 amino acid sequences set forth in SEQ ID NOs: 10, 11, and 12; 16, 17, and 18; or 22, 23, and 24, respectively, and the second antigen-binding region comprises a second VH comprising the CDRH1, CDRH2, and CDRH3 amino acid sequences set forth in SEQ ID NOs: 28, 29, and 30, respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding molecule comprises a first VL comprising the CDRH1, CDRH2, and CDRH3 amino acid sequences set forth in SEQ ID NOs: 13, 14, and 15; 19, 20, and 21; or 25, 26, and 27, respectively, and the second antigen-binding region comprises a second VL comprising the CDRH1, CDRH2, and CDRH3 amino acid sequences set forth in SEQ ID NOs: 31, 32, and 33, respectively.

In certain embodiments, the instant disclosure provides a multispecific molecule comprising a first antigen-binding region that specifically binds to CD96 (e.g., human CD96 or cynomolgus CD96), and a second antigen-binding region that specifically binds to TIGIT (e.g., human TIGIT or cynomolgus TIGIT), wherein the first antigen-binding molecule comprises a first VH comprising CDRH1, CDRH2, and CDRH3 regions, and a first VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 10, 11, 12, 13, 14, and 15; 16, 17, 18, 19, 20, and 21; or 22, 23, 24, 25, 26, and 27, respectively, and the second antigen-binding region comprises a second VH comprising CDRH1, CDRH2, and CDRH3 regions, and a second VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 28, 29, 30, 31, 32, and 33, respectively.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 34, 36, or 38, and the second antigen-binding region comprises a second VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 40. In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VH comprising an amino acid sequence set forth in SEQ ID NO: 34, 36, or 38, and the second antigen-binding region comprises a second VH comprising an amino acid sequence set forth in SEQ ID NO: 40. In certain embodiments, the amino acid sequence of the first VH consists of the amino acid sequence selected from the group consisting of SEQ ID NO: 34, 36, and 38, and the amino acid sequence of the second VH consists of the amino acid sequence set forth in SEQ ID NO: 40.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 35, 37, or 39, and the second antigen-binding region comprises a second VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 41. In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VL comprising an amino acid sequence set forth in SEQ ID NO: 35, 37, or 39, and the second antigen-binding region comprises a second VL comprising an amino acid sequence set forth in SEQ ID NO: 41. In certain embodiments, the amino acid sequence of the first VL consists of an amino acid sequence selected from the group consisting of SEQ ID NO: 35, 37, and 39, and the amino acid sequence of the second VL consists of the amino acid sequence set forth in SEQ ID NO: 41.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 34, 36, or 38, and a first VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 35, 37, or 39, and the second antigen-binding region comprises a second VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 40, and a second VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 41. In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VH comprising an amino acid sequence of SEQ ID NO: 34, 36, or 38, and a first VL comprising an amino acid sequence of SEQ ID NO: 35, 37, or 39, the second antigen-binding region comprises a second VH comprising an amino acid sequence of SEQ ID NO: 40, and a second VL comprising an amino acid sequence of SEQ ID NO: 41. In certain embodiments, the amino acid sequence of the first VH consists of an amino acid sequence selected from the group consisting of SEQ ID NOs: 34, 36, and 38; and the amino acid sequence of the first VL consists of an amino acid sequence selected from the group consisting of SEQ ID NOs: 35, 37, and 39, and the amino acid sequence of the second VH consists of the amino acid sequence set forth in SEQ ID NO: 40; and the amino acid sequence of the second VL consists of the amino acid sequence set forth in SEQ ID NO: 41.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), wherein the first antigen-binding region comprises a first VH and a first VL comprising the amino acid sequences set forth in SEQ ID NOs: 34 and 35; 36 and 37; or 38 and 39, respectively, and the second antigen-binding region comprises a second VH and a second VL comprising the amino acid sequences set forth in SEQ ID NOs: 40 and 41, respectively. In certain embodiments, the amino acid sequences of the first VH and the first VL consist of amino acid sequences selected from the groups consisting of SEQ ID NOs: 34 and 35; 36 and 37; and 38 and 39, respectively, and the amino acid sequences of the second VH and the second VL consist of the amino acid sequences set forth in SEQ ID NOs: 40 and 41, respectively.

In certain embodiments, the instant disclosure provides a multispecific molecule comprising a first antigen-binding region that cross-competes for binding to CD96 (e.g., human CD96 or cynomolgus CD96) with a multispecific molecule comprising the VH and VL amino acid sequences set forth in SEQ ID NOs: 34 and 35; 36 and 37; or 38 and 39, respectively, and a second antigen-binding region that cross-competes for binding to TIGIT (e.g., human TIGIT or cynomolgus TIGIT) with a multispecific molecule comprising the VH and VL amino acid sequences set forth in SEQ ID NOs: 40 and 41, respectively.

In certain embodiments, the instant disclosure provides a multispecific molecule that comprises a first antigen-binding region that binds to the same or an overlapping epitope of CD96 (e.g., an epitope of human CD96 or an epitope of cynomolgus CD96) as a multispecific molecule described herein, e.g., a multispecific molecule comprising the VH and VL amino acid sequences set forth in SEQ ID NOs: 34 and 35; 36 and 37; or 38 and 39, respectively, and a second antigen-binding region that binds to the same or an overlapping epitope of TIGIT (e.g., an epitope of human TIGIT or an epitope of cynomolgus TIGIT) as a multispecific molecule described herein, e.g., a multispecific molecule comprising the VH and VL amino acid sequences set forth in SEQ ID NOs: 40 and 41, respectively.

In certain embodiments, the instant disclosure provides an isolated antibody that specifically binds to TIGIT (e.g., human TIGIT or cynomolgus TIGIT), wherein the isolated antibody comprises a VH comprising the CDRH1, CDRH2, and CDRH3 amino acid sequences set forth in SEQ ID NOs: 28, 29, and 30, respectively.

In certain embodiments, the instant disclosure provides an isolated antibody that specifically binds to TIGIT (e.g., human TIGIT or cynomolgus TIGIT), wherein the isolated antibody comprises a VL comprising the CDRL1, CDRL2, and CDRL3 amino acid sequences set forth in SEQ ID NOs: 31, 32, and 33, respectively.

In certain embodiments, the instant disclosure provides an isolated antibody that specifically binds to TIGIT (e.g., human TIGIT or cynomolgus TIGIT), wherein the isolated antibody comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 28, 29, 30, 31, 32, and 33, respectively.

In certain embodiments, the instant disclosure provides an isolated antibody that specifically binds to TIGIT (e.g., human TIGIT or cynomolgus TIGIT) comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 40. In certain embodiments, the instant disclosure provides an isolated antibody that specifically binds to TIGIT (e.g., human TIGIT or cynomolgus TIGIT), comprising a VH comprising an amino acid sequence set forth in SEQ ID NO: 40. In certain embodiments, the amino acid sequence of the VH consists of the amino acid sequence set forth in SEQ ID NO: 40.

In certain embodiments, the instant disclosure provides an isolated antibody that specifically binds to TIGIT (e.g., human TIGIT or cynomolgus TIGIT), comprising a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 41. In certain embodiments, the instant disclosure provides an isolated antibody that specifically binds to TIGIT (e.g., human TIGIT or cynomolgus TIGIT), comprising a VL comprising an amino acid sequence set forth in SEQ ID NO: 41. In certain embodiments, the amino acid sequence of the VL consists of the amino acid sequence set forth in SEQ ID NO: 41.

In certain embodiments, the instant disclosure provides an isolated antibody that specifically binds to TIGIT (e.g., human TIGIT or cynomolgus TIGIT), comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 40, and a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 41. In certain embodiments, the instant disclosure provides an isolated antibody that specifically binds to TIGIT (e.g., human TIGIT or cynomolgus TIGIT), comprising a VH comprising an amino acid sequence of SEQ ID NO: 40, and a VL comprising an amino acid sequence of SEQ ID NO: 41. In certain embodiments, the amino acid sequence of the VH consists of the amino acid sequence set forth in SEQ ID NO: 40; and the amino acid sequence of the VL consists of the amino acid sequence set forth in SEQ ID NO: 41.

In certain embodiments, the instant disclosure provides an isolated antibody that specifically binds to TIGIT (e.g., human TIGIT or cynomolgus TIGIT), comprising the VH and VL amino acid sequences set forth in SEQ ID NOs: 40 and 41, respectively. In certain embodiments, the amino acid sequences of VH and VL consist of the amino acid sequences set forth in SEQ ID NOs: 40 and 41, respectively.

In certain embodiments, the instant disclosure provides an isolated antibody that cross-competes for binding to TIGIT (e.g., human TIGIT or cynomolgus TIGIT) with an antibody comprising the VH and VL amino acid sequences set forth in SEQ ID NOs: 40 and 41, respectively.

In certain embodiments, the instant disclosure provides an isolated antibody that binds to the same or an overlapping epitope of TIGIT (e.g., an epitope of human TIGIT or an epitope of cynomolgus TIGIT) as an antibody described herein, e.g., an antibody comprising the VH and VL amino acid sequences set forth in SEQ ID NOs: 40 and 41, respectively.

In certain embodiments, the epitope of a multispecific molecule or an antibody can be determined by, e.g., NMR spectroscopy, surface plasmon resonance)(BIAcore®, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Multispecific molecule:antigen or antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds. Wyckoff H W et al.; U.S. Patent Application No. 2004/0014194), and BUSTER (Bricogne G (1993) Acta Crystallogr D Biol Crystallogr 49 (Pt 1): 37-60; Bricogne G (1997) Meth Enzymol 276A: 361-423, ed. Carter C W; Roversi P et al., (2000) Acta Crystallogr D Biol Crystallogr 56 (Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of a multispecific molecule or an antibody is determined using alanine scanning mutagenesis studies. In addition, multispecific molecules or antibodies that recognize and bind to the same or overlapping epitopes of CD96 (e.g., human CD96 or cynomolgus CD96) and/or TIGIT (e.g., human TIGIT or cynomolgus TIGIT) can be identified using routine techniques such as an immunoassay, for example, by showing the ability of one multispecific molecule or antibody to block the binding of another multispecific molecule or antibody to a target antigen, i.e., a competitive binding assay. Competition binding assays also can be used to determine whether two multispecific molecules or antibodies have similar binding specificity for an epitope. Competitive binding can be determined in an assay in which the immunoglobulin under test inhibits specific binding of a reference multispecific molecule or antibody to a common antigen, such as CD96 (e.g., human CD96 or cynomolgus CD96) and/or TIGIT (e.g., human TIGIT or cynomolgus TIGIT). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., CD96, such as human CD96 or cynomolgus CD96, or TIGIT, such as human TIGIT or cynomolgus TIGIT) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually, the test immunoglobulin is present in excess. Usually, when a competing multispecific molecule or antibody is present in excess, it will inhibit specific binding of a reference multispecific molecule or antibody to a common antigen by at least 50-55%, 55-60%, 60-65%, 65-70%, 70-75% or more. A competition binding assay can be configured in a large number of different formats using either labeled antigen or labeled multispecific molecule or antibody. In a common version of this assay, the antigen is immobilized on a 96-well plate. The ability of unlabeled multispecific molecule or antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, eds. Harlow E & Lane D, supra, pp. 386-389, all of which are herein incorporated by reference in their entireties.

In certain embodiments, the multispecific molecule inhibits the binding of human CD96 to human CD155 (also known as poliovirus receptor (PVR)). In certain embodiments, the binding of human CD96 to human CD155 is reduced by more than 50%, 55%, 60%, 65%, 70%, 75%, 80%, 85%, 90%, 95%, 96%, 97%, 98%, or 99% in the presence of the multispecific molecule relative to the binding of human CD96 to human CD155 in the absence of the multispecific molecule.

In certain embodiments, the multispecific molecule inhibits a soluble fragment of human CD96 from binding to a soluble fragment of human CD155. In certain embodiments, the binding of a soluble fragment of human CD96 to a soluble fragment of human CD155 is reduced by more than 50%, 55%, 60%, 65%, 70%, 75%, 80%, 85%, 90%, 95%, 96%, 97%, 98%, or 99% in the presence of the multispecific molecule relative to the binding of a soluble fragment of human CD96 to a soluble fragment of human CD155 in the absence of the multispecific molecule.

In certain embodiments, the antibody inhibits a CD96-expressing cell from binding to a soluble fragment of human CD155. In certain embodiments, the binding of a CD96-expressing cell to a soluble fragment of human CD155 is reduced by more than 50%, 55%, 60%, 65%, 70%, 75%, 80%, 85%, 90%, 95%, 96%, 97%, 98%, or 99% in the presence of the multispecific molecule relative to the binding of a CD96-expressing cell to a soluble fragment of human CD155 in the absence of the multispecific molecule.

In certain embodiments, the multispecific molecule inhibits a CD96-expressing cell from binding to a cell expressing human CD155. In certain embodiments, the binding of a CD96-expressing cell to a CD155-expressing cell is reduced by more than 50%, 55%, 60%, 65%, 70%, 75%, 80%, 85%, 90%, 95%, 96%, 97%, 98%, or 99% in the presence of the multispecific molecule relative to the binding of a CD96-expressing cell to a CD155-expressing cell in the absence of the multispecific molecule.

In certain embodiments, the instant disclosure provides a multispecific molecule comprising a first antigen-binding region that specifically binds to CD96 (e.g., human CD96 or cynomolgus CD96) and a second antigen-binding region that specifically binds to an antigen other than CD96, the first antigen-binding region comprising a heavy chain comprising the amino acid sequence set forth in SEQ ID NO: 1, 3, 5, or 67-99. In certain embodiments, the amino acid sequence of the heavy chain consists of an amino acid sequence selected from the group consisting of SEQ ID NOs: 1, 3, 5, and 67-99.

In certain embodiments, the instant disclosure provides a multispecific molecule comprising a first antigen-binding region that specifically binds to CD96 (e.g., human CD96 or cynomolgus CD96) and a second antigen-binding region that specifically binds to an antigen other than CD96, the first antigen-binding region comprising a light chain comprising the amino acid sequence set forth in SEQ ID NO: 2, 4, or 6. In certain embodiments, the amino acid sequence of the light chain consists of an amino acid sequence selected from the group consisting of SEQ ID NOs: 2, 4, and 6.

In certain embodiments, the instant disclosure provides a multispecific molecule comprising a first antigen-binding region that specifically binds to CD96 (e.g., human CD96 or cynomolgus CD96) and a second antigen-binding region that specifically binds to an antigen other than CD96, the first antigen-binding region comprising a heavy chain and a light chain, wherein the heavy chain and light chain comprise the amino acid sequences of SEQ ID NOs: 1 and 2; 3 and 4; or 5 and 6, respectively. In certain embodiments, the amino acid sequences of the heavy chain and light chain consist of amino acid sequences selected from the groups consisting of SEQ ID NOs: 1 and 2; 3 and 4; and 5 and 6, respectively.

In certain embodiments, the multispecific molecule inhibits the binding of human TIGIT to human CD155 (also known as poliovirus receptor (PVR)). In certain embodiments, the binding of human TIGIT to human CD155 is reduced by more than 50%, 55%, 60%, 65%, 70%, 75%, 80%, 85%, 90%, 95%, 96%, 97%, 98%, or 99% in the presence of the multispecific molecule relative to the binding of human TIGIT to human CD155 in the absence of the multispecific molecule.

In certain embodiments, the multispecific molecule inhibits a soluble fragment of human TIGIT from binding to a soluble fragment of human CD155. In certain embodiments, the binding of a soluble fragment of human TIGIT to a soluble fragment of human CD155 is reduced by more than 50%, 55%, 60%, 65%, 70%, 75%, 80%, 85%, 90%, 95%, 96%, 97%, 98%, or 99% in the presence of the multispecific molecule relative to the binding of a soluble fragment of human TIGIT to a soluble fragment of human CD155 in the absence of the multispecific molecule.

In certain embodiments, the multispecific molecule inhibits a TIGIT-expressing cell from binding to a soluble fragment of human CD155. In certain embodiments, the binding of a TIGIT-expressing cell to a soluble fragment of human CD155 is reduced by more than 50%, 55%, 60%, 65%, 70%, 75%, 80%, 85%, 90%, 95%, 96%, 97%, 98%, or 99% in the presence of the multispecific molecule relative to the binding of a TIGIT-expressing cell to a soluble fragment of human CD155 in the absence of the multispecific molecule.

In certain embodiments, the multispecific molecule inhibits a TIGIT-expressing cell from binding to a cell expressing human CD155. In certain embodiments, the binding of a TIGIT-expressing cell to a CD155-expressing cell is reduced by more than 50%, 55%, 60%, 65%, 70%, 75%, 80%, 85%, 90%, 95%, 96%, 97%, 98%, or 99% in the presence of the multispecific molecule relative to the binding of a TIGIT-expressing cell to a CD155-expressing cell in the absence of the multispecific molecule.

In certain embodiments, the instant disclosure provides a multispecific molecule comprising a first antigen-binding region that specifically binds to an antigen other than TIGIT and a second antigen-binding region that specifically binds to TIGIT (e.g., human TIGIT or cynomolgus TIGIT), the second antigen-binding region comprising a heavy chain comprising the amino acid sequence set forth in SEQ ID NO: 7 or 100-110. In certain embodiments, the amino acid sequence of the heavy chain consists of an amino acid sequence selected from the group consisting of SEQ ID NOs: 7 and 100-110.

In certain embodiments, the instant disclosure provides a multispecific molecule comprising a first antigen-binding region that specifically binds an antigen other than TIGIT and a second antigen-binding region that specifically binds to TIGIT (e.g., human TIGIT or cynomolgus TIGIT), the second antigen-binding region comprising a light chain comprising the amino acid sequence set forth in SEQ ID NO: 8 or 9. In certain embodiments, the amino acid sequence of the light chain consists of an amino acid sequence selected from the group consisting of SEQ ID NOs: 8 and 9.

In certain embodiments, the instant disclosure provides a multispecific molecule comprising a first antigen-binding region that specifically binds to an antigen other than TIGIT and a second antigen-binding region that specifically binds to TIGIT (e.g., human TIGIT or cynomolgus TIGIT), the second antigen-binding region comprising a heavy chain and a light chain, wherein the heavy chain and light chain comprise the amino acid sequences of SEQ ID NOs: 7 and 8; or 7 and 9, respectively. In certain embodiments, the amino acid sequences of the heavy chain and light chain consist of amino acid sequences selected from the groups consisting of SEQ ID NOs: 7 and 8; and 7 and 9, respectively.

In certain embodiments, the multispecific molecule inhibits the binding of human CD96 and human TIGIT to human CD155 (also known as poliovirus receptor (PVR)). In certain embodiments, the binding of human CD96 and human TIGIT to human CD155 is reduced by more than 50%, 55%, 60%, 65%, 70%, 75%, 80%, 85%, 90%, 95%, 96%, 97%, 98%, or 99% in the presence of the multispecific molecule relative to the binding of human CD96 and human TIGIT to human CD155 in the absence of the multispecific molecule.

In certain embodiments, the multispecific molecule inhibits a soluble fragment of human CD96 and a soluble fragment of human TIGIT from binding to a soluble fragment of human CD155. In certain embodiments, the binding of a soluble fragment of human CD96 and a soluble fragment of human TIGIT to a soluble fragment of human CD155 is reduced by more than 50%, 55%, 60%, 65%, 70%, 75%, 80%, 85%, 90%, 95%, 96%, 97%, 98%, or 99% in the presence of the multispecific molecule relative to the binding of a soluble fragment of human CD96 and a soluble fragment of human TIGIT to a soluble fragment of human CD155 in the absence of the multispecific molecule.

In certain embodiments, the multispecific molecule inhibits a cell expressing CD96, TIGIT, or CD96 and TIGIT from binding to a soluble fragment of human CD155. In certain embodiments, the binding of a cell expressing CD96, TIGIT, or CD96 and TIGIT to a soluble fragment of human CD155 is reduced by more than 50%, 55%, 60%, 65%, 70%, 75%, 80%, 85%, 90%, 95%, 96%, 97%, 98%, or 99% in the presence of the multispecific molecule relative to the binding of a cell expressing CD96, TIGIT, or CD96 and TIGIT to a soluble fragment of human CD155 in the absence of the multispecific molecule.

In certain embodiments, the multispecific molecule inhibits a cell expressing CD96, TIGIT, or CD96 and TIGIT from binding to a cell expressing human CD155. In certain embodiments, the binding of a cell expressing CD96, TIGIT, or CD96 and TIGIT to a CD155-expressing cell is reduced by more than 50%, 55%, 60%, 65%, 70%, 75%, 80%, 85%, 90%, 95%, 96%, 97%, 98%, or 99% in the presence of the multispecific molecule relative to the binding of a cell expressing CD96, TIGIT, or CD96 and TIGIT to a CD155-expressing cell in the absence of the multispecific molecule.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), the first antigen-binding region comprising a first heavy chain comprising the amino acid sequence set forth in SEQ ID NO: 1, 2, 3, or 67-99, and a second antigen-binding region comprising a second heavy chain comprising the amino acid sequence set forth in SEQ ID NO: 7 or 100-110. In certain embodiments, the amino acid sequence of the first heavy chain consists of an amino acid sequence selected from the group consisting of SEQ ID NOs: 1, 2, 3, and 67-99, and the amino acid sequence of the second heavy chain consists of an amino acid sequence selected from the group consisting of SEQ ID NOs: 7 and 100-110.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), the first antigen-binding region comprising a first light chain comprising the amino acid sequence set forth in SEQ ID NO: 2, 4, or 6, and a second antigen-binding region comprising a second light chain comprising the amino acid sequence set forth in SEQ ID NO: 8 or 9. In certain embodiments, the amino acid sequence of the first light chain consists of an amino acid sequence selected from the group consisting of SEQ ID NOs: 2, 4, and 6, and the amino acid sequence of the second light chain consists of an amino acid sequence selected from the group consisting of SEQ ID NOs: 8 and 9.

In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), the first antigen-binding region comprising a first heavy chain and a first light chain, wherein the first heavy chain and first light chain comprise the amino acid sequences of SEQ ID NOs: 1 and 2; 3 and 4; or 5 and 6, respectively, and the second antigen-binding region comprising a second heavy chain and a second light chain, wherein the second heavy chain and second light chain comprise the amino acid sequences of SEQ ID NOs: 7 and 8; or 7 and 9, respectively. In certain embodiments, the amino acid sequences of the first heavy chain and the first light chain consist of amino acid sequences selected from the groups consisting of SEQ ID NOs: 1 and 2; 3 and 4; and 5 and 6, respectively, and the amino acid sequences of the second heavy chain and the second light chain consist of amino acid sequences selected from the groups consisting of SEQ ID NOs: 7 and 8; and 7 and 9, respectively.

In certain embodiments, the antibody inhibits the binding of human TIGIT to human CD155 (also known as poliovirus receptor (PVR)). In certain embodiments, the binding of human TIGIT to human CD155 is reduced by more than 50%, 55%, 60%, 65%, 70%, 75%, 80%, 85%, 90%, 95%, 96%, 97%, 98%, or 99% in the presence of the antibody relative to the binding of human TIGIT to human CD155 in the absence of the antibody.

In certain embodiments, the antibody inhibits a soluble fragment of human TIGIT from binding to a soluble fragment of human CD155. In certain embodiments, the binding of a soluble fragment of human TIGIT to a soluble fragment of human CD155 is reduced by more than 50%, 55%, 60%, 65%, 70%, 75%, 80%, 85%, 90%, 95%, 96%, 97%, 98%, or 99% in the presence of the antibody relative to the binding of a soluble fragment of human TIGIT to a soluble fragment of human CD155 in the absence of the antibody.

In certain embodiments, the antibody inhibits a TIGIT-expressing cell from binding to a soluble fragment of human CD155. In certain embodiments, the binding of a TIGIT-expressing cell to a soluble fragment of human CD155 is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a soluble fragment of human CD155 in the absence of the antibody.

In certain embodiments, the antibody inhibits a TIGIT-expressing cell from binding to a cell expressing human CD155. In certain embodiments, the binding of a TIGIT-expressing cell to a CD155-expressing cell is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a CD155-expressing cell in the absence of the antibody.

In certain embodiments, the instant disclosure provides an isolated antibody that specifically binds to TIGIT (e.g., human TIGIT or cynomolgus TIGIT), the antibody comprising a heavy chain comprising the amino acid sequence set forth in SEQ ID NO: 107, 108, 109, or 110. In certain embodiments, the amino acid sequence of the heavy chain consists of the amino acid sequence set forth in SEQ ID NO: 107, 108, 109, or 110.

In certain embodiments, the instant disclosure provides an isolated antibody that specifically binds to TIGIT (e.g., human TIGIT or cynomolgus TIGIT), the antibody comprising a light chain comprising the amino acid sequence set forth in SEQ ID NO: 8 or 9. In certain embodiments, the amino acid sequence of the light chain consists of an amino acid sequence selected from the group consisting of SEQ ID NOs: 8 and 9.

In certain embodiments, the instant disclosure provides an isolated antibody that specifically binds to TIGIT (e.g., human TIGIT or cynomolgus TIGIT), comprising the heavy chain and light chain, wherein the heavy chain and light chain comprise the amino acid sequences of SEQ ID NOs: 107 and 8; 107, and 9; 108 and 8; 108 and 9; 109 and 8; 109 and 9; 110 and 8; or 110 and 9, respectively.

In certain embodiments, the amino acid sequences of the heavy chain and light chain consist of amino acid sequences selected from the groups consisting of SEQ ID NOs: 107 and 8; 107, and 9; 108 and 8; 108 and 9; 109 and 8; 109 and 9; 110 and 8; or 110 and 9, respectively.

In certain embodiments, the multispecific molecule or antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$, and $^{186}Re$. In certain embodiments, the detectable label comprises a fluorescent moiety or a click chemistry handle.

Any immunoglobulin (Ig) constant region can be used in the multispecific molecules or antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_2a$ and $IgG_2b$) of immunoglobulin molecule.

In certain embodiments, the instant disclosure provides a multispecific molecule comprising a first antigen-binding region that specifically binds to CD96 (e.g., human CD96 or cynomolgus CD96) and a second antigen-binding that specifically binds to an antigen other than CD96, the first antigen-binding region comprising a heavy chain constant region comprising the amino acid sequence of any one of SEQ ID NOs: 49-60. In certain embodiments, the instant disclosure provides a multispecific molecule comprising a first antigen-binding region that specifically binds to CD96 (e.g., human CD96 or cynomolgus CD96) and a second antigen-binding region that specifically binds to an antigen other than CD96, the first antigen-binding region comprising a light chain constant region comprising the amino acid sequence of SEQ ID NO: 42.

In certain embodiments, the instant disclosure provides a multispecific molecule comprising a first antigen-binding region that specifically binds to an antigen other than TIGIT and a second antigen-binding region that specifically binds to TIGIT (e.g., human TIGIT or cynomolgus TIGIT), the second antigen-binding region comprising a heavy chain constant region comprising the amino acid sequence of any one of SEQ ID NOs: 49-60. In certain embodiments, the instant disclosure provides a multispecific molecule comprising a first antigen-binding region that specifically binds to an antigen other than TIGIT and a second antigen-binding region that specifically binds to TIGIT (e.g., human TIGIT or cynomolgus TIGIT), the first antigen-binding region comprising a comprising a light chain constant region comprising the amino acid sequence of SEQ ID NO: 43 or 44.

In certain embodiments, the multispecific molecule comprises a first antigen-binding region that specifically binds to CD96 (e.g., human CD96 or cynomolgus CD96) and a second antigen-binding region that specifically binds to TIGIT (e.g., human TIGIT or cynomolgus TIGIT), the first antigen-binding region comprising a heavy chain constant region comprising the amino acid sequence of SEQ ID NO: 50, and the second antigen-binding region comprising a heavy chain constant region comprising the amino acid sequence of SEQ ID NO: 56. In certain embodiments, the instant disclosure provides a multispecific molecule comprising a first antigen-binding region that specifically binds to CD96 (e.g., human CD96 or cynomolgus CD96) and a second antigen-binding region that specifically binds to TIGIT (e.g., human TIGIT or cynomolgus TIGIT), the first antigen-binding region comprising a comprising a light chain constant region comprising the amino acid sequence of SEQ ID NO: 42, and the second antigen-binding region comprising a comprising a light chain constant region comprising the amino acid sequence of SEQ ID NO: 43 or 44.

In certain embodiments, the instant disclosure provides an isolated antibody that specifically binds to TIGIT (e.g., human TIGIT or cynomolgus TIGIT), the antibody comprising a heavy chain constant region comprising the amino acid sequence of SEQ ID NO: 57, 58, 59, or 60. In certain embodiments, the instant disclosure provides an isolated antibody that specifically binds to TIGIT (e.g., human TIGIT or cynomolgus TIGIT), the antibody comprising a light chain constant region comprising the amino acid sequence of SEQ ID NO: 43 or 44.

In certain embodiments, one, two, or more mutations (e.g., amino acid substitutions) are introduced into an Fc region (e.g., a CH2 domain (residues 231-340 of human $IgG_1$) and/or a CH3 domain (residues 341-447 of human $IgG_1$), numbered according to the EU numbering system) and/or a hinge region (residues 216-230, numbered according to the EU numbering system) of a multispecific molecule or an antibody described herein, to alter one or more functional properties of the multispecific molecule or antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of a multispecific molecule or an antibody described herein, such that the number of cysteine residues in the hinge region is altered (e.g., increased or decreased) as described in, e.g., U.S. Pat. No. 5,677,425, herein incorporated by reference in its entirety. The number of cysteine residues in the hinge region may be altered to, e.g., facilitate assembly of the light and heavy chains, or to alter (e.g., increase or decrease) the stability of the multispecific molecule or antibody.

In a specific embodiment, one, two, or more amino acid mutations (e.g., substitutions, insertions, or deletions) are introduced into an IgG constant region, or FcRn-binding fragment thereof (preferably an Fc or hinge-Fc fragment) to alter (e.g., decrease or increase) half-life of the multispecific molecule or antibody in vivo. See, e.g., International Publication Nos. WO 02/060919; WO 98/23289; and WO 97/34631; and U.S. Pat. Nos. 5,869,046, 6,121,022, 6,277,375, and 6,165,745, all of which are herein incorporated by reference in their entireties, for examples of mutations that will alter (e.g., decrease or increase) the half-life of a multispecific molecule or an antibody in vivo. In certain embodiments, one, two, or more amino acid mutations (e.g., substitutions, insertions, or deletions) are introduced into an IgG constant region, or FcRn-binding fragment thereof (preferably an Fc or hinge-Fc fragment) to decrease the half-life of the multispecific molecule or antibody in vivo. In other embodiments, one, two, or more amino acid mutations (e.g., substitutions, insertions or deletions) are introduced into an IgG constant region, or FcRn-binding fragment thereof (preferably an Fc or hinge-Fc fragment) to increase the half-life of the multispecific molecule or antibody in vivo. In a specific embodiment, the multispecific molecules or antibodies may have one or more amino acid mutations (e.g., substitutions) in the second constant (CH2) domain (residues 231-340 of human $IgG_1$) and/or the third constant (CH3) domain (residues 341-447 of human IgG$_1$), numbered according to the EU numbering system. In a specific embodiment, the constant region of the IgG$_1$ of a multispecific molecule or antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same multispecific molecule or antibody (see Dall'Acqua W F et al., (2006) J Biol Chem 281: 23514-24, which is herein incorporated by reference in its entirety). In certain embodiments, a multispecific molecule or an antibody comprises an IgG constant region comprising one, two, three, or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into an Fc region (e.g., a CH2 domain (residues 231-340 of human IgG$_1$) and/or a CH3 domain (residues 341-447 of human IgG$_1$), numbered according to the EU numbering system) and/or a hinge region (residues 216-230, numbered according to the EU numbering system) of a multispecific molecule or an antibody described herein, to increase or decrease the affinity of the multispecific molecule or antibody for an Fc receptor (e.g., an activated Fc receptor) on the surface of an effector cell. Mutations in the Fc region of a multispecific molecule or an antibody that decrease or increase the affinity of a multispecific molecule or an antibody for an Fc receptor and techniques for introducing such mutations into the Fc receptor or fragment thereof are known to one of skill in the art. Examples of mutations in the Fc receptor of a multispecific molecule or an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the multispecific molecule or antibody comprises a heavy chain constant region that is a variant of a wild type heavy chain constant region, wherein the variant heavy chain constant region binds to FcγRIIB with higher affinity than the wild type heavy chain constant region binds to FcγRIIB. In certain embodiments, the variant heavy chain constant region is a variant human heavy chain constant region, e.g., a variant human IgG$_1$, a variant human IgG$_2$, or a variant human IgG$_4$ heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant region Fc region to alter the effector function(s) of the multispecific molecule or antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the multispecific molecule or antibody has an altered affinity for an effector ligand but retains the antigen-binding ability of the parent multispecific molecule or antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating multispecific molecule or antibody thereby increasing tumor localization. See, e.g., U.S. Pat. Nos. 5,585,097 and 8,591,886, each of which is herein incorporated by reference in its entirety, for a description of mutations that delete or inactivate the constant region and thereby increase tumor localization. In certain embodiments, one or more amino acid substitutions may be introduced into the Fc region of a multispecific molecule or an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of a multispecific molecule or an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A330L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of a multispecific molecule or an antibody described herein. In certain embodiments, a mutation selected from the group consisting of L235A, L237A, and a combination thereof, numbered according to the EU numbering system, may be made in the constant region of a multispecific molecule or an antibody described herein. In certain embodiments, a mutation selected from the group consisting of S267E, L328F, and a combination thereof, numbered according to the EU numbering system, may be made in the constant region of a multispecific molecule or an antibody described herein. In certain embodiments, a mutation selected from the group consisting of S239D, I332E, optionally A330L, and a combination thereof, numbered according to the EU numbering system, may be made in the constant region of a multispecific molecule or an antibody described herein. In certain embodiments, a mutation selected from the group consisting of L235V, F243L, R292P, Y300L, P396L, and a combination thereof, numbered according to the EU numbering system, may be made in the constant region of a multispecific molecule or an antibody described herein. In certain embodiments, a mutation selected from the group consisting of S267E, L328F, and a combination thereof, numbered according to the EU numbering system, may be made in the constant region of a multispecific molecule or an antibody described herein.

In a specific embodiment, a multispecific molecule or an antibody described herein comprises the constant region of an IgG$_1$ with an N297Q or N297A amino acid substitution, numbered according to the EU numbering system. In certain embodiments, a multispecific molecule or an antibody described herein comprises the constant region of an IgG$_1$ with a mutation selected from the group consisting of D265A, P329A, and a combination thereof, numbered according to the EU numbering system. In another embodiment, a multispecific molecule or an antibody described herein comprises the constant region of an IgG$_1$ with a mutation selected from the group consisting of L234A, L235A, and a combination thereof, numbered according to the EU numbering system. In another embodiment, a multispecific molecule or an antibody described herein comprises the constant region of an IgG$_1$ with a mutation selected from the group consisting of L234F, L235F, N297A, and a combination thereof, numbered according to the EU numbering system. In certain embodiments, amino acid residues in the constant region of multispecific molecule or an antibody described herein in the positions corresponding to positions L234, L235, and D265 in a human IgG$_1$ heavy chain, numbered according to the EU numbering system, are not L, L, and D, respectively. This approach is described in detail in International Publication No. WO 14/108483, which is herein incorporated by reference in its entirety. In certain embodiments, the amino acids corresponding to positions L234, L235, and D265 in a human IgG$_1$ heavy chain are F, E, and A; or A, A, and A, respectively, numbered according to the EU numbering system.

In certain embodiments, one or more amino acids selected from amino acid residues 329, 331, and 322 in the constant region of a multispecific molecule or an antibody described herein, numbered according to the EU numbering system, can be replaced with a different amino acid residue such that the multispecific molecule or antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of a multispecific molecule or an antibody described herein are altered to thereby alter the ability of the multispecific molecule or antibody to fix complement, numbered according to the EU numbering system. This approach is described further in International Publication No. WO 94/29351, which is herein incorporated by reference in its entirety. In certain embodiments, the Fc region of a multispecific molecule or an antibody described herein is modified to increase the ability of the multispecific molecule or antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, a multispecific molecule or an antibody described herein comprises a modified constant region of an IgG$_1$, wherein the modification increases the ability of the multispecific molecule or antibody to mediate antibody dependent cellular cytotoxicity (ADCC). In certain embodiments, 0.1, 1, or 10 μg/mL of the multispecific molecule or antibody is capable of inducing cell death of at least 20%, 25%, 30%, 35%, 40%, 45%, 50%, 55%, or 60% of CD96-expressing and/or TIGIT-expressing cells within 1, 2, or 3 hours, as assessed by methods described herein and/or known to a person of skill in the art. In certain embodiments, the modified constant region of an IgG$_1$ comprises S239D and I332E substitutions, numbered according to the EU numbering system. In certain embodiments, the modified constant region of an IgG$_1$ comprises S239D, A330L, and I332E substitutions, numbered according to the EU numbering system. In certain embodiments, the modified constant region of an IgG$_1$ comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, a multispecific molecule described herein comprises a first and a second heavy chain constant region, wherein the first heavy chain constant region and the second heavy chain constant region comprise different amino acid substitutions.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising an S239D mutation, and the second antigen-binding region comprises a heavy chain constant region that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D and I332E mutations, and the second antigen-binding region comprises a heavy chain constant region that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, and I332E mutations, and the second antigen-binding region comprises a heavy chain constant region that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising an S239D mutation, and the second antigen-binding region comprises a heavy chain constant region comprising S239D and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising an S239D mutation, and the second antigen-binding region comprises a heavy chain constant region comprising S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D and I332E mutations, and the second antigen-binding region comprises a heavy chain constant region comprising an S239D mutation.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D and I332E mutations, and the second antigen-binding region comprises a heavy chain constant region comprising S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, and I332E mutations, and the second antigen-binding region comprises a heavy chain constant region comprising an S239D mutation.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, and I332E mutations, and the second antigen-binding region comprises a heavy chain constant region comprising S239D and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region that does not comprise S239D, A330L, and I332E mutations, and the second antigen-binding region comprises a heavy chain constant region comprising an S239D mutation.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region that does not comprise S239D, A330L, and I332E mutations, and the second antigen-binding region comprises a heavy chain constant region comprising S239D and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region that does not comprise S239D, A330L, and I332E mutations, and the second antigen-binding region comprises a heavy chain constant region comprising S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising an S239D mutation, and the second antigen-binding region comprises a heavy chain constant region that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D and I332E mutations, and the second antigen-binding region comprises a heavy chain constant region that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, and I332E mutations, and the second antigen-binding region comprises a heavy chain constant region that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising an S239D mutation, and the second antigen-binding region comprises a heavy chain constant region comprising S239D and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising an S239D mutation, and the second antigen-binding region comprises a heavy chain constant region comprising S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D and I332E mutations, and the second antigen-binding region comprises a heavy chain constant region comprising an S239D mutation.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D and I332E mutations, and the second antigen-binding region comprises a heavy chain constant region comprising S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, and I332E mutations, and the second antigen-binding region comprises a heavy chain constant region comprising an S239D mutation.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, and I332E mutations, and the second antigen-binding region comprises a heavy chain constant region comprising S239D and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region that does not comprise S239D, A330L, and I332E mutations, and the second antigen-binding region comprises a heavy chain constant region comprising an S239D mutation.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region that does not comprise S239D, A330L, and I332E mutations, and the second antigen-binding region comprises a heavy chain constant region comprising S239D and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region that does not comprise S239D, A330L, and I332E mutations, and the second antigen-binding region comprises a heavy chain constant region comprising S239D, A330L, and I332E mutations.

In certain embodiments, a multispecific molecule that binds to CD96 and/or TIGIT comprises "knob-into-holes" mutations wherein the multispecific molecule comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain"; R409D, K370E mutations in the "knobs chain" and D399K, E357K mutations in the "hole chain"; R409D, K370E mutations in the "knobs chain" and D399K, E357K mutations in the "hole chain"; a T366W mutation in the "knobs chain" and T366S, L368A, Y407V mutations in the "hole chain"; R409D, K370E mutations in the "knobs chain" and D399K, E357K mutations in the "hole chain"; Y349C, T366W mutations in one of the chains and E356C, T366S, L368A, Y407V mutations in the counterpart chain; Y349C, T366W mutations in one chain and S354C, T366S, L368A, Y407V mutations in the counterpart chain; Y349C, T366W mutations in one chain and S354C, T366S, L368A, Y407V mutations in the counterpart chain; and Y349C, T366W mutations in one chain and S354C, T366S, L368A, Y407V mutations in the counterpart chain (numbering according to the EU numbering system).

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising a T366W mutation, and the second antigen-binding region comprises a heavy chain constant region comprising T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising T366S, L368A, and Y407V mutations, and the second antigen-binding region comprises a heavy chain constant region comprising a T366W mutation.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising a T366W mutation, and the second antigen-binding region comprises a heavy chain constant region comprising T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising T366S, L368A, and Y407V mutations, and the second antigen-binding region comprises a heavy chain constant region comprising a T366W mutation.

In certain embodiments, a multispecific molecule described herein comprises a first and a second heavy chain constant region, wherein the first heavy chain constant region and the second heavy chain constant region comprise knobs-into-holes substitutions, and further comprise additional amino acid substitutions that are different in the first antigen-binding region and the second antigen-binding region.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, T366S, L368A, and Y407V mutations, and the second antigen-binding region comprises a heavy chain constant region comprising a T366W mutation, but that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, I332E, T366S, L368A, and Y407V mutations, and the second antigen-binding region comprises a heavy chain constant region comprising a T366W mutation, but that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, I332E, T366S, L368A, and Y407V mutations, and the second antigen-binding region comprises a heavy chain constant region comprising a T366W mutation, but that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, T366S, L368A, and Y407V mutations, and the second antigen-binding region comprises a heavy chain constant region comprising S239D, I332E, and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, T366S, L368A, and Y407V mutations, and the second antigen-binding region comprises a heavy chain constant region comprising S239D, A330L, I332E, and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, I332E, T366S, L368A, and Y407V mutations, and the second antigen-binding region comprises a heavy chain constant region comprising S239D and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, I332E, T366S, L368A, and Y407V mutations, and the second antigen-binding region comprises a heavy chain constant region comprising S239D, A330L, I332E, and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, I332E, T366S, L368A, and Y407V mutations, and the second antigen-binding region comprises a heavy chain constant region comprising S239D and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, I332E, T366S, L368A, and Y407V mutations, and the second antigen-binding region comprises a heavy chain constant region comprising S239D, I332E, and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising T366S, L368A, and Y407V mutations, but that does not comprise S239D, A330L, and I332E mutations, and the second antigen-binding region comprises a heavy chain constant region comprising S239D and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising T366S, L368A, and Y407V mutations, but that does not comprise S239D, A330L, and I332E mutations, and the second antigen-binding region comprises a heavy chain constant region comprising S239D, I332E, and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising T366S, L368A, and Y407V mutations, but that does not comprise S239D, A330L, and I332E mutations, and the second antigen-binding region comprises a heavy chain constant region comprising S239D, A330L, I332E, and T366W mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D and T366W mutations, and the second antigen-binding region comprises a heavy chain constant region comprising T366S, L368A, and Y407V mutations, but that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, I332E, and T366W mutations, and the second antigen-binding region comprises a heavy chain constant region comprising T366S, L368A, and Y407V mutations, but that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, I332E, and T366W mutations, and the second antigen-binding region comprises a heavy chain constant region comprising T366S, L368A, and Y407V mutations, but that does not comprise S239D, A330L, and I332E mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D and T366W mutations, and the second antigen-binding region comprises a heavy chain constant region comprising S239D, I332E, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D and T366W mutations, and the second antigen-binding region comprises a heavy chain constant region comprising S239D, A330L, I332E, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, I332E, and T366W mutations, and the second antigen-binding region comprises a heavy chain constant region comprising S239D, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, I332E, and T366W mutations, and the second antigen-binding region comprises a heavy chain constant region comprising S239D, A330L, I332E, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, I332E, and T366W mutations, and the second antigen-binding region comprises a heavy chain constant region comprising S239D, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising S239D, A330L, I332E, and T366W mutations, and the second antigen-binding region comprises a heavy chain constant region comprising S239D, I332E, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising a T366W mutation, but that does not comprise S239D, A330L, and I332E mutations, and the second antigen-binding region comprises a heavy chain constant region comprising S239D, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising a T366W mutation, but that does not comprise S239D, A330L, and I332E mutations, and the second antigen-binding region comprises a heavy chain constant region comprising S239D, I332E, T366S, L368A, and Y407V mutations.

In certain embodiments, the instant disclosure provides a multispecific molecule comprising a first antigen-binding region that specifically binds to CD96 (e.g., human CD96 or cynomolgus CD96), and a second antigen-binding region that specifically binds to an antigen other than CD96 (e.g., TIGIT, e.g., human TIGIT or cynomolgus TIGIT), wherein the first antigen-binding region comprises a heavy chain constant region comprising a T366W mutation, but that does not comprise S239D, A330L, and I332E mutations, and the second antigen-binding region comprises a heavy chain constant region comprising S239D, A330L, I332E, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, T366S, L368A, and Y407V mutations, and the second antigen-binding region comprises a heavy chain constant region comprising a T366W mutation, but that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, I332E, T366S, L368A, and Y407V mutations, and the second antigen-binding region comprises a heavy chain constant region comprising a T366W mutation, but that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, I332E, T366S, L368A, and Y407V mutations, and the second antigen-binding region comprises a heavy chain constant region comprising a T366W mutation, but that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, T366S, L368A, and Y407V mutations, and the second antigen-binding region comprises a heavy chain constant region comprising S239D, I332E, and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, T366S, L368A, and Y407V mutations, and the second antigen-binding region comprises a heavy chain constant region comprising S239D, A330L, I332E, and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, I332E, T366S, L368A, and Y407V mutations, and the second antigen-binding region comprises a heavy chain constant region comprising S239D and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, I332E, T366S, L368A, and Y407V mutations, and the second antigen-binding region comprises a heavy chain constant region comprising S239D, A330L, I332E, and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, I332E, T366S, L368A, and Y407V mutations, and the second antigen-binding region comprises a heavy chain constant region comprising S239D and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, I332E, T366S, L368A, and Y407V mutations, and the second antigen-binding region comprises a heavy chain constant region comprising S239D, I332E, and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising T366S, L368A, and Y407V mutations, but that does not comprise S239D, A330L, and I332E mutations, and the second antigen-binding region comprises a heavy chain constant region comprising S239D and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising T366S, L368A, and Y407V mutations, but that does not comprise S239D, A330L, and I332E mutations, and the second antigen-binding region comprises a heavy chain constant region comprising S239D, I332E, and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising T366S, L368A, and Y407V mutations, but that does not comprise S239D, A330L, and I332E mutations, and the second antigen-binding region comprises a heavy chain constant region comprising S239D, A330L, I332E, and T366W mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D and T366W mutations, and the second antigen-binding region comprises a heavy chain constant region comprising T366S, L368A, and Y407V mutations, but that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, I332E, and T366W mutations, and the second antigen-binding region comprises a heavy chain constant region comprising T366S, L368A, and Y407V mutations, but that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, I332E, and T366W mutations, and the second antigen-binding region comprises a heavy chain constant region comprising T366S, L368A, and Y407V mutations, but that does not comprise S239D, A330L, and I332E mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D and T366W mutations, and the second antigen-binding region comprises a heavy chain constant region comprising S239D, I332E, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D and T366W mutations, and the second antigen-binding region comprises a heavy chain constant region comprising S239D, A330L, I332E, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, I332E, and T366W mutations, and the second antigen-binding region comprises a heavy chain constant region comprising S239D, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, I332E, and T366W mutations, and the second antigen-binding region comprises a heavy chain constant region comprising S239D, A330L, I332E, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, I332E, and T366W mutations, and the second antigen-binding region comprises a heavy chain constant region comprising S239D, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising S239D, A330L, I332E, and T366W mutations, and the second antigen-binding region comprises a heavy chain constant region comprising S239D, I332E, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising a T366W mutation, but that does not comprise S239D, A330L, and I332E mutations, and the second antigen-binding region comprises a heavy chain constant region comprising S239D, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising a T366W mutation, but that does not comprise S239D, A330L, and I332E mutations, and the second antigen-binding region comprises a heavy chain constant region comprising S239D, I332E, T366S, L368A, and Y407V mutations.

In certain embodiments, the instant disclosure provides a multispecific molecule comprising a first antigen-binding region that specifically binds to an antigen other than TIGIT (e.g., CD96, e.g., human CD96 or cynomolgus CD96), and a second antigen-binding region that specifically binds to TIGIT (e.g., human TIGIT or cynomolgus TIGIT), wherein the first antigen-binding region comprises a heavy chain constant region comprising a T366W mutation, but that does not comprise S239D, A330L, and I332E mutations, and the second antigen-binding region comprises a heavy chain constant region comprising S239D, A330L, I332E, T366S, L368A, and Y407V mutations.

In certain embodiments, a multispecific molecule or an antibody described herein comprises the constant region of an IgG$_4$ antibody and the serine at amino acid residue 228 of the heavy chain, numbered according to the EU numbering system, is substituted for proline.

In certain embodiments, the instant disclosure provides a multispecific molecule that specifically binds to CD96 (e.g., human CD96 or cynomolgus CD96), the multispecific molecule comprising a heavy chain constant region comprising the amino acid sequence of any one of SEQ ID NOs: 49-60.

In certain embodiments, any of the constant region mutations or modifications described herein can be introduced into one or both heavy chain constant regions of a multispecific molecule or an antibody described herein having two heavy chain constant regions.

In certain embodiments, the instant disclosure provides a multispecific molecule that specifically binds to CD96 (e.g., human CD96 or cynomolgus CD96) and functions as an antagonist (e.g., decreases or inhibits CD96 activity).

In certain embodiments, the instant disclosure provides a multispecific molecule that specifically binds to CD96 (e.g., human CD96 or cynomolgus CD96) and decreases or inhibits CD96 (e.g., human CD96 or cynomolgus CD96) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to CD96 (e.g., human CD96 or cynomolgus CD96) activity without any multispecific molecule or with an unrelated multispecific molecule (e.g., a multispecific molecule that does not specifically bind to CD96 (e.g., human CD96 or cynomolgus CD96)). In certain embodiments, the instant disclosure provides a multispecific molecule that specifically binds to CD96 (e.g., human CD96 or cynomolgus CD96) and decreases or inhibits CD96 (e.g., human CD96 or cynomolgus CD96) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to CD96 (e.g., human CD96 or cynomolgus CD96) activity without any multispecific molecule or with an unrelated multispecific molecule (e.g., a multispecific molecule that does not specifically bind to CD96 (e.g., human CD96)). Non-limiting examples of CD96 (e.g., human CD96 or cynomolgus CD96) activity can include CD96 (e.g., human CD96 or cynomolgus CD96) signaling; CD96 (e.g., human CD96 or cynomolgus CD96) binding to its ligand (e.g., CD155) or a fragment and/or fusion protein thereof; activation of a T cell (e.g., a T cell expressing human CD96); activation of a natural killer (NK) cell; decrease or inhibition of a Treg; increase of cytokine (e.g., IL-2) production; increase of the activity of CD155 (e.g., human CD155). In specific embodiments, an increase in a CD96 (e.g., human CD96 or cynomolgus CD96) activity is assessed as described in the Examples.

In specific embodiments, the instant disclosure provides a multispecific molecule that specifically binds to CD96 (e.g., human CD96 or cynomolgus CD96) and decreases or inhibits CD96 (e.g., human CD96 or cynomolgus CD96) binding to its ligand (e.g., CD155) or a fragment and/or fusion protein thereof, by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to CD96 (e.g., human CD96 or cynomolgus CD96) binding to this ligand without any multispecific molecule or with an unrelated multispecific molecule (e.g., a multispecific molecule that does not specifically bind to CD96 (e.g., human CD96 or cynomolgus CD96)). In specific embodiments, the instant disclosure provides a multispecific molecule that specifically binds to CD96 (e.g., human CD96 or cynomolgus CD96) and increases CD96 (e.g., human CD96 or cynomolgus CD96) binding to its ligand (e.g., CD155 (e.g., human or cynomolgus CD155) or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to CD96 (e.g., human CD96) binding to this ligand without any multispecific molecule or with an unrelated multispecific molecule (e.g., an antibody that does not specifically bind to CD96 (e.g., human CD96 or cynomolgus CD96)).

In specific embodiments, the instant disclosure provides a multispecific molecule that specifically binds to CD96 (e.g., human CD96 or cynomolgus CD96) and activates a T cell (e.g., a T cell expressing human CD96). In certain embodiments, the T cell is a memory T cell. In certain embodiments, the T cell is a primary CD3-expressing T cell. In certain embodiments, the T cell is a CD96-expressing Jurkat cell. In certain embodiments, the multispecific molecule disclosed herein increases the activity of nuclear factor of activated T cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to NFAT activity without any multispecific molecule or with an unrelated multispecific molecule (e.g., a multispecific molecule that does not specifically bind to CD96 (e.g., human CD96 or cynomolgus CD96)). In certain embodiments, the multispecific molecule disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to NFAT activity without any multispecific molecule or with an unrelated multispecific molecule (e.g., a multispecific molecule that does not specifically bind to CD96 (e.g., human CD96 or cynomolgus CD96)). In certain embodiments, the multispecific molecule increases NFAT activity in the presence of a ligand of CD96 (e.g., CD155) or a fragment and/or fusion protein thereof, and/or a cell expressing a ligand of CD96 (e.g., a monocyte or a dendritic cell).

In specific embodiments, the instant disclosure provides a multispecific molecule that specifically binds to CD96 (e.g., human CD96 or cynomolgus CD96) and increases cytokine production (e.g., IL-2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production without any multispecific molecule or with an unrelated multispecific molecule (e.g., a multispecific molecule that does not specifically bind to CD96 (e.g., human CD96 or cynomolgus CD96)). In specific embodiments, the instant disclosure provides a multispecific molecule that specifically binds to CD96 (e.g., human CD96 or cynomolgus CD96) and increases cytokine production (e.g., IL-2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production without any multispecific molecule or with an unrelated multispecific molecule (e.g., a multispecific molecule that does not specifically bind to CD96 (e.g., human CD96 or cynomolgus CD96)). In certain embodiments, the multispecific molecule increases cytokine production (e.g., IL-2) in the presence of a ligand of CD96 (e.g., CD155) or a fragment and/or fusion protein thereof, and/or a cell expressing a ligand of CD96 (e.g., a monocyte or a dendritic cell). In certain embodiments, the multispecific molecule increases the production of IL-2 relative to IL-2 production without any multispecific molecule or with an unrelated multispecific molecule (e.g., an antibody that does not specifically bind to CD96 (e.g., human CD96 or cynomolgus CD96)).

In certain embodiments, the instant disclosure provides a multispecific molecule that specifically binds to CD96 (e.g., human CD96 or cynomolgus CD96) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to IFNγ and/or IL-2 production without any multispecific molecule or with an unrelated multispecific molecule (e.g., a multispecific molecule that does not specifically bind to CD96 (e.g., human CD96 or cynomolgus CD96)).

In certain embodiments, human peripheral blood mononuclear cells (PBMCs) stimulated with *Staphylococcus* Enterotoxin A (SEA) in the presence of a multispecific molecule described herein, which specifically binds to CD96 (e.g., human CD96 or cynomolgus CD96), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any multispecific molecule or with an unrelated multispecific molecule (e.g., multispecific molecule that does not specifically bind to CD96 (e.g., human CD96 or cynomolgus CD96)), as assessed by methods described herein or known to one of skill in the art.

In certain embodiments, the instant disclosure provides a multispecific molecule that specifically binds to CD96 (e.g., human CD96 or cynomolgus CD96) and increases or promotes memory recall of a memory T cell. In certain embodiments, the memory T cell is a CD8 effector memory T cell. In certain embodiments, the memory T cell is a CD4 effector memory T cell. In certain embodiments, the multispecific molecule increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the number of proliferating memory T cells when the memory T cells are in contact with their cognate antigen(s) in the absence of any multispecific molecule or in the presence of an unrelated multispecific molecule (e.g., a multispecific molecule that does not specifically bind to CD96 (e.g., human CD96 or cynomolgus CD96)). In certain embodiments, the multispecific molecule increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the production of the cytokine from a memory T cell when the memory T cell is in contact with its cognate antigen in the absence of any multispecific molecule or in the presence of an unrelated multispecific molecule (e.g., a multispecific molecule that does not specifically bind to CD96 (e.g., human CD96 or cynomolgus CD96)).

In certain embodiments, the instant disclosure provides a multispecific molecule that specifically binds to CD96 (e.g., human CD96 or cynomolgus CD96) and activates an NK cell. In certain embodiments, the NK cells are isolated. In certain embodiments, the NK cells are in a mixed culture of PBMCs. In certain embodiments, the multispecific molecule disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to the expression level of CD107a in NK cells without any multispecific molecule or with an unrelated multispecific molecule (e.g., an antibody that does not specifically bind to CD96 (e.g., human CD96 or cynomolgus CD96)). In certain embodiments, the multispecific molecule disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to the expression level of CD107a in NK cells without any multispecific molecule or with an unrelated multispecific molecule (e.g., a multispecific molecule that does not specifically bind to CD96 (e.g., human CD96 or cynomolgus CD96)). In certain embodiments, the multispecific molecule disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production (e.g., IFNγ and/or TNFα) from NK cells without any multispecific molecule or with an unrelated multispecific molecule (e.g., a multispecific molecule that does not specifically bind to CD96 (e.g., human CD96 or cynomolgus CD96)). In certain embodiments, the multispecific molecule disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production (e.g., IFNγ and/or TNFα) from NK cells without any multispecific molecule or with an unrelated multispecific molecule (e.g., a multispecific molecule that does not specifically bind to CD96 (e.g., human CD96 or cynomolgus CD96)).

In certain embodiments, the instant disclosure provides a multispecific molecule that specifically binds to TIGIT (e.g., human TIGIT or cynomolgus TIGIT) and functions as an antagonist (e.g., decreases or inhibits TIGIT activity).

In certain embodiments, the instant disclosure provides a multispecific molecule that specifically binds to TIGIT (e.g., human TIGIT or cynomolgus TIGIT) and decreases or inhibits TIGIT (e.g., human TIGIT or cynomolgus TIGIT) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to TIGIT (e.g., human TIGIT or cynomolgus TIGIT) activity without any multispecific molecule or with an unrelated multispecific molecule (e.g., a multispecific molecule that does not specifically bind to TIGIT (e.g., human TIGIT or cynomolgus TIGIT)). In certain embodiments, the instant disclosure provides a multispecific molecule that specifically binds to TIGIT (e.g., human TIGIT or cynomolgus TIGIT) and decreases or inhibits TIGIT (e.g., human TIGIT or cynomolgus TIGIT) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to TIGIT (e.g., human TIGIT or cynomolgus TIGIT) activity without any multispecific molecule or with an unrelated multispecific molecule (e.g., a multispecific molecule that does not specifically bind to TIGIT (e.g., human TIGIT)). Non-limiting examples of TIGIT (e.g., human TIGIT or cynomolgus TIGIT) activity can include TIGIT (e.g., human TIGIT or cynomolgus TIGIT) signaling; TIGIT (e.g., human TIGIT or cynomolgus TIGIT) binding to its ligand (e.g., CD155) or a fragment and/or fusion protein thereof; activation of a T cell (e.g., a T cell expressing human TIGIT); activation of a natural killer (NK) cell; decrease or inhibition of a Treg; increase of cytokine (e.g., IL-2) production; increase of the activity of CD155 (e.g., human CD155). In specific embodiments, an increase in a TIGIT (e.g., human TIGIT or cynomolgus TIGIT) activity is assessed as described in the Examples.

In specific embodiments, the instant disclosure provides a multispecific molecule that specifically binds to TIGIT (e.g., human TIGIT or cynomolgus TIGIT) and decreases or inhibits TIGIT (e.g., human TIGIT or cynomolgus TIGIT) binding to its ligand (e.g., CD155) or a fragment and/or fusion protein thereof, by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to TIGIT (e.g., human TIGIT or cynomolgus TIGIT) binding to this ligand without any multispecific molecule or with an unrelated multispecific molecule (e.g., a multispecific molecule that does not specifically bind to TIGIT (e.g., human TIGIT or cynomolgus TIGIT)). In specific embodiments, the instant disclosure provides a multispecific molecule that specifically binds to TIGIT (e.g., human TIGIT or cynomolgus TIGIT) and increases TIGIT (e.g., human TIGIT or cynomolgus TIGIT) binding to its ligand (e.g., CD155 (e.g., human or cynomolgus CD155) or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to TIGIT (e.g., human TIGIT) binding to this ligand without any multispecific molecule or with an unrelated multispecific molecule (e.g., an antibody that does not specifically bind to TIGIT (e.g., human TIGIT or cynomolgus TIGIT)).

In specific embodiments, the instant disclosure provides a multispecific molecule that specifically binds to TIGIT (e.g., human TIGIT or cynomolgus TIGIT) and activates a T cell (e.g., a T cell expressing human TIGIT). In certain embodiments, the T cell is a memory T cell. In certain embodiments, the T cell is a primary CD3-expressing T cell. In certain embodiments, the T cell is a TIGIT-expressing Jurkat cell. In certain embodiments, the multispecific molecule disclosed herein increases the activity of nuclear factor of activated T cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to NFAT activity without any multispecific molecule or with an unrelated multispecific molecule (e.g., a multispecific molecule that does not specifically bind to TIGIT (e.g., human TIGIT or cynomolgus TIGIT)). In certain embodiments, the multispecific molecule disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to NFAT activity without any multispecific molecule or with an unrelated multispecific molecule (e.g., a multispecific molecule that does not specifically bind to TIGIT (e.g., human TIGIT or cynomolgus TIGIT)). In certain embodiments, the multispecific molecule increases NFAT activity in the presence of a ligand of TIGIT (e.g., CD155) or a fragment and/or fusion protein thereof, and/or a cell expressing a ligand of TIGIT (e.g., a monocyte or a dendritic cell).

In specific embodiments, the instant disclosure provides a multispecific molecule that specifically binds to TIGIT (e.g., human TIGIT or cynomolgus TIGIT) and increases cytokine production (e.g., IL-2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production without any multispecific molecule or with an unrelated multispecific molecule (e.g., a multispecific molecule that does not specifically bind to TIGIT (e.g., human TIGIT or cynomolgus TIGIT)). In specific embodiments, the instant disclosure provides a multispecific molecule that specifically binds to TIGIT (e.g., human TIGIT or cynomolgus TIGIT) and increases cytokine production (e.g., IL-2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production without any multispecific molecule or with an unrelated multispecific molecule (e.g., a multispecific molecule that does not specifically bind to TIGIT (e.g., human TIGIT or cynomolgus TIGIT)). In certain embodiments, the multispecific molecule increases cytokine production (e.g., IL-2) in the presence of a ligand of TIGIT (e.g., CD155) or a fragment and/or fusion protein thereof, and/or a cell expressing a ligand of TIGIT (e.g., a monocyte or a dendritic cell). In certain embodiments, the multispecific molecule increases the production of IL-2 relative to IL-2 production without any multispecific molecule or with an unrelated multispecific molecule (e.g., an antibody that does not specifically bind to TIGIT (e.g., human TIGIT or cynomolgus TIGIT)).

In certain embodiments, the instant disclosure provides a multispecific molecule that specifically binds to TIGIT (e.g., human TIGIT or cynomolgus TIGIT) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to IFNγ and/or IL-2 production without any multispecific molecule or with an unrelated multispecific molecule (e.g., a multispecific molecule that does not specifically bind to TIGIT (e.g., human TIGIT or cynomolgus TIGIT)).

In certain embodiments, human peripheral blood mononuclear cells (PBMCs) stimulated with *Staphylococcus* Enterotoxin A (SEA) in the presence of a multispecific molecule described herein, which specifically binds to TIGIT (e.g., human TIGIT or cynomolgus TIGIT), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any multispecific molecule or with an unrelated multispecific molecule (e.g., multispecific molecule that does not specifically bind to TIGIT (e.g., human TIGIT or cynomolgus TIGIT)), as assessed by methods described herein or known to one of skill in the art.

In certain embodiments, the instant disclosure provides a multispecific molecule that specifically binds to TIGIT (e.g., human TIGIT or cynomolgus TIGIT) and increases or promotes memory recall of a memory T cell. In certain embodiments, the memory T cell is a CD8 effector memory T cell. In certain embodiments, the memory T cell is a CD4 effector memory T cell. In certain embodiments, the multispecific molecule increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the number of proliferating memory T cells when the memory T cells are in contact with their cognate antigen(s) in the absence of any multispecific molecule or in the presence of an unrelated multispecific molecule (e.g., a multispecific molecule that does not specifically bind to TIGIT (e.g., human TIGIT or cynomolgus TIGIT)). In certain embodiments, the multispecific molecule increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the production of the cytokine from a memory T cell when the memory T cell is in contact with its cognate antigen in the absence of any multispecific molecule or in the presence of an unrelated multispecific molecule (e.g., a multispecific molecule that does not specifically bind to TIGIT (e.g., human TIGIT or cynomolgus TIGIT)).

In certain embodiments, the instant disclosure provides a multispecific molecule that specifically binds to TIGIT (e.g., human TIGIT or cynomolgus TIGIT) and activates an NK cell. In certain embodiments, the NK cells are isolated. In certain embodiments, the NK cells are in a mixed culture of PBMCs. In certain embodiments, the multispecific molecule disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to the expression level of CD107a in NK cells without any multispecific molecule or with an unrelated multispecific molecule (e.g., an antibody that does not specifically bind to TIGIT (e.g., human TIGIT or cynomolgus TIGIT)). In certain embodiments, the multispecific molecule disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to the expression level of CD107a in NK cells without any multispecific molecule or with an unrelated multispecific molecule (e.g., a multispecific molecule that does not specifically bind to TIGIT (e.g., human TIGIT or cynomolgus TIGIT)). In certain embodiments, the multispecific molecule disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production (e.g., IFNγ and/or TNFα) from NK cells without any multispecific molecule or with an unrelated multispecific molecule (e.g., a multispecific molecule that does not specifically bind to TIGIT (e.g., human TIGIT or cynomolgus TIGIT)). In certain embodiments, the multispecific molecule disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production (e.g., IFNγ and/or TNFα) from NK cells without any multispecific molecule or with an unrelated multispecific molecule (e.g., a multispecific molecule that does not specifically bind to TIGIT (e.g., human TIGIT or cynomolgus TIGIT)).

In certain embodiments, the instant disclosure provides a multispecific molecule that specifically binds to CD96 (e.g., human CD96 or cynomolgus CD96) and TIGIT (e.g., human TIGIT or cynomolgus TIGIT) and functions as an antagonist (e.g., decreases or inhibits CD96 and TIGIT activity).

In certain embodiments, the instant disclosure provides a multispecific molecule that specifically binds to CD96 (e.g., human CD96 or cynomolgus CD96) and TIGIT (e.g., human TIGIT or cynomolgus TIGIT) and decreases or inhibits CD96 (e.g., human CD96 or cynomolgus CD96) and TIGIT (e.g., human TIGIT or cynomolgus TIGIT) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to CD96 (e.g., human CD96 or cynomolgus CD96) and TIGIT (e.g., human TIGIT or cynomolgus TIGIT) activity without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the instant disclosure provides a multispecific molecule that specifically binds to CD96 (e.g., human CD96 or cynomolgus CD96) and TIGIT (e.g., human TIGIT or cynomolgus TIGIT) and decreases or inhibits CD96 (e.g., human CD96 or cynomolgus CD96) and TIGIT (e.g., human TIGIT or cynomolgus TIGIT) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to CD96 (e.g., human CD96 or cynomolgus CD96) and TIGIT (e.g., human TIGIT or cynomolgus TIGIT) activity without any multispecific molecule or with an unrelated multispecific molecule (e.g., a multispecific molecule that does not specifically bind to CD96 (e.g., human CD96) or TIGIT (e.g., human TIGIT)). Non-limiting examples of CD96 (e.g., human CD96 or cynomolgus CD96) and TIGIT (e.g., human TIGIT or cynomolgus TIGIT) activity can include CD96 (e.g., human CD96 or cynomolgus CD96) and TIGIT (e.g., human TIGIT or cynomolgus TIGIT) signaling; CD96 (e.g., human CD96 or cynomolgus CD96) and TIGIT (e.g., human TIGIT or cynomolgus TIGIT) binding to its ligand (e.g., CD155) or a fragment and/or fusion protein thereof; activation of a T cell (e.g., a T cell expressing human CD96 and/or TIGIT); activation of a natural killer (NK) cell; decrease or inhibition of a Treg; increase of cytokine (e.g., IL-2) production; increase of the activity of CD155 (e.g., human CD155). In specific embodiments, an increase in a CD96 (e.g., human CD96 or cynomolgus CD96) and TIGIT (e.g., human TIGIT or cynomolgus TIGIT) activity is assessed as described in the Examples.

In specific embodiments, the instant disclosure provides a multispecific molecule that specifically binds to CD96 (e.g., human CD96 or cynomolgus CD96) and TIGIT (e.g., human TIGIT or cynomolgus TIGIT) and decreases or inhibits CD96 (e.g., human CD96 or cynomolgus CD96) or TIGIT (e.g., human TIGIT or cynomolgus TIGIT) binding to its ligand (e.g., CD155) or a fragment and/or fusion protein thereof, by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to CD96 (e.g., human CD96 or cynomolgus CD96) and TIGIT (e.g., human TIGIT or cynomolgus TIGIT) binding to this ligand without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In specific embodiments, the instant disclosure provides a multispecific molecule that specifically binds to CD96 (e.g., human CD96 or cynomolgus CD96) and TIGIT (e.g., human TIGIT or cynomolgus TIGIT) and increases CD96 (e.g., human CD96 or cynomolgus CD96) and TIGIT (e.g., human TIGIT or cynomolgus TIGIT) binding to its ligand (e.g., CD155 (e.g., human or cynomolgus CD155) or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to CD96 (e.g., human CD96) and TIGIT (e.g., human TIGIT) binding to this ligand without any multispecific molecule or with an unrelated multispecific molecule (e.g., an antibody that does not specifically bind to CD96 (e.g., human CD96 or cynomolgus CD96) or TIGIT (e.g., human TIGIT or cynomolgus TIGIT)).

In specific embodiments, the instant disclosure provides a multispecific molecule that specifically binds to CD96 (e.g., human CD96 or cynomolgus CD96) and TIGIT (e.g., human TIGIT or cynomolgus TIGIT) and activates a T cell (e.g., a T cell expressing human CD96 and/or human TIGIT). In certain embodiments, the T cell is a memory T cell. In certain embodiments, the T cell is a primary CD3-expressing T cell. In certain embodiments, the T cell is a CD96-expressing and/or TIGIT-expressing Jurkat cell. In certain embodiments, the multispecific molecule disclosed herein increases the activity of nuclear factor of activated T cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to NFAT activity without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the multispecific molecule disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to NFAT activity without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the multispecific molecule increases NFAT activity in the presence of a ligand of CD96 and/or TIGIT (e.g., CD155) or a fragment and/or fusion protein thereof, and/or a cell expressing a ligand of CD96 and/or TIGIT (e.g., a monocyte or a dendritic cell).

In specific embodiments, the instant disclosure provides a multispecific molecule that specifically binds to CD96 (e.g., human CD96 or cynomolgus CD96) and TIGIT (e.g., human TIGIT or cynomolgus TIGIT) and increases cytokine production (e.g., IL-2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In specific embodiments, the instant disclosure provides a multispecific molecule that specifically binds to CD96 (e.g., human CD96 or cynomolgus CD96) and TIGIT (e.g., human TIGIT or cynomolgus TIGIT) and increases cytokine production (e.g., IL-2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the multispecific molecule increases cytokine production (e.g., IL-2) in the presence of a ligand of CD96 and/or TIGIT (e.g., CD155) or a fragment and/or fusion protein thereof, and/or a cell expressing a ligand of CD96 and/or TIGIT (e.g., a monocyte or a dendritic cell). In certain embodiments, the multispecific molecule increases the production of IL-2 relative to IL-2 production without any multispecific molecule or with an unrelated multispecific molecule (e.g., an antibody that does not specifically bind to CD96 (e.g., human CD96 or cynomolgus CD96) or TIGIT (e.g., human TIGIT or cynomolgus TIGIT)).

In certain embodiments, the instant disclosure provides a multispecific molecule that specifically binds to CD96 (e.g., human CD96 or cynomolgus CD96) and TIGIT (e.g., human TIGIT or cynomolgus TIGIT) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to IFNγ and/or IL-2 production without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)).

In certain embodiments, human peripheral blood mononuclear cells (PBMCs) stimulated with *Staphylococcus* Enterotoxin A (SEA) in the presence of a multispecific molecule described herein, which specifically binds to CD96 (e.g., human CD96 or cynomolgus CD96) and TIGIT (e.g., human TIGIT or cynomolgus TIGIT), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any multispecific molecule or with an unrelated multispecific molecule (e.g., multispecific molecule that does not specifically bind to CD96 (e.g., human CD96 or cynomolgus CD96) or TIGIT (e.g., human TIGIT or cynomolgus TIGIT)), as assessed by methods described herein or known to one of skill in the art.

In certain embodiments, the instant disclosure provides a multispecific molecule that specifically binds to CD96 (e.g., human CD96 or cynomolgus CD96) and TIGIT (e.g., human TIGIT or cynomolgus TIGIT) and increases or promotes memory recall of a memory T cell. In certain embodiments, the memory T cell is a CD8 effector memory T cell. In certain embodiments, the memory T cell is a CD4 effector memory T cell. In certain embodiments, the multispecific molecule increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the number of proliferating memory T cells when the memory T cells are in contact with their cognate antigen(s) in the absence of any multispecific molecule or in the presence of an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the multispecific molecule increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the production of the cytokine from a memory T cell when the memory T cell is in contact with its cognate antigen in the absence of any multispecific molecule or in the presence of an unrelated multispecific molecule (e.g., a multispecific molecule that does not specifically bind to CD96 (e.g., human CD96 or cynomolgus CD96) or TIGIT (e.g., human TIGIT or cynomolgus TIGIT)).

In certain embodiments, the instant disclosure provides a multispecific molecule that specifically binds to CD96 (e.g., human CD96 or cynomolgus CD96) and TIGIT (e.g., human TIGIT or cynomolgus TIGIT) and activates an NK cell. In certain embodiments, the NK cells are isolated. In certain embodiments, the NK cells are in a mixed culture of PBMCs. In certain embodiments, the multispecific molecule disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to the expression level of CD107a in NK cells without any multispecific molecule or with an unrelated multispecific molecule (e.g., an antibody that does not specifically bind to CD96 (e.g., human CD96 or cynomolgus CD96) or TIGIT (e.g., human TIGIT or cynomolgus TIGIT)). In certain embodiments, the multispecific molecule disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to the expression level of CD107a in NK cells without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the multispecific molecule disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production (e.g., IFNγ and/or TNFα) from NK cells without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)). In certain embodiments, the multispecific molecule disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production (e.g., IFNγ and/or TNFα) from NK cells without any multispecific molecule or with an unrelated multispecific molecule (e.g., a multispecific molecule that does not specifically bind to CD96 (e.g., human CD96 or cynomolgus CD96) or TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and functions as an antagonist (e.g., decreases or inhibits TIGIT activity).

In certain embodiments, the instant disclosure provides an isolated antibody that specifically binds to TIGIT (e.g., human TIGIT or cynomolgus TIGIT) and decreases or inhibits TIGIT (e.g., human TIGIT or cynomolgus TIGIT) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to TIGIT (e.g., human TIGIT or cynomolgus TIGIT) activity without any antibody or with an unrelated antibody (e.g., an antibody that does not specifically bind to TIGIT (e.g., human TIGIT or cynomolgus TIGIT)). In certain embodiments, the instant disclosure provides an isolated antibody that specifically binds to TIGIT (e.g., human TIGIT or cynomolgus TIGIT) and decreases or inhibits TIGIT (e.g., human TIGIT or cynomolgus TIGIT) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to TIGIT (e.g., human TIGIT or cynomolgus TIGIT) activity without any antibody or with an unrelated antibody (e.g., an antibody that does not specifically bind to TIGIT (e.g., human TIGIT or cynomolgus TIGIT)). Non-limiting examples of TIGIT (e.g., human TIGIT or cynomolgus TIGIT) activity can include TIGIT (e.g., human TIGIT or cynomolgus TIGIT) signaling; TIGIT (e.g., human TIGIT or cynomolgus TIGIT) binding to its ligand (e.g., CD155) or a fragment and/or fusion protein thereof; activation of a T cell (e.g., a T cell expressing human TIGIT); activation of a natural killer (NK) cell; decrease or inhibition of a Treg; increase of cytokine (e.g., IL-2) production; increase of the activity of CD155 (e.g., human CD155). In specific embodiments, an increase in a TIGIT (e.g., human TIGIT or cynomolgus TIGIT) activity is assessed as described in the Examples.

In specific embodiments, the instant disclosure provides an isolated antibody that specifically binds TIGIT (e.g., human TIGIT or cynomolgus TIGIT) and decreases or inhibits TIGIT (e.g., human TIGIT or cynomolgus TIGIT) binding to its ligand (e.g., CD155) or a fragment and/or fusion protein thereof, by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to TIGIT (e.g., human TIGIT or cynomolgus TIGIT) binding to this ligand without any antibody or with an unrelated antibody (e.g., an antibody that does not specifically bind to TIGIT (e.g., human TIGIT or cynomolgus TIGIT)). In specific embodiments, the instant disclosure provides an isolated antibody that specifically binds to TIGIT (e.g., human TIGIT or cynomolgus TIGIT) and increases TIGIT (e.g., human TIGIT or cynomolgus TIGIT) binding to its ligand (e.g., CD155 (e.g., human or cynomolgus CD155) or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to TIGIT (e.g., human TIGIT) binding to this ligand without any antibody or with an unrelated antibody (e.g., an antibody that does not specifically bind to TIGIT (e.g., human TIGIT or cynomolgus TIGIT)).

In specific embodiments, the instant disclosure provides an isolated antibody that specifically binds to TIGIT (e.g., human TIGIT or cynomolgus TIGIT) and activates a T cell (e.g., a T cell expressing human TIGIT). In certain embodiments, the T cell is a memory T cell. In certain embodiments, the T cell is a primary CD3-expressing T cell. In certain embodiments, the T cell is a TIGIT-expressing Jurkat cell. In certain embodiments, the antibody disclosed herein increases the activity of nuclear factor of activated T cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to NFAT activity without any antibody or with an unrelated antibody (e.g., an antibody that does not specifically bind to TIGIT (e.g., human TIGIT or cynomolgus TIGIT)). In certain embodiments, the antibody disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to NFAT activity without any antibody or with an unrelated antibody (e.g., an antibody that does not specifically bind to TIGIT (e.g., human TIGIT or cynomolgus TIGIT)). In certain embodiments, the antibody increases NFAT activity in the presence of a ligand of TIGIT (e.g., CD155) or a fragment and/or fusion protein thereof, and/or a cell expressing a ligand of TIGIT (e.g., a monocyte or a dendritic cell).

In specific embodiments, the instant disclosure provides an isolated antibody that specifically binds to TIGIT (e.g., human TIGIT or cynomolgus TIGIT) and increases cytokine production (e.g., IL-2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production without any antibody or with an unrelated antibody (e.g., an antibody that does not specifically bind to TIGIT (e.g., human TIGIT or cynomolgus TIGIT)). In specific embodiments, the instant disclosure provides an isolated antibody that specifically binds to TIGIT (e.g., human TIGIT or cynomolgus TIGIT) and increases cytokine production (e.g., IL-2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production without any antibody or with an unrelated antibody (e.g., an antibody that does not specifically bind to TIGIT (e.g., human TIGIT or cynomolgus TIGIT)). In certain embodiments, the antibody increases cytokine production (e.g., IL-2) in the presence of a ligand of TIGIT (e.g., CD155) or a fragment and/or fusion protein thereof, and/or a cell expressing a ligand of TIGIT (e.g., a monocyte or a dendritic cell). In certain embodiments, the antibody increases the production of IL-2 relative to IL-2 production without any antibody or with an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to IFNγ and/or IL-2 production without any antibody or with an unrelated antibody (e.g., an antibody that does not specifically bind to TIGIT (e.g., human TIGIT or cynomolgus TIGIT)).

In certain embodiments, human peripheral blood mononuclear cells (PBMCs) stimulated with *Staphylococcus* Enterotoxin A (SEA) in the presence of an antibody described herein, which specifically binds to TIGIT (e.g., human TIGIT or cynomolgus TIGIT), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any antibody or with an unrelated antibody (e.g., an antibody that does not specifically bind to TIGIT (e.g., human TIGIT or cynomolgus TIGIT)), as assessed by methods described herein or known to one of skill in the art.

In certain embodiments, the instant disclosure provides an isolated antibody that specifically binds to TIGIT (e.g., human TIGIT or cynomolgus TIGIT) and increases or promotes memory recall of a memory T cell. In certain embodiments, the memory T cell is a CD8 effector memory T cell. In certain embodiments, the memory T cell is a CD4 effector memory T cell. In certain embodiments, the antibody increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the number of proliferating memory T cells when the memory T cells are in contact with their cognate antigen(s) in the absence of any antibody or in the presence of an unrelated antibody (e.g., an antibody that does not specifically bind to TIGIT (e.g., human TIGIT or cynomolgus TIGIT)). In certain embodiments, the antibody increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the production of the cytokine from a memory T cell when the memory T cell is in contact with its cognate antigen in the absence of any antibody or in the presence of an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and activates an NK cell. In certain embodiments, the NK cells are isolated. In certain embodiments, the NK cells are in a mixed culture of PBMCs. In certain embodiments, the antibody disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to the expression level of CD107a in NK cells without any antibody or with an unrelated antibody (e.g., an antibody that does not specifically bind to TIGIT (e.g., human TIGIT or cynomolgus TIGIT)). In certain embodiments, the antibody disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to the expression level of CD107a in NK cells without any antibody or with an unrelated antibody (e.g., an antibody that does not specifically bind to TIGIT (e.g., human TIGIT or cynomolgus TIGIT)). In certain embodiments, the antibody disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production (e.g., IFNγ and/or TNFα) from NK cells without any antibody or with an unrelated antibody (e.g., an antibody that does not specifically bind to TIGIT (e.g., human TIGIT or cynomolgus TIGIT)). In certain embodiments, the antibody disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production (e.g., IFNγ and/or TNFα) from NK cells without any antibody or with an unrelated antibody (e.g., an antibody that does not specifically bind to TIGIT (e.g., human TIGIT or cynomolgus TIGIT)).

7.3 Pharmaceutical Compositions

Provided herein are compositions comprising an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein having the desired degree of purity in a physiologically acceptable carrier, excipient, or stabilizer (see, e.g., Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein, and optionally one or more additional prophylactic or therapeutic agents, in a pharmaceutically acceptable carrier. In a specific embodiment, pharmaceutical compositions comprise an effective amount of an anti-CD96 (e.g., human CD96 or cynomolgus CD96) and/or anti-TIGIT (e.g., human TIGIT or cynomolgus TIGIT) multispecific molecule or an isolated anti-TIGIT antibody herein, and optionally one or more additional prophylactic or therapeutic agents, in a pharmaceutically acceptable carrier. In certain embodiments, the multispecific molecule or antibody is the only active ingredient included in the pharmaceutical composition. Pharmaceutical compositions described herein can be useful in increasing or promoting CD96 (e.g., human CD96 or cynomolgus CD96) and/or TIGIT (e.g., human TIGIT or cynomolgus TIGIT) activity and treating a condition, such as cancer or an infectious disease. In certain embodiments, the present invention relates to a pharmaceutical composition of the present invention comprising an anti-CD96 (e.g., human CD96 or cynomolgus CD96) and/or anti-TIGIT (e.g., human TIGIT or cynomolgus TIGIT) multispecific molecule or an isolated anti-TIGIT antibody of the present invention for use as a medicament. In another embodiment, the present invention relates to a pharmaceutical composition of the present invention for use in a method for the treatment of cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringer's Injection, Isotonic Dextrose Injection, Sterile Water Injection, Dextrose and Lactated Ringer's Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol, and propylene glycol for water miscible vehicles; and sodium hydroxide, hydrochloric acid, citric acid, or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular, or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol, or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of a multispecific molecule or antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

An anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in certain embodiments, have diameters of less than 50 microns, In certain embodiments less than 10 microns.

An anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising a multispecific molecule or antibody described herein is a lyophilized powder, which can be reconstituted for administration as solutions, emulsions, and other mixtures. It may also be reconstituted and formulated as solids or gels. The lyophilized powder is prepared by dissolving a multispecific molecule or antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose, or other suitable agent. The solvent may also contain a buffer, such as citrate, sodium or potassium phosphate or other such buffer known to those of skill in the art at, In certain embodiments, about neutral pH. Subsequent sterile filtration of the solution followed by lyophilization under standard conditions known to those of skill in the art provides the desired formulation. In certain embodiments, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-CD96 (e.g., human CD96 or cynomolgus CD96) and/or anti-TIGIT (e.g., human TIGIT or cynomolgus TIGIT) multispecific molecules and isolated anti-TIGIT antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874, all of which are herein incorporated by reference in their entireties. In a specific embodiment, a multispecific molecule or an antibody described herein is targeted to a tumor.

The compositions to be used for in vivo administration can be sterile. This is readily accomplished by filtration through, e.g., sterile filtration membranes.

7.4 Methods of Use and Uses

In another aspect, the instant disclosure provides a method of treating a subject using the anti-CD96 (e.g., human CD96 or cynomolgus CD96) and/or anti-TIGIT (e.g., human TIGIT or cynomolgus TIGIT) multispecific molecule and isolated anti-TIGIT antibodies disclosed herein. Any disease or disorder in a subject that would benefit from decrease of CD96 (e.g., human CD96 or cynomolgus CD96) and/or TIGIT (e.g., human TIGIT or cynomolgus TIGIT) function can be treated using the anti-CD96 (e.g., human CD96 or cynomolgus CD96) and/or anti-TIGIT (e.g., human TIGIT or cynomolgus TIGIT) multispecific molecules and isolated anti-TIGIT antibodies disclosed herein. In certain embodiments, the disease or disorder is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the disease or disorder is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

The anti-CD96 (e.g., human CD96 or cynomolgus CD96) and/or anti-TIGIT (e.g., human TIGIT or cynomolgus TIGIT) multispecific molecule and isolated anti-TIGIT antibodies disclosed herein are particularly useful for inhibiting immune system tolerance to tumors, and accordingly can be used as an immunotherapy for subjects with cancer. For example, in certain embodiments, the instant disclosure provides a method of increasing T cell (e.g., $CD8^+$ cytotoxic T cells, $CD4^+$ helper T cells, NKT cells, effector T cells, or memory T cells) activation in response to an antigen in a subject, the method comprising administering to the subject an effective amount of an anti-CD96 (e.g., human CD96 or cynomolgus CD96) and/or anti-TIGIT (e.g., human TIGIT or cynomolgus TIGIT) multispecific molecule or an isolated anti-TIGIT antibody, or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the anti-CD96 (e.g., human CD96 or cynomolgus CD96) and/or anti-TIGIT (e.g., human TIGIT or cynomolgus TIGIT) multispecific molecules or an isolated anti-TIGIT antibodies or pharmaceutical compositions disclosed herein include, without limitation, a solid tumor, a hematological cancer (e.g., leukemia, lymphoma, myeloma, e.g., multiple myeloma), and a metastatic lesion. In certain embodiments, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage, or metastatic cancer. In certain embodiments, the cancer is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the cancer is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

In certain embodiments, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC)), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In a specific embodiment, the cancer is a cervical cancer.

In certain embodiments, the cancer is a hematological cancer, for example, a leukemia, a lymphoma, or a myeloma. In certain embodiments, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In certain embodiments, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In certain embodiments the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In certain embodiments, the cancer is a lung cancer, e.g., a lung adenocarcinoma, non-small cell lung cancer, or small cell lung cancer.

In certain embodiments, the cancer is a melanoma, e.g., an advanced melanoma. In certain embodiments, the cancer is an advanced or unresectable melanoma that does not respond to other therapies. In other embodiments, the cancer is a melanoma with a BRAF mutation (e.g., a BRAF V600 mutation). In yet other embodiments, the anti-CD96 (e.g., human CD96 or cynomolgus CD96) and/or anti-TIGIT (e.g., human TIGIT or cynomolgus TIGIT) multispecific molecules, isolated anti-TIGIT antibodies, or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an anti-CD96 (e.g., human CD96 or cynomolgus CD96) and/or anti-TIGIT (e.g., human TIGIT or cynomolgus TIGIT) multispecific molecule or an isolated anti-TIGIT antibody, or pharmaceutical composition thereof, as disclosed herein. In certain embodiments, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a composition thereof is the only active agent administered to a subject. In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a composition thereof is used in combination with anti-infective interventions (e.g., antivirals, antibacterials, antifungals, or anti-helminthics) for the treatment of infectious diseases. Therefore, in a one embodiment, the present invention relates to a multispecific molecule or an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by anti-CD96 (e.g., human CD96 or cynomolgus CD96) and/or anti-TIGIT (e.g., human TIGIT or cynomolgus TIGIT) multispecific molecules, isolated anti-TIGIT antibodies, or pharmaceutical compositions disclosed herein are caused by infectious agents including but not limited to bacteria, parasites, fungi, protozoa, and viruses. In a specific embodiment, the infectious disease treated and/or prevented by anti-CD96 (e.g., human CD96 or cynomolgus CD96) and/or anti-TIGIT (e.g., human TIGIT or cynomolgus TIGIT) multispecific molecules, isolated anti-TIGIT antibodies, or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, small pox, Epstein-Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli*, *Klebsiella pneumoniae*, *Staphylococcus aureus*, *Enterococcus faecalis*, *Proteus vulgaris*, *Staphylococcus viridans*, and *Pseudomonas aeruginosa*. Bacterial diseases caused by bacteria (e.g., *Escherichia coli*, *Klebsiella pneumoniae*, *Staphylococcus aureus*, *Enterococcus faecalis*, *Proteus vulgaris*, *Staphylococcus viridans*, and *Pseudomonas aeruginosa*) that can be prevented and/or treated in accordance with the methods described herein include, but are not limited to, *Mycobacteria rickettsia*, *Mycoplasma*, *Neisseria*, *S. pneumonia*, *Borrelia burgdorferi* (Lyme disease), *Bacillus antracis* (anthrax), tetanus, *Streptococcus*, *Staphylococcus*, *mycobacterium*, pertussis, cholera, plague, diphtheria, *Chlamydia*, *S. aureus*, and *Legionella*.

Protozoal diseases or protozoal infections caused by protozoa that can be prevented and/or treated in accordance with the methods described herein include, but are not limited to, leishmaniasis, coccidiosis, trypanosoma schistosoma, or malaria. Parasitic diseases or parasitic infections caused by parasites that can be prevented and/or treated in accordance with the methods described herein include, but are not limited to, *Chlamydia* and *Rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the chemotherapeutic agent is a DNA damage-inducing agent (e.g., gemcitabine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an agonist anti-CD137 antibody, an agonist anti-GITR antibody, and an agonist anti-OX40 antibody. In certain embodiments, the checkpoint targeting agent is selected from the group consisting of an antagonist anti-CTLA-4 antibody, an antagonist anti-PD-L1 antibody, an antagonist anti-PD-L2 antibody, and an antagonist anti-PD-1 antibody, wherein the anti-CD96 (e.g., human CD96 or cynomolgus CD96) antibodies or pharmaceutical compositions disclosed herein synergize with the checkpoint targeting agent.

In certain embodiments, the present invention relates to a multispecific molecule, antibody, and/or pharmaceutical composition of the present invention for use in a method of the present invention, wherein the method further comprises administering an additional therapeutic agent to the subject. In certain embodiments, the present invention relates to (a) a multispecific molecule, an antibody, and/or pharmaceutical composition of the present invention, and (b) an additional therapeutic agent for use as a medicament. In certain embodiments, the present invention relates to (a) a multispecific molecule, an antibody, and/or pharmaceutical composition of the present invention, and (b) an additional therapeutic agent for use in a method for the treatment of cancer. In a further embodiment, the present invention relates to a pharmaceutical composition, kit or kit-of-parts comprising (a) a multispecific molecule, or an antibody, and/or pharmaceutical composition of the present invention, and (b) an additional therapeutic agent. In certain embodiments, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by MedImmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene, and MedImmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. U.S. 2010/0203056 A1; U.S. Publication No. U.S. 2003/0232323 A1; U.S. Publication No. U.S. 2013/0323249 A1; U.S. Publication No. U.S. 2014/0341917 A1; U.S. Publication No. U.S. 2014/0044738 A1; U.S. Publication No. U.S. 2015/0203580 A1; U.S. Publication No. U.S. 2015/0225483 A1; U.S. Publication No. U.S. 2015/0346208 A1; U.S. Publication No. U.S. 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in certain embodiments, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In certain embodiments, the compound is epacadostat. In another embodiment, the compound is F001287. In another embodiment, the compound is indoximod. In another embodiment, the compound is NLG919. In a specific embodiment, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with an IDO inhibitor for treating cancer. The IDO inhibitor as described herein for use in treating cancer is present in a solid dosage form of a pharmaceutical composition such as a tablet, a pill, or a capsule, wherein the pharmaceutical composition includes an IDO inhibitor and a pharmaceutically acceptable excipient. As such, the multispecific molecule or antibody as described herein and the IDO inhibitor as described herein can be administered separately, sequentially, or concurrently as separate dosage forms. In certain embodiments, the multispecific molecule or antibody is administered parenterally, and the IDO inhibitor is administered orally. In certain embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In certain embodiments, the inhibitor is epacadostat. In another embodiment, the inhibitor is F001287. In another embodiment, the inhibitor is indoximod. In another embodiment, the inhibitor is NLG919.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a vaccine. The vaccine can be, e.g., a peptide vaccine, a DNA vaccine, or an RNA vaccine. In certain embodiments, the vaccine is a heat shock protein-based tumor vaccine or a heat shock protein-based pathogen vaccine. In a specific embodiment, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a heat shock protein-based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress, or glucose deprivation. Five families have been classified according to molecular weight: HSP-110, -90, -70, -60, and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in certain embodiments, the present invention relates to (a) a multispecific molecule, an antibody, and/or pharmaceutical composition of the present invention and (b) a vaccine for use as a medicament, for example for use in a method for the treatment of cancer. In certain embodiments, the present invention relates to a pharmaceutical composition, kit or kit-of-parts comprising (a) a multispecific molecule, an antibody, and/or pharmaceutical composition of the present invention and (b) a vaccine. In certain embodiments, the vaccine is a heat shock protein-based tumor vaccine. In certain embodiments, the vaccine is a heat shock protein-based pathogen vaccine. In certain embodiments, the vaccine is as described in WO 2016/183486, incorporated herein by reference in its entirety.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding region thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in certain embodiments, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In certain embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436,404, 6,447,780, 6,447,781, and 6,610,659.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, Toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In certain embodiments, the adjuvant used herein is QS-21 STIMULON.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in certain embodiments, the present invention relates to a multispecific molecule, an antibody, and/or pharmaceutical composition of the present invention in combination with an additional therapeutic agent comprising a TCR for use as a medicament and/or for use in a method for the treatment of cancer.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a cell expressing a chimeric antigen receptor (CAR). In certain embodiments, the cell is a T cell.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), optionally wherein the BiTE and/or DART comprises the VH and VL sequences of cetuximab. In certain embodiments, the tumor-associated antigen is Her2 (e.g., human Her2), optionally wherein the BiTE and/or DART comprises the VH and VL sequences of trastuzumab. In certain embodiments, the tumor-associated antigen is CD20 (e.g., human CD20).

The anti-CD96 (e.g., human CD96 or cynomolgus CD96) and/or anti-TIGIT (e.g., human TIGIT or cynomolgus TIGIT) multispecific molecule or isolated anti-TIGIT antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the multispecific molecule, antibody, or pharmaceutical composition described herein is delivered subcutaneously or intravenously. In certain embodiments, the multispecific molecule, antibody, or pharmaceutical composition described herein is delivered intra-arterially. In certain embodiments, the multispecific molecule, antibody, or pharmaceutical composition described herein is delivered intratumorally. In certain embodiments, the multispecific molecule, antibody, or pharmaceutical composition described herein is delivered into a tumor draining lymph node.

The amount of a multispecific molecule, antibody, or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-CD96 (e.g., human CD96 or cynomolgus CD96) and/or anti-TIGIT (e.g., human TIGIT or cynomolgus TIGIT) multispecific molecule or an isolated anti-TIGIT antibody described herein can also be used to assay CD96 (e.g., human CD96 or cynomolgus CD96) and/or TIGIT (e.g., human TIGIT or cynomolgus TIGIT) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label a multispecific molecule or antibody described herein. Alternatively, a second multispecific molecule or antibody that recognizes an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein can be labeled and used in combination with an anti-CD96 (e.g., human CD96 or cynomolgus CD96) and/or anti-TIGIT (e.g., human TIGIT or cynomolgus TIGIT) multispecific molecule or an isolated anti-TIGIT antibody to detect CD96 (e.g., human CD96 or cynomolgus CD96) and/or TIGIT (e.g., human TIGIT or cynomolgus TIGIT) protein levels. Therefore, in certain embodiments, the present invention relates to the use of an anti-CD96 (e.g., human CD96 or cynomolgus CD96) and/or anti-TIGIT (e.g., human TIGIT or cynomolgus TIGIT) multispecific molecule or an isolated anti-TIGIT antibody of the present invention for in vitro detection of CD96 (e.g., human CD96 or cynomolgus CD96) and/or TIGIT (e.g., human TIGIT or cynomolgus TIGIT) protein in a biological sample. In a further embodiment, the present invention relates to the use of an anti-CD96 (e.g., human CD96 or cynomolgus CD96) and/or anti-TIGIT (e.g., human TIGIT or cynomolgus TIGIT) multispecific molecule or an isolated anti-TIGIT antibody of the invention, for assaying and/or detecting CD96 (e.g., human CD96 or cynomolgus CD96) and/or TIGIT (e.g., human TIGIT or cynomolgus TIGIT) protein levels in a biological sample in vitro, optionally wherein the anti-CD96 (e.g., human CD96 or cynomolgus CD96) and/or anti-TIGIT (e.g., human TIGIT or cynomolgus TIGIT) multispecific molecule or isolated anti-TIGIT antibody is conjugated to a radionuclide or detectable label, and/or carries a label described herein, and/or wherein an immunohistological method is used.

Assaying for the expression level of CD96 (e.g., human CD96 or cynomolgus CD96) and/or TIGIT (e.g., human TIGIT or cynomolgus TIGIT) protein is intended to include qualitatively or quantitatively measuring or estimating the level of CD96 (e.g., human CD96 or cynomolgus CD96) and/or TIGIT (e.g., human TIGIT or cynomolgus TIGIT) protein in a first biological sample either directly (e.g., by determining or estimating absolute protein level) or relatively (e.g., by comparing to the disease associated protein level in a second biological sample). CD96 (e.g., human CD96 or cynomolgus CD96) and/or TIGIT (e.g., human TIGIT or cynomolgus TIGIT) polypeptide expression level in the first biological sample can be measured or estimated and compared to a standard CD96 (e.g., human CD96 or cynomolgus CD96) and/or TIGIT (e.g., human TIGIT or cynomolgus TIGIT) protein level, the standard being taken, for example, from a second biological sample obtained from an individual not having the disorder or being determined by averaging levels from a population of individuals not having the disorder. As will be appreciated in the art, once the "standard" CD96 (e.g., human CD96 or cynomolgus CD96) and/or TIGIT (e.g., human TIGIT or cynomolgus TIGIT) polypeptide level is known, it can be used repeatedly as a standard for comparison. Therefore, in a further embodiment, the present invention relates to an in vitro method for assaying and/or detecting CD96 and/or TIGIT protein levels, for example human CD96 and/or TIGIT protein levels, in a biological sample, comprising qualitatively or quantitatively measuring or estimating the level of CD96 and/or TIGIT protein, for example of human CD96 and/or TIGIT protein, in a biological sample, by an immunohistological method.

As used herein, the term "biological sample" refers to any biological sample obtained from a subject, cell line, tissue, or other source of cells potentially expressing CD96 (e.g., human CD96 or cynomolgus CD96) and/or TIGIT (e.g., human TIGIT or cynomolgus TIGIT). Methods for obtaining tissue biopsies and body fluids from animals (e.g., humans or cynomolgus monkeys) are well known in the art. Biological samples include peripheral blood mononuclear cells (PBMCs).

An anti-CD96 (e.g., human CD96 or cynomolgus CD96) and/or anti-TIGIT (e.g., human TIGIT or cynomolgus TIGIT) multispecific molecule or an isolated anti-TIGIT antibody described herein can be used for prognostic, diagnostic, monitoring and screening applications, including in vitro and in vivo applications well known and standard to the skilled artisan and based on the present description. Prognostic, diagnostic, monitoring, and screening assays and kits for in vitro assessment and evaluation of immune system status and/or immune response may be utilized to predict, diagnose, and monitor to evaluate patient samples including those known to have or suspected of having an immune system-dysfunction or with regard to an anticipated or desired immune system response, antigen response, or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in certain embodiments, the present invention relates to an anti-CD96 antibody and/or pharmaceutical composition of the present invention for use as a diagnostic. In certain embodiments, the present invention relates to an anti-CD96 (e.g., human CD96 or cynomolgus CD96) and/or anti-TIGIT (e.g., human TIGIT or cynomolgus TIGIT) multispecific molecule or an isolated anti-TIGIT antibody, and/or pharmaceutical composition of the present invention for use in a method for the prediction, diagnosis, and/or monitoring of a subject having or suspected to have an immune system-dysfunction and/or with regard to an anticipated or desired immune system response, antigen response, or vaccine response. In another embodiment, the present invention relates to the use of an anti-CD96 (e.g., human CD96 or cynomolgus CD96) and/or anti-TIGIT (e.g., human TIGIT or cynomolgus TIGIT) multispecific molecule or an isolated anti-TIGIT antibody of the invention, for predicting, diagnosing, and/or monitoring of a subject having or suspected to have an immune system-dysfunction and/or with regard to an anticipated or desired immune system response, antigen response, or vaccine response, by assaying and/or detecting human CD96 and/or TIGIT protein levels in a biological sample of the subject in vitro.

In certain embodiments, an anti-CD96 (e.g., human CD96 or cynomolgus CD96) and/or anti-TIGIT (e.g., human TIGIT or cynomolgus TIGIT) multispecific molecule or an isolated anti-TIGIT antibody can be used in immunohistochemistry of biopsy samples. In certain embodiments, the method is an in vitro method. In another embodiment, an anti-CD96 (e.g., human CD96 or cynomolgus CD96) and/or anti-TIGIT (e.g., human TIGIT or cynomolgus TIGIT) multispecific molecule or an isolated anti-TIGIT antibody can be used to detect levels of CD96 (e.g., human CD96 or cynomolgus CD96) and/or TIGIT (e.g., human TIGIT or cynomolgus TIGIT), or levels of cells which contain CD96 (e.g., human CD96 or cynomolgus CD96) and/or TIGIT (e.g., human TIGIT or cynomolgus TIGIT) on their membrane surface, the levels of which can then be linked to certain disease symptoms. Anti-CD96 (e.g., human CD96 or cynomolgus CD96) and/or anti-TIGIT (e.g., human TIGIT or cynomolgus TIGIT) multispecific molecules and isolated anti-TIGIT antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-CD96 (e.g., human CD96 or cynomolgus CD96) and/or anti-TIGIT (e.g., human TIGIT or cynomolgus TIGIT) multispecific molecules and isolated anti-TIGIT antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes, and DyLight dyes. An anti-CD96 (e.g., human CD96 or cynomolgus CD96) and/or anti-TIGIT (e.g., human TIGIT or cynomolgus TIGIT) multispecific molecule or an isolated anti-TIGIT antibody may carry or may be conjugated to a radioactive label or radionuclide, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{124}I$, $^{131}I$, $^{198}Au$, $^{211}At$, $^{213}Bi$, $^{225}Ac$, and $^{186}Re$. When radioactive labels are used, currently available counting procedures known in the art may be utilized to identify and quantitate the specific binding of an anti-CD96 (e.g., human CD96 or cynomolgus CD96) and/or anti-TIGIT (e.g., human TIGIT or cynomol-gus TIGIT) multispecific molecule to CD96 (e.g., human CD96 or cynomolgus CD96) or TIGIT (e.g., human TIGIT or cynomolgus TIGIT), or an isolated anti-TIGIT antibody to TIGIT (e.g., human TIGIT or cynomolgus TIGIT). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-CD96 (e.g., human CD96 or cynomolgus CD96) and/or anti-TIGIT (e.g., human TIGIT or cynomolgus TIGIT) multispecific molecule or an isolated anti-TIGIT antibody under conditions that allow for the formation of a complex between the anti-CD96 and/or anti-TIGIT multispecific molecule and CD96 (e.g., human CD96 or cynomolgus CD96) and/or TIGIT (e.g., human TIGIT or cynomolgus TIGIT), or the anti-TIGIT antibody and TIGIT (e.g., human TIGIT or cynomolgus TIGIT). Any complexes formed between the anti-CD96 and/or anti-TIGIT multispecific molecule and CD96 (e.g., human CD96 or cynomolgus CD96) and/or TIGIT (e.g., human TIGIT or cynomolgus TIGIT), or the anti-TIGIT antibody and TIGIT (e.g., human TIGIT or cynomolgus TIGIT), are detected and compared in the sample and the control. In light of the specific binding of the multispecific molecules described herein for CD96 (e.g., human CD96 or cynomolgus CD96) and/or TIGIT (e.g., human TIGIT or cynomolgus TIGIT), and the anti-TIGIT antibodies described herein for TIGIT (e.g., human TIGIT or cynomolgus TIGIT), the multispecific molecules can be used to specifically detect CD96 (e.g., human CD96 or cynomolgus CD96) and/or TIGIT (e.g., human TIGIT or cynomolgus TIGIT) expression on the surface of cells, and the anti-TIGIT antibodies can be used to specifically detect TIGIT (e.g., human TIGIT or cynomolgus TIGIT). The anti-CD96 and/or anti-TIGIT multispecific molecules described herein can also be used to purify CD96 (e.g., human CD96 or cynomolgus CD96) and/or TIGIT (e.g., human TIGIT or cynomolgus TIGIT) via immunoaffinity purification. The anti-TIGIT antibodies described herein can also be used to purify TIGIT (e.g., human TIGIT or cynomolgus TIGIT) via immunoaffinity purification. Also included herein is an assay system which may be prepared in the form of a test kit, kit, or kit-of-parts for the quantitative analysis of the extent of the presence of, for instance, CD96 (e.g., human CD96 or cynomolgus CD96) and/or TIGIT (e.g., human TIGIT or cynomolgus TIGIT), or CD96 (e.g., human CD96 or cynomolgus CD96)/CD96 (e.g., human CD96 or cynomolgus CD96) ligand complexes and/or TIGIT (e.g., human TIGIT or cynomolgus TIGIT)/TIGIT (e.g., human TIGIT or cynomolgus TIGIT) ligand complexes. The system, test kit, kit, or kit-of-parts may comprise a labeled component, e.g., a labeled antibody, and one or more additional immunochemical reagents.

7.5 Polynucleotides, Vectors, and Methods of Producing Multispecific Molecules and Antibodies In another aspect, provided herein are polynucleotides comprising a nucleotide sequence encoding a multispecific molecule or an antibody, or a portion thereof, described herein or a fragment thereof (e.g., a VL and/or VH; and a light chain and/or heavy chain) that specifically binds to a CD96 (e.g., human CD96 or cynomolgus CD96) and/or TIGIT (e.g., human TIGIT or cynomolgus TIGIT) antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular, less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding multispecific molecules and antibodies, which specifically bind to a CD96 (e.g., human CD96 or cynomolgus CD96) and/or TIGIT (e.g., human TIGIT or cynomolgus TIGIT) polypeptide and comprises an amino acid sequence as described herein, as well as multispecific molecules and antibodies which compete with such multispecific molecules and antibodies for binding to a CD96 (e.g., human CD96 or cynomolgus CD96) and/or TIGIT (e.g., human TIGIT or cynomolgus TIGIT) polypeptide (e.g., in a dose-dependent manner), or which binds to the same epitope as that of such multispecific molecules and antibodies.

In certain aspects, provided herein are polynucleotides comprising a nucleotide sequence encoding the light chain or heavy chain of a multispecific molecule or antibody described herein. The polynucleotides can comprise nucleotide sequences encoding a light chain comprising the VL FRs and CDRs of multispecific molecules or antibodies described herein (see, e.g., Table 1 and Table 2) or nucleotide sequences encoding a heavy chain comprising the VH FRs and CDRs of multispecific molecules or antibodies described herein (see, e.g., Table 1 and Table 2). In certain embodiments, a polynucleotide encodes a VH, VL, heavy chain, and/or light chain of a multispecific molecule described herein. In another embodiment, a polynucleotide encodes the first VH and the first VL of a multispecific molecule described herein. In another embodiment, a polynucleotide encodes the second VH and the second VL of a multispecific molecule described herein. In another embodiment, a polynucleotide encodes the first heavy chain and the first light chain of a multispecific molecule described herein. In another embodiment, a polynucleotide encodes the second heavy chain and the second light chain of a multispecific molecule described herein. In another embodiment, a polynucleotide encodes the VH and/or the VL, or the heavy chain and/or the light chain, of an isolated antibody described herein.

Also provided herein are polynucleotides encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody that are optimized, e.g., by codon/RNA optimization, replacement with heterologous signal sequences, and elimination of mRNA instability elements. Methods to generate optimized nucleic acids encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-CD96 (e.g., human CD96 or cynomolgus CD96) and/or anti-TIGIT (e.g., human TIGIT or cynomolgus TIGIT) multispecific molecule or an isolated anti-TIGIT antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-CD96 (e.g., human CD96 or cynomolgus CD96) and/or anti-TIGIT (e.g., human TIGIT or cynomolgus TIGIT) multispecific molecule or an isolated anti-TIGIT antibody encoded by polynucleotides that have not been optimized.

In certain embodiments, an optimized polynucleotide sequence encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a fragment thereof (e.g., VL domain and/or VH domain) can hybridize to an antisense (e.g., complementary) polynucleotide of an unoptimized polynucleotide sequence encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a fragment thereof (e.g., VL domain and/or VH domain). In specific embodiments, an optimized nucleotide sequence encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a fragment hybridizes under high stringency conditions to antisense polynucleotide of an unoptimized polynucleotide sequence encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a fragment thereof. In a specific embodiment, an optimized nucleotide sequence encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a fragment thereof hybridizes under high stringency, intermediate or lower stringency hybridization conditions to an antisense polynucleotide of an unoptimized nucleotide sequence encoding an anti-CD96 (e.g., human CD96 or cynomolgus CD96) and/or anti-TIGIT (e.g., human TIGIT or cynomolgus TIGIT) multispecific molecule or an isolated anti-TIGIT antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding multispecific molecules and antibodies described herein, e.g., multispecific molecules and antibodies described in Table 1 and Table 2, and modified versions of these multispecific molecules and antibodies can be determined using methods well known in the art, i.e., nucleotide codons known to encode particular amino acids are assembled in such a way to generate a nucleic acid that encodes the multispecific molecule or antibody. Such a polynucleotide encoding the multispecific molecule or antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the multispecific molecule or antibody, annealing and ligating of those oligonucleotides, and then amplification of the ligated oligonucleotides by PCR.

Alternatively, a polynucleotide encoding an antigen-binding region of a multispecific molecule described here or an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of a multispecific molecule or an antibody. Such PCR amplification methods can be used to obtain nucleic acids comprising the sequence encoding the variable light chain region and/or the variable heavy chain region of multispecific molecule or an antibody. The amplified nucleic acids can be cloned into vectors for expression in host cells and for further cloning.

If a clone containing a nucleic acid encoding a particular antigen-binding region or antibody is not available, but the sequence of the antigen-binding region or antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-CD96 (e.g., human CD96 or cynomolgus CD96) and/or anti-TIGIT (e.g., human TIGIT or cynomolgus TIGIT) multispecific molecules, or antigen-binding fragments thereof, or isolated anti-TIGIT (e.g., human TIGIT or cynomolgus TIGIT) antibodies described herein can be readily isolated and sequenced using conventional procedures (e.g., by using oligonucleotide probes that are capable of binding specifically to genes encoding the heavy and light chains of the anti-CD96 (e.g., human CD96 or cynomolgus CD96) antigen-binding region, anti-TIGIT (e.g., human TIGIT or cynomolgus TIGIT) antigen-binding region, or anti-TIGIT (e.g., human TIGIT or cynomolgus TIGIT) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-CD96 and/or anti-TIGIT multispecific molecules or anti-TIGIT antibodies in the recombinant host cells.

To generate whole antibodies or antigen-binding regions, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant regions, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant regions in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) multispecific molecules, or antigen-binding regions thereof, described herein which specifically bind to CD96 (e.g., human CD96 or cynomolgus CD96) and/or TIGIT (e.g., human TIGIT or cynomolgus TIGIT), cells (e.g., host cells) expressing (e.g., recombinantly) antibodies described herein which specifically bind to TIGIT (e.g., human TIGIT or cynomolgus TIGIT), and related polynucleotides and expression vectors. Provided herein are vectors (e.g., expression vectors) comprising polynucleotides comprising nucleotide sequences encoding anti-CD96 (e.g., human CD96 or cynomolgus CD96) and/or anti-TIGIT (e.g., human TIGIT or cynomolgus TIGIT) multispecific molecules, or antigen-binding regions thereof, and anti-TIGIT antibodies or a fragment for recombinant expression in host cells, preferably in mammalian cells (e.g., CHO cells). Also provided herein are host cells comprising such vectors for recombinantly expressing anti-CD96 (e.g., human CD96 or cynomolgus CD96) and/or anti-TIGIT (e.g., human TIGIT or cynomolgus TIGIT) multispecific molecules, and anti-TIGIT antibodies described herein (e.g., human or humanized antibody). In a particular aspect, provided herein are methods for producing a multispecific molecule or an antibody described herein, comprising expressing the multispecific molecule, or antigen-binding regions thereof, or the antibody from a host cell.

Recombinant expression of a multispecific molecule, or antigen-binding region thereof, or an antibody described herein (e.g., a full-length antigen-binding region or antibody or heavy and/or light chain of an antibody described herein) that specifically binds to CD96 (e.g., human CD96 or cynomolgus CD96) and/or TIGIT (e.g., human TIGIT or cynomolgus TIGIT) generally involves construction of an expression vector containing a polynucleotide that encodes the multispecific molecule, or antigen-binding region thereof, or antibody. Once a polynucleotide encoding a multispecific molecule, or antigen-binding region thereof, or an antibody molecule, heavy and/or light chain of a multispecific molecule or an antibody, or a fragment thereof (e.g., heavy and/or light chain variable regions) described herein has been obtained, the vector for the production of the multispecific molecule, or antigen-binding region thereof, or antibody molecule can be produced by recombinant DNA technology using techniques well known in the art. Thus, methods for preparing a protein by expressing a polynucleotide containing a multispecific molecule, or antigen-binding region thereof, or an antibody or antibody fragment (e.g., light chain or heavy chain) encoding nucleotide sequence are described herein. Methods which are well known to those skilled in the art can be used to construct expression vectors containing a multispecific molecule, or antigen-binding region thereof, or an antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding containing a multispecific molecule, or antigen-binding region thereof, or an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the multispecific molecule or antibody molecule (see, e.g., International Publication Nos. WO 86/05807 and WO 89/01036; and U.S. Pat. No. 5,122,464, which are herein incorporated by reference in their entireties) and variable regions of the multispecific molecule or antibody can be cloned into such a vector for expression of the entire heavy, the entire light chain, or both the entire heavy and light chains.

In certain embodiments, a vector comprises a polynucleotide encoding a VH, VL, heavy chain, and/or light chain of a multispecific molecule described herein. In another embodiment, a vector comprises a polynucleotide encoding the first VH and the first VL of a multispecific molecule described herein. In another embodiment, a vector comprises a polynucleotide encoding the second VH and the second VL of a multispecific molecule described herein. In another embodiment, a vector comprises a polynucleotide encoding the first heavy chain and the first light chain of a multispecific molecule described herein. In another embodiment, a vector comprises a polynucleotide encoding the second heavy chain and the second light chain of a multispecific molecule described herein. In another embodiment, a vector comprises a polynucleotide encoding the VH and/or the VL, or the heavy chain and/or the light chain, of an isolated antibody described herein.

An expression vector can be transferred to a cell (e.g., host cell) by conventional techniques and the resulting cells can then be cultured by conventional techniques to produce containing a multispecific molecule, or antigen-binding region thereof, or an antibody described herein or a fragment thereof. Thus, provided herein are host cells containing a polynucleotide encoding containing a multispecific molecule, or antigen-binding region thereof, or an antibody described herein or fragments thereof, or a heavy or light chain thereof, or fragment thereof, or a single chain antibody described herein, operably linked to a promoter for expression of such sequences in the host cell.

In certain embodiments, a host cell comprises a polynucleotide encoding a VH, VL, heavy chain, and/or light chain of a multispecific molecule described herein. In another embodiment, a host cell comprises a polynucleotide encoding the first VH and the first VL of a multispecific molecule described herein. In another embodiment, a host cell comprises a polynucleotide encoding the second VH and the second VL of a multispecific molecule described herein. In another embodiment, a host cell comprises a polynucleotide encoding the first heavy chain and the first light chain of a multispecific molecule described herein. In another embodiment, a host cell comprises a polynucleotide encoding the second heavy chain and the second light chain of a multispecific molecule described herein. In another embodiment, a host cell comprises a polynucleotide encoding the VH and/or the VL, or the heavy chain and/or the light chain, of an isolated antibody described herein.

In certain embodiments, a host cell comprises a vector comprising a polynucleotide encoding a VH, VL, heavy chain, and/or light chain of a multispecific molecule described herein. In another embodiment, a host cell comprises a vector comprising a polynucleotide encoding the first VH and the first VL of a multispecific molecule described herein. In another embodiment, a host cell comprises a vector comprising a polynucleotide encoding the second VH and the second VL of a multispecific molecule described herein. In another embodiment, a host cell comprises a vector comprising a polynucleotide encoding the first heavy chain and the first light chain of a multispecific molecule described herein. In another embodiment, a host cell comprises a vector comprising a polynucleotide encoding the second heavy chain and the second light chain of a multispecific molecule described herein. In another embodiment, a host cell comprises a vector comprising a polynucleotide encoding the VH and/or the VL, or the heavy chain and/or the light chain, of an isolated antibody described herein.

In certain embodiments, a host cell comprises a first polynucleotide encoding the VH and VL of the first antigen-binding region of a multispecific molecule described herein, and a second polynucleotide encoding the VH and VL of the second antigen-binding region of a multispecific molecule described herein. In another embodiment, a host cell comprises a first vector comprising a first polynucleotide encoding the VH and VL of the first antigen-binding region of a multispecific molecule described herein, and a second vector comprising a second polynucleotide encoding the VH and VL of the second antigen-binding region of a multispecific molecule described herein. In another embodiment, a host cell comprises a first polynucleotide encoding the VH of the first antigen-binding region of a multispecific molecule described herein, and a second polynucleotide encoding the VL of the first antigen-binding region of a multispecific molecule described herein, a third polynucleotide encoding the VH of the second antigen-binding region of a multispecific molecule described herein, and a fourth polynucleotide encoding the VL of the second antigen-binding region of a multispecific molecule described herein. In another embodiment, a host cell comprises a first vector comprising a first polynucleotide encoding the VH of the first antigen-binding region of a multispecific molecule described herein, and a second vector comprising a second polynucleotide encoding the VL of the first antigen-binding region of a multispecific molecule described herein, a third vector comprising a third polynucleotide encoding the VH of the second antigen-binding region of a multispecific molecule described herein, and a fourth vector comprising a fourth polynucleotide encoding the VL of the second antigen-binding region of a multispecific molecule described herein.

In certain embodiments, a host cell comprises a first polynucleotide encoding the heavy chain and light chain of the first antigen-binding region of a multispecific molecule described herein, and a second polynucleotide encoding the heavy chain and light chain of the second antigen-binding region of a multispecific molecule described herein. In another embodiment, a host cell comprises a first vector comprising a first polynucleotide encoding the heavy chain and light chain of the first antigen-binding region of a multispecific molecule described herein, and a second vector comprising a second polynucleotide encoding the heavy chain and light chain of the second antigen-binding region of a multispecific molecule described herein. In another embodiment, a host cell comprises a first polynucleotide encoding the heavy chain of the first antigen-binding region of a multispecific molecule described herein, and a second polynucleotide encoding the light chain of the first antigen-binding region of a multispecific molecule described herein, a third polynucleotide encoding the heavy chain of the second antigen-binding region of a multispecific molecule described herein, and a fourth polynucleotide encoding the light chain of the second antigen-binding region of a multispecific molecule described herein. In another embodiment, a host cell comprises a first vector comprising a first polynucleotide encoding the heavy chain of the first antigen-binding region of a multispecific molecule described herein, and a second vector comprising a second polynucleotide encoding the light chain of the first antigen-binding region of a multispecific molecule described herein, a third vector comprising a third polynucleotide encoding the heavy chain of the second antigen-binding region of a multispecific molecule described herein, and a fourth vector comprising a fourth polynucleotide encoding the light chain of the second antigen-binding region of a multispecific molecule described herein.

In certain embodiments, a host cell comprises a polynucleotide encoding the VH and VL of an isolated antibody described herein. In another embodiment, a host cell comprises a vector comprising a polynucleotide encoding the VH and VL of an isolated antibody described herein. In another embodiment, a host cell comprises a first polynucleotide encoding the VH of an isolated antibody described herein, and a second polynucleotide encoding the VL of an isolated antibody described herein. In another embodiment, a host cell comprises a first vector comprising a first polynucleotide encoding the VH of an isolated antibody described herein, and a second vector comprising a second polynucleotide encoding the VL of an isolated antibody described herein.

In specific embodiments, a heavy chain/heavy chain variable region expressed by a first cell associated with a light chain/light chain variable region of a second cell to form an anti-CD96 (e.g., human CD96 or cynomolgus CD96) and/or anti-TIGIT (e.g., human TIGIT or cynomolgus TIGIT) multispecific molecule described herein, or antigen-binding region thereof, or an anti-TIGIT (e.g., human TIGIT or cynomolgus TIGIT) antibody described herein. In certain embodiments, provided herein is a population of host cells comprising such first host cell and such second host cell.

In certain embodiments, provided herein is a population of vectors comprising a first vector comprising a polynucleotide encoding a light chain/light chain variable region of an anti-CD96 (e.g., human CD96 or cynomolgus CD96) and/or anti-TIGIT (e.g., human TIGIT or cynomolgus TIGIT) multispecific molecule described herein, or antigen-binding region thereof, or an anti-TIGIT (e.g., human TIGIT or cynomolgus TIGIT) antibody described herein, and a second vector comprising a polynucleotide encoding a heavy chain/heavy chain variable region of an anti-CD96 (e.g., human CD96 or cynomolgus CD96) and/or anti-TIGIT (e.g., human TIGIT or cynomolgus TIGIT) multispecific molecule described herein, or antigen-binding region thereof, or an anti-TIGIT (e.g., human TIGIT or cynomolgus TIGIT) antibody described herein.

A variety of host-expression vector systems can be utilized to express multispecific molecules described herein, or antigen-binding regions thereof, or antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express a multispecific molecule described herein, or antigen-binding region thereof, or an antibody molecule described herein in situ. These include but are not limited to microorganisms such as bacteria (e.g., *E. coli* and *B. subtilis*) transformed with, e.g., recombinant bacteriophage DNA, plasmid DNA, or cosmid DNA expression vectors containing coding sequences of multispecific molecules, or antigen-binding regions thereof, or antibody coding sequences; yeast (e.g., *Saccharomyces* and *Pichia*) transformed with, e.g., recombinant yeast expression vectors containing antibody coding sequences; insect cell systems infected with, e.g., recombinant virus expression vectors (e.g., baculovirus) containing coding sequences of multispecific molecules, or antigen-binding regions thereof, or antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing coding sequences of multispecific molecules, or antigen-binding regions thereof, or antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of a multispecific molecule, or antigen-binding region thereof, or an antibody produced by a CHO cell may have an N-terminal glutamine or glutamate residue replaced by pyroglutamate. In certain embodiments, cells for expressing antibodies described herein are human cells, e.g., human cell lines. In a specific embodiment, a mammalian expression vector is pOptiVEC™ or pcDNA3.3. In certain embodiments, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus, are an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, multispecific molecules described herein, or antigen-binding region thereof, or antibodies described herein are produced by CHO cells or NS0 cells. In a specific embodiment, the expression of nucleotide sequences encoding anti-CD96 (e.g., human CD96 or cynomolgus CD96) and/or anti-TIGIT (e.g., human TIGIT or cynomolgus TIGIT) multispecific molecules described herein, or antigen-binding region thereof, or antibodies described herein which specifically bind to TIGIT (e.g., human TIGIT or cynomolgus TIGIT) is regulated by a constitutive promoter, inducible promoter, or tissue specific promoter.

In bacterial systems, a number of expression vectors can be advantageously selected depending upon the use intended for the multispecific molecule or antibody molecule being expressed. For example, when a large quantity of such a multispecific molecule or an antibody is to be produced, for the generation of pharmaceutical compositions of a multispecific molecule or an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (see, e.g., Logan J & Shenk T (1984) PNAS 81(12): 3655-9, which is herein incorporated by reference in its entirety). Specific initiation signals can also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O, and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10, and HsS78Bst cells. In certain embodiments, anti-CD96 (e.g., human CD96 or cynomolgus CD96) and/or anti-TIGIT (e.g., human TIGIT or cynomolgus TIGIT) multispecific molecules or anti-TIGIT (e.g., human TIGIT or cynomolgus TIGIT) antibodies described herein are produced in mammalian cells, such as CHO cells.

In a specific embodiment, the multispecific molecules or antibodies described herein have reduced fucose content or no fucose content. Such multispecific molecules or antibodies can be produced using techniques known to one skilled in the art. For example, the multispecific molecules, or antigen-binding regions thereof, or antibodies can be expressed in cells deficient or lacking the ability of to fucosylate. In a specific example, cell lines with a knockout of both alleles of α1,6-fucosyltransferase can be used to produce multispecific molecules, or antigen-binding regions thereof, or antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-CD96 (e.g., human CD96 or cynomolgus CD96) and/or anti-TIGIT (e.g., human TIGIT or cynomolgus TIGIT) multispecific molecule, or antigen-binding region thereof, or an anti-TIGIT (e.g., human TIGIT or cynomolgus TIGIT) antibody described herein can be engineered. In specific embodiments, a cell provided herein stably expresses a light chain/light chain variable region and a heavy chain/heavy chain variable region which associate to form an antigen-binding region or an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CD96 (e.g., human CD96 or cynomolgus CD96) and/or anti-TIGIT (e.g., human TIGIT or cynomolgus TIGIT) multispecific molecule, or antigen-binding region thereof, or an anti-TIGIT (e.g., human TIGIT or cynomolgus TIGIT) described herein or a fragment thereof. Such engineered cell lines can be particularly useful in screening and evaluation of compositions that interact directly or indirectly with the multispecific molecule or antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N.C. et al., (eds.), Current Protocols in Human Genetics, John Wiley & Sons, N Y (1994); Colbère-Garapin F et al., (1981) J Mol Biol 150: 1-14, all of which are herein incorporated by reference in their entireties.

The expression levels of a multispecific molecule, or antigen-binding region thereof, or an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system is amplifiable, increase in the level of inhibitor present in culture of host cell will increase the number of copies of the marker gene. Since the amplified region is associated with the gene of interest, production of the protein will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Kohler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10, or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once a multispecific molecule, or antigen-binding region thereof, or an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the multispecific molecules and antibodies described herein can be fused to heterologous polypeptide sequences described herein or otherwise known in the art to facilitate purification.

In specific embodiments, a multispecific molecule described herein, or antigen-binding region thereof, or an antibody described herein is isolated or purified. In certain embodiments, an isolated antibody is one that is substantially free of other antibodies with different antigenic specificities than the isolated antibody. For example, in certain embodiments, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Anti-CD96 (e.g., human CD96 or cynomolgus CD96) and/or anti-TIGIT (e.g., human TIGIT or cynomolgus TIGIT) multispecific molecules, or antigen-binding regions thereof, or anti-TIGIT (e.g., human TIGIT or cynomolgus TIGIT) antibodies or fragments thereof can be produced by any method known in the art for the synthesis of proteins or antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, a multispecific molecule described herein, or an antigen-binding region thereof, or an antibody described herein is prepared, expressed, created, or isolated by any means that involves creation, e.g., via synthesis, genetic engineering of DNA sequences. In certain embodiments, such a multispecific molecule, or antigen-binding region thereof, or an antibody comprises sequences (e.g., DNA sequences or amino acid sequences) that do not naturally exist within the antibody germline repertoire of an animal or mammal (e.g., human) in vivo.

In one aspect, provided herein is a method of making an anti-CD96 (e.g., human CD96 or cynomolgus CD96) and/or anti-TIGIT (e.g., human TIGIT or cynomolgus TIGIT) multispecific molecule, or antigen-binding region thereof, or an anti-TIGIT (e.g., human TIGIT or cynomolgus TIGIT) antibody comprising culturing a cell or host cell described herein. In certain embodiments, the method is performed in vitro. In a certain aspect, provided herein is a method of making an anti-CD96 (e.g., human CD96 or cynomolgus CD96) and/or anti-TIGIT (e.g., human TIGIT or cynomolgus TIGIT) multispecific molecule, or antigen-binding region thereof, or an anti-TIGIT (e.g., human TIGIT or cynomolgus TIGIT) antibody comprising expressing (e.g., recombinantly expressing) the multispecific molecule, or antigen-binding region thereof, or the antibody using a cell or host cell described herein (e.g., a cell or a host cell comprising polynucleotides encoding an antibody described herein). In certain embodiments, the cell is an isolated cell. In certain embodiments, the exogenous polynucleotides have been introduced into the cell. In certain embodiments, the method further comprises the step of purifying the multispecific molecule, or antigen-binding region thereof, or the antibody obtained from the cell or host cell.

In certain embodiments, a multispecific molecule is produced by expressing in a cell a first polynucleotide encoding the VH and VL of a first antigen-binding region of a multispecific molecule described herein, and a second polynucleotide encoding the VH and VL of a second antigen-binding region of a multispecific molecule described herein under suitable conditions so that the polynucleotides are expressed and the multispecific molecule is produced. In certain embodiments, a multispecific molecule is produced by expressing in a cell a first polynucleotide encoding the heavy chain and light chain of a first antigen-binding region of a multispecific molecule described herein, and a second polynucleotide encoding the heavy chain and light chain of a second antigen-binding region of a multispecific molecule described herein under suitable conditions so that the polynucleotides are expressed and the multispecific molecule is produced.

In certain embodiments, a multispecific molecule is produced by expressing in a cell a first polynucleotide encoding the VH of the first antigen-binding region of a multispecific molecule described herein, a second polynucleotide encoding the VL of the first antigen-binding region of a multispecific molecule described herein, a third polynucleotide encoding the VH of the second antigen-binding region of a multispecific molecule described herein, and a fourth polynucleotide encoding the VL of the second antigen-binding region of a multispecific molecule described herein under suitable conditions so that the polynucleotides are expressed and the multispecific molecule is produced. In certain embodiments, a multispecific molecule is produced by expressing in a cell a first polynucleotide encoding the heavy chain of the first antigen-binding region of a multispecific molecule described herein, a second polynucleotide encoding the light chain of the first antigen-binding region of a multispecific molecule described herein, a third polynucleotide encoding the heavy chain of the second antigen-binding region of a multispecific molecule described herein, and a fourth polynucleotide encoding the light chain of the second antigen-binding region of a multispecific molecule described herein under suitable conditions so that the polynucleotides are expressed and the multispecific molecule is produced.

In certain embodiments, a multispecific molecule is produced by contacting the first antigen-binding region and the second antigen-binding region of a multispecific molecule described herein under conditions so that the multispecific molecule is produced. For example, in certain embodiments, a multispecific molecule is produced by expressing in a first cell a first polynucleotide encoding the VH and VL of a first antigen-binding region of a multispecific molecule described herein, under conditions whereby the first antigen-binding region is produced, and expressing in a second cell a second polynucleotide encoding the VH and VL of a second antigen-binding region of a multispecific molecule described herein under conditions whereby the second antigen-binding region is produced, and contacting the first and second antigen-binding regions under suitable conditions so that the multispecific molecule is produced. Alternatively, in certain embodiments, a multispecific molecule is produced by expressing in a first cell a first polynucleotide encoding the VH of a first antigen-binding region of a multispecific molecule described herein, and a second polynucleotide encoding the VL of a first antigen-binding region of a multispecific molecule described herein, under conditions whereby the first antigen-binding region is produced, and expressing in a second cell a third polynucleotide encoding the VH a second antigen-binding region of a multispecific molecule described herein, and a fourth polynucleotide encoding the VL of a second antigen-binding region of a multispecific molecule described herein, under conditions whereby the second antigen-binding region is produced, and contacting the first and second antigen-binding regions under suitable conditions so that the multispecific molecule is produced. Suitable methodologies and conditions for contacting the first and second antigen-binding regions to produce the multispecific molecule include, without limitation, those methodologies and conditions described in WO 2011/131746, WO 2011/147986, WO 2008/119353, and WO 2013/060867, and in Labrijn A F et al., (2013) PNAS 110(13): 5145-5150, each of which is incorporated by reference herein in its entirety.

In certain embodiments, an isolated antibody is produced by expressing in a cell a polynucleotide encoding the VH and VL of an antibody described herein under suitable conditions so that the polynucleotides are expressed and the antibody is produced. In another embodiment, an isolated antibody is produced by expressing in a cell a polynucleotide encoding the heavy chain and light chain of an antibody described herein under suitable conditions so that the polynucleotides are expressed and the antibody is produced. In certain embodiments, an isolated antibody is produced by expressing in a cell a first polynucleotide encoding the VH of an antibody described herein, and a second polynucleotide encoding the VH of an antibody described herein, under suitable conditions so that the polynucleotides are expressed and the antibody is produced. In certain embodiments, an isolated antibody is produced by expressing in a cell a first polynucleotide encoding the heavy chain of an antibody described herein, and a second polynucleotide encoding the light chain of an antibody described herein, under suitable conditions so that the polynucleotides are expressed and the antibody is produced.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd Ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to CD96 (e.g., human CD96 or cynomolgus CD96) as determined, e.g., by ELISA or other antigen-binding or competitive binding assay known in the art or in the examples provided herein. In certain embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding regions, each monovalent binding region capable of binding to an epitope on the antigen. Each monovalent binding region can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster, or macaque monkey, is immunized to elicit lymphocytes that produce or are capable of producing antibodies that will specifically bind to the protein (e.g., CD96 (e.g., human CD96 or cynomolgus CD96)) used for immunization. Alternatively, lymphocytes may be immunized in vitro. Lymphocytes then are fused with myeloma cells using a suitable fusing agent, such as polyethylene glycol, to form a hybridoma cell (Goding J W (ed.), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., CD96 (e.g., human CD96 or cynomolgus CD96)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against TIGIT (e.g., human TIGIT or cynomolgus TIGIT). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (ed.), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize TIGIT (e.g., human TIGIT or cynomolgus TIGIT), and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antigen-binding region that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108, all of which are herein incorporated by reference in their entireties.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab', and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) A m J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In certain embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA, and IgE, and any isotype, including $IgG_1$, $IgG_2$, $IgG_3$, and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10; and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is herein incorporated by reference in its entirety.

Methods for making multispecific molecules and multispecific antibodies (e.g., bispecific antibodies) have been described, see, for example, U.S. Pat. Nos. 7,951,917; 7,183,076; 8,227,577; 5,837,242; 5,989,830; 5,869,620; 6,132,992; and 8,586,713, all of which are herein incorporated by reference in their entireties.

Bispecific, bivalent antibodies, and methods of making them, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

A multispecific molecule or a bispecific antibody as described herein can be generated according to the DuoBody technology platform (Genmab A/S) as described, e.g., in International Publication Nos. WO 2011/131746, WO 2011/147986, WO 2008/119353, and WO 2013/060867, and in Labrijn A F et al., (2013) PNAS 110(13): 5145-5150. The DuoBody technology can be used to combine one half of a first monospecific antibody, or first antigen-binding region, containing two heavy and two light chains with one half of a second monospecific antibody, or second antigen-binding region, containing two heavy and two light chains. The resultant heterodimer contains one heavy chain and one light chain from the first antibody, or first antigen-binding region, paired with one heavy chain and one light chain from the second antibody, or second antigen-binding region. When both of the monospecific antibodies, or antigen-binding regions, recognize different epitopes on different antigens, the resultant heterodimer is a multispecific molecule or bispecific antibody.

The DuoBody technology requires that each of the monospecific antibodies, or antigen-binding regions includes a heavy chain constant region with a single point mutation in the CH3 domain. The point mutations allow for a stronger interaction between the CH3 domains in the resultant bispecific antibody than between the CH3 domains in either of the monospecific antibodies, or antigen-binding regions. The single point mutation in each monospecific antibody, or antigen-binding region, is at residue 366, 368, 370, 399, 405, 407, or 409, numbered according to the EU numbering system, in the CH3 domain of the heavy chain constant region, as described, e.g., in International Publication No. WO 2011/131746. Moreover, the single point mutation is located at a different residue in one monospecific antibody, or antigen-binding region, as compared to the other monospecific antibody, or antigen-binding region. For example, one monospecific antibody, or antigen-binding region, can comprise the mutation F405L (i.e., a mutation from phenylalanine to leucine at residue 405), while the other monospecific antibody, or antigen-binding region, can comprise the mutation K409R (i.e., a mutation from lysine to arginine at residue 409), numbered according to the EU numbering system. The heavy chain constant regions of the monospecific antibodies, or antigen-binding regions, can be an $IgG_1$, $IgG_2$, $IgG_3$, or $IgG_4$ isotype (e.g., a human $IgG_1$ isotype), and a bispecific antibody, or multispecific molecule, produced by the DuoBody technology can retain Fc-mediated effector functions.

Another method for generating multispecific molecules or bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides so as to preferentially form a bispecific antibody. The bispecific antibodies, or multispecific molecules, can be composed of immunoglobulin chains of the same subclass (e.g., $IgG_1$ or $IgG_3$) or different subclasses (e.g., $IgG_1$ and $IgG_3$, or $IgG_3$ and $IgG_4$).

Multispecific molecules that bind to CD96 and/or TIGIT can, in some instances contain, $IgG_4$ and $IgG_1$, $IgG_4$ and $IgG_2$, $IgG_4$ and $IgG_2$, $IgG_4$ and $IgG_3$, or $IgG_1$ and $IgG_3$ chain heterodimers. Such heterodimeric heavy chain antibodies can routinely be engineered by, for example, modifying selected amino acids forming the interface of the CH3 domains in human $IgG_4$ and the $IgG_1$ or $IgG_3$, so as to favor heterodimeric heavy chain formation.

In certain embodiments, an antibody described herein, which binds to the same epitope of TIGIT (e.g., human TIGIT or cynomolgus TIGIT) as an anti-TIGIT (e.g., human TIGIT or cynomolgus TIGIT) antibody described herein, is a human antibody. In certain embodiments, an antibody described herein, which competitively blocks (e.g., in a dose-dependent manner) any one of the antibodies described herein, from binding to TIGIT (e.g., human TIGIT or cynomolgus TIGIT), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., TIGIT (e.g., human TIGIT or cynomolgus TIGIT)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598, all of which are herein incorporated by reference in their entireties. Examples of mice capable of producing human antibodies include the XenoMouse™ (Abgenix, Inc.; U.S. Pat. Nos. 6,075,181 and 6,150,184), the HuAb-Mouse™ (Medarex, Inc./Gen Pharm; U.S. Pat. Nos. 5,545,806 and 5,569,825), the Trans-Chromo Mouse™ (Kirin) and the KM Mouse™ (Medarex/Kirin), all of which are herein incorporated by reference in their entireties.

Human antibodies that specifically bind to TIGIT (e.g., human TIGIT or cynomolgus TIGIT) can be made by a variety of methods known in the art including the phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., TIGIT (e.g., human TIGIT or cynomolgus TIGIT)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

7.6 Kits

Also provided are kits comprising one or more multispecific molecules or antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more multispecific molecules or antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use, or sale for human administration.

Also provided, are kits that can be used in the above methods. In certain embodiments, a kit comprises an antibody described herein, preferably a multispecific molecule or purified antibody, in one or more containers. In a specific embodiment, kits described herein contain a substantially isolated CD96 (e.g., human CD96 or cynomolgus CD96) antigen and/or TIGIT (e.g., human TIGIT or cynomolgus TIGIT) antigen as a control. In another specific embodiment, the kits described herein further comprise a control antibody which does not react with a CD96 (e.g., human CD96 or cynomolgus CD96) antigen and/or TIGIT (e.g., human TIGIT or cynomolgus TIGIT) antigen. In another specific embodiment, kits described herein contain one or more elements for detecting the binding of a multispecific molecule or an antibody to a CD96 (e.g., human CD96 or cynomolgus CD96) antigen and/or TIGIT (e.g., human TIGIT or cynomolgus TIGIT) antigen (e.g., the multispecific molecule or antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CD96 (e.g., human CD96 or cynomolgus CD96) antigen and/or TIGIT (e.g., human TIGIT or cynomolgus TIGIT) antigen. The CD96 (e.g., human CD96 or cynomolgus CD96) antigen and/or TIGIT (e.g., human TIGIT or cynomolgus TIGIT) antigen provided in the kit can also be attached to a solid support. In a more specific embodiment, the detecting means of the above-described kit includes a solid support to which a CD96 (e.g., human CD96 or cynomolgus CD96) antigen and/or TIGIT (e.g., human TIGIT or cynomolgus TIGIT) antigen is attached. Such a kit can also include a non-attached reporter-labeled anti-human antibody or anti-mouse/rat antibody. In this embodiment, binding of the multispecific molecule or antibody to the CD96 (e.g., human CD96 or cynomolgus CD96) antigen and/or TIGIT (e.g., human TIGIT or cynomolgus TIGIT) antigen can be detected by binding of the said reporter-labeled antibody. In certain embodiments, the present invention relates to the use of a kit of the present invention for in vitro assaying and/or detecting CD96 antigen (e.g., human CD96 or cynomolgus CD96) and/or TIGIT (e.g., human TIGIT or cynomolgus TIGIT) antigen in a biological sample.

8. EXAMPLES

The examples in this Section (i.e., Section 6) are offered by way of illustration and not by way of limitation.

Table 5 provides details of the various multispecific molecules and monospecific antibodies used in the following Examples.

TABLE 5

Exemplary multispecific molecules and monospecific antibodies.

| Description | Anti-CD96 Antigen-Binding Region SEQ ID NOs | | Anti-TIGIT Antigen-Binding Region SEQ ID NOs | |
|---|---|---|---|---|
| | HC | LC | HC | LC |
| BA123 | 1 | 2 | 7 | 9 |
| BA125 | 3 | 4 | 7 | 9 |
| BA127 | 5 | 6 | 7 | 9 |
| BA128 | isotype control | | isotype control | |
| BA129 | 1 | 2 | isotype control | |
| BA130 | 3 | 4 | isotype control | |
| BA131 | 5 | 6 | isotype control | |

TABLE 5-continued

Exemplary multispecific molecules and monospecific antibodies.

| Description | Anti-CD96 Antigen-Binding Region SEQ ID NOs | | Anti-TIGIT Antigen-Binding Region SEQ ID NOs | |
|---|---|---|---|---|
| | HC | LC | HC | LC |
| BA133 | isotype control | | 7 | 9 |
| BA134 | anti-CD96 reference | | isotype control | |
| BA136 | anti-CD96 reference | | 7 | 9 |
| BA143 | 47 | 6 | N/A | N/A |
| BA144 | 46 | 4 | N/A | N/A |
| BA145 | 45 | 2 | N/A | N/A |
| BA146 | isotype control | | N/A | N/A |
| BA148 | N/A | N/A | 48 | 9 |
| BA149 | N/A | N/A | isotype control | |

8.1 Example 1: Characterization of Anti-TIGIT×CD96 Multispecific Molecules

8.1.1 Anti-TIGIT×CD96 Multispecific Molecules Binding to Purified Human and Cynomolgus Monkey CD96 Protein Binding to His-Tagged Isoform 2 of Human CD96 with a C89S Mutation The binding affinity of the multispecific molecules BA123, BA125, and BA127 to a variant of the full-length extracellular domain (ECD) of human isoform 2 of CD96 comprising a C89S mutation (SEQ ID NO: 63) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 2 µg/mL of BA123, BA125, and BA127 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Multispecific molecules were captured using a 30-sec injection at a flow rate of 10 µl/min to reach about 350 resonance units (RUs). Full-length isoform 2 ECD of human CD96 with a C89S mutation (SEQ ID NO: 63) was diluted to a concentration of 0, 0.41, 1.23, 3.7, 11.1, 33.3, and 100 nM and flowed over the chip surface at a flow rate of 30 µl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 6.

TABLE 6

Kinetic parameters of anti-TIGIT × CD96 multispecific molecules binding
to full-length isoform 2 ECD of human CD96 with a C89S mutation (SEQ ID NO: 63).

| Multispecific Molecule | Experiment #1 | | | Experiment #2 | | | Geomean $K_D$ |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | |
| BA123 | 1.58E+04 | 1.25E−03 | 7.90E−08 | 9.76E+03 | 8.30E−04 | 8.50E−08 | 81.9 nM |
| BA125 | 6.51E+05 | 1.81E−02 | 2.78E−08 | 4.38E+05 | 7.96E−03 | 1.82E−08 | 22.5 nM |
| BA127 | 5.92E+04 | 1.16E−03 | 1.96E−08 | 4.05E+04 | 7.96E−04 | 1.97E−08 | 19.6 nM |

Binding to His-Tagged Isoform 2 of Cynomolgus Monkey CD96

The binding affinity of the multispecific molecules BA123, BA125, and BA127 to the full-length ECD of cynomolgus monkey isoform 2 of CD96 (SEQ ID NO: 111) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 2 µg/mL of BA123, BA125, and BA127 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Multispecific molecules were captured using a 30-sec injection at a flow rate of 10 µl/min to reach about 350 resonance units (RUs). Full-length isoform 2 ECD of cynomolgus monkey CD96 (SEQ ID NO: 111) was diluted to a concentration of 0, 0.41, 1.23, 3.7, 11.1, 33.3, and 100 nM and flowed over the chip surface at a flow rate of 30 µl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 7.

8.1.2 Anti-TIGIT×CD96 Multispecific Molecules Binding to Purified Human and Cynomolgus Monkey TIGIT Protein Binding to His-Tagged Human TIGIT The binding affinity of the multispecific molecules BA123, BA125, and BA127 to the full-length ECD of human TIGIT (SEQ ID NO: 113) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 4 µg/mL of BA123, BA125, and BA127 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Multispecific molecules were captured using a 30-sec injection at a flow rate of 10 µl/min to reach about 1000 resonance units (RUs). Full-length ECD of human TIGIT (SEQ ID NO: 113) was diluted to a concentration of 0, 0.41, 1.23, 3.7, 11.1, 33.3, and 100 nM and flowed over the chip surface at a flow rate of 30 µl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 8.

TABLE 7

Kinetic parameters of anti-TIGIT × CD96 multispecific molecules binding
to full-length isoform 2 ECD of cynomolgus monkey CD96 (SEQ ID NO: 111).

| Multispecific Molecule | Experiment #1 | | | Experiment #2 | | | Geomean $K_D$ |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | |
| BA123 | 7.90E+04 | 3.79E−03 | 4.80E−08 | 7.59E+04 | 3.24E−03 | 4.27E−08 | 45.3 nM |
| BA125 | No significant binding | | | No significant binding | | | — |
| BA127 | No significant binding | | | No significant binding | | | — |

TABLE 8

Kinetic parameters of anti-TIGIT × CD96 multispecific molecules
binding to full-length ECD of human TIGIT (SEQ ID NO: 113).

| Multispecific Molecule | Experiment #1 | | | Experiment #2 | | | Geomean $K_D$ |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | |
| BA123 | 6.02E+05 | 4.44E−04 | 7.37E−10 | 6.60E+05 | 4.87E−04 | 7.37E−10 | 0.74 nM |
| BA125 | 5.86E+05 | 3.67E−04 | 6.26E−10 | 6.00E+05 | 3.99E−04 | 6.65E−10 | 0.64 nM |
| BA127 | 6.10E+05 | 3.56E−04 | 5.84E−10 | 6.31E+05 | 3.85E−04 | 6.11E−10 | 0.59 nM |

Binding to His-Tagged Cynomolgus Monkey TIGIT

The binding affinity of the multispecific molecule BA123, BA125, and BA127 to the full-length ECD of cynomolgus monkey TIGIT (SEQ ID NO: 114) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 4 μg/mL of BA123, BA125, and BA127 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Multispecific molecules were captured using a 30-sec injection at a flow rate of 10 μl/min to reach about 350 resonance units (RUs). Full-length ECD of cynomolgus monkey TIGIT (SEQ ID NO: 114) was diluted to a concentration of 0, 0.41, 1.23, 3.7, 11.1, 33.3, and 100 nM and flowed over the chip surface at a flow rate of 30 μl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 9.

8.2 Example 2: Anti-CD96 Antibodies Binding to Purified Human and Cynomolgus Monkey CD96 Protein Binding to His-Tagged Isoform 2 of Human CD96 with a C89S Mutation The binding affinity of the monospecific antibodies BA143, BA144, and BA145 to the full-length ECD of human isoform 2 of CD96 with a C89S mutation (SEQ ID NO: 63) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 1 μg/mL of BA143, BA144, and BA145 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Antibodies were captured using a 30-sec injection at a flow rate of 10 μl/min to reach about 175 resonance units (RUs). Full-length isoform 2 ECD of human CD96 with a C89S mutation (SEQ ID NO: 63) was diluted to a concentration of 0, 0.41, 1.23, 3.7, 11.1, 33.3, and 100 nM was flowed over the chip surface at a flow rate of 30 μl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 10.

TABLE 9

Kinetic parameters of anti-TIGIT × CD96 multispecific molecules
binding to full-length ECD of cynomolgus monkey TIGIT (SEQ ID NO: 114).

| Multispecific Molecule | Experiment #1 | | | Experiment #2 | | | Geomean $K_D$ |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | |
| BA123 | 2.77E+05 | 1.32E−03 | 4.78E−09 | 3.15E+05 | 1.35E−03 | 4.27E−09 | 4.5 nM |
| BA125 | 2.92E+05 | 1.29E−03 | 4.43E−09 | 3.37E+05 | 1.31E−03 | 3.89E−09 | 4.2 nM |
| BA127 | 2.94E+05 | 1.26E−03 | 4.29E−09 | 3.48E+05 | 1.29E−03 | 3.70E−09 | 4.0 nM |

TABLE 10

Kinetic parameters of anti-CD96 antibodies binding to full-length
isoform 2 ECD of human CD96 with a C89S mutation (SEQ ID NO: 63).

| Multispecific Molecule | Experiment #1 | | | Experiment #2 | | | Geomean $K_D$ |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | |
| BA143 | 4.40E+04 | 5.83E-04 | 1.33E-08 | 4.31E+04 | 5.72E-04 | 1.33E-08 | 13.3 nM |
| BA144 | 1.19E+05 | 2.95E-03 | 2.48E-08 | 1.28E+05 | 3.02E-03 | 2.36E-08 | 24.2 nM |
| BA145 | 1.18E+04 | 1.05E-03 | 8.91E-08 | 1.26E+04 | 9.07E-04 | 7.18E-08 | 80.0 nM |

Binding to His-Tagged Isoform 2 of Cynomolgus Monkey CD96

The binding affinity of the monospecific antibodies BA143, BA144, and BA145 to the full-length ECD of cynomolgus monkey isoform 2 of CD96 (SEQ ID NO: 111) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 1 µg/mL of BA143, BA144, and BA145 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Antibodies were captured using a 30-sec injection at a flow rate of 10 µl/min to reach about 175 resonance units (RUs). Full-length isoform 2 ECD of cynomolgus monkey CD96 (SEQ ID NO: 111) was diluted to a concentration of 0, 0.41, 1.23, 3.7, 11.1, 33.3, and 100 nM and flowed over the chip surface at a flow rate of 30 µl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 11.

8.3 Example 3: Anti-TIGIT Antibodies Binding to Purified Human and Cynomolgus Monkey TIGIT Protein Binding to His-Tagged Human TIGIT The binding affinity of the monospecific antibody BA148 to the full-length ECD of human TIGIT (SEQ ID NO: 113) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 2 µg/mL of BA148 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as reference. Antibodies were captured using a 30-sec injection at a flow rate of 10 µl/min to reach about 500 resonance units (RUs). Full-length ECD of human TIGIT (SEQ ID NO: 113) was diluted to a concentration of 0, 0.41, 1.23, 3.7, 11.1, 33.3, and 100 nM and flowed over the chip surface at a flow rate of 30 µl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 12.

TABLE 11

Kinetic parameters of anti-CD96 antibodies binding to full-length
isoform 2 ECD of cynomolgus monkey CD96 (SEQ ID NO: 111).

| Antibody | Experiment #1 | | | Experiment #2 | | | Geomean $K_D$ |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | |
| BA143 | No significant binding | | | No significant binding | | | — |
| BA144 | No significant binding | | | No significant binding | | | — |
| BA145 | 6.68E+04 | 6.16E-03 | 9.23E-08 | 7.26E+04 | 5.84E-03 | 8.05E-08 | 86.2 nM |

TABLE 12

Kinetic parameters of anti-TIGIT antibodies binding to full-length ECD of human TIGIT (SEQ ID NO: 113).

| | Experiment #1 | | | Experiment #2 | | | |
|---|---|---|---|---|---|---|---|
| Antibody | $k_a$ (1/Ms) | $k_d$ (1/s) | $K_D$ (M) | $k_a$ (1/Ms) | $k_d$ (1/s) | $K_D$ (M) | Geomean $K_D$ |
| BA148 | 7.73E+05 | 4.13E−04 | 5.35E−10 | 7.70E+05 | 4.22E−04 | 5.48E−10 | 0.54 nM |

Binding to His-Tagged Cynomolgus Monkey TIGIT

The binding affinity of the monospecific antibody BA148 to the full-length ECD of cynomolgus monkey TIGIT (SEQ ID NO: 114) was assessed by surface plasmon resonance.

Briefly, surface plasmon resonance experiments were performed using a Biacore T200 instrument, and the association rate ($k_a$), dissociation rate ($k_d$), and dissociation constant ($K_D$) were calculated from each experiment using a 1:1 binding model with Biacore T200 Evaluation Software.

Approximately 4 µg/mL of BA148 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as reference. Antibodies were captured using a 30-sec injection at a flow rate of 10 µl/min to reach about 500 resonance units (RUs). Full-length ECD of cynomolgus monkey TIGIT (SEQ ID NO: 114) was diluted to a concentration of 0, 0.41, 1.23, 3.7, 11.1, 33.3, and 100 nM was flowed over the chip surface at a flow rate of 30 µl/min with a 3-min association phase and a 10-min dissociation phase. The sensor chip was regenerated between cycles with two 30-sec injections of 10 mM glycine, pH 1.5. Sensorgrams were evaluated and fit to a simple Langmuir 1:1 interaction model using the global data analysis option of BIAevaluation 3.0 software. Data quality was verified by visually inspecting deviations and curve fitting, and by evaluating the parameters of $R_{max}$, Chi2, and Tc. The binding kinetics ($k_a$, $k_d$, and $K_D$) were determined from the sensorgram analyses and are shown in Table 13.

Briefly, surface plasmon resonance experiments were performed using a Biacore T200 instrument, and sensorgrams were visually inspected using Biacore T200 Evaluation Software.

Approximately 4 µg/mL of BA123, BA125, and BA127 diluted in running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56), keeping a single flow cell as a reference. Multispecific Molecules were captured using a 30-sec injection at a flow rate of 10 µl/min to reach about 1000 resonance units (RUs). The Biacore T200's Dual Injection protocol was then used for two separate injections of different TIGIT and/or CD96 samples, one immediately after the other. The first injection was with 100 nM of the full-length ECD of human TIGIT (SEQ ID NO: 113) for a 3-min association phase, followed immediately by the second 3-min injection of either buffer, 100 nM of the full-length ECD of human TIGIT (SEQ ID NO: 113), a mixture of 100 nM of the full-length ECD of human TIGIT (SEQ ID NO: 113) and 100 nM of the full-length ECD of human isoform 2 of CD96 with a C89S mutation (SEQ ID NO: 63), or 100 nM of the full-length ECD of human isoform 2 of CD96 with a C89S mutation (SEQ ID NO: 63). The second injection was followed by a 10-min dissociation phase. The sensor chip was regenerated between cycles with two 30-sec injections of 10 mM glycine, pH 1.5. Sensorgrams were evaluated using BIAevaluation 3.0 software.

Figure 1A:
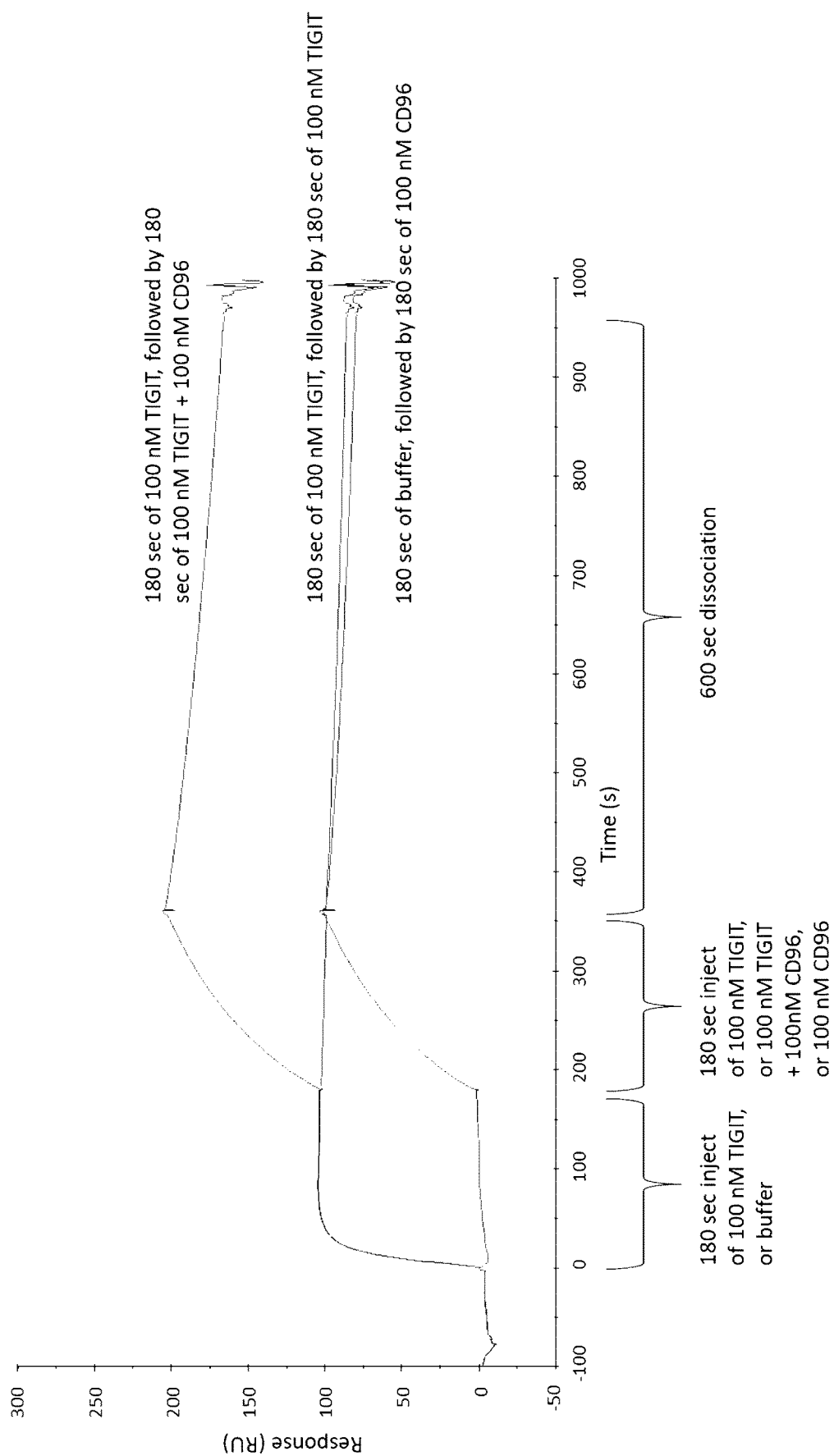
Figure 1B:
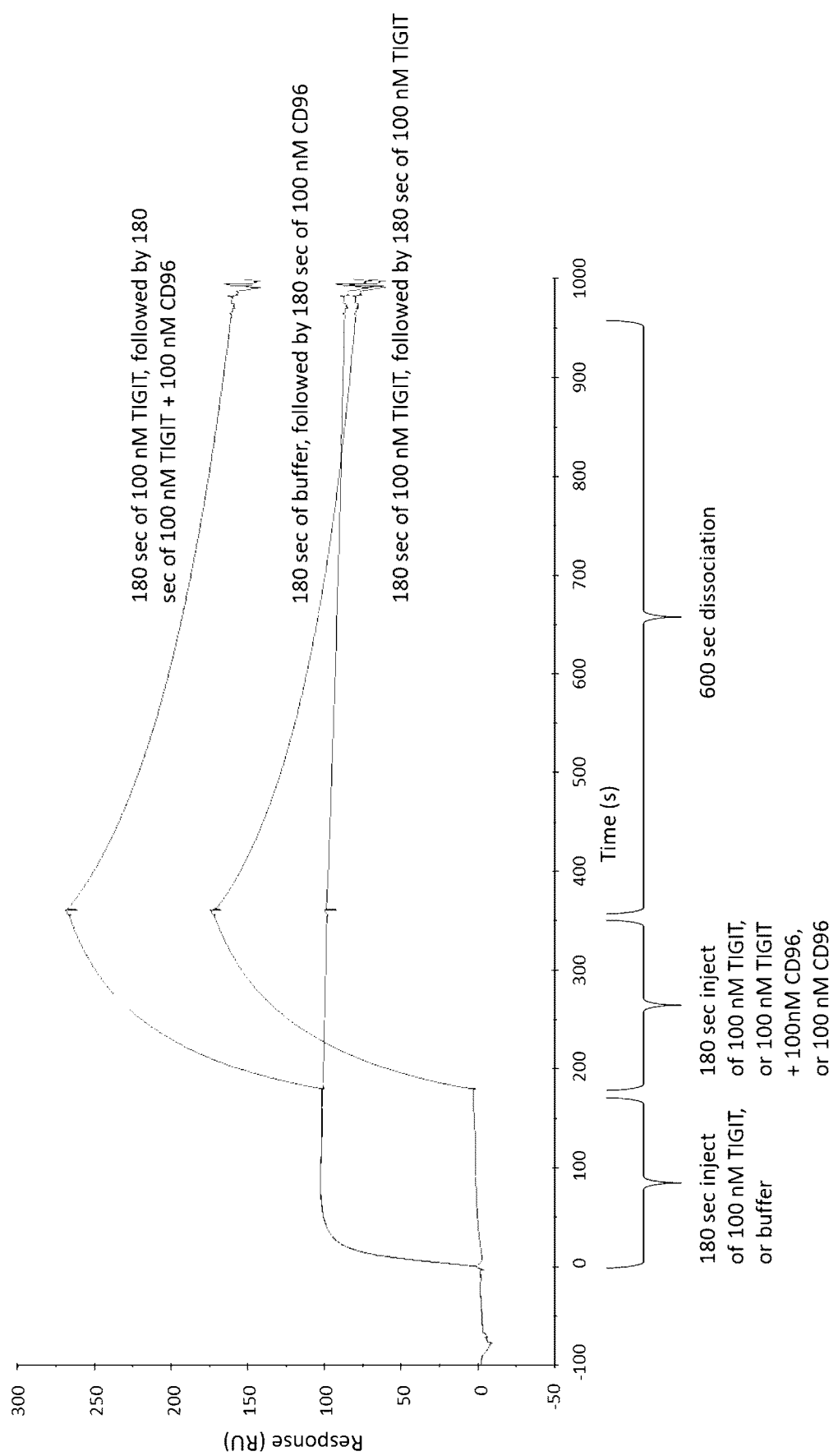
Figure 1C:
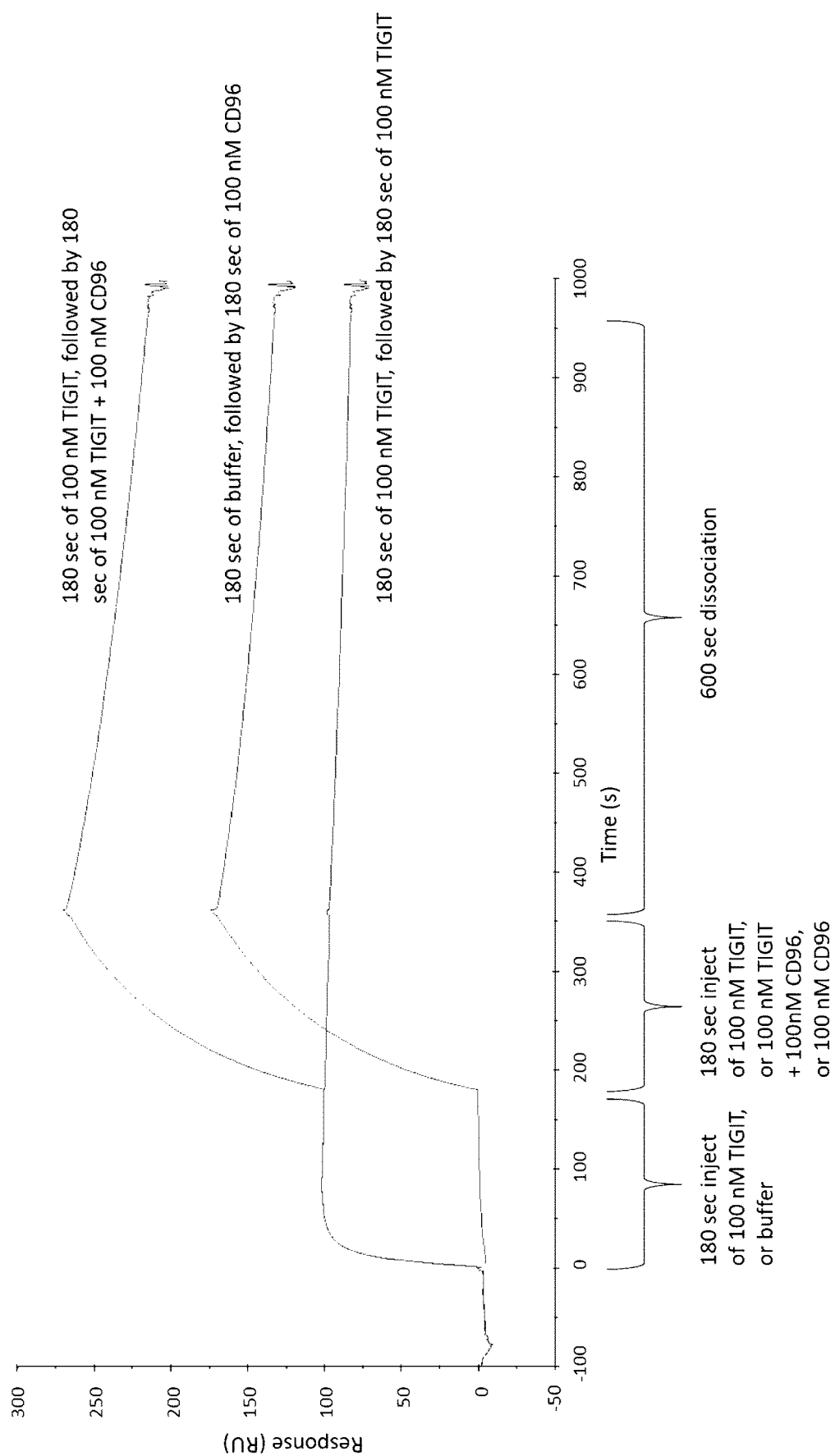

As shown in FIGS. 1A-1C, BA123 (FIG. 1A), BA125 (FIG. 1B), and BA127 (FIG. 1C) are able to simultaneously bind to human TIGIT and human CD96 proteins, as dem-

TABLE 13

Kinetic parameters of anti-TIGIT antibodies binding to full-length ECD of cynomolgus monkey TIGIT (SEQ ID NO: 114).

| | Experiment #1 | | | Experiment #2 | | | |
|---|---|---|---|---|---|---|---|
| Antibody | $k_a$ (1/Ms) | $k_d$ (1/s) | $K_D$ (M) | $k_a$ (1/Ms) | $k_d$ (1/s) | $K_D$ (M) | Geomean $K_D$ |
| BA148 | 3.34E+05 | 1.27E−03 | 3.80E−09 | 3.10E+05 | 1.26E−03 | 4.06E−09 | 3.9 nM |

8.4 Example 4: Simultaneous Dual Binding of Purified Human TIGIT and CD96 Proteins to Anti-TIGIT×CD96 Multispecific Molecules Surface Plasmon Resonance Binding Assay The ability of the multispecific molecules BA123, BA125, and BA127 to simultaneously bind to the full-length ECD of human TIGIT (SEQ ID NO: 113) and the full-length ECD of human isoform 2 of CD96 with a C89S mutation (SEQ ID NO: 63) was confirmed using surface plasmon resonance.

onstrated by the increase in signal (RU) that occurs when the TIGIT-bound multispecific molecule has a mixture of TIGIT and CD96 subsequently flowed over it, indicating binding of CD96 to the other antigen-binding region of the multispecific molecule.

Cell Binding Assay

In this example, simultaneous binding of the anti-TIGIT× CD96 multispecific molecule BA127 to CHO cells engineered to express human TIGIT or human CD96 as compared control multispecific molecules BA128, BA131, and BA133.

CHO cell lines expressing human TIGIT or human CD96 were cultured in Power CHO-2 medium containing 1 µg/mL Puromycin in shaker flasks at 37° C. For the antibody binding assay, human TIGIT or CD96-CHO cells were retrieved from the incubator and transferred to a tube containing cell culture. Cells were centrifuged at 300 g for five minutes. The supernatant was discarded, and cells resuspended in FACS buffer (cold PBS supplement with 2% Fetal Bovine Serum) were seeded in a 96-well U-bottom tissue culture plate at a density of $1\times10^5$ cells per well in 50 µL.

Antibodies were prepared in a separate microplate. Antibodies were serially diluted 1-to-3 in FACS buffer. A total of 12 working dilutions ranging from 90 µg/mL to 0.0005 µg/mL for binding to CHO-human TIGIT or 30 µg/mL to 0.0002 µg/mL for binding to CHO-human CD96 were prepared. Cells were centrifuged at 300 g for five minutes, the supernatant discarded, and cells resuspended in 50 µl of antibody mixture. Cells were incubated at 4° C. for 45 minutes. After 45 minutes the cells were washed 2× with FACS buffer and the supernatant discarded.

Figure 2A:
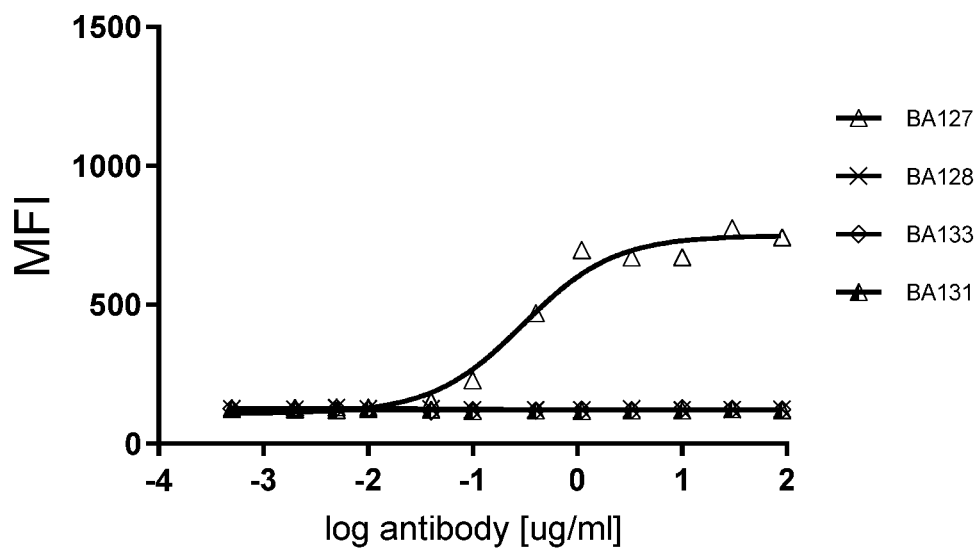
Figure 2B:
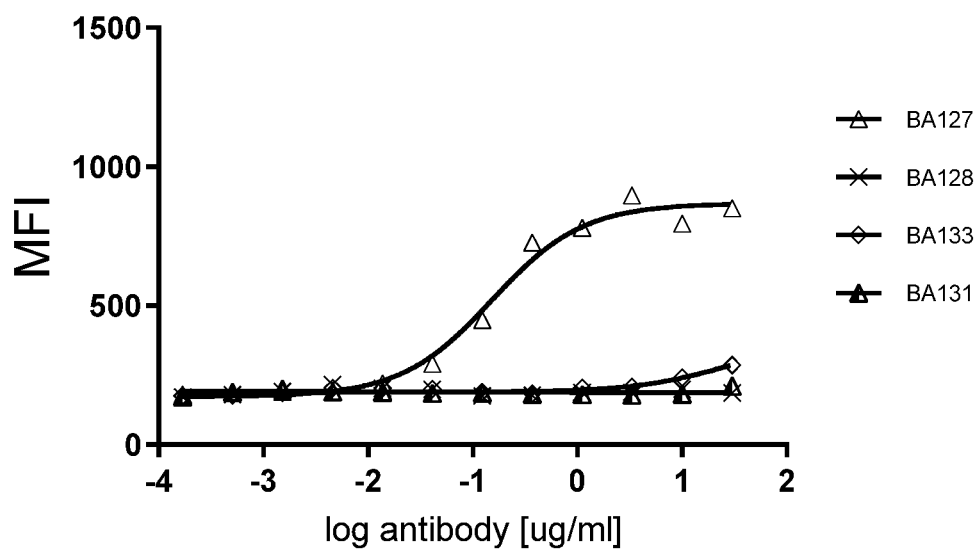
Figure 3A:
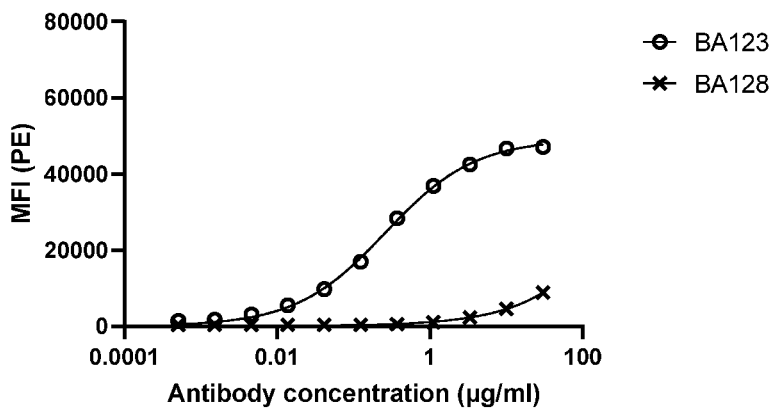
Figure 3B:
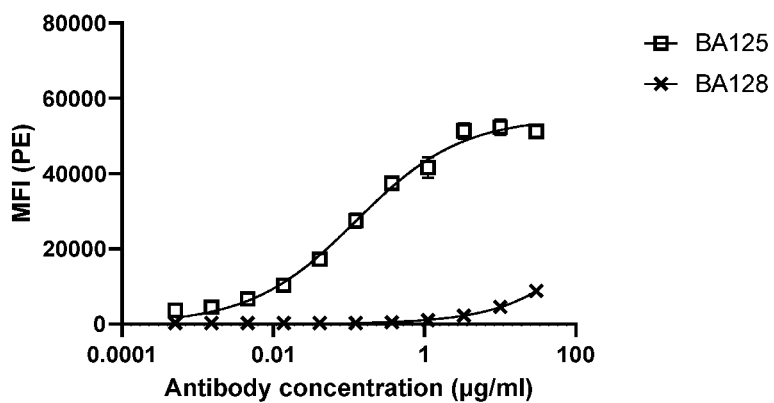
Figure 3C:
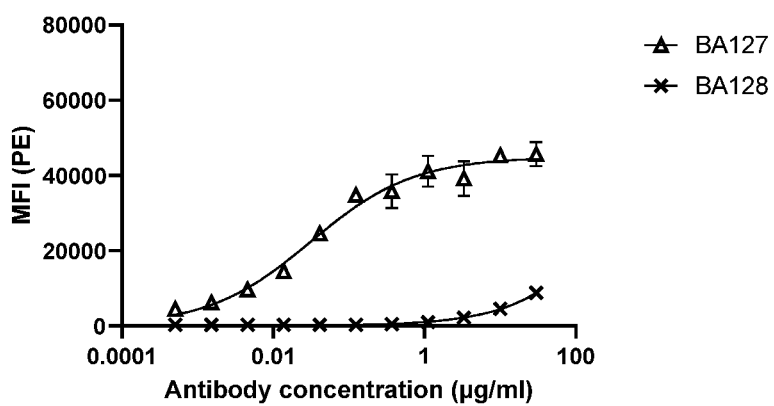
Figure 3D:
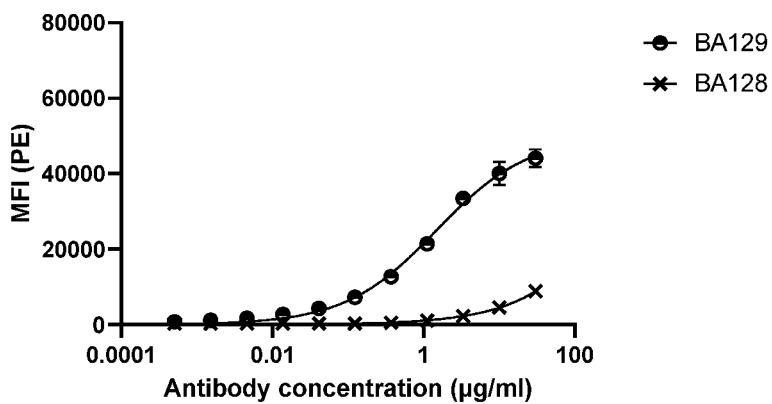
Figure 3E:
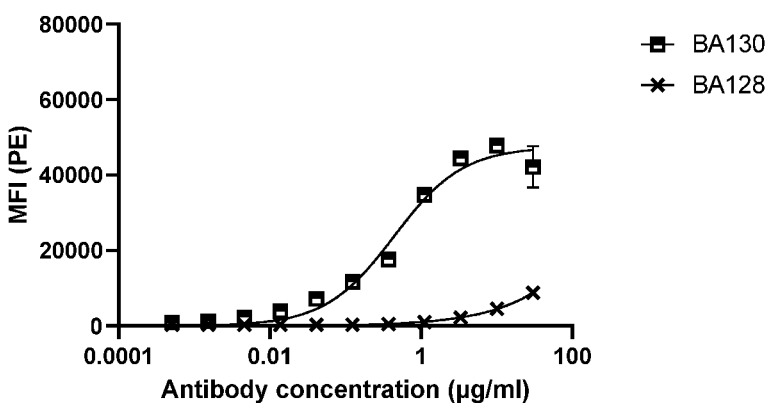
Figure 3F:
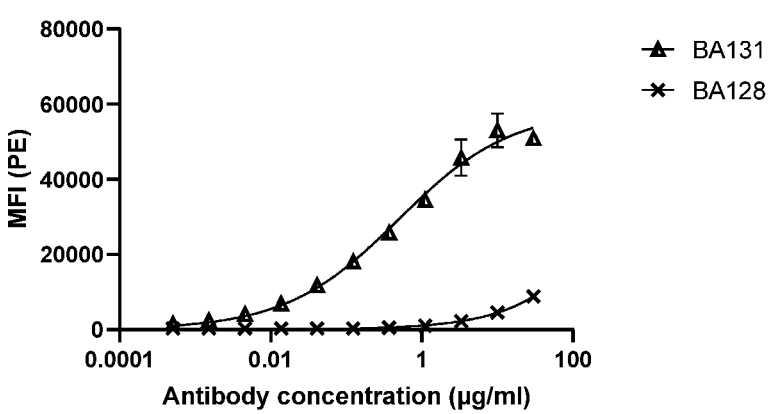
Figure 3G:
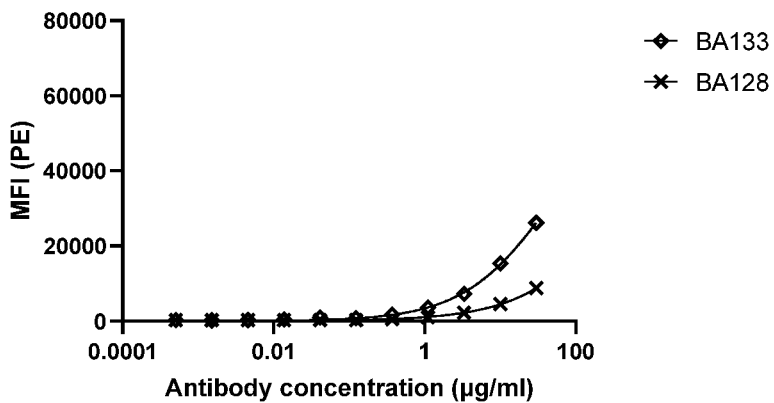
Figure 3H:
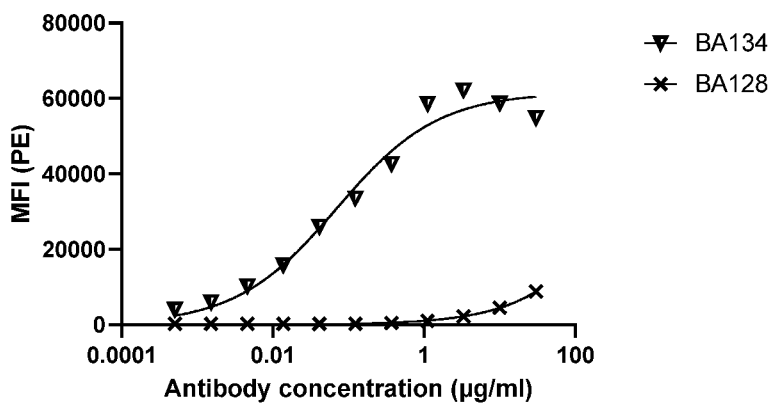
Figure 3I:
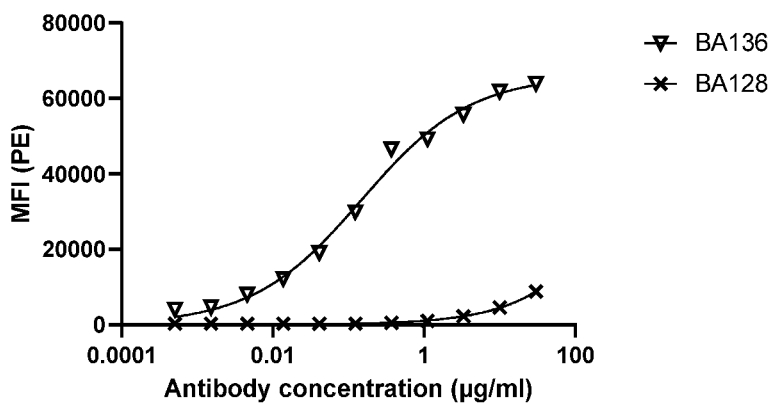
Figure 4A:
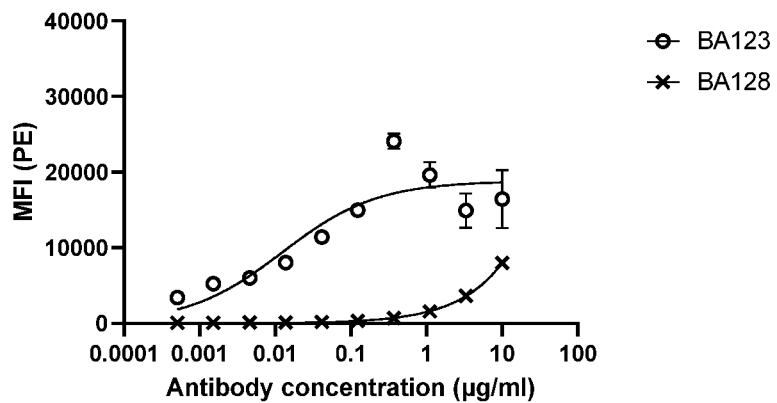
Figure 4B:
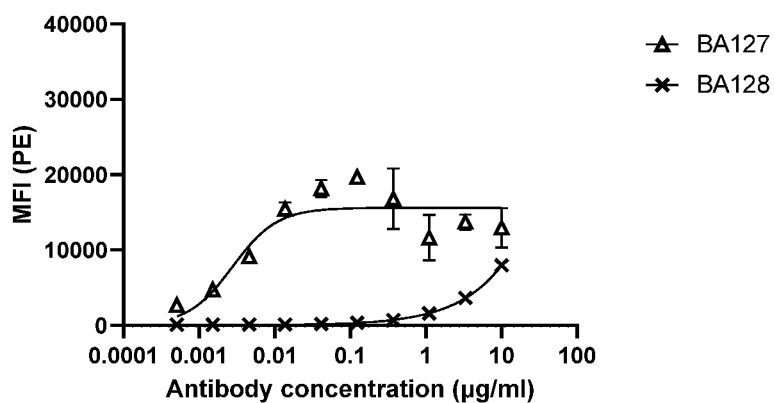
Figure 4C:
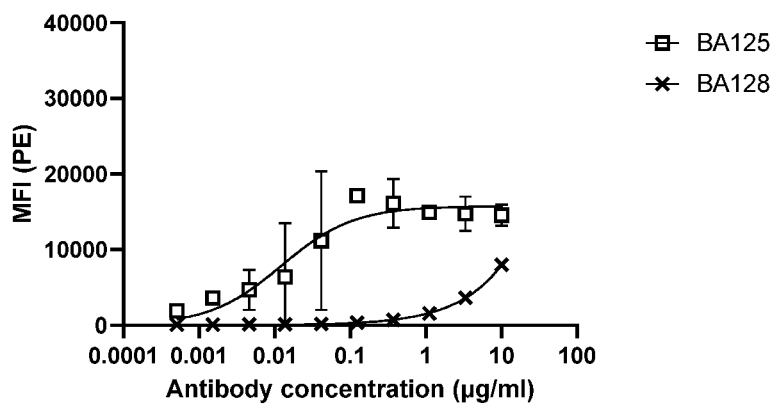
Figure 4D:
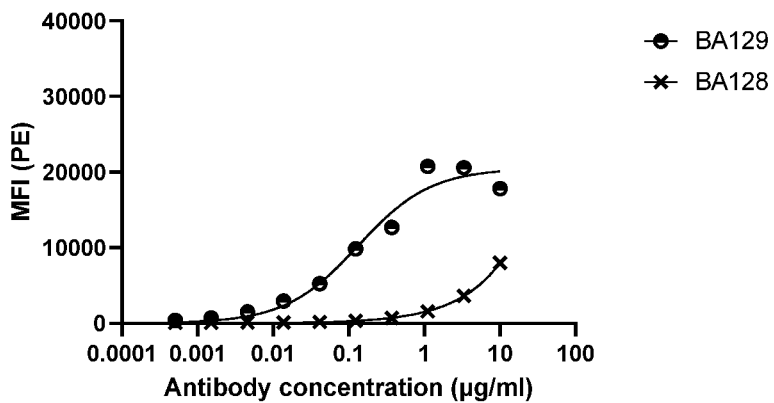
Figure 4E:
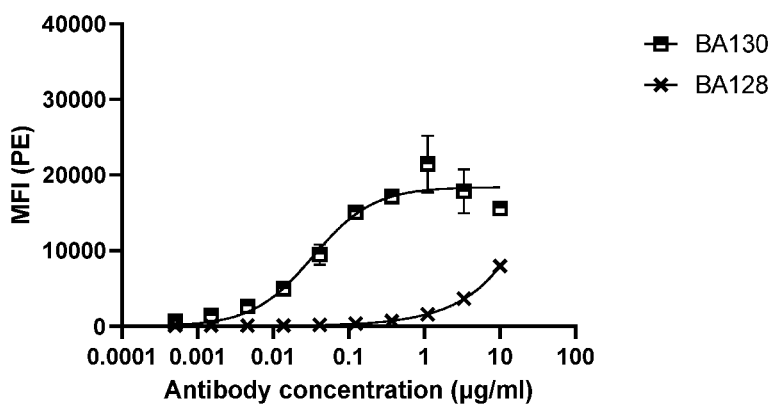
Figure 4F:
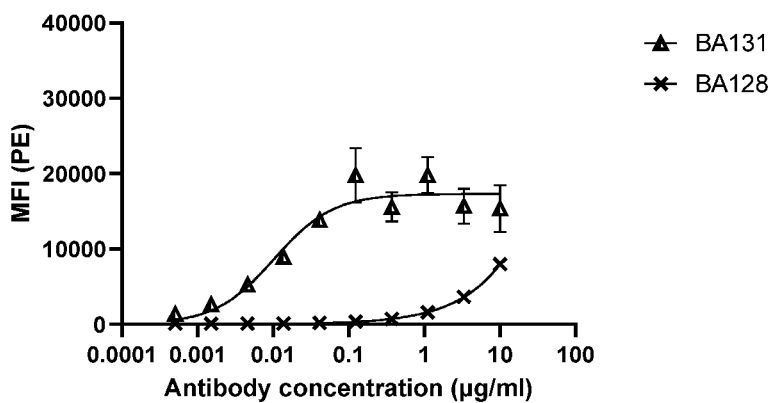
Figure 4G:
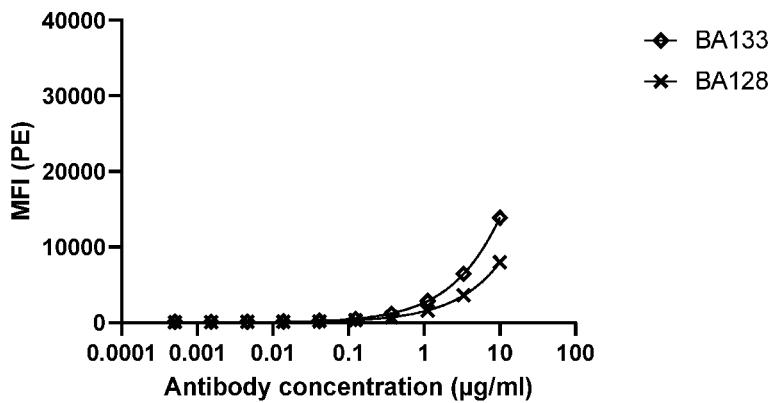
Figure 4H:
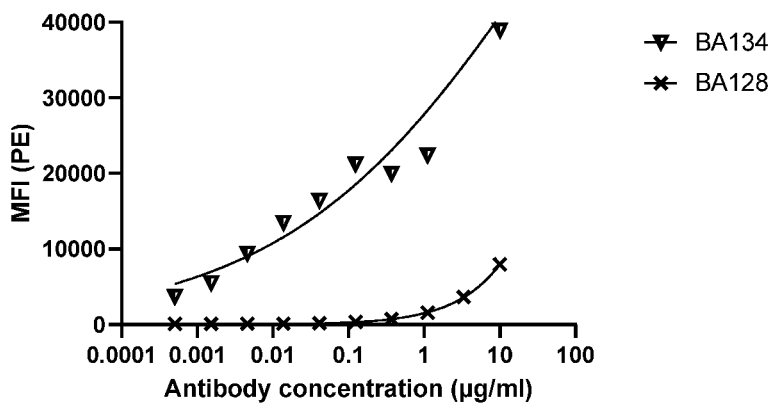
Figure 4I:
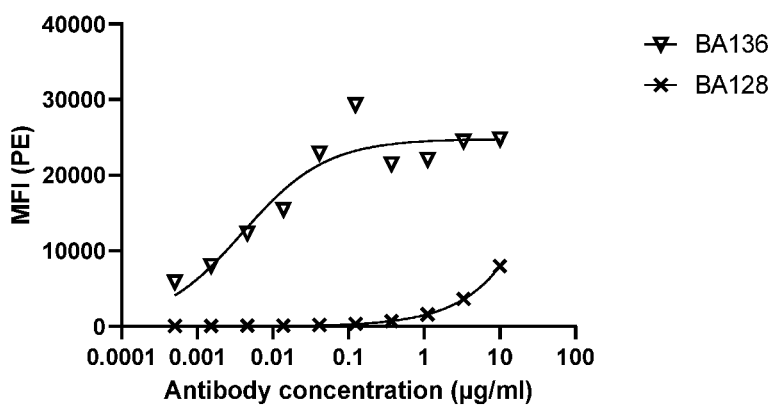
Figure 5A:
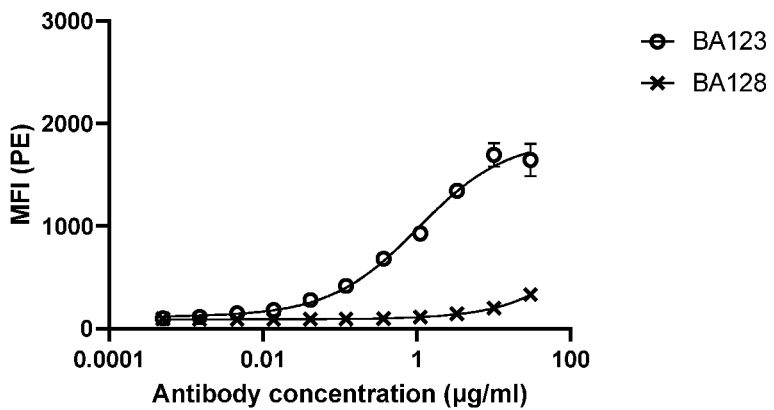
Figure 5B:
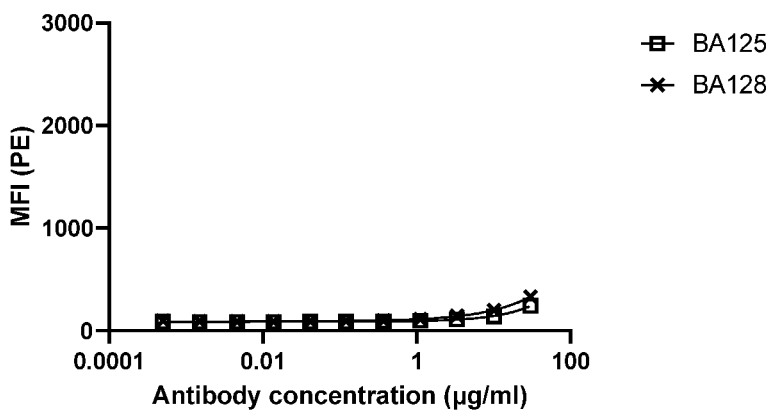
Figure 5C:
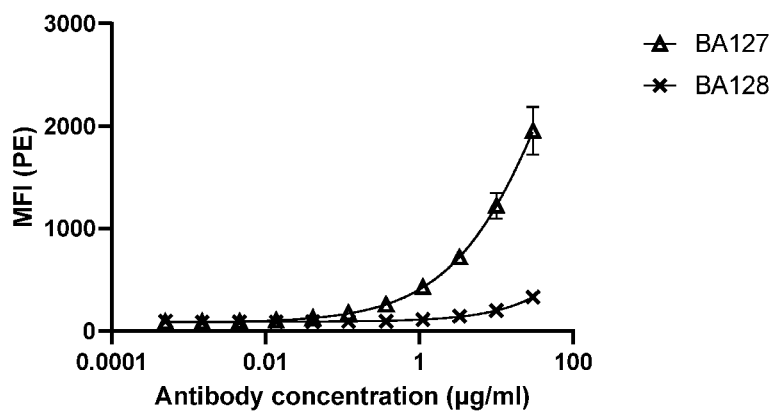
Figure 5D:
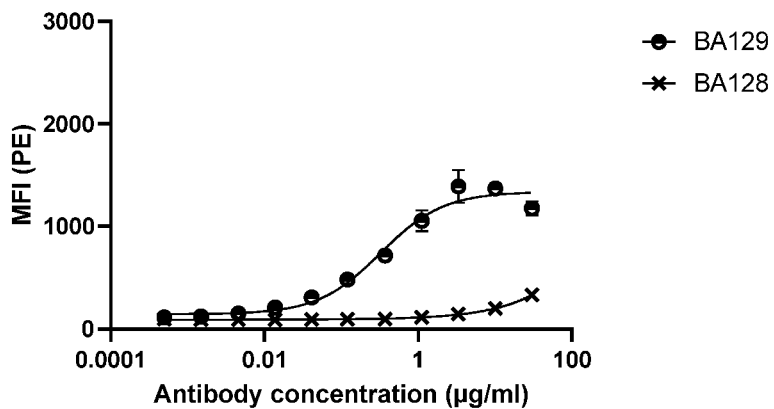
Figure 5E:
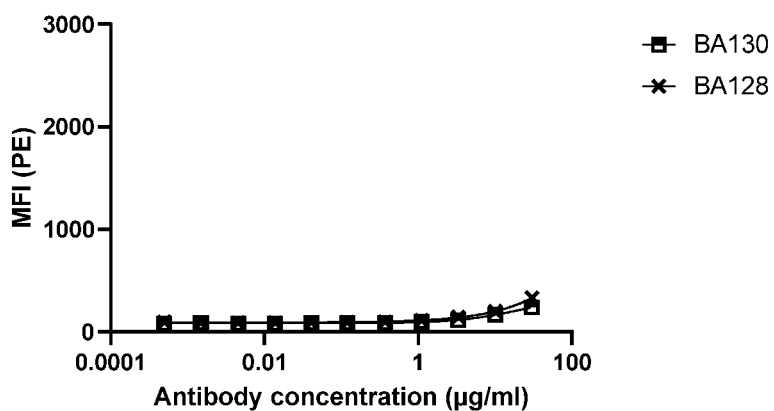
Figure 5F:
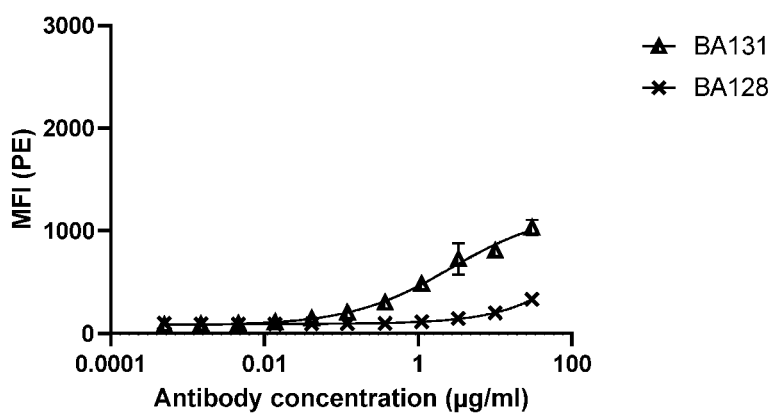
Figure 5G:
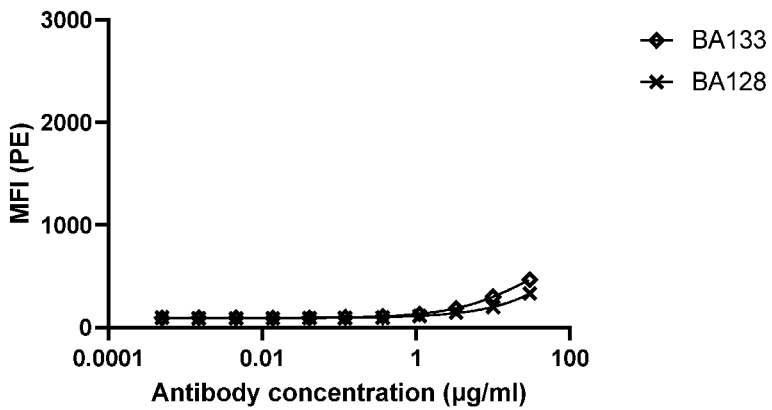
Figure 5H:
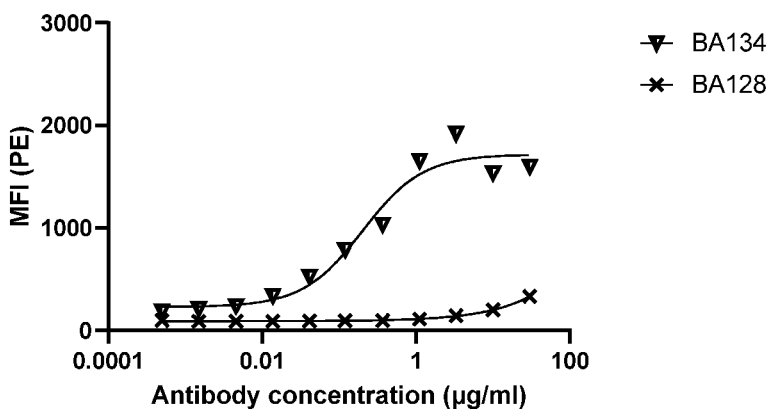
Figure 5I:
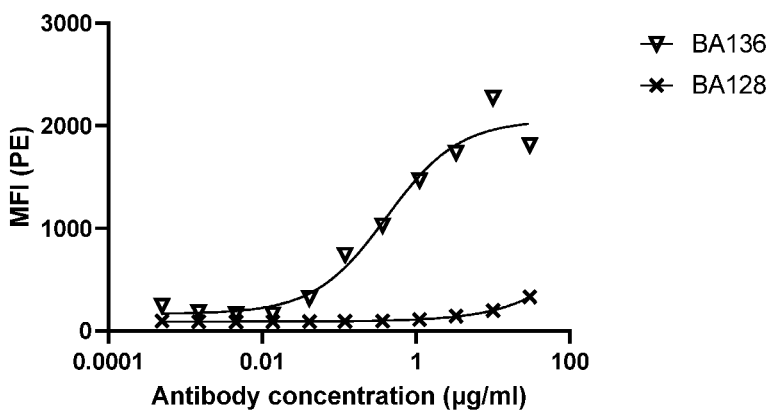
Figure 6A:
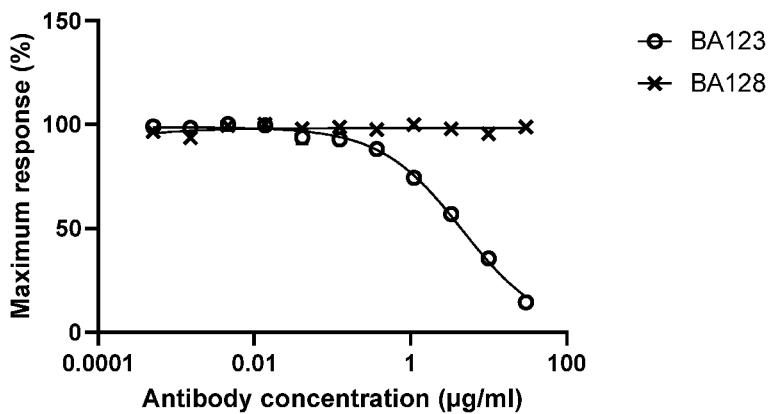
Figure 6B:
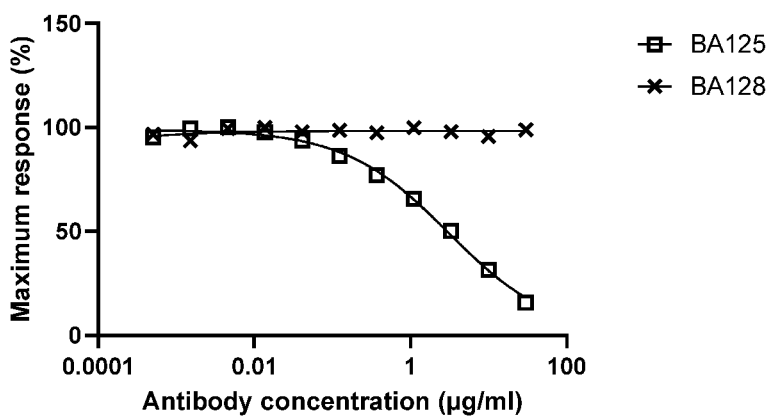
Figure 6C:
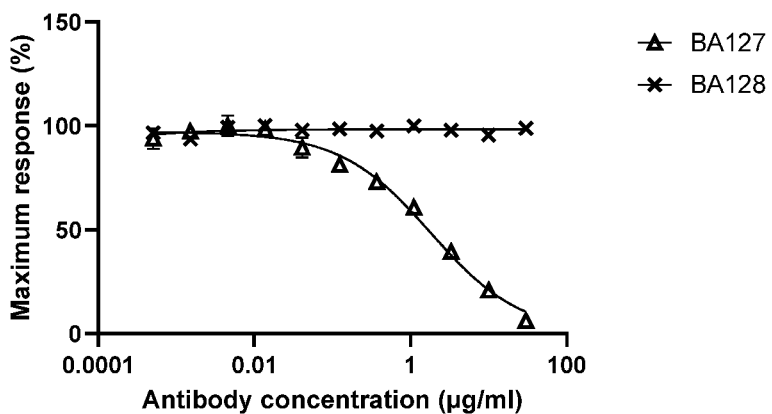
Figure 6D:
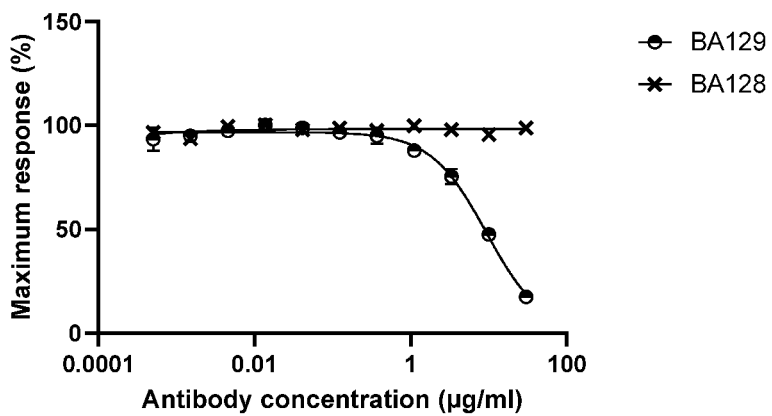
Figure 6E:
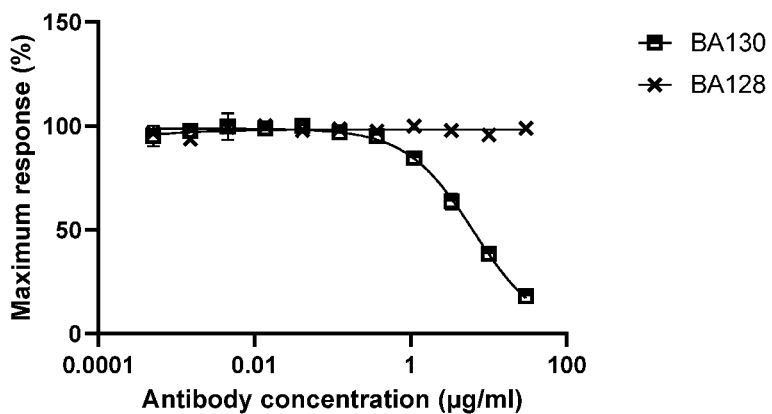
Figure 6F:
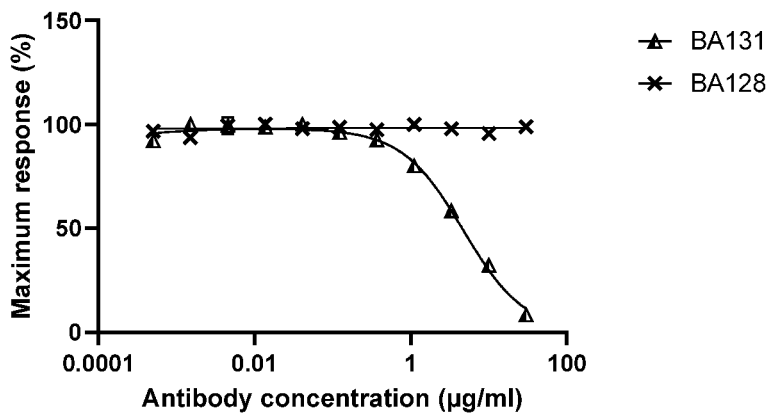
Figure 6G:
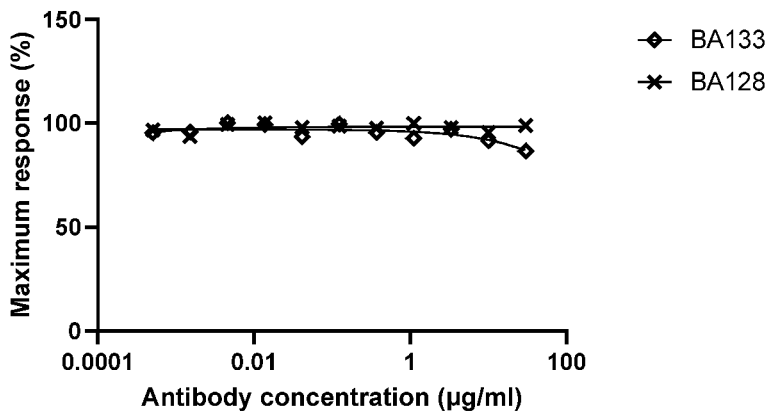
Figure 6H:
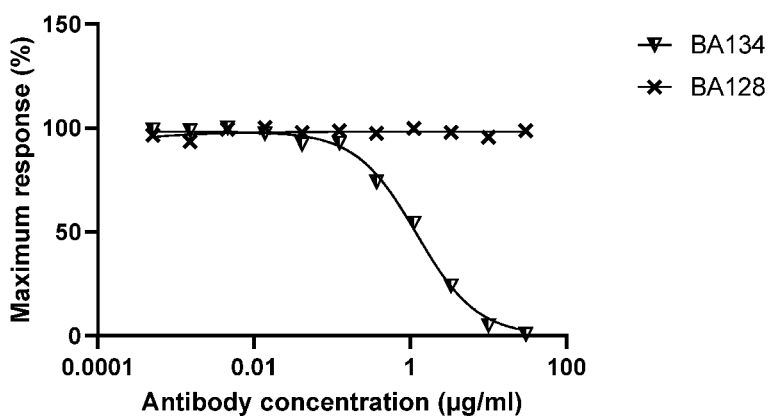
Figure 6I:
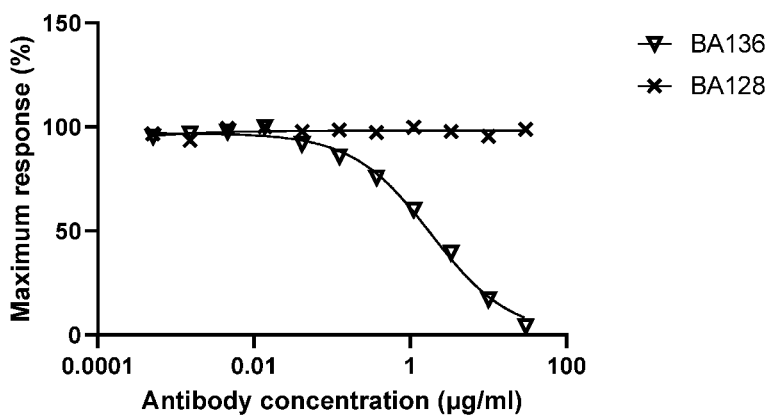
Figure 7A:
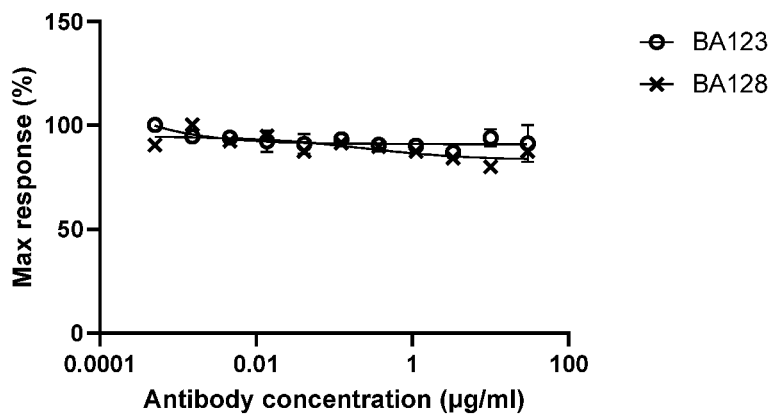
Figure 7B:
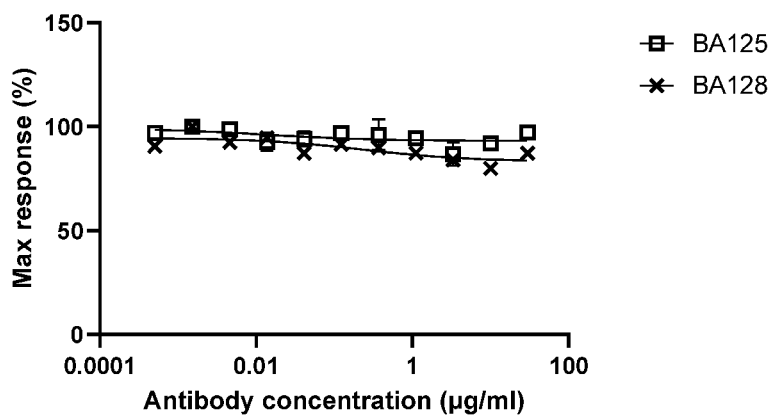
Figure 7C:
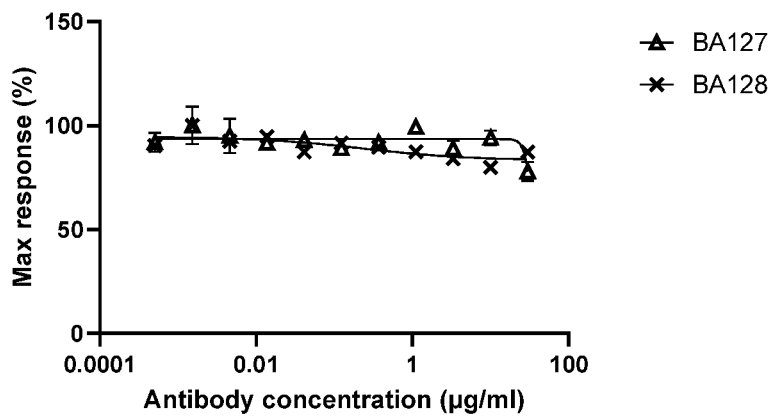
Figure 7D:
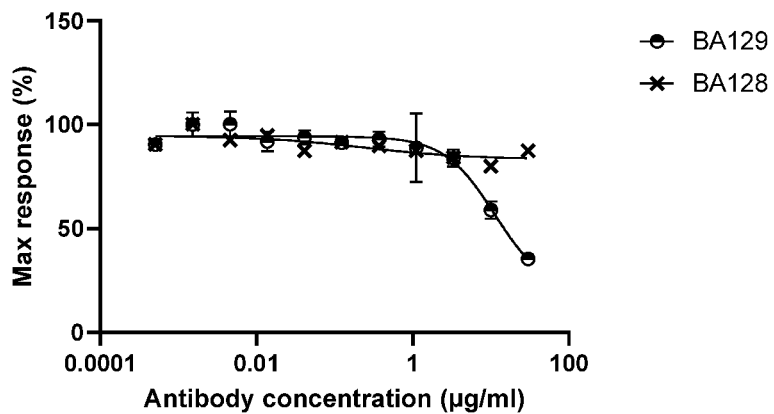
Figure 7E:
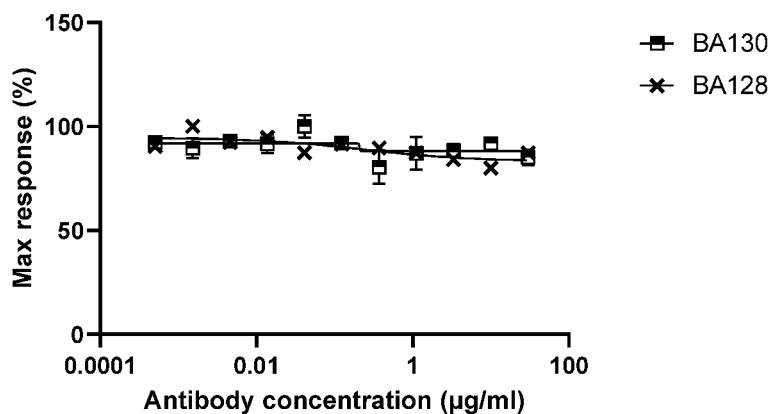
Figure 7F:
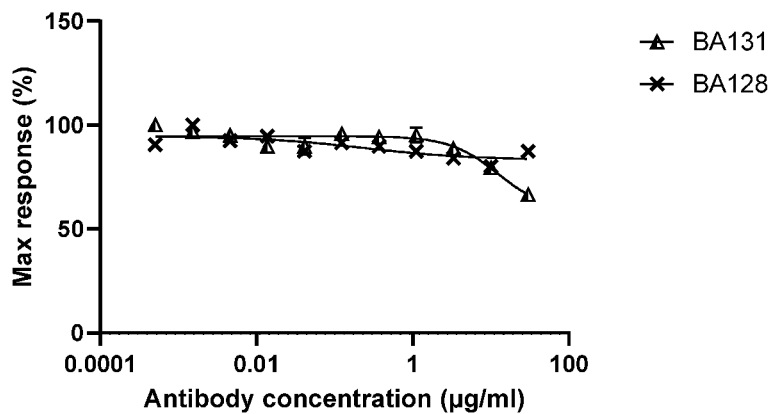
Figure 7G:
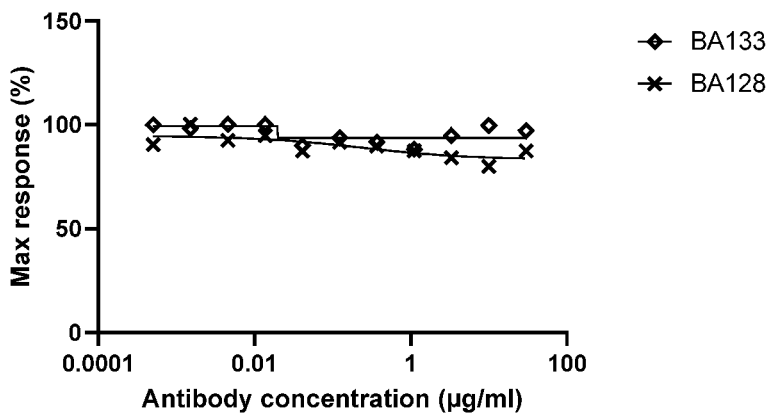
Figure 7H:
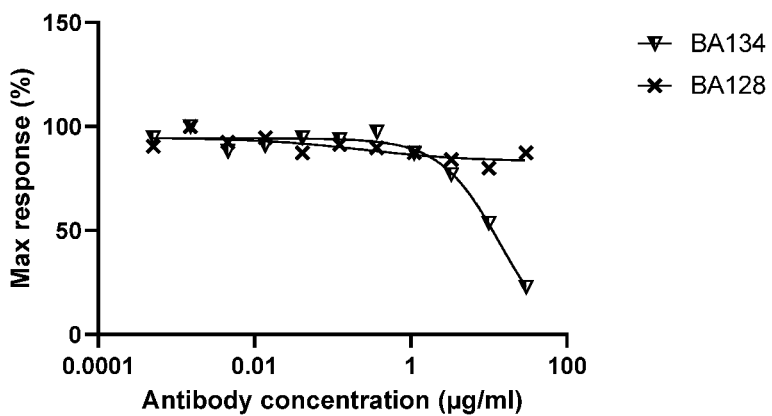
Figure 7I:
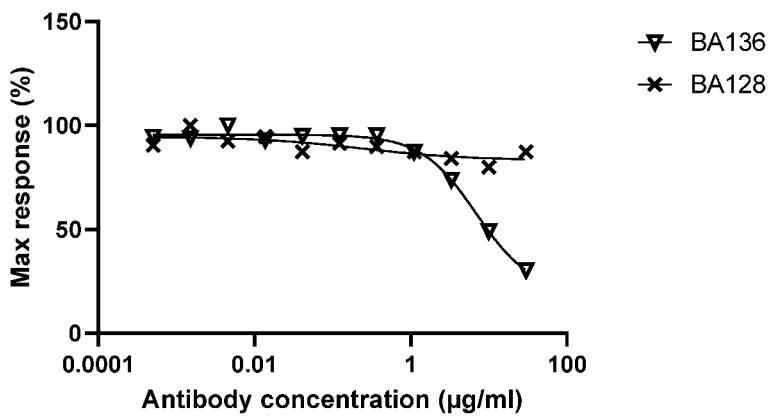
Figure 8A:
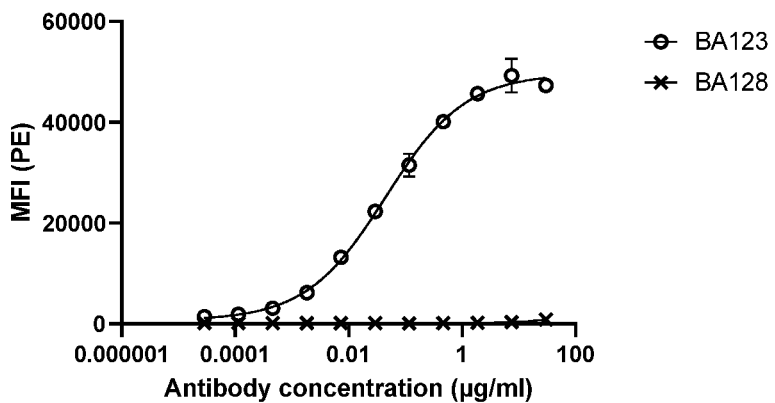
Figure 8B:
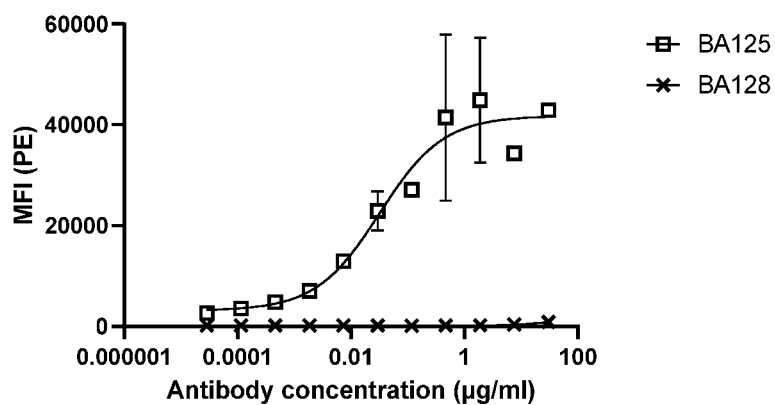
Figure 8C:
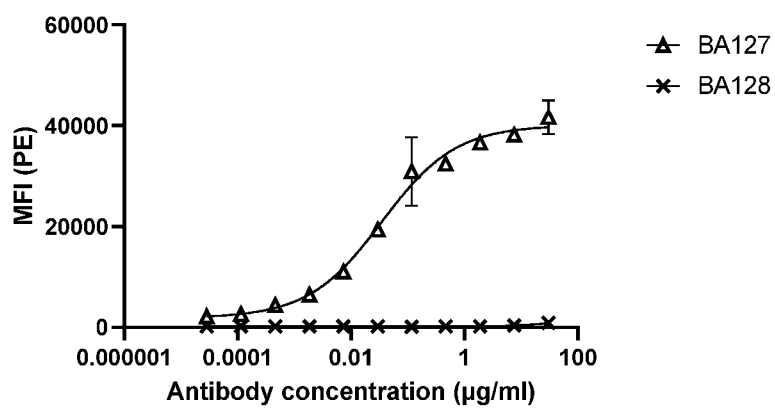
Figure 8D:
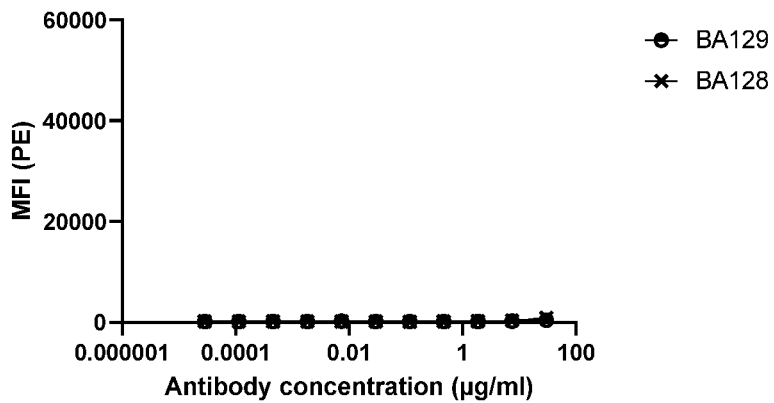
Figure 8E:
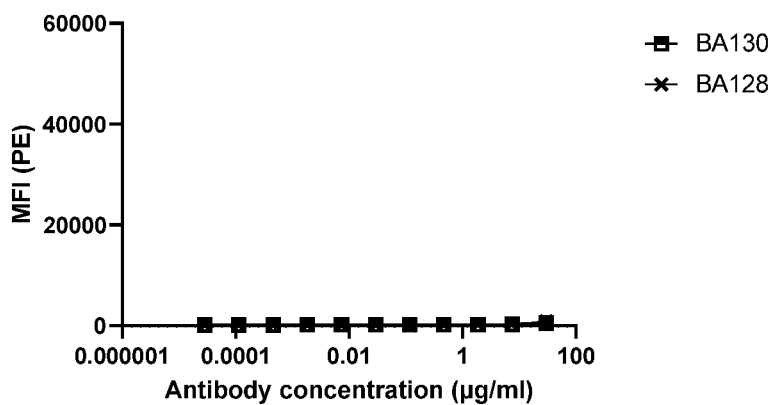
Figure 8F:
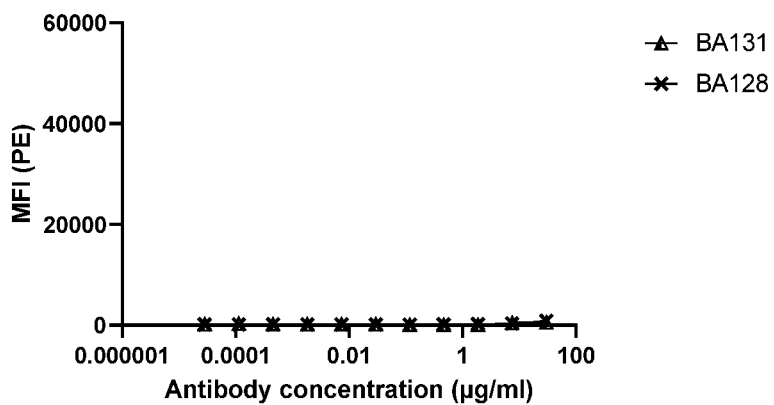
Figure 8G:
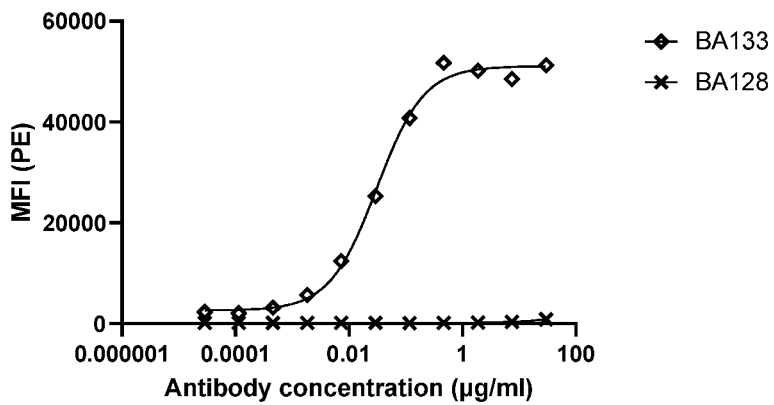
Figure 8H:
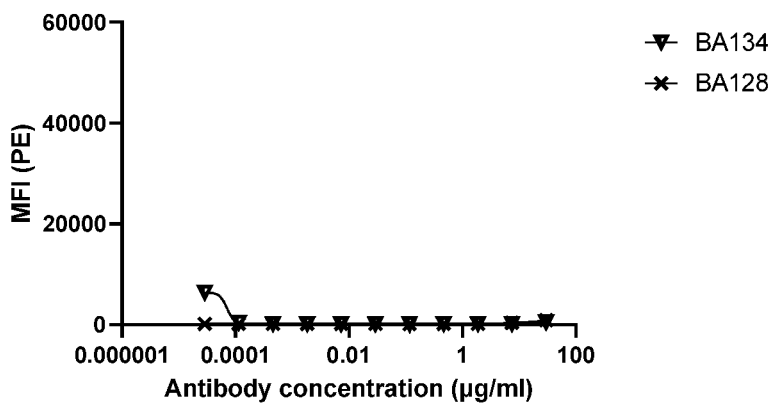
Figure 8I:
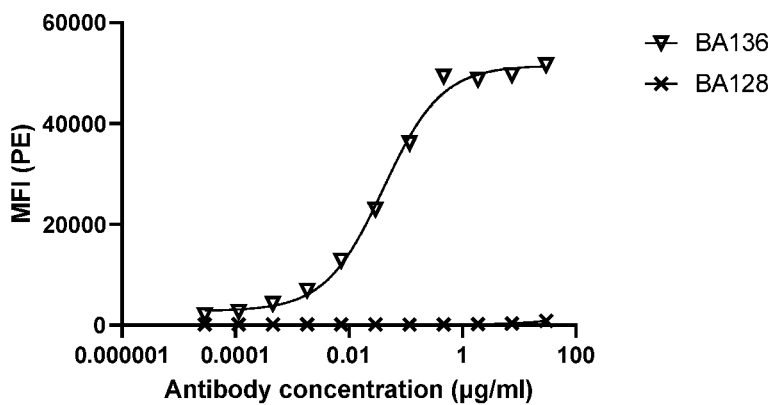
Figure 9A:
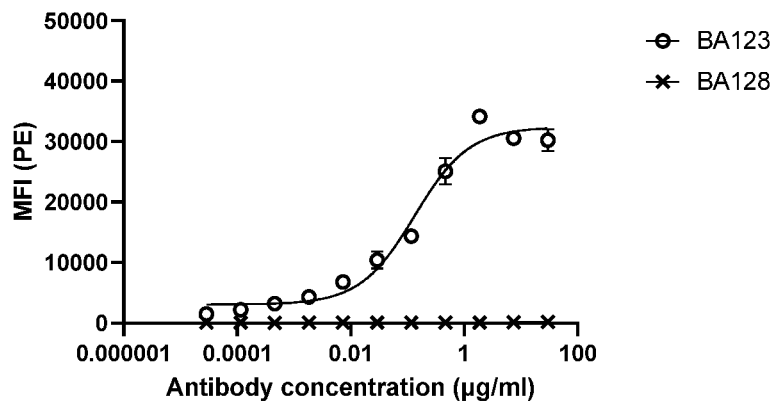
Figure 9B:
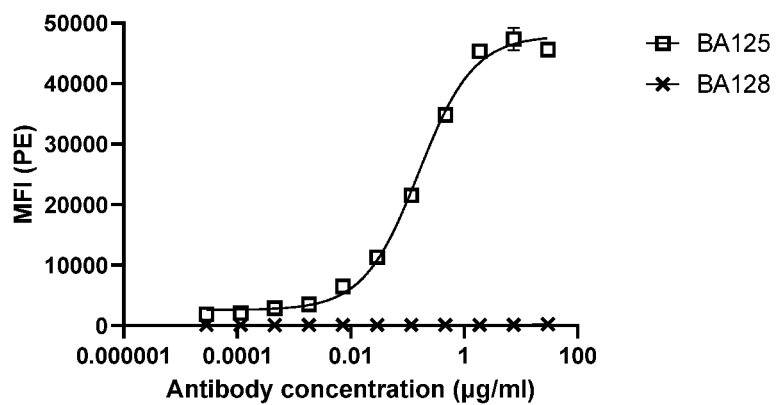
Figure 9C:
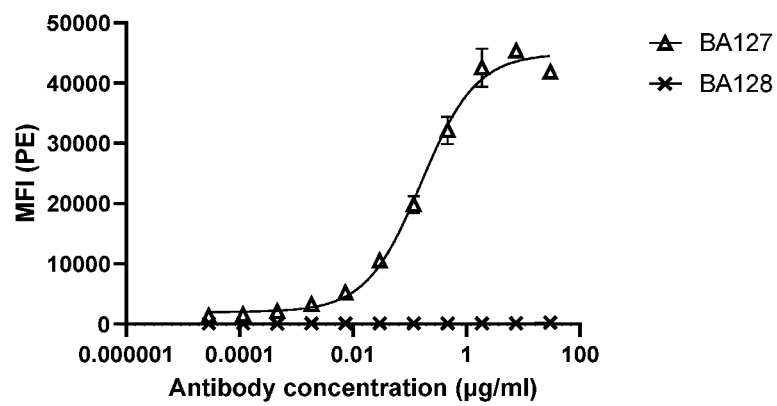
Figure 9D:
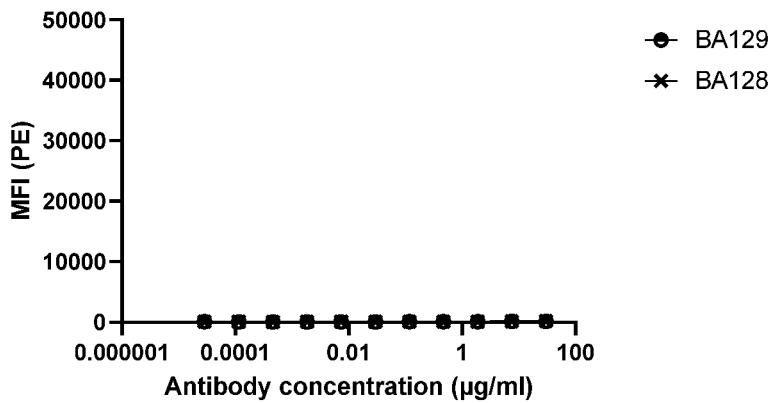
Figure 9E:
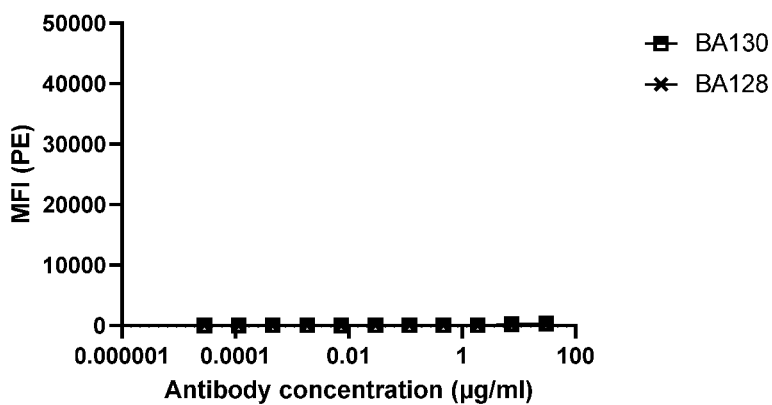
Figure 9F:
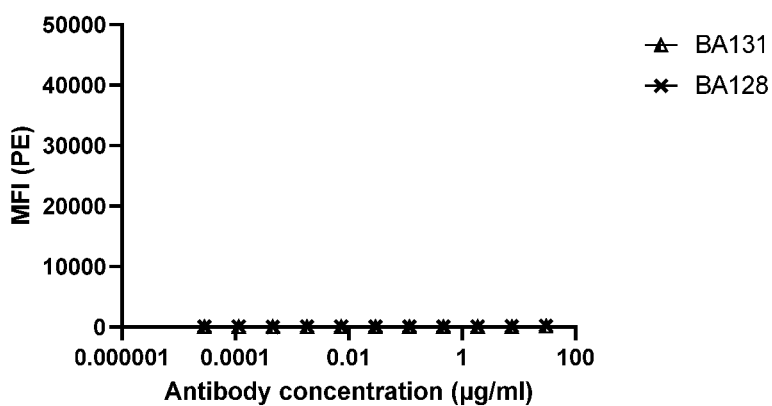
Figure 9G:
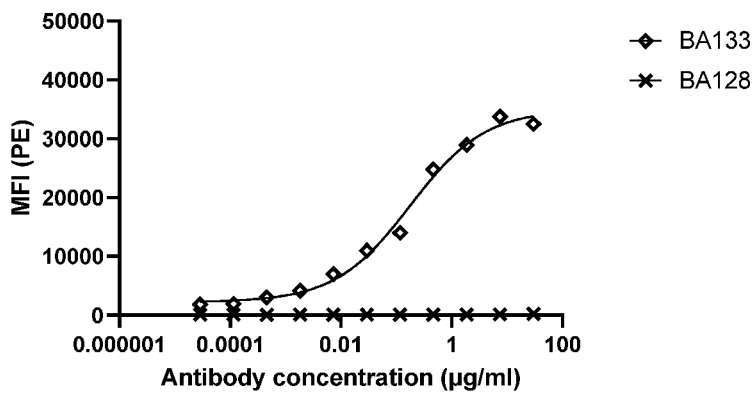
Figure 9H:
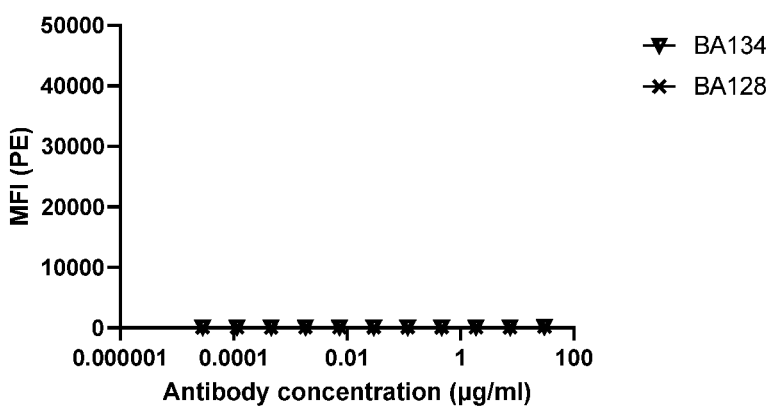
Figure 9I:
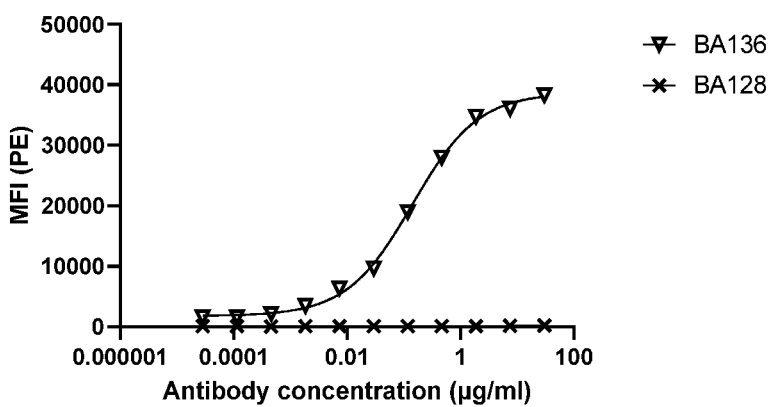
Figure 10A:
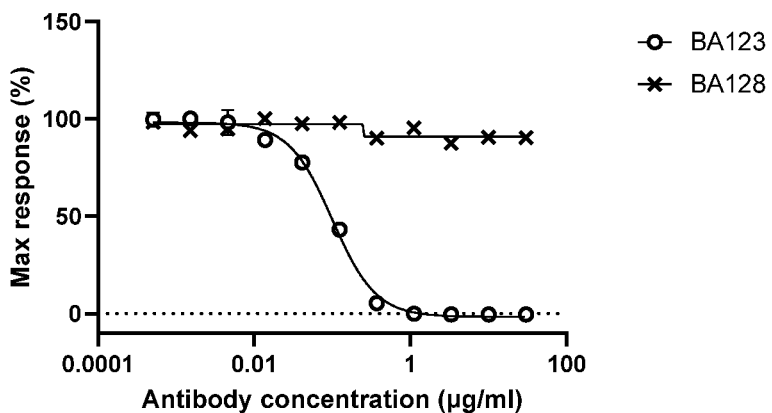
Figure 10B:
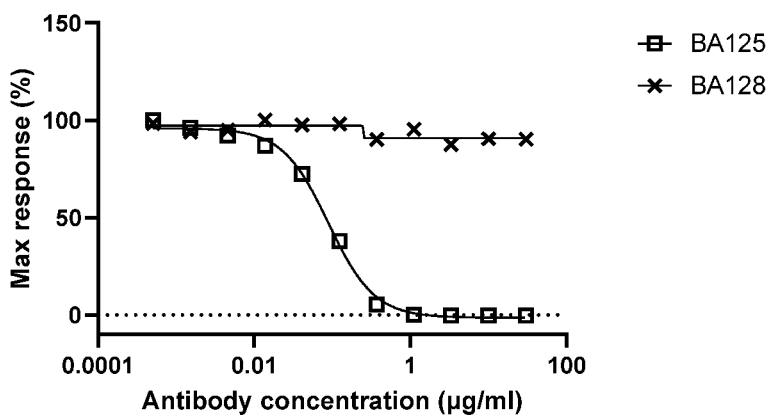
Figure 10C:
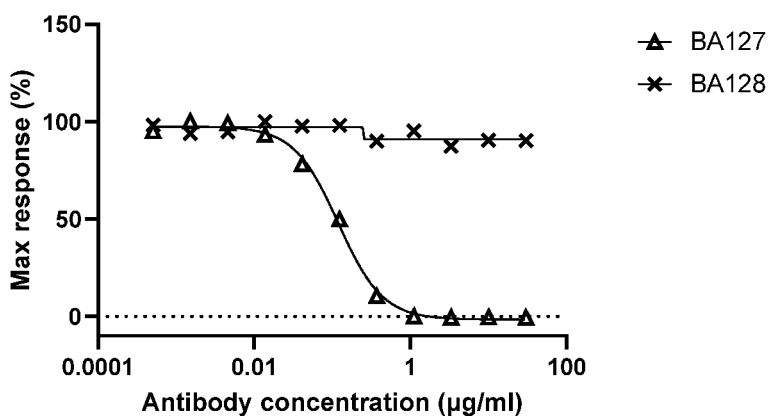
Figure 10D:
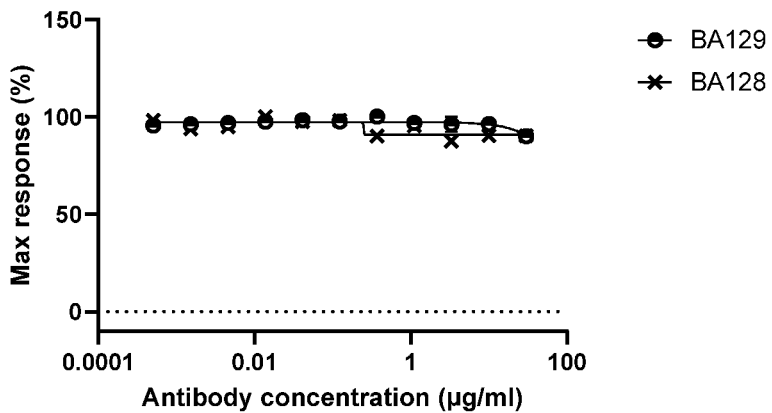
Figure 10E:
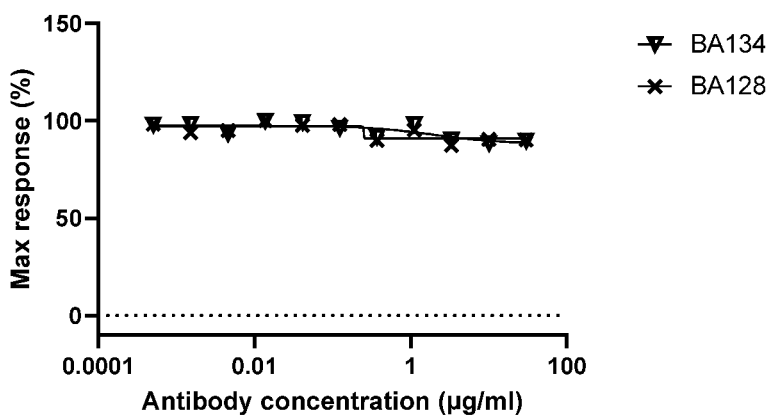
Figure 10F:
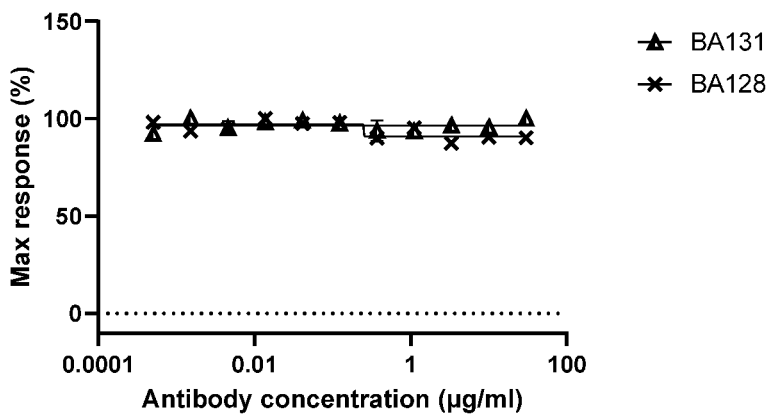
Figure 10G:
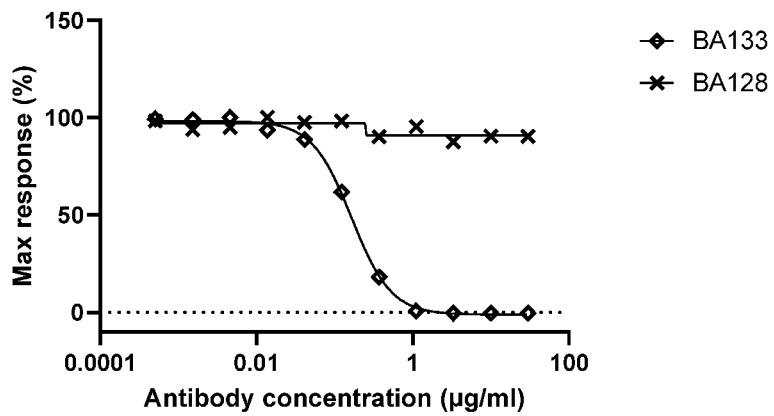
Figure 10H:
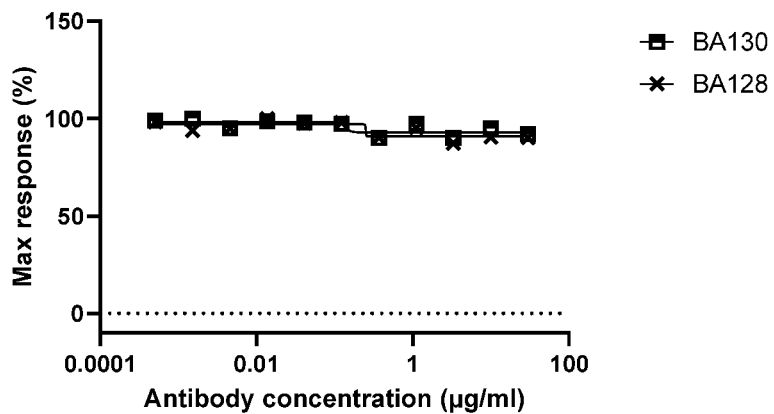
Figure 10I:
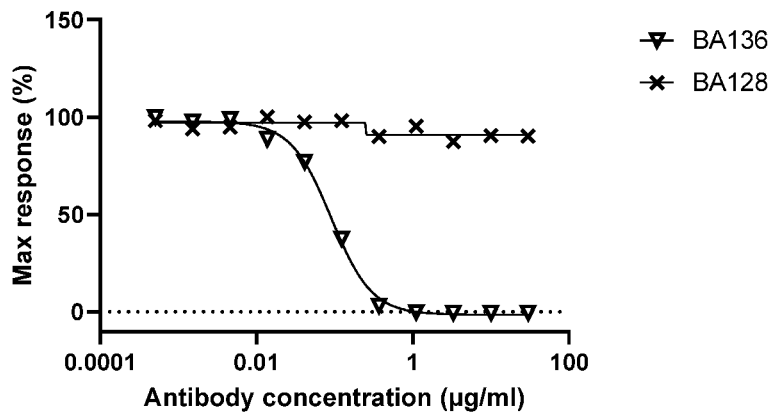
Figure 11A:
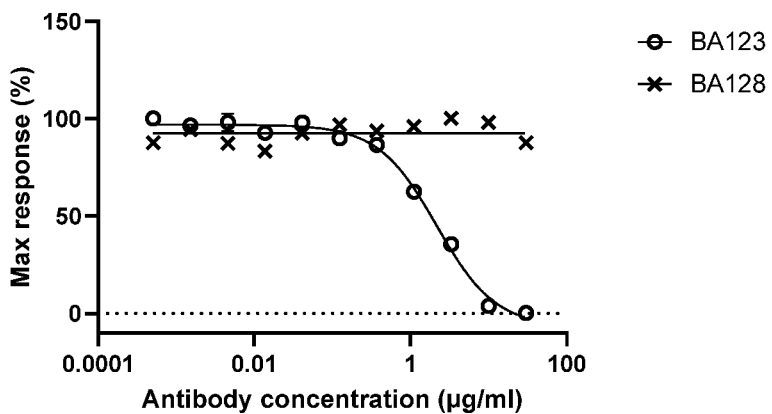
Figure 11B:
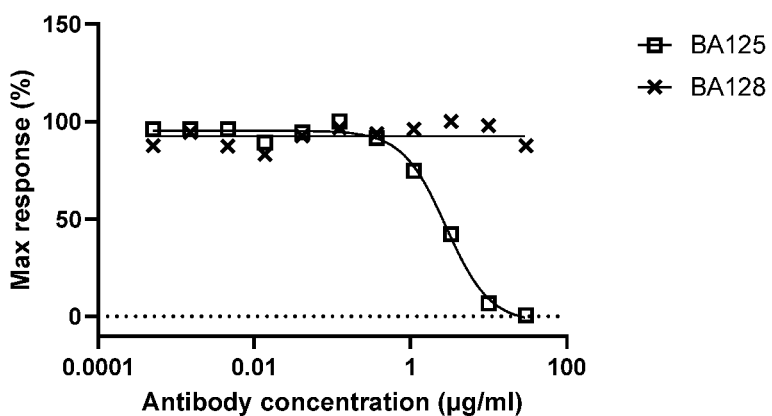
Figure 11C:
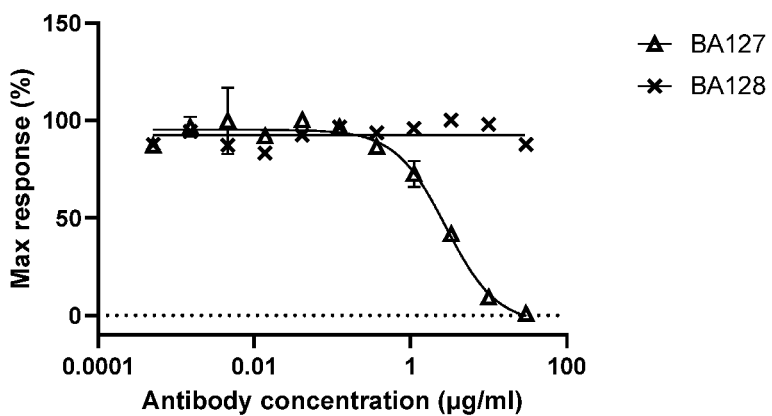
Figure 11D:
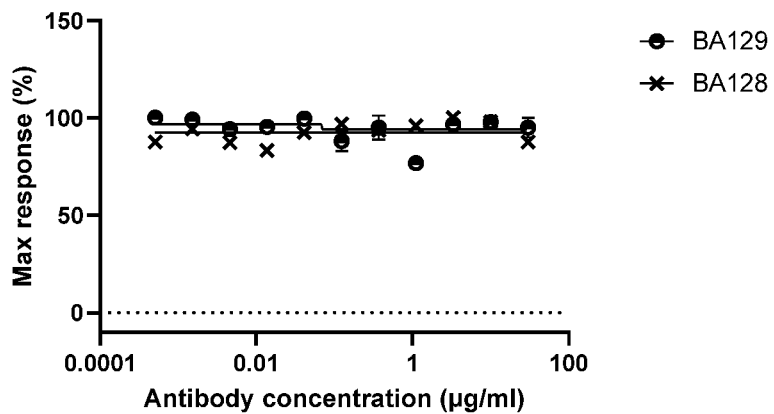
Figure 11E:
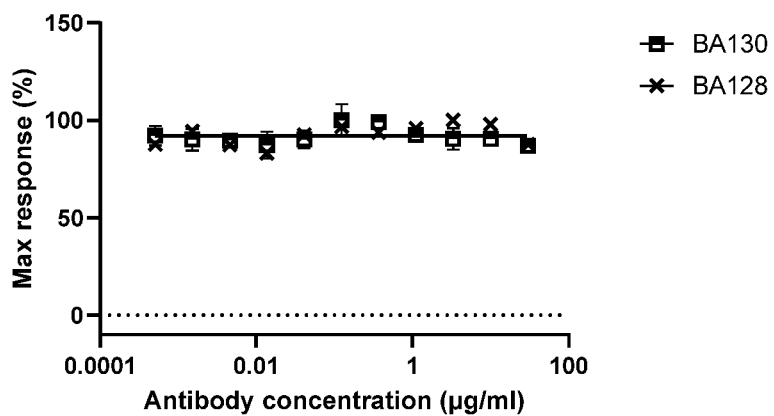
Figure 11F:
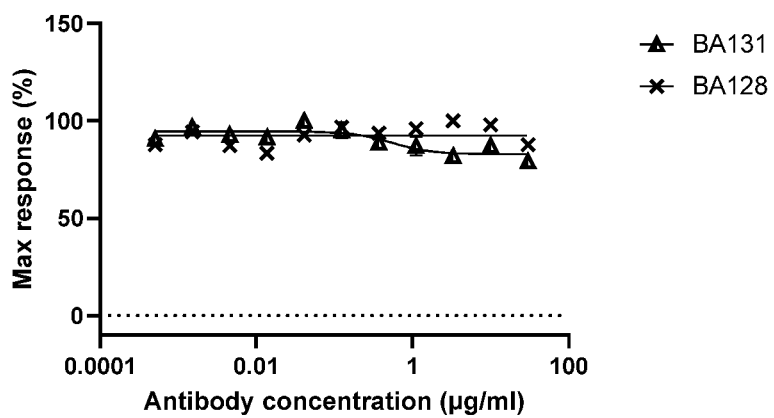
Figure 11G:
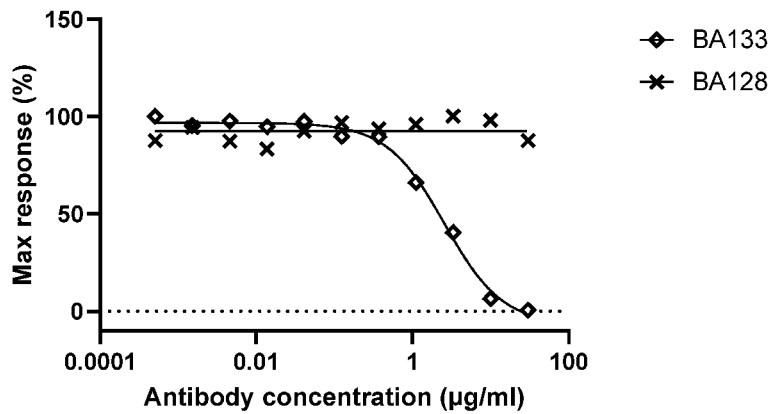
Figure 11H:
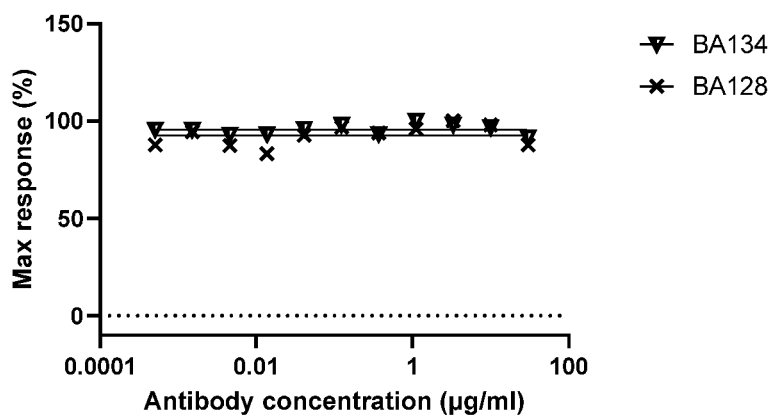
Figure 11I:
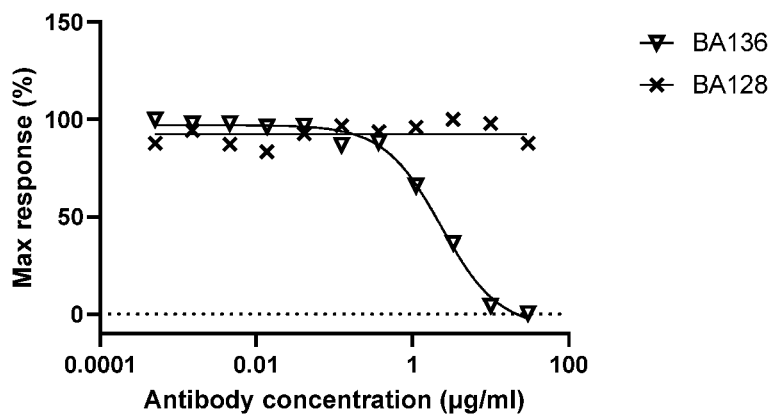
Figure 12A:
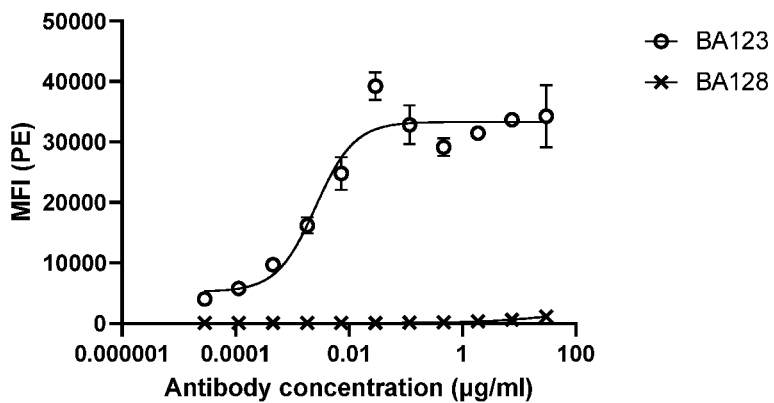
Figure 12B:
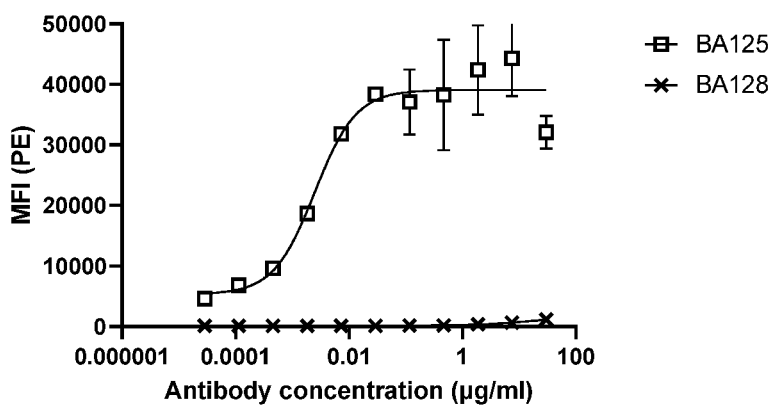
Figure 12C:
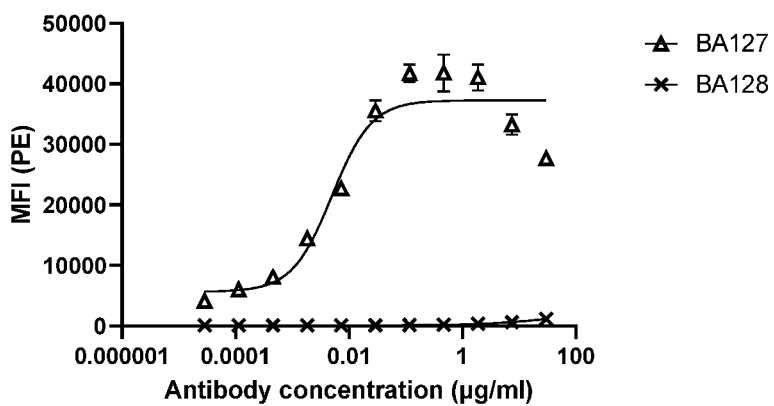
Figure 12D:
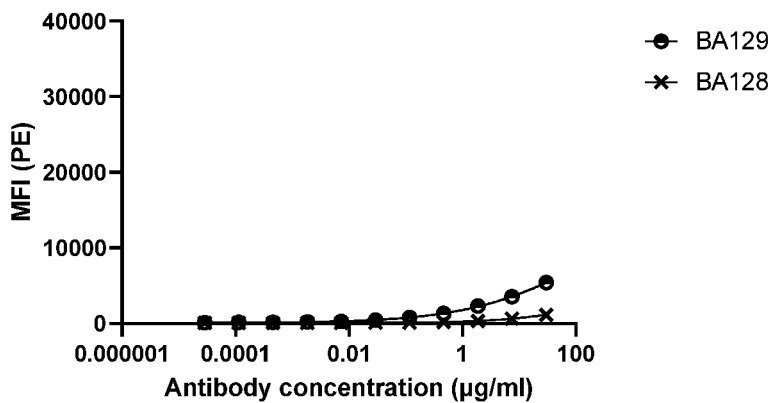
Figure 12E:
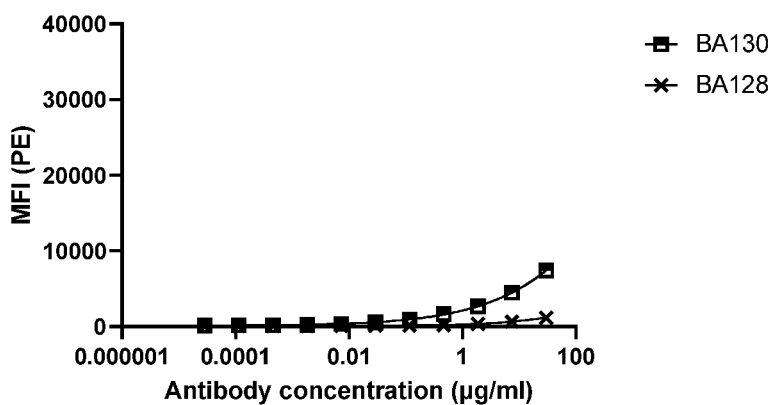
Figure 12F:
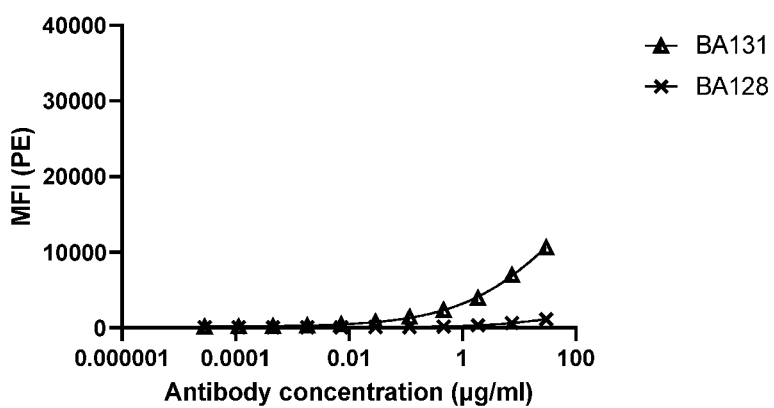
Figure 12G:
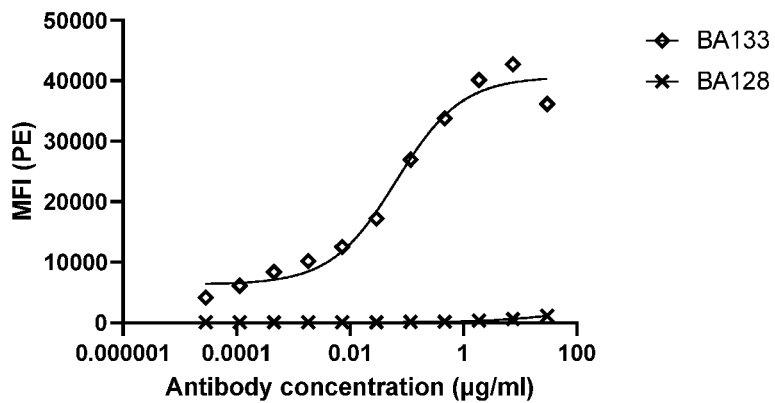
Figure 12H:
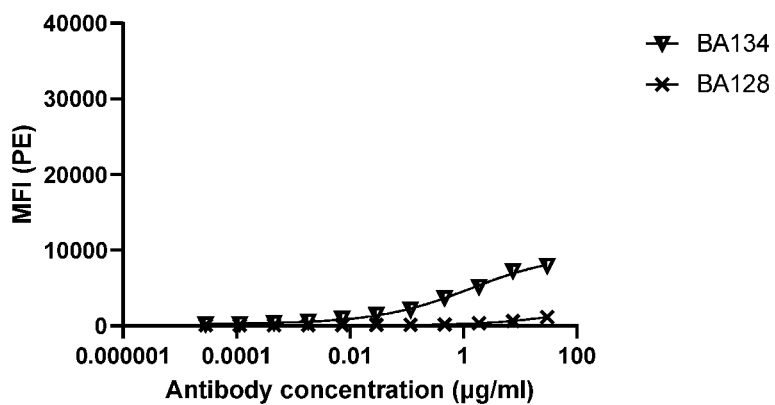
Figure 12I:
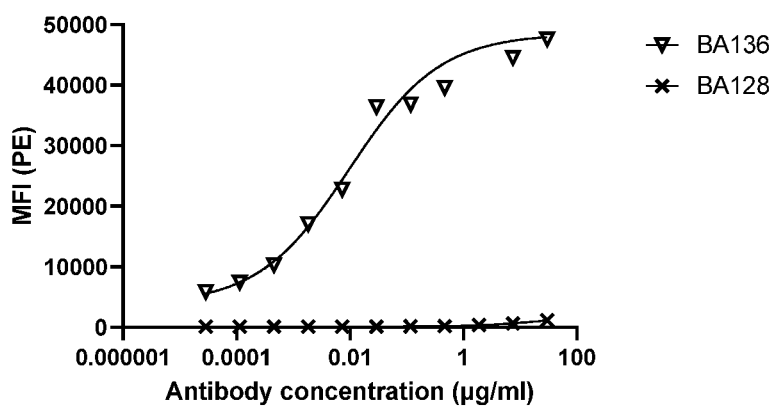
Figure 13A:
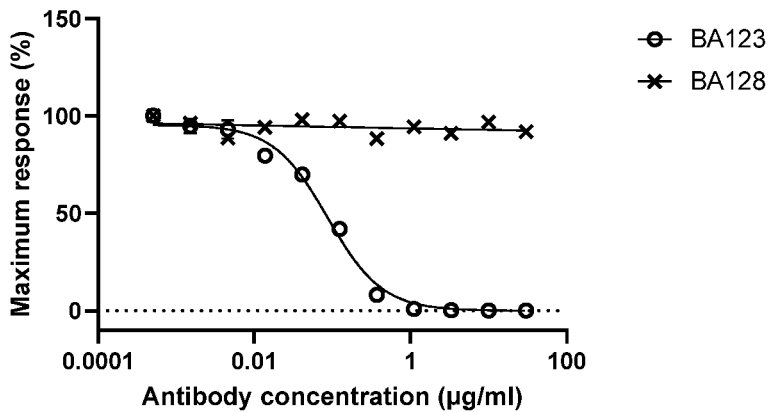
Figure 13B:
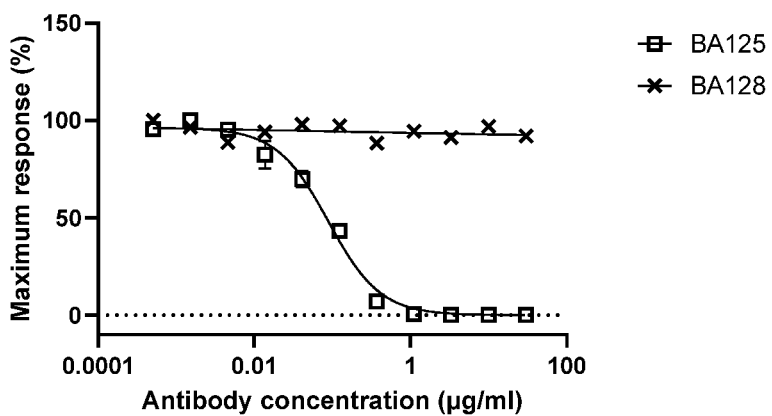
Figure 13C:
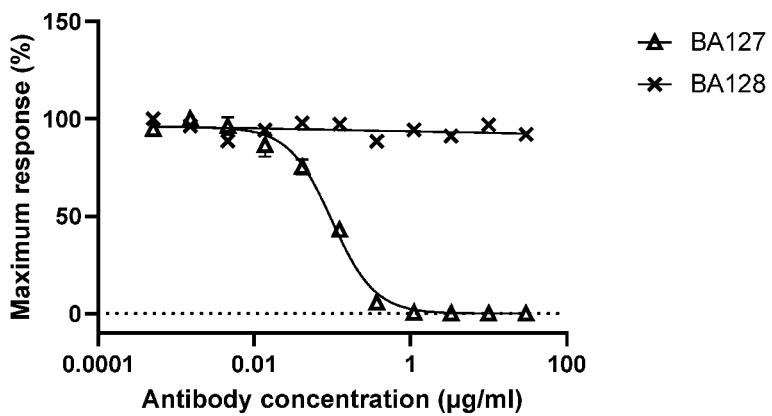
Figure 13D:
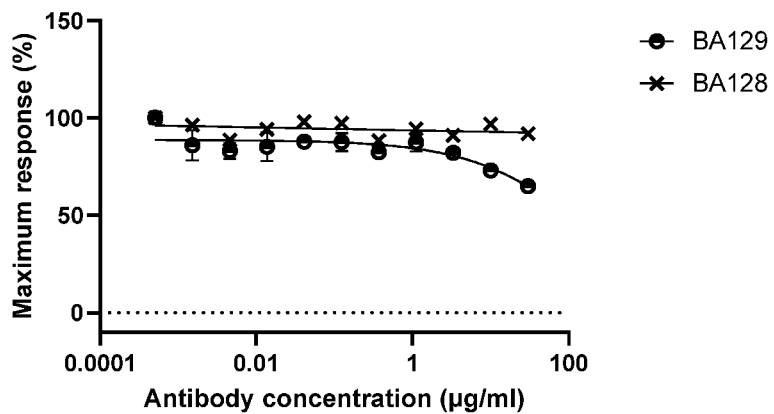
Figure 13E:
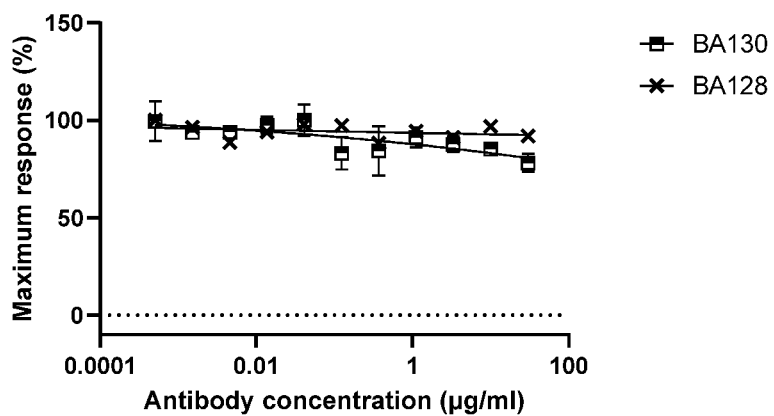
Figure 13F:
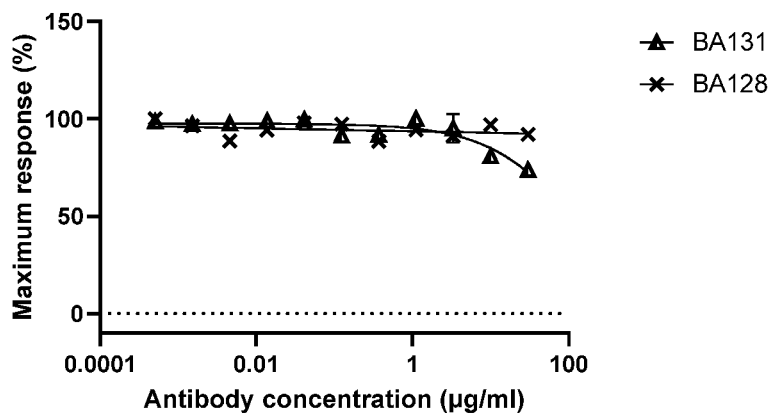
Figure 13G:
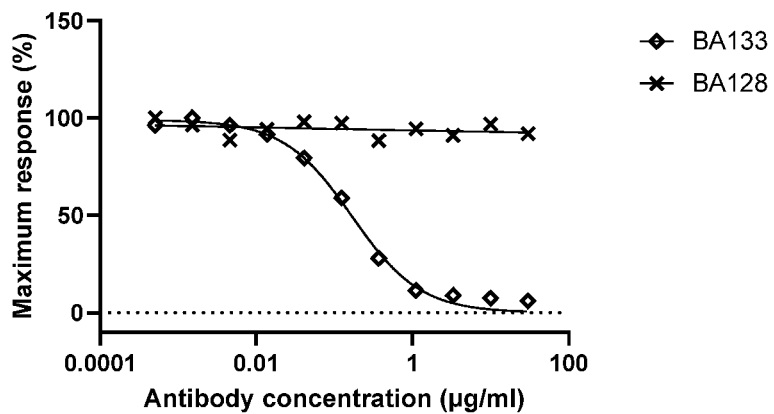
Figure 13H:
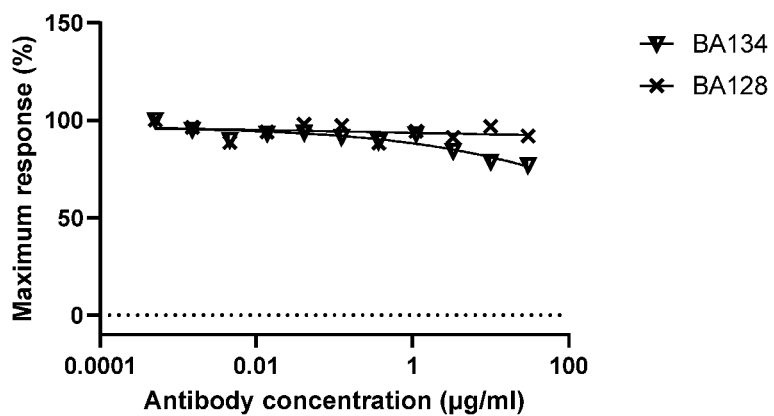
Figure 13I:
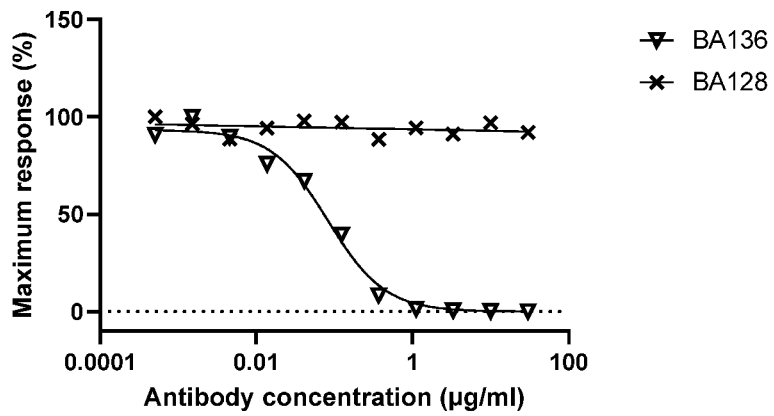
Figure 14A:
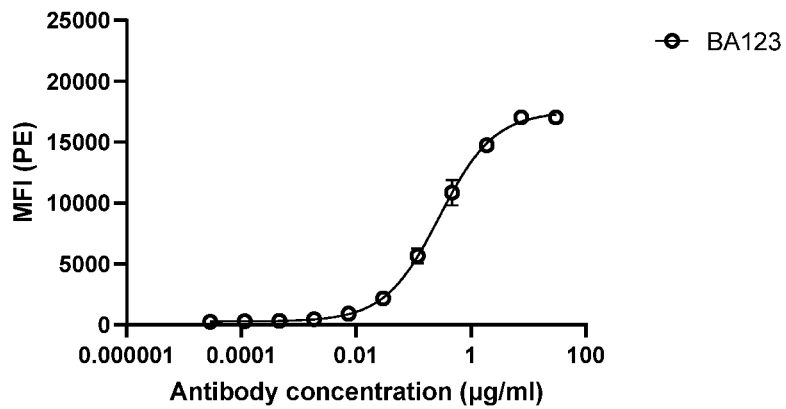
Figure 14B:
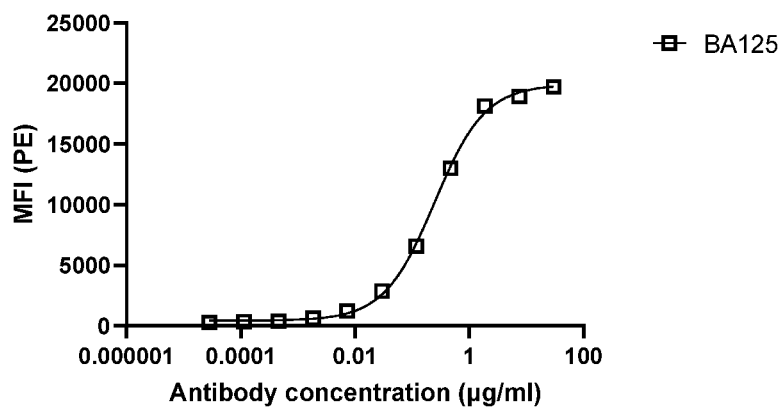
Figure 14C:
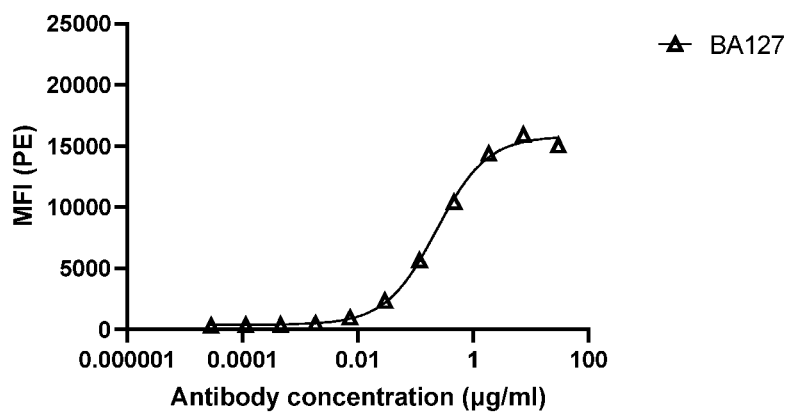
Figure 14D:
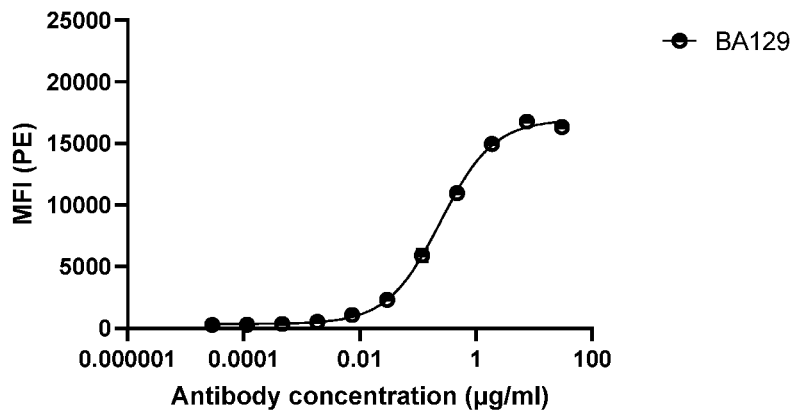
Figure 14E:
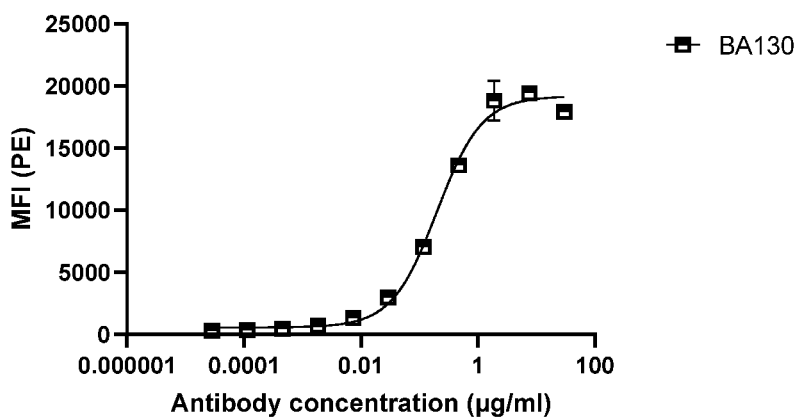
Figure 14F:
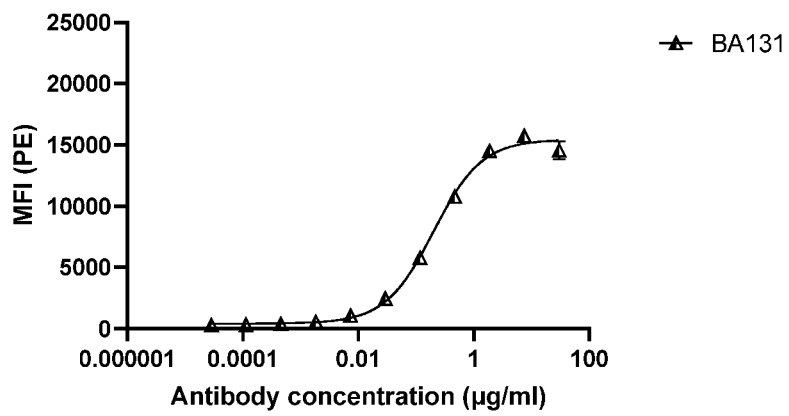
Figure 15A:
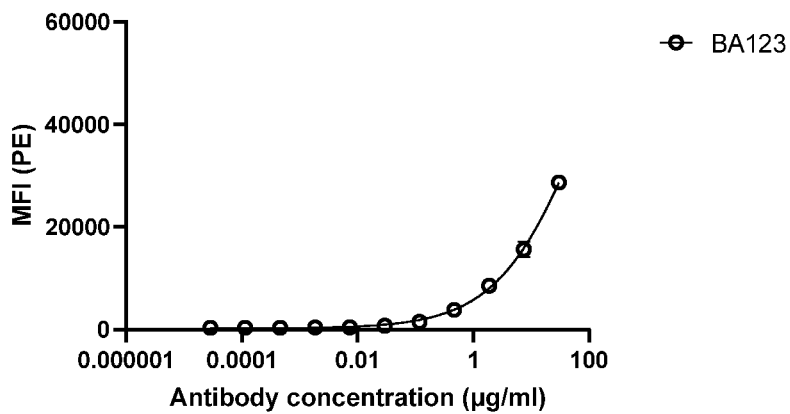
Figure 15B:
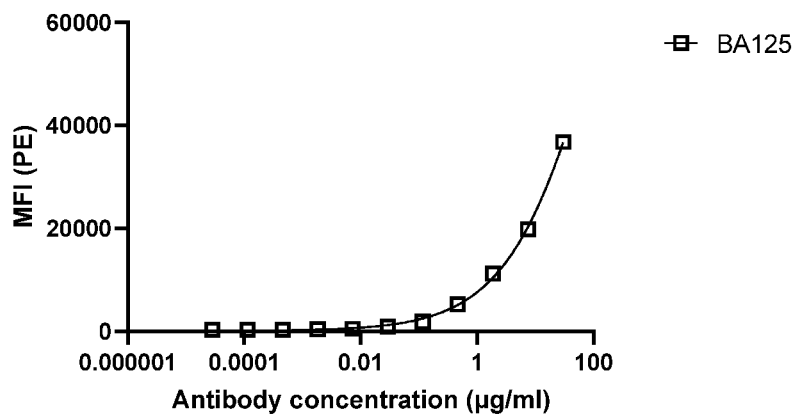
Figure 15C:
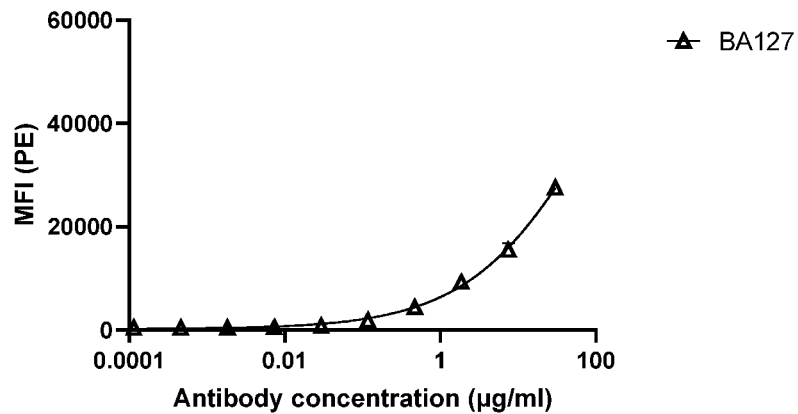
Figure 15D:
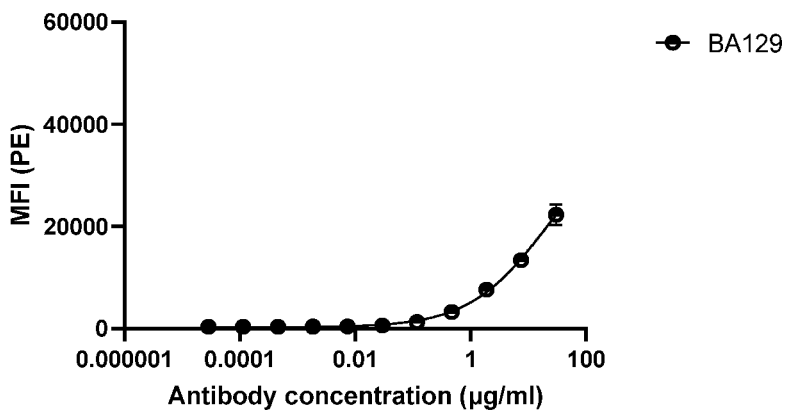
Figure 15E:
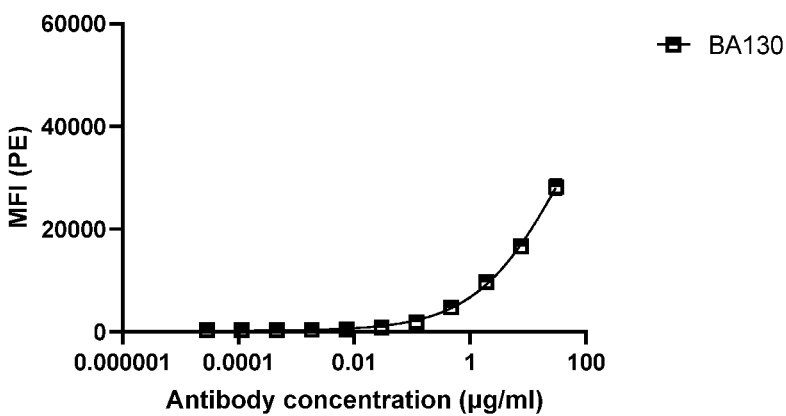
Figure 15F:
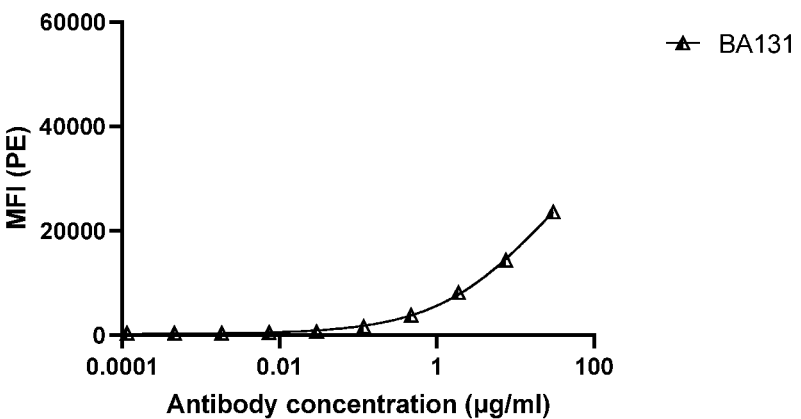

As shown in FIGS. 2A and 2B, the anti-TIGIT×CD96 multispecific molecule BA127 was able to simultaneous binding to human TIGIT and human CD96 as compared control multispecific molecules BA128, BA131, and BA133. Dual binding of cell-expressed human TIGIT and soluble His-tagged human CD96 (FIG. 2A) or cell-expressed human CD96 and soluble His-tagged human TIGIT (FIG. 2B) was detected by flow cytometry using fluorochrome-conjugated (Alex Fluor 488) anti-His antibody.

8.5 Example 5: Characterization of Lead Panel of Anti-TIGIT×CD96 Multispecific Molecules

8.5.1 Anti-TIGIT×CD96 Multispecific Molecules Bind to Cells Expressing Human and Cynomolgus Monkey CD96

In this example, the capacity of anti-TIGIT×CD96 multispecific molecules to bind to wild type human CD96 or wild type cynomolgus monkey CD96 on the surface of various cell types was tested in vitro by flow cytometry.
Binding to Human CD96-Expressing CHO Cells The ability of anti-TIGIT×CD96 multispecific molecules to bind to human CD96 expressed on the surface of CHO cells was assessed. Briefly, CHO cells were transfected with a vector encoding wild type full-length human CD96 (human CD96-CHO) isoform 1 or isoform 2, and clones stably expressing wild type CD96 isoform 1 or isoform 2 were selected. Stable cell lines were cultured in Power CHO-2 medium containing 4 mM L-Glutamine, 100 U/mL 1×HT-Supplement, and 2.5 µg/mL Puromycin.

For the antibody binding assay, a frozen aliquot of human CD96-CHO cells (isoform 1 or isoform 2) was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of $2\times10^5$ cells per well in 50 pt. In a separate microplate, a 2× concentrated intermediate stock of each antibody was prepared. Antibodies were serially diluted 1-to-3 in FACS buffer. A total of 11 working dilutions ranging from 60 µg/mL to 0.001 µg/mL were prepared. Fifty microlitres of each dilution were then transferred to the microplate containing human CD96-CHO cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')₂ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of multispecific molecule resulting in 50% of maximal binding (Effective Concentration 50, [EC50]) by curve fitting using a four-parameter logistic equation.

As shown in FIGS. 3A-3I (isoform 2) and FIGS. 4A-4I (isoform 1), BA123, BA125, BA127, BA129, BA130, BA131, BA134, and BA136 bound to human CD96-expressing CHO cells in a dose-dependent manner. Mean EC50 values were calculated for each antibody and are reported in Tables 14 and 16 (for isoform 2 and isoform 1 respectively). The area under the curve (AUC) was calculated for a representative experiment and is reported in Tables 15 and 17 (for isoform 2 and isoform 1 respectively).

TABLE 14

EC50 values for anti-TIGIT × CD96 multispecific molecules binding to human CD96-CHO (isoform 2) cells.*

| Multispecific molecule | EC50 (Geomean), ng/mL |
|---|---|
| BA123 | 196.3 |
| BA125 | 81.1 |
| BA127 | 95.1 |
| BA129 | 1921.7 |
| BA130 | 468.1 |
| BA131 | 697.4 |
| BA133 | No binding |
| BA134 | 123.4 |
| BA136 | 341.3 |

*Calculated from 2 experiments.

TABLE 15

AUC values for a representative experiment showing anti-TIGIT × CD96 multispecific molecules binding to human CD96-CHO (isoform 2) cells.

| Multispecific molecule | Area under the curve (AUC) | Standard error |
|---|---|---|
| BA123 | 102640 | N/A |
| BA125 | 131901 | 1551 |
| BA127 | 131867 | 2754 |
| BA128 | 6875 | N/A |
| BA129 | 70253 | 1258 |
| BA130 | 91914 | 1450 |
| BA131 | 109014 | 2236 |
| BA133 | 21002 | N/A |
| BA134 | 163929 | N/A |
| BA136 | 153274 | N/A |

TABLE 16

EC50 values for anti-TIGIT × CD96 multispecific molecules binding to human CD96-CHO (isoform 1) cells.

| Multispecific molecule | EC50, ng/mL |
|---|---|
| BA123 | 11.3 |
| BA125 | 108.4 |

TABLE 16-continued

EC50 values for anti-TIGIT × CD96 multispecific
molecules binding to human CD96-CHO (isoform 1) cells.

| Multispecific molecule | EC50, ng/mL |
| --- | --- |
| BA127 | 48.9 |
| BA129 | 123.3 |
| BA130 | 30.2 |
| BA131 | 9.9 |
| BA133 | No binding |
| BA134 | 8.1 |
| BA136 | 10.7 |

*Calculated from 1 experiment.

TABLE 17

AUC values for a representative experiment showing anti-TIGIT × CD96 multispecific molecules binding to human CD96-CHO (isoform 1) CHO cells.

| Multispecific molecule | Area under the curve (AUC) | Standard error |
| --- | --- | --- |
| BA123 | 92383 | 2595 |
| BA125 | 132860 | 2507 |
| BA127 | 143733 | 4872 |
| BA128 | 5149 | N/A |
| BA129 | 39804 | 425.4 |
| BA130 | 46824 | 1692 |
| BA131 | 52417 | 1935 |
| BA133 | 19339 | N/A |
| BA134 | 81530 | N/A |
| BA136 | 152868 | N/A |

Binding to Cynomolgus Monkey CD96-Expressing CHO Cells

In similar experiments, the capacity of anti-TIGIT×CD96 multispecific molecules to bind to CHO cells engineered to express wild type cynomolgus monkey CD96 (isoform 2) on their cell surfaces (cynomolgus CD96-CHO cells) was tested. Briefly, CHO cells were transfected with a vector encoding wild type full-length cynomolgus monkey CD96 isoform 2, and a clone stably expressing CD96 was selected. The stable cell line was cultured in Power CHO-2 medium containing 4 mM L-Glutamine, 100 U/mL 1× HT-Supplement, and 2.5 μg/mL Puromycin. The ability of anti-TIGIT× CD96 multispecific molecules to bind to cynomolgus CD96-CHO was determined as described for human CD96-CHO cells above.

As shown in FIGS. 5A-5I, anti-TIGIT×CD96 multispecific molecules BA123, BA127, BA129, BA131, BA134, and BA136 bound to CHO cells expressing cynomolgus monkey CD96 in a dose-dependent manner. The EC50 values for the binding of anti-TIGIT×CD96 multispecific molecules to cynomolgus CD96-CHO cells were calculated for each antibody and are reported in Table 18. The area under the curve (AUC) was calculated and is reported in Table 19.

TABLE 18

EC50 values for anti-TIGIT × CD96 multispecific molecules binding to cynomolgus CD96-CHO (isoform 2) cells.*

| Multispecific molecule | EC50, ng/mL |
| --- | --- |
| BA123 | 1039 |
| BA125 | No binding |
| BA127 | Not fit |
| BA129 | 323.8 |
| BA130 | No binding |
| BA131 | Not fit |
| BA133 | No binding |
| BA134 | 202.2 |
| BA136 | 415.3 |

*Calculated from 1 experiment.

TABLE 19

AUC values for a representative experiment showing anti-TIGIT × CD96 multispecific molecules binding to cynomolgus CD96-CHO (isoform 2) cells.

| Multispecific molecule | Area under the curve (AUC) | Standard error |
| --- | --- | --- |
| BA123 | 3179 | 59.2 |
| BA125 | 486 | 3.6 |
| BA127 | 2016 | 72.8 |
| BA128 | 580 | N/A |
| BA129 | 3076 | 69.5 |
| BA130 | 499 | 8.7 |
| BA131 | 1667 | 56.4 |
| BA133 | 708 | N/A |
| BA134 | 4357 | N/A |
| BA136 | 4350 | N/A |

8.5.2 Anti-TIGIT×CD96 Multispecific Molecules Block Ligand Binding to Human CD96

The capacity of anti-TIGIT×CD96 multispecific molecules to block binding between wild type human CD96 (isoform 2) or wild type cynomolgus monkey CD96 (isoform 2) and its ligand CD155 was tested in vitro by flow cytometry.

Blocking of Human CD96-CHO Cells Binding to Soluble Human CD155

Anti-TIGIT×CD96 multispecific molecules were tested in vitro for their ability to block binding between wild type human CD96 (isoform 2) over-expressed on CHO cells and soluble human CD155 in vitro by flow cytometry.

Briefly, a solution containing 2 μg/mL of human CD155-Fc conjugated to R-Phycoerythrin (CD155-Fc-PE) was prepared in FACS buffer. Fifty microlitres of this working stock of human CD155-Fc-PE were then added to the wells of a 96-well U-bottom microplate. A 4× concentrated intermediate stock of each multispecific molecule was prepared in a microplate. Antibodies were serially diluted 1-to-3 in FACS buffer. A total of 11 working dilutions ranging from 120 μg/mL to 0.002 μg/mL were prepared. Twenty-five microlitres of each dilution were added to the microplate containing CD155-Fc-PE. Lastly, 25 μL of wild type human CD96-CHO cells (isoform 2), prepared as described above, were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs. SSC-A. Mean fluorescence intensity (MFI) values for PE were calculated, and the data were plotted by GraphPad Prism software and analyzed as described above. For each antibody concentration, experimental data were normalized using MFI values obtained for human CD96-CHO cells incubated with CD155-Fc-PE in the absence of multispecific molecules and MFI values for human CD96-CHO cell autofluorescence (background) according to equation 1.

% Maximal signal=(MFI "multispecific molecule"−MFI "background")/(MFI "total"−MFI "background")     Equation 1 where

"Multispecific molecule" is BA123, BA125, BA127, BA129, BA130, BA131, BA133, BA134, or BA136

"Background" is cells alone (no antibody or CD155-Fc-PE)

"Total" is cells incubated with CD155-Fc-PE in absence of antibodies

The concentration of multispecific molecule inhibiting 50% (IC50) of CD155-Fc-PE binding to human CD96-CHO cells was determined. IC50 values were calculated using GraphPad Prism software by curve fitting using a four-parameter logistic equation.

As shown in FIGS. 6A-6I, BA123, BA125, BA127, BA129, BA130, BA131, BA134, and BA136 blocked human CD96 binding to CD155. Mean IC50 values were calculated for each antibody and are reported in Table 20. The area under the curve (AUC) was calculated for a representative experiment and is reported in Table 21.

TABLE 20

IC50 values for anti-TIGIT × CD96 multispecific molecules blocking human CD96-CHO (isoform 2) cells binding to human CD155.*

| Multispecific molecule | IC50 (Geomean), ng/mL |
|---|---|
| BA123 | 5633 |
| BA125 | 3489 |
| BA127 | 1992 |
| BA129 | 11460 |
| BA130 | 7603 |
| BA131 | 4698 |
| BA133 | Non blocker |
| BA134 | 1363 |
| BA136 | 983 |

*Calculated from 3 experiments.

TABLE 21

AUC values for a representative experiment showing anti-TIGIT × CD96 multispecific molecules blocking human CD96-CHO (isoform 2) binding to human CD155.

| Multispecific molecule | Area under the curve (AUC) | Standard error |
|---|---|---|
| BA123 | 379.7 | 1.66 |
| BA125 | 360.8 | 2.02 |
| BA127 | 338.6 | 2.94 |
| BA128 | 466.4 | N/A |
| BA129 | 404.8 | 2.78 |
| BA130 | 396.3 | 3.25 |
| BA131 | 385.0 | 1.98 |
| BA133 | 455.9 | N/A |
| BA134 | 328.8 | N/A |
| BA136 | 340.7 | N/A |

Blocking of Cynomolgus CD96-CHO Cells Binding to Soluble Human CD155

In similar experiments, anti-TIGIT×CD96 multispecific molecules were tested in vitro for their ability to block binding between wild type cynomolgus monkey CD96 (isoform 2) over-expressed on CHO cells and soluble human CD155 in vitro by flow cytometry as described for human CD96-CHO cells above.

The concentration of antibody inhibiting 50% (IC50) of CD155-Fc-PE binding to human CD96-CHO cells was determined. IC50 values were calculated using GraphPad Prism software by curve fitting using a four-parameter logistic equation.

As shown in FIGS. 7A-7I, anti-TIGIT×CD96 multispecific molecules BA129, BA131, BA134, and BA136 partially block the interaction between wild type cynomolgus monkey CD96 and human CD155. The IC50 values could not be calculated as the multispecific molecules are partial blockers. The area under the curve (AUC) was calculated and is reported in Table 22.

TABLE 22

AUC values for a representative experiment showing anti-TIGIT × CD96 multispecific molecules blocking cynomolgus CD96-CHO (isoform 2) cells binding to human CD155.

| Multispecific molecule | Area under the curve (AUC) | Standard error |
|---|---|---|
| BA123 | 440.0 | 3.74 |
| BA125 | 452.7 | 3.94 |
| BA127 | 442.8 | 5.07 |
| BA128 | 427.3 | N/A |
| BA129 | 412.2 | 7.08 |
| BA130 | 430.6 | 5.12 |
| BA131 | 432.9 | 2.23 |
| BA133 | 455.2 | N/A |
| BA134 | 401.4 | N/A |
| BA136 | 403.2 | N/A |

8.5.3 Anti-TIGIT×CD96 Multispecific Molecules Bind to Cells Expressing Human and Cynomolgus Monkey TIGIT The capacity of anti-TIGIT×CD96 multispecific molecules to bind to wild type human TIGIT or wild type cynomolgus monkey TIGIT on the surface of various cell types was tested in vitro by flow cytometry.

Binding to Human TIGIT-Expressing CHO Cells

The ability of anti-TIGIT×CD96 multispecific molecules to bind to wild type human TIGIT expressed on the surface of CHO cells was assessed. Briefly, CHO cells were transfected with a vector encoding wild type full-length human TIGIT (human TIGIT-CHO), and clones stably expressing TIGIT were selected. Stable cell lines were cultured in Power CHO-2 medium containing 4 mM L-Glutamine, 100 U/mL 1× HT-Supplement, and 2.5 µg/mL Puromycin.

For the antibody binding assay, a frozen aliquot of human TIGIT-CHO cells was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of $2 \times 10^5$ cells per well in 50 pt. In a separate microplate, a 2× concentrated intermediate stock of each antibody was prepared. Antibodies were serially diluted 1-to-4 in FACS buffer. A total of 11 working dilutions ranging from 60 µg/mL to 0.000057 µg/mL were prepared. Fifty microlitres of each dilution were then transferred to the microplate containing human TIGIT-CHO cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')$_2$ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of multispecific molecule resulting in 50% of maximal binding (Effective Concentration 50, [EC50]) by curve fitting using a four-parameter logistic equation.

As shown in FIGS. 8A-8I, BA123, BA125, BA127, BA133, and BA136 bound to human TIGIT-expressing CHO cells in a dose-dependent manner. Mean EC50 values were calculated for each multispecific molecule and are reported in Table 23. The area under the curve (AUC) was calculated for a representative experiment and is reported in Table 24.

TABLE 23

EC50 values for multispecific molecules
binding to human TIGIT CHO cells.*

| Multispecific molecule | EC50 (Geomean), ng/mL |
| --- | --- |
| BA123 | 44.9 |
| BA125 | 30.7 |
| BA127 | 33.0 |
| BA129 | No binding |
| BA130 | No binding |
| BA131 | No binding |
| BA133 | 27.1 |
| BA134 | No binding |
| BA136 | 28.4 |

*Calculated from 2 experiments.

TABLE 24

AUC values for a representative experiment showing anti-TIGIT × CD96 multispecific molecules binding to human TIGIT-CHO cells.

| Multispecific molecule | Area under the curve (AUC) | Standard error |
| --- | --- | --- |
| BA123 | 143147 | 1866 |
| BA125 | 133572 | 8920 |
| BA127 | 122832 | 3169 |
| BA128 | 1304 | N/A |
| BA129 | 1197 | 75.4 |
| BA130 | 1437 | 94.2 |
| BA131 | 1297 | 148.5 |
| BA133 | 160549 | N/A |
| BA134 | 3073 | N/A |
| BA136 | 156823 | N/A |

Binding to Cynomolgus Monkey TIGIT-Expressing CHO Cells

In similar experiments, the capacity of anti-TIGIT×CD96 multispecific molecules to bind to CHO cells engineered to express wild type cynomolgus monkey TIGIT on their cell surfaces (cynomolgus TIGIT-CHO cells) was tested. Briefly, CHO cells were transfected with a vector encoding wild type full-length cynomolgus monkey TIGIT, and a clone stably expressing TIGIT was selected. The stable cell line was cultured in Power CHO-2 medium containing 4 mM L-Glutamine, 100 U/mL 1× HT-Supplement, and 2.5 µg/mL Puromycin. The ability of anti-TIGIT×CD96 multispecific molecules to bind to cynomolgus TIGIT-CHO was determined as described for human TIGIT-CHO cells above.

As shown in FIGS. 9A-9I, BA123, BA125, BA127, BA133, and BA136 bound to CHO cells expressing cynomolgus monkey TIGIT in a dose-dependent manner. Mean EC50 values for the binding of antibodies to cynomolgus TIGIT-CHO cells were calculated for each antibody and are reported in Table 25. The area under the curve (AUC) was calculated for a representative experiment and is reported in Table 26.

TABLE 25

EC50 values for anti-TIGIT × CD96 multispecific
molecules binding to cynomolgus TIGIT-CHO cells.*

| Multispecific molecule | EC50 (Geomean), ng/mL |
| --- | --- |
| BA123 | 165.0 |
| BA125 | 406.1 |
| BA127 | 257.7 |
| BA129 | No binding |
| BA130 | No binding |
| BA131 | No binding |
| BA133 | 235.1 |
| BA134 | No binding |
| BA136 | 456.9 |

*Calculated from 2 experiments.

TABLE 26

AUC values for a representative experiment
showing anti-TIGIT × CD96 multispecific
molecules binding to cynomolgus TIGIT-CHO cells.

| Multispecific molecule | Area under the curve (AUC) | Standard error |
| --- | --- | --- |
| BA123 | 88592 | 1340 |
| BA125 | 119819 | 1077 |
| BA127 | 110887 | 1811 |
| BA128 | 594 | N/A |
| BA129 | 546 | 18 |
| BA130 | 715 | 114 |
| BA131 | 554 | 5 |
| BA133 | 87757 | N/A |
| BA134 | 584 | N/A |
| BA136 | 96962 | N/A |

8.5.4 Anti-TIGIT×CD96 Multispecific Molecules Block Ligand Binding to TIGIT The capacity of anti-TIGIT×CD96 multispecific molecules to block binding between wild type human TIGIT or wild type cynomolgus monkey TIGIT and its ligand human CD155 was tested in vitro by flow cytometry.

Blocking of Human TIGIT-CHO Cells Binding to Soluble Human CD155

In this example, the capacity of anti-TIGIT×CD96 multispecific molecules to block binding between wild type human TIGIT and its ligand human CD155 (also referred to as PVR) was tested. Specifically, antibodies were tested in vitro for their ability to block binding between human TIGIT over-expressed on CHO cells and soluble human CD155 by flow cytometry.

Briefly, a solution containing 2 µg/mL of human CD155-Fc conjugated to R-Phycoerythrin (CD155-Fc-PE) was prepared in FACS buffer. Fifty microliters of this working stock of human CD155-Fc-PE were then added to the wells of a 96-well U-bottom microplate. A 4× concentrated intermediate stock of each multispecific molecule was prepared in a microplate. Antibodies were serially diluted 1-to-3 in FACS buffer. A total of 11 working dilutions ranging from 120 µg/mL to 0.002 µg/mL were prepared. Twenty-five microlitres of each dilution were added to the microplate containing CD155-Fc-PE. Lastly, 25 µL of human TIGIT-CHO cells, prepared as described above, were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs. SSC-A. Mean fluorescence intensity (MFI) values for PE were calculated, and the data were plotted by GraphPad Prism software and analyzed as described above. For each antibody concentration, experimental data were normalized using MFI values obtained for human TIGIT-CHO cells incubated with CD155-Fc-PE in the absence of multispecific molecules and MFI values for human TIGIT-CHO cell autofluorescence (background) according to equation 2.

% Maximal signal=(MFI "multispecific molecule"−MFI "background")/(MFI "total"−MFI "background")      Equation 2 where

"Multispecific molecule" is BA123, BA125, BA127, BA129, BA130, BA131, BA133, BA134, or BA136

"Background" is cells alone (no antibody or CD155-Fc-PE)

"Total" is cells incubated with CD155-Fc-PE in absence of antibodies

The concentration of multispecific molecule inhibiting 50% (IC50) of CD155-Fc-PE binding to human TIGIT-CHO cells was determined. IC50 values were calculated using GraphPad Prism software by curve fitting using a four-parameter logistic equation.

As shown in FIGS. 10A-10I, BA123, BA125, BA127, BA133, and BA136 blocked human TIGIT binding to CD155. Mean IC50 values were calculated for each antibody and are reported in Table 27. The area under the curve (AUC) was calculated for a representative experiment and is reported in Table 28.

TABLE 27

IC50 values for anti-TIGIT × CD96 multispecific molecules blocking human TIGIT-CHO binding to human CD155.*

| Multispecific molecule | IC50 (Geomean), ng/mL |
|---|---|
| BA123 | 142 |
| BA125 | 135 |
| BA127 | 164 |
| BA129 | Non blocker |
| BA130 | Non blocker |
| BA131 | Non blocker |
| BA133 | 200 |
| BA134 | Non blocker |
| BA136 | 144 |

*Calculated from 3 experiments.

TABLE 28

AUC values for a representative experiment showing anti-TIGIT × CD96 multispecific molecules blocking human TIGIT-CHO binding to human CD155.

| Multispecific molecule | Area under the curve (AUC) | Standard error |
|---|---|---|
| BA123 | 221.4 | 2.53 |
| BA125 | 210.7 | 0.93 |
| BA127 | 228.9 | 1.32 |
| BA128 | 449.3 | N/A |
| BA129 | 462.1 | 2.14 |
| BA130 | 456.7 | 2.01 |
| BA131 | 460.4 | 2.83 |
| BA133 | 244.5 | N/A |
| BA134 | 453.5 | N/A |
| BA136 | 216.8 | N/A |

Blocking of Cynomolgus TIGIT-CHO Cells Binding to Soluble Human CD155

In similar experiments, the capacity of anti-TIGIT×CD96 multispecific molecules to block binding between wild type cynomolgus monkey TIGIT and its ligand human CD155 (also referred to as PVR) was tested. Briefly, antibodies were tested in vitro for their ability to block binding between wild type cynomolgus monkey TIGIT over-expressed on CHO cells and soluble human CD155 by flow cytometry as described for human TIGIT-CHO cells above.

The concentration of antibody inhibiting 50% (IC50) of CD155-Fc-PE binding to human TIGIT-CHO cells was determined. IC50 values were calculated using GraphPad Prism software by curve fitting using a four-parameter logistic equation.

As shown in FIGS. 11A-11I, anti-TIGIT×CD96 multispecific molecules BA123, BA125, BA127, BA133, and BA136 block the interaction between cynomolgus monkey CD96 and CD155. Mean IC50 values were calculated for each antibody and are reported in Table 29. The area under the curve (AUC) was calculated for a representative experiment and is reported in Table 30.

TABLE 29

IC50 values for anti-TIGIT × CD96 multispecific molecules blocking cynomolgus TIGIT-CHO cells binding to human CD155.*

| Multispecific molecule | IC50 (Geomean), ng/mL |
|---|---|
| BA123 | 2354 |
| BA125 | 2763 |
| BA127 | 2811 |
| BA129 | Non blocker |
| BA130 | Non blocker |
| BA131 | Non blocker |
| BA133 | 2641 |
| BA134 | Non blocker |
| BA136 | 2538 |

*Calculated from 2 experiments

TABLE 30

AUC values for a representative experiment showing anti-TIGIT × CD96 multispecific molecules blocking cynomolgus TIGIT-CHO binding to human CD155.

| Multispecific molecule | Area under the curve (AUC) | Standard error |
|---|---|---|
| BA123 | 104427 | 784.1 |
| BA125 | 114383 | 675.9 |

TABLE 30-continued

AUC values for a representative experiment showing anti-TIGIT × CD96 multispecific molecules blocking cynomolgus TIGIT-CHO binding to human CD155.

| Multispecific molecule | Area under the curve (AUC) | Standard error |
|---|---|---|
| BA127 | 352.6 | 6.715 |
| BA128 | 156744 | N/A |
| BA129 | 128554 | 963.7 |
| BA130 | 137195 | 1610 |
| BA131 | 432.4 | 2.426 |
| BA133 | 115364 | N/A |
| BA134 | 155862 | N/A |
| BA136 | 110003 | N/A |

8.5.5 Anti-TIGIT×CD96 Multispecific Molecules Bind to Cells Co-Expressing Human TIGIT and Human CD96

The capacity of anti-TIGIT×CD96 multispecific molecules to bind to human TIGIT or human CD96 on the surface of various cell types was tested in vitro by flow cytometry.

Binding to CHO Cells Co-Expressing Human TIGIT and Human CD96

The ability of anti-TIGIT×CD96 multispecific molecules to bind to wild type human TIGIT and wild type human CD96 co-expressed on the surface of CHO cells was assessed. Briefly, CHO cells were transfected with a vector encoding wild type human TIGIT (human TIGIT-CHO), and clones stably expressing TIGIT were selected. These cells were then transfected with a vector encoding wild type human CD96 (isoform 2) to produce a cell line expressing both human TIGIT and human CD96 (human TIGIT-CD96-CHO). These stable cell lines were cultured in Power CHO-2 medium containing 4 mM L-Glutamine, 100 U/mL 1× HT-Supplement, and 2.5 µg/mL Puromycin. Expression was confirmed by flow cytometry. Cells were clonal for high level TIGIT expression, but had a range of CD96 expression.

For the antibody binding assay, a frozen aliquot of human TIGIT-CD96 CHO cells was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of 2×10⁵ cells per well in 50 pt. In a separate microplate, a 2× concentrated intermediate stock of each antibody was prepared. Antibodies were serially diluted 1-to-3 in FACS buffer. A total of 11 working dilutions ranging from 60 µg/mL to 0.001 µg/mL were prepared. Fifty microlitres of each dilution were then transferred to the microplate containing human TIGIT-CD96-CHO cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')₂ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of multispecific molecule resulting in 50% of maximal binding (Effective Concentration 50, [EC50]) by curve fitting using a four-parameter logistic equation.

As shown in FIGS. 12A-12I, BA123, BA125, BA127, BA129, BA130, BA131, BA133, BA134, and BA136 bound to human TIGIT-CD96 expressing CHO cells in a dose-dependent manner. Mean EC50 values were calculated for each multispecific antibody and are reported in Table 31. The area under the curve (AUC) was calculated for a representative experiment and is reported in Table 32.

TABLE 31

EC50 values for anti-TIGIT × CD96 multispecific molecules binding to human TIGIT-CD96-CHO cells.*

| Multispecific molecule | EC50 (Geomean), ng/mL |
|---|---|
| BA123 | 2.36 |
| BA125 | 2.58 |
| BA127 | 11.91 |
| BA129 | Not fit |
| BA130 | Not fit |
| BA131 | Not fit |
| BA133 | 24.37 |
| BA134 | Not fit |
| BA136 | 4.40 |

*Calculated from 2 experiments

TABLE 32

AUC values for a representative experiment showing anti-TIGIT × CD96 multispecific molecules binding to human TIGIT-CD96 CHO cells.

| Multispecific molecule | Area under the curve (AUC) | Standard error |
|---|---|---|
| BA123 | 145831 | 2716 |
| BA125 | 172085 | 6165 |
| BA127 | 156923 | 2020 |
| BA128 | 1458 | N/A |
| BA129 | 7233 | 128.9 |
| BA130 | 8971 | 122.6 |
| BA131 | 13367 | 374.9 |
| BA133 | 131494 | N/A |
| BA134 | 15662 | N/A |
| BA136 | 177760 | N/A |

8.5.6 Anti-TIGIT×CD96 Multispecific Molecules Block Ligand Binding to Cells Co-Expressing Human TIGIT and Human CD96

The capacity of anti-TIGIT×CD96 multispecific molecules to block binding between human TIGIT and human CD96 on the surface of various cell types was tested in vitro by flow cytometry.

Blocking of Soluble Human CD155 Binding to CHO Cells Expressing Human TIGIT and Human CD96

In this example, the capacity of anti-TIGIT×CD96 multispecific molecules to block binding between wild type human TIGIT and wild type human CD96 and their ligand human CD155 (also referred to as PVR) was tested. Specifically, antibodies were tested in vitro for their ability to block binding between human TIGIT and human CD96 over-expressed on CHO cells and soluble human CD155 by flow cytometry.

Briefly, a solution containing 2 µg/mL of human CD155-Fc conjugated to R-Phycoerythrin (CD155-Fc-PE) was prepared in FACS buffer. Fifty microlitres of this working stock of human CD155-Fc-PE were then added to the wells of a 96-well U-bottom microplate. A 4× concentrated intermediate stock of each multispecific molecule was prepared in a microplate. Antibodies were serially diluted 1-to-3 in FACS buffer. A total of 11 working dilutions ranging from 120 μg/mL to 0.002 μg/mL were prepared. Twenty-five microlitres of each dilution were added to the microplate containing CD155-Fc-PE. Lastly, 25 μL of human TIGIT-CHO cells, prepared as described above, were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs. SSC-A. Mean fluorescence intensity (MFI) values for PE were calculated, and the data were plotted by GraphPad Prism software and analyzed as described above. For each multispecific molecule concentration, experimental data were normalized using MFI values obtained for human TIGIT-CHO cells incubated with CD155-Fc-PE in the absence of multispecific molecule and MFI values for human TIGIT-CHO cell autofluorescence (background) according to equation 3.

% Maximal signal=(MFI "multispecific molecule"−MFI "background")/(MFI "total"−MFI "background")   Equation 3 where

"Multispecific molecule" is BA123, BA125, BA127, BA129, BA130, BA131, BA133, BA134, or BA136

"Background" is cells alone (no antibody or CD155-Fc-PE)

"Total" is cells incubated with CD155-Fc-PE in absence of antibodies

The concentration of multispecific molecule inhibiting 50% (IC50) of CD155-Fc-PE binding to human TIGIT-CD96-CHO cells was determined. IC50 values were calculated using GraphPad Prism software by curve fitting using a four-parameter logistic equation.

As shown in FIGS. 13A-13I, BA123, BA125, BA127, BA133, and BA136 blocked human TIGIT-CD96 binding to CD155. BA129, BA130, BA131, and BA134 partially blocked human TIGIT-CD96 binding to CD155. Mean IC50 values were calculated for each multispecific molecule and are reported in Table 33. The area under the curve (AUC) was calculated for a representative experiment and is reported in Table 34.

TABLE 33

IC50 values for anti-TIGIT × CD96 multispecific molecules blocking human TIGIT-CD96-CHO binding to human CD155.*

| Multispecific molecule | IC50 (Geomean), ng/mL |
|---|---|
| BA123 | 111.6 |
| BA125 | 143.2 |
| BA127 | 141.2 |
| BA129 | Not fit |
| BA130 | Not fit |
| BA131 | Not fit |
| BA133 | 266.6 |
| BA134 | Not fit |
| BA136 | 113.7 |

*Calculated from 2 experiments.

TABLE 34

AUC values for a representative experiment showing anti-TIGIT × CD96 multispecific molecules blocking human TIGIT-CD96-CHO binding to human CD155.

| Multispecific molecule | Area under the curve (AUC) | Standard error |
|---|---|---|
| BA123 | 209.2 | 2.406 |
| BA125 | 213.0 | 3.209 |
| BA127 | 217.1 | 2.936 |
| BA128 | 448.9 | N/A |
| BA129 | 399.1 | 4.603 |
| BA130 | 432.1 | 7.002 |
| BA131 | 447.6 | 3.035 |
| BA133 | 254.2 | N/A |
| BA134 | 428.1 | N/A |
| BA136 | 204.6 | N/A |

8.6 Example 6: Anti-TIGIT×CD96 Multispecific Molecules Bind to Cells Expressing Human FcγRIIIa The capacity of anti-TIGIT×CD96 multispecific molecules to bind to variant V/V or variant F/F of human FcγRIIIa on the surface of various cell types was tested in vitro by flow cytometry.

Binding to Human FcγRIIIa—Expressing CHO Cells

The ability of anti-TIGIT×CD96 multispecific molecules to bind to variant V/V or variant F/F of human FcγRIIIa expressed on the surface of CHO cells was assessed. Briefly, CHO cells were transfected with a vector encoding full-length human FcγRIIIa (human FcγRIIIa-CHO) variant V/V or F/F, and clones stably expressing FcγRIIIa (variant V/V or variant F/F) were selected. Stable cell lines were cultured in Power CHO-2 medium containing 4 mM L-Glutamine, 100 U/mL 100 U/mL 1× HT-Supplement, and 2.5 μg/mL Puromycin.

For the antibody binding assay, a frozen aliquot of human FcγRIIIa-CHO (variant V/V or variant F/F) cells was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of 2×10⁵ cells per well in 50 pL. In a separate microplate, a 2× concentrated intermediate stock of each multispecific molecule was prepared. Multispecific molecules were serially diluted 1-to-4 in FACS buffer. A total of 11 working dilutions ranging from 60 μg/mL to 0.000057 μg/mL were prepared. Fifty microlitres of each dilution were then transferred to the microplate containing human FcγRIIIa-CHO (variant V/V or variant F/F) cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')₂ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of multispecific molecule resulting in 50% of maximal binding (Effective Concentration 50, [EC50]) by curve fitting using a four-parameter logistic equation.

As shown in FIGS. 14A-14F (variant V/V) and 15A-15F (variant F/F), BA123, BA125, BA127, BA129, BA130, and BA131 bound to human FcγRIIIa-expressing CHO cells in a dose-dependent manner. Mean EC50 values were calculated for each multispecific molecule and are reported in Table 35 for variant V/V. The area under the curve (AUC) was calculated for a representative experiment and is reported in Tables 36 and 37 (for variant V/V and variant F/F respectively).

TABLE 35

EC50 values for anti-TIGIT × CD96 multispecific molecules binding to human FcγRIIIa-CHO (variant V/V) cells.*

| Multispecific molecule | EC50 (Geomean), ng/mL |
|---|---|
| BA123 | 188.8 |
| BA125 | 153.3 |
| BA127 | 147.8 |
| BA129 | 126.5 |
| BA130 | 118.4 |
| BA131 | 123.6 |

*Calculated from 2 experiments.

TABLE 36

AUC values for a representative experiment showing anti-TIGIT × CD96 multispecific molecules binding to human FcγRIIIa-CHO (variant V/V) cells.

| Multispecific molecule | Area under the curve (AUC) | Standard error |
|---|---|---|
| BA123 | 36722 | 545.6 |
| BA125 | 43351 | 167.6 |
| BA127 | 35159 | 97.1 |
| BA129 | 36957 | 317.6 |
| BA130 | 44399 | 701.1 |
| BA131 | 35486 | 267.1 |

TABLE 37

AUC values for experiment showing anti-TIGIT × CD96 multispecific molecules binding to human FcγRIIIa-CHO (variant F/F) cells.

| Multispecific molecule | Area under the curve (AUC) | Standard error |
|---|---|---|
| BA123 | 27774 | 732 |
| BA125 | 35798 | 426 |
| BA127 | 28498 | 653 |
| BA129 | 23351 | 695 |
| BA130 | 29783 | 689 |
| BA131 | 25318 | 434 |

8.7 Example 7: Characterization of Anti-CD96 Antibodies

8.7.1 Anti-Human CD96 Antibodies Bind to Cells Expressing Human and Cynomolgus Monkey CD96 (Isoform 2)

The capacity of anti-CD96 antibodies to bind to wild type human CD96 or wild type cynomolgus monkey CD96 on the surface of various cell types was tested in vitro by flow cytometry.

Binding to Human CD96-Expressing CHO Cells

The ability of anti-CD96 antibodies to bind to wild type human CD96 expressed on the surface of CHO cells was assessed. Briefly, CHO cells were transfected with a vector encoding human CD96 (human CD96-CHO) isoform 2, and clones stably expressing CD96 isoform 2 were selected. Stable cell lines were cultured in Power CHO-2 medium containing 4 mM L-Glutamine, 100 U/mL 1× HT-Supplement, and 2.5 μg/mL Puromycin.

For the antibody binding assay, a frozen aliquot of human CD96-CHO cells (isoform 2) was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of $2 \times 10^5$ cells per well in 50 μt. In a separate microplate, a 2× concentrated intermediate stock of each antibody was prepared. Antibodies were serially diluted 1-to-4 in FACS buffer. A total of 11 working dilutions ranging from 60 μg/mL to 0.000057 μg/mL were prepared. Fifty microlitres of each dilution were then transferred to the microplate containing human CD96-CHO cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')$_2$ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of antibody resulting in 50% of maximal binding (Effective Concentration 50, [EC50]) by curve fitting using a four-parameter logistic equation.

Figure 16A:
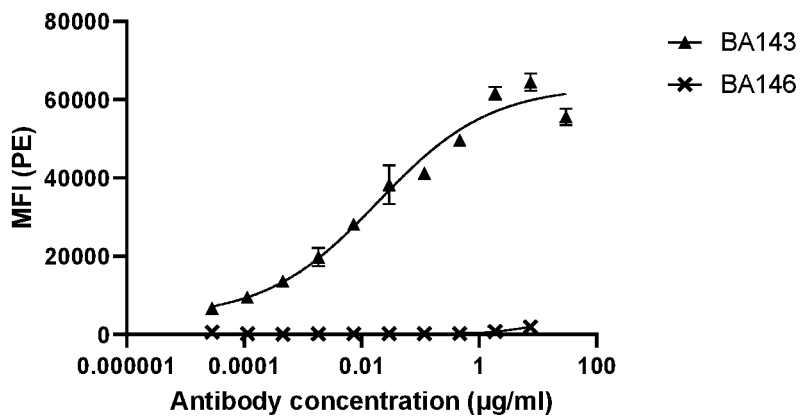
Figure 16B:
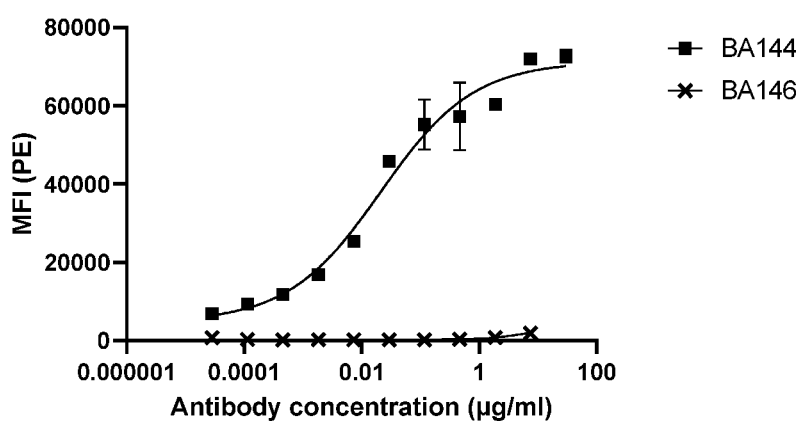
Figure 16C:
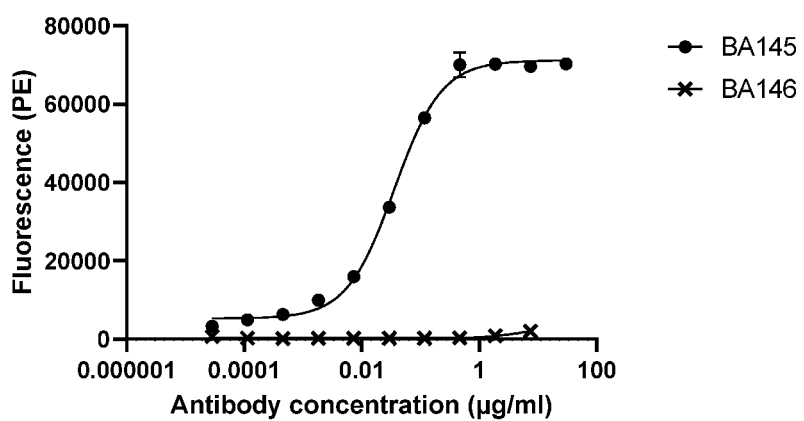

As shown in FIGS. 16A-16C, anti-CD96 antibodies BA143, BA144, and BA145 bound to human CD96-expressing CHO cells (isoform 2) in a dose-dependent manner. Mean EC50 values were calculated for each antibody and are reported in Table 38. The area under the curve (AUC) was calculated for a representative experiment and is reported in Table 39.

TABLE 38

EC50 values for anti-CD96 antibodies binding to human CD96 (iso2) CHO cells.*

| Multispecific molecule | EC50 (Geomean), ng/mL |
|---|---|
| BA143 | 5.9 |
| BA144 | 21.1 |
| BA145 | 26.7 |

*Calculated from 2 experiments.

TABLE 39

AUC values for a representative experiment showing anti-CD96 antibodies binding to human CD96 (iso2) CHO cells.

| Multispecific molecule | Area under the curve (AUC) | Standard error |
|---|---|---|
| BA143 | 215277 | 2774 |
| BA144 | 236887 | 4647 |

TABLE 39-continued

AUC values for a representative experiment showing anti-CD96 antibodies binding to human CD96 (iso2) CHO cells.

| Multispecific molecule | Area under the curve (AUC) | Standard error |
|---|---|---|
| BA145 | 225036 | 1556 |
| BA146 | 2057 | N/A |

Binding to Cynomolgus Monkey CD96-Expressing CHO Cells

In similar experiments, the capacity of anti-CD96 antibodies to bind to CHO cells engineered to express wild type cynomolgus monkey CD96 (isoform 2) on their cell surfaces (cynomolgus CD96-CHO cells) was tested. Briefly, CHO cells were transfected with a vector encoding wild type cynomolgus monkey CD96 isoform 2, and a clone stably expressing cynomolgus monkey CD96 was selected. The stable cell line was cultured in Power CHO-2 medium containing 4 mM L-Glutamine, 100 U/mL 1× HT-Supplement, and 2.5 µg/mL Puromycin. The ability of anti-CD96 antibodies to bind to cynomolgus CD96-CHO was determined as described for human CD96-CHO cells above.

Figure 17A:
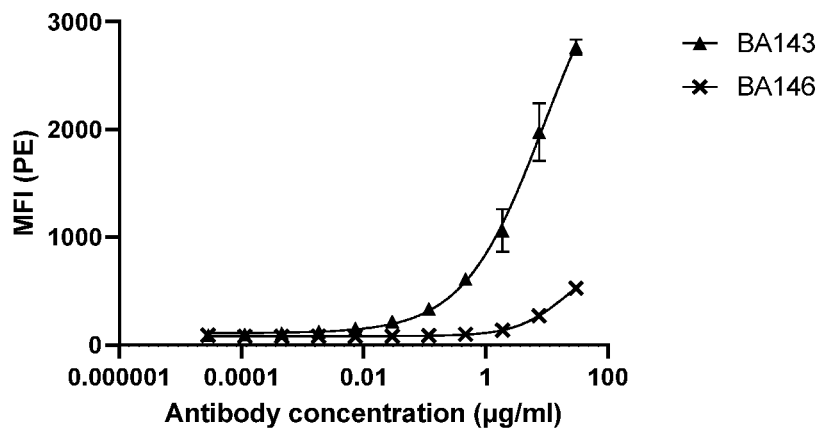
Figure 17B:
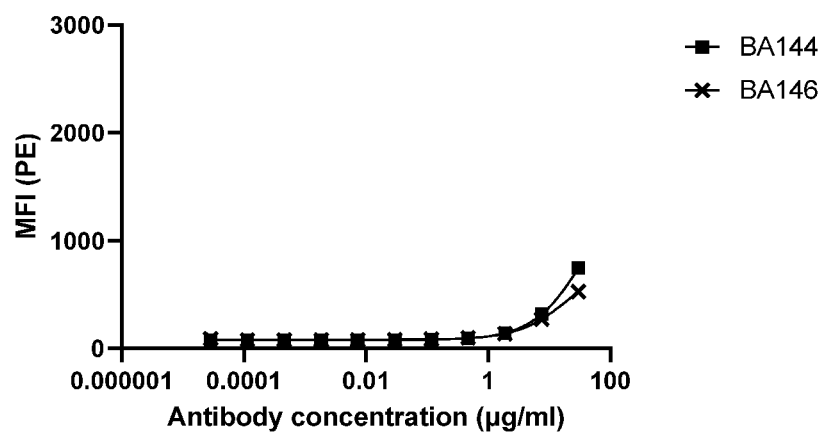
Figure 17C:
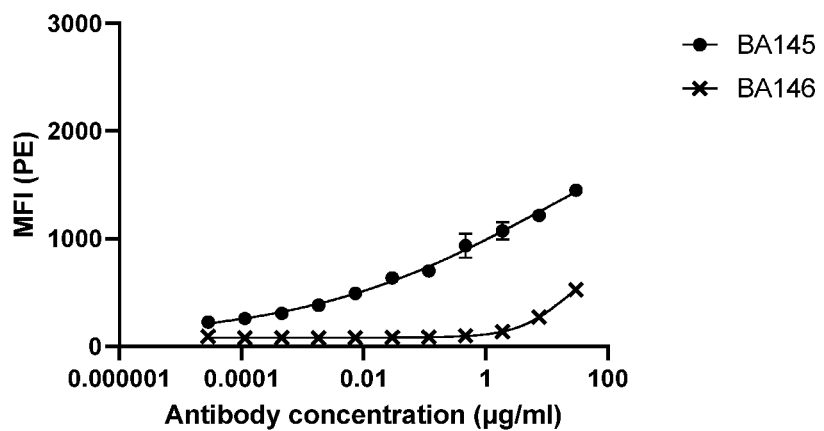

As shown in FIGS. 17A-17C, anti-CD96 antibodies BA143 and BA145 bound to CHO cells expressing cynomolgus monkey CD96 in a dose-dependent manner. Mean EC50 values for the binding of anti-CD96 antibodies to cynomolgus CD96-CHO cells were calculated for each antibody and are reported in Table 40. The area under the curve (AUC) was calculated for a representative experiment and is reported in Table 41.

TABLE 40

EC50 values for anti-CD96 antibodies binding to cynomolgus CD96-CHO cells.*

| Multispecific molecule | EC50 (Geomean), ng/mL |
|---|---|
| BA143 | Not fit |
| BA144 | No binding |
| BA145 | 1046 |

*Calculated from 2 experiments.

TABLE 41

AUC values for a representative experiment showing anti-CD96 antibodies binding to cynomolgus CD96-CHO cells.

| Multispecific molecule | Area under the curve (AUC) | Standard error |
|---|---|---|
| BA143 | 3675 | 144.9 |
| BA144 | 862.3 | 11.65 |
| BA145 | 4115 | 62.17 |
| BA146 | 781.4 | N/A |

8.7.2 Anti-Human CD96 Antibodies Block Ligand Binding to Human CD96

Blocking of human CD96-CHO cells binding to soluble human CD155

In this example, the capacity of anti-CD96 antibodies to block binding between wild type human CD96 and its ligand human CD155 (also referred to as PVR) was tested. Specifically, antibodies were tested in vitro for their ability to block binding between human CD96 (isoform 2) overexpressed on CHO cells and soluble human CD155 by flow cytometry.

Briefly, a solution containing 2 µg/mL of human CD155-Fc conjugated to R-Phycoerythrin (CD155-Fc-PE) was prepared in FACS buffer. Fifty microlitres of this working stock of human CD155-Fc-PE were then added to the wells of a 96-well U-bottom microplate. A 4× concentrated intermediate stock of each antibody was prepared in a microplate. Antibodies were serially diluted 1-to-4 in FACS buffer. A total of 11 working dilutions ranging from 120 µg/mL to 0.0001 µg/mL were prepared. Twenty-five microlitres of each dilution were added to the microplate containing CD155-Fc-PE. Lastly, 25 µL of human CD96-CHO cells (isoform 2), prepared as described above, were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs. SSC-A. Mean fluorescence intensity (MFI) values for PE were calculated, and the data were plotted by GraphPad Prism software and analyzed as described above.

For each antibody concentration, experimental data were normalized using MFI values obtained for human CD96-CHO cells incubated with CD155-Fc-PE in absence of antibody and MFI values for human CD96-CHO cell autofluorescence (background) according to equation 4.

$$\% \text{ Maximal signal} = (\text{MFI "antibody"} - \text{MFI "background"})/(\text{MFI "total"} - \text{MFI "background"}) \quad \text{Equation 4}$$

where

"Antibody" is BA143, BA144, or BA145

"Background" is cells alone (no antibody or CD155-Fc-PE)

"Total" is cells incubated with CD155-Fc-PE in absence of antibodies

The concentration of antibody inhibiting 50% (IC50) of CD155-Fc-PE binding to human CD96-CHO cells was determined. IC50 values were calculated using GraphPad Prism software by curve fitting using a four-parameter logistic equation.

Figure 18A:
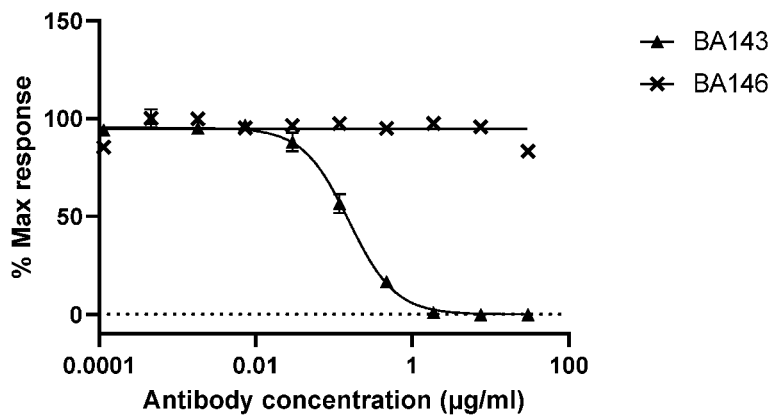
Figure 18B:
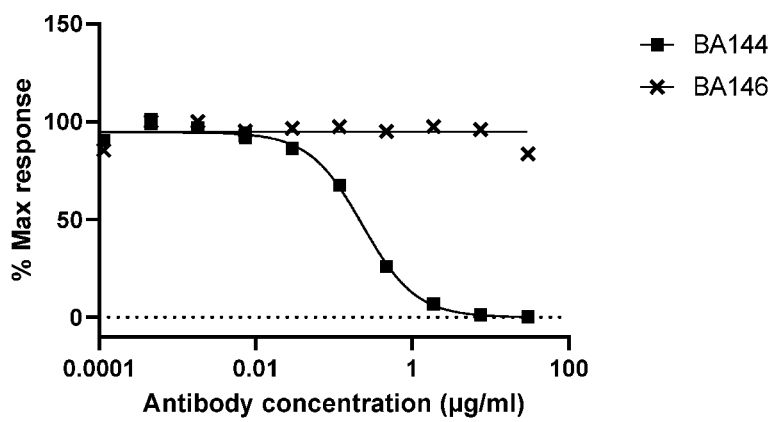
Figure 18C:
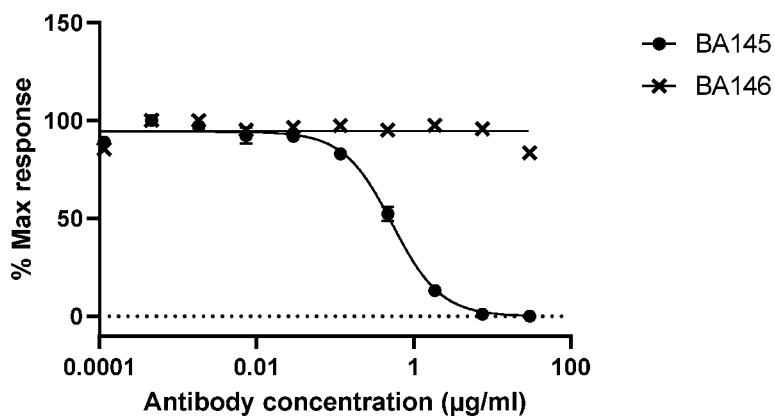

As shown in FIGS. 18A-18C, BA143, BA144, and BA145 blocked human CD96-CHO binding to CD155. Mean IC50 values were calculated for each antibody and are reported in Table 42. The area under the curve (AUC) was calculated for a representative experiment and is reported in Table 43.

TABLE 42

IC50 values for anti-CD96 antibodies blocking human CD96-CHO (isoform 2) binding to human CD155.*

| Antibody | IC50 (Geomean), ng/mL |
|---|---|
| BA143 | 152.4 |
| BA144 | 257.2 |
| BA145 | 542.1 |

*Calculated from 3 experiments.

TABLE 43

AUC values for a representative experiment showing anti-CD96 antibodies blocking human CD96-CHO (isoform 2) binding to human CD155.

| Antibody | Area under the curve (AUC) | Standard error |
|---|---|---|
| BA143 | 357.2 | 3.61 |
| BA144 | 370.2 | 3.53 |
| BA145 | 401.7 | 2.58 |
| BA146 | 573.5 | N/A |

Blocking of Cynomolgus CD96-CHO Cells Binding to Soluble Human CD155

In similar experiments, the capacity of anti-CD96 antibodies to block binding between wild type cynomolgus monkey CD96 and its ligand human CD155 (also referred to as PVR) was tested. Briefly, antibodies were tested in vitro for their ability to block binding between wild type cynomolgus monkey CD96 (isoform 2) over-expressed on CHO cells and soluble human CD155 by flow cytometry as described for human CD96-CHO cells above.

The concentration of antibody inhibiting 50% (IC50) of CD155-Fc-PE binding to human CD96-CHO cells was determined. IC50 values were calculated using GraphPad Prism software by curve fitting using a four-parameter logistic equation.

Figure 19A:
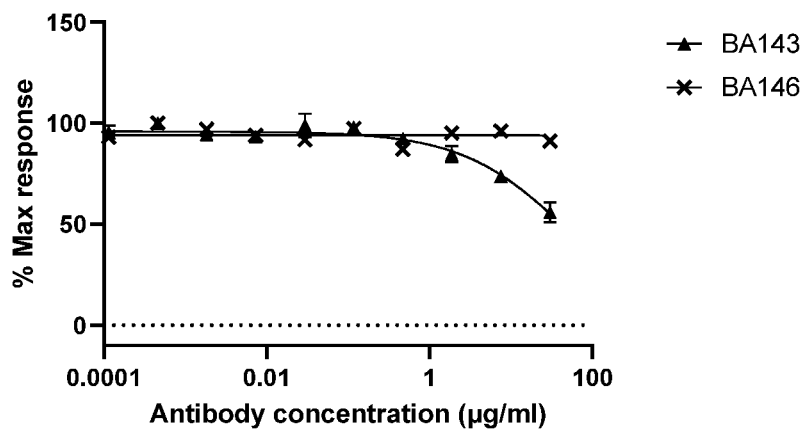
Figure 19B:
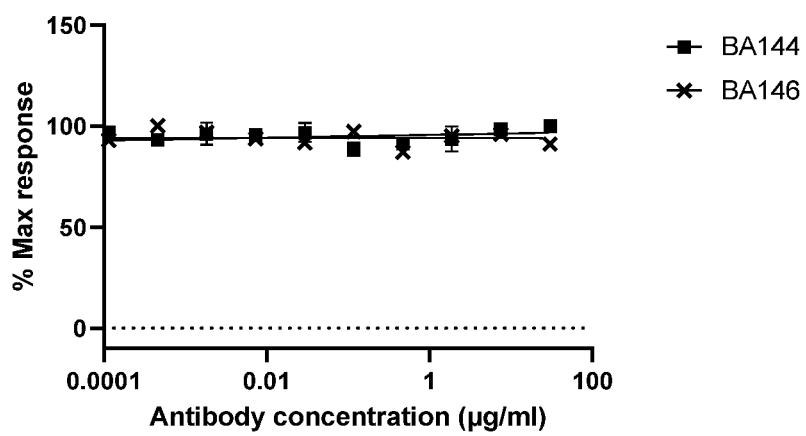
Figure 19C:
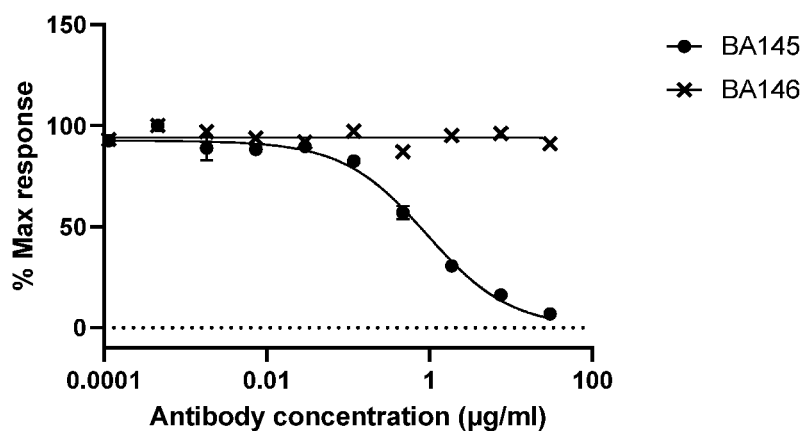

As shown in FIGS. 19A-19C, anti-CD96 antibodies BA145 block, and BA143 partially block the interaction between cynomolgus monkey CD96 and CD155. Mean IC50 values were calculated for BA145 and are reported in Table 44. IC50 value could not be calculated for BA143 due to partial blocking. The area under the curve (AUC) was calculated for a representative experiment and is reported in Table 45.

TABLE 44

IC50 values for anti-CD96 antibodies blocking cynomolgus monkey CD96 (isoform 2) binding to human CD155.*

| Antibody | IC50 (Geomean), ng/mL |
|---|---|
| BA143 | Not fit |
| BA144 | No blocking |
| BA145 | 794.8 |

*Calculated from 3 experiments.

TABLE 45

AUC values for a representative experiment showing anti-CD96 blocking cynomolgus monkey CD96 (isoform 2) binding to human CD155.

| Multispecific molecule | Area under the curve (AUC) | Standard error |
|---|---|---|
| BA143 | 543.9 | 4.19 |
| BA144 | 569.5 | 4.70 |
| BA145 | 417.0 | 4.70 |
| BA146 | 567.0 | N/A |

8.8 Example 8: Characterization of Anti-TIGIT Antibodies 8.8.1 Anti-Human TIGIT Antibodies Bind to Cells Expressing Human and Cynomolgus Monkey TIGIT The capacity of anti-TIGIT antibodies to bind to wild type human TIGIT or wild type cynomolgus monkey TIGIT on the surface of various cell types was tested in vitro by flow cytometry.

Binding to Human TIGIT-Expressing CHO Cells

The ability of anti-TIGIT antibodies to bind to wild type human TIGIT expressed on the surface of CHO cells was assessed. Briefly, CHO cells were transfected with a vector encoding wild type human TIGIT (human TIGIT-CHO), and clones stably expressing TIGIT were selected. Stable cell lines were cultured in Power CHO-2 medium containing 4 mM L-Glutamine, 100 U/mL 1× HT-Supplement, and 2.5 µg/mL Puromycin.

For the antibody binding assay, a frozen aliquot of human TIGIT-CHO cells was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of $2 \times 10^5$ cells per well in 50 µt. In a separate microplate, a 2× concentrated intermediate stock of each antibody was prepared. Antibodies were serially diluted 1-to-4 in FACS buffer. A total of 11 working dilutions ranging from 60 µg/mL to 0.000057 µg/mL were prepared. Fifty microliters of each dilution were then transferred to the microplate containing human TIGIT-CHO cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')$_2$ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of antibody resulting in 50% of maximal binding (Effective Concentration 50, [EC50]) by curve fitting using a four-parameter logistic equation.

Figure 20:
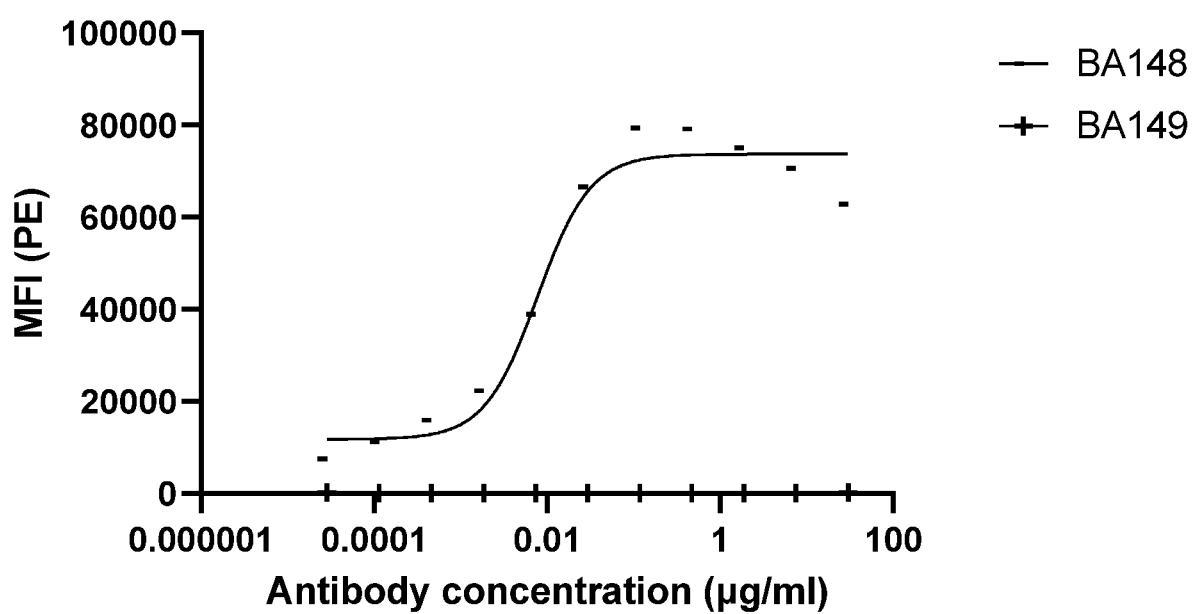

As shown in FIG. 20, BA148 bound to human TIGIT-expressing CHO cells in a dose-dependent manner. Mean EC50 values were calculated for each antibody and are reported in Table 46. The area under the curve (AUC) was calculated for a representative experiment and is reported in Table 47.

TABLE 46

EC50 values for anti-TIGIT antibodies binding to human TIGIT CHO cells.*

| Antibody | EC50 (Geomean), ng/mL |
|---|---|
| BA148 | 8.2 |

*Calculated from 2 experiments.

TABLE 47

AUC values for a representative experiment showing anti-
TIGIT antibodies binding to human TIGIT CHO cells.

| Antibody | Area under the curve (AUC) | Standard error |
|---|---|---|
| BA148 | 297761 | 1286 |
| BA149 | 653.3 | 49.26 |

Binding to Cynomolgus Monkey TIGIT-Expressing CHO Cells

In similar experiments, the capacity of anti-TIGIT antibodies to bind to CHO cells engineered to express wild type cynomolgus monkey TIGIT on their cell surfaces (cynomolgus TIGIT-CHO cells) was tested. Briefly, CHO cells were transfected with a vector encoding wild type cynomolgus monkey TIGIT, and a clone stably expressing cynomolgus monkey TIGIT was selected. The stable cell line was cultured in Power CHO-2 medium containing 4 mM L-Glutamine, 100 U/mL 1× HT-Supplement, and 2.5 µg/mL Puromycin. The ability of anti-TIGIT antibodies to bind to cynomolgus TIGIT-CHO was determined as described for human TIGIT-CHO cells above.

Figure 21:
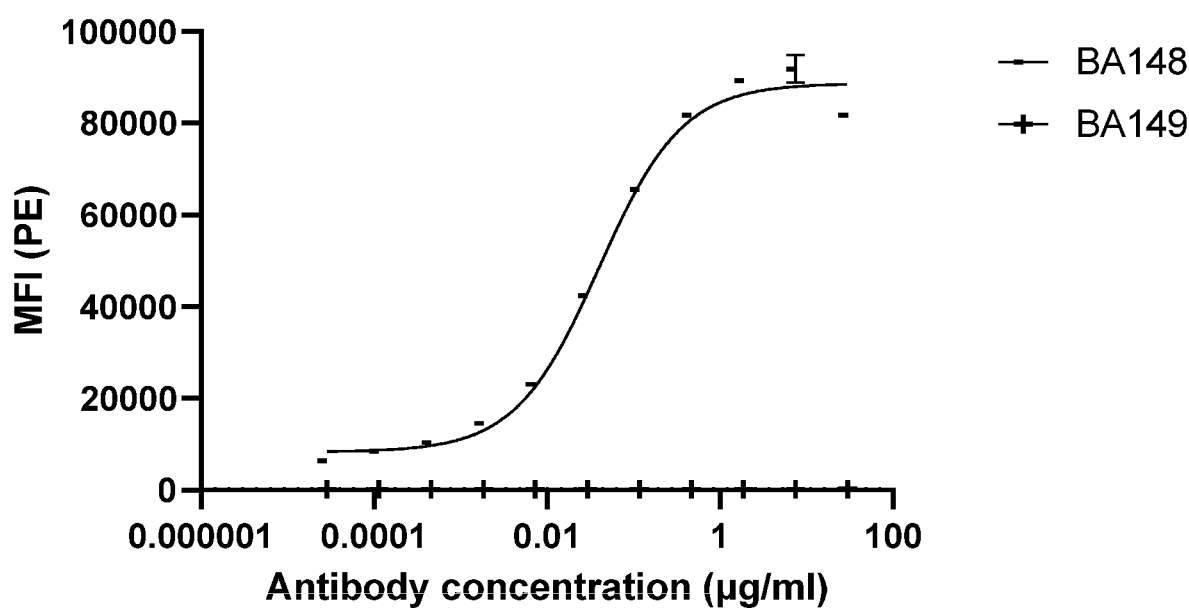

As shown in FIG. 21, BA148 bound to CHO cells expressing cynomolgus monkey TIGIT in a dose-dependent manner. Mean EC50 values for the binding of BA148 to cynomolgus TIGIT-CHO cells were calculated for each antibody and are reported in Table 48. The area under the curve (AUC) was calculated for a representative experiment and is reported in Table 49.

TABLE 48

EC50 values for anti-TIGIT antibodies
binding to cynomolgus TIGIT-CHO cells.*

| Antibody | EC50 (Geomean), ng/mL |
|---|---|
| BA148 | 53.42 |

*Calculated from 2 experiments.

TABLE 49

AUC values for a representative experiment showing anti-
TIGIT antibodies binding to cynomolgus TIGIT-CHO cells.

| Antibody | Area under the curve (AUC) | Standard error |
|---|---|---|
| BA148 | 283737 | 1822 |
| BA149 | 578.8 | 31.16 |

8.8.2 Anti-Human TIGIT Antibodies Block Ligand Binding to TIGIT

Blocking of Human TIGIT-CHO Cells Binding to Soluble Human CD155

In this example, the capacity of anti-TIGIT antibodies to block binding between wild type human TIGIT and its ligand human CD155 (also referred to as PVR) was tested. Specifically, antibodies were tested in vitro for their ability to block binding between wild type human TIGIT overexpressed on CHO cells and soluble human CD155 by flow cytometry.

Briefly, a solution containing 2 µg/mL of human CD155-Fc conjugated to R-Phycoerythrin (CD155-Fc-PE) was prepared in FACS buffer. Fifty microlitres of this working stock of human CD155-Fc-PE were then added to the wells of a 96-well U-bottom microplate. A 4× concentrated intermediate stock of each antibody was prepared in a microplate. Antibodies were serially diluted 1-to-4 in FACS buffer. A total of 11 working dilutions ranging from 120 µg/mL to 0.0001 µg/mL were prepared. Twenty-five microlitres of each dilution were added to the microplate containing CD155-Fc-PE. Lastly, 25 µL of human TIGIT-CHO cells, prepared as described above, were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs. SSC-A. Mean fluorescence intensity (MFI) values for PE were calculated, and the data were plotted by GraphPad Prism software and analyzed as described above.

For each antibody concentration, experimental data were normalized using MFI values obtained for human TIGIT-CHO cells incubated with CD155-Fc-PE in absence of antibody and MFI values for human TIGIT-CHO cell autofluorescence (background) according to equation 5.

$$\% \text{ Maximal signal} = (\text{MFI "antibody"} - \text{MFI "background"})/(\text{MFI "total"} - \text{MFI "background"}) \quad \text{Equation 5}$$

where

"Antibody" is BA148

"Background" is cells alone (no antibody or CD155-Fc-PE)

"Total" is cells incubated with CD155-Fc-PE in absence of antibodies

The concentration of antibody inhibiting 50% (IC50) of CD155-Fc-PE binding to wild type human TIGIT-CHO cells was determined. IC50 values were calculated using GraphPad Prism software by curve fitting using a four-parameter logistic equation.

Figure 22:
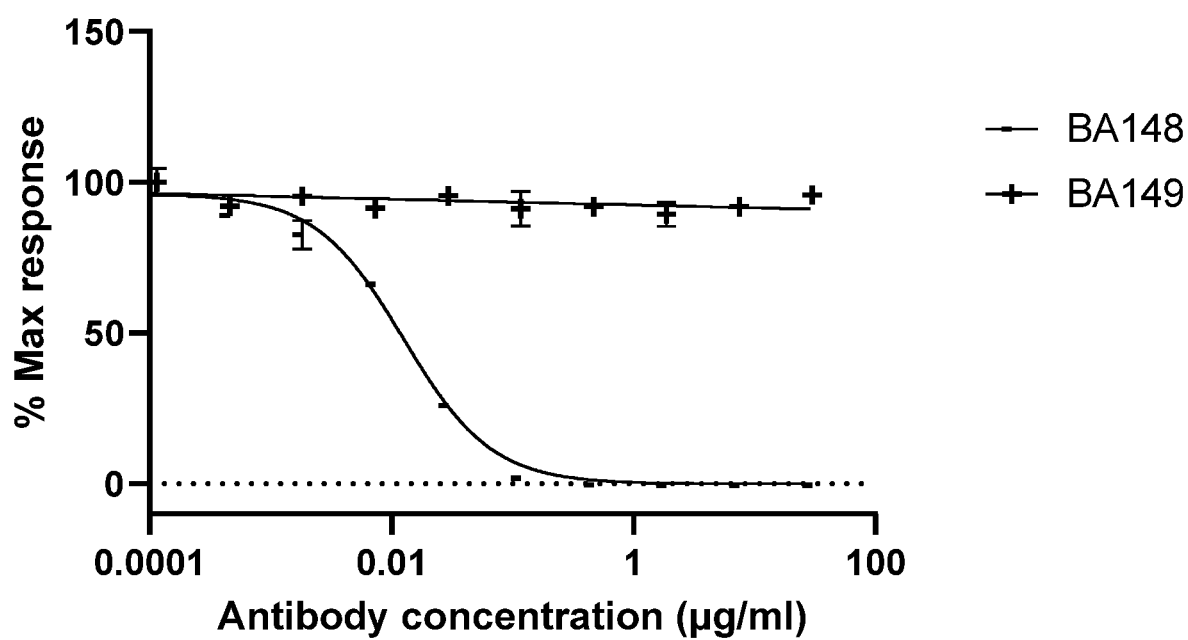

As shown in FIG. 22, BA148 blocked wild type human TIGIT binding to CD155. Mean IC50 values were calculated for each antibody and are reported in Table 50. The area under the curve (AUC) was calculated for a representative experiment and is reported in Table 51.

TABLE 50

IC50 values for anti-TIGIT antibodies blocking
human TIGIT-CHO binding to human CD155.*

| Antibody | IC50 (Geomean), ng/mL |
|---|---|
| BA148 | 8.4 |

*Calculated from 3 experiments.

TABLE 51

AUC values for a representative experiment showing anti-TIGIT
antibodies blocking human TIGIT-CHO binding to human CD155.

| Antibody | Area under the curve (AUC) | Standard error |
|---|---|---|
| BA148 | 250.9 | 3.24 |
| BA149 | 563.7 | 3.60 |

Blocking of Cynomolgus TIGIT-CHO Cells Binding to Soluble Human CD155

In this example, the capacity of anti-TIGIT antibodies to block binding between wild type cynomolgus monkey TIGIT and its ligand human CD155 (also referred to as PVR) was tested. Specifically, antibodies were tested in vitro for their ability to block binding between wild type cynomolgus monkey TIGIT over-expressed on CHO cells and soluble human CD155 by flow cytometry.

Briefly, a solution containing 2 µg/mL of human CD155-Fc conjugated to R-Phycoerythrin (CD155-Fc-PE) was prepared in FACS buffer. Fifty microlitres of this working stock of human CD155-Fc-PE were then added to the wells of a 96-well U-bottom microplate. A 4× concentrated intermediate stock of each multispecific molecule was prepared in a microplate. Antibodies were serially diluted 1-to-4 in FACS buffer. A total of 11 working dilutions ranging from 120 µg/mL to 0.0001 µg/mL were prepared. Twenty-five microlitres of each dilution were added to the microplate containing CD155-Fc-PE. Lastly, 25 µL of cynomolgus TIGIT-CHO cells, prepared as described above, were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs. SSC-A. Mean fluorescence intensity (MFI) values for PE were calculated, and the data were plotted by GraphPad Prism software and analyzed as described above.

Figure 23:
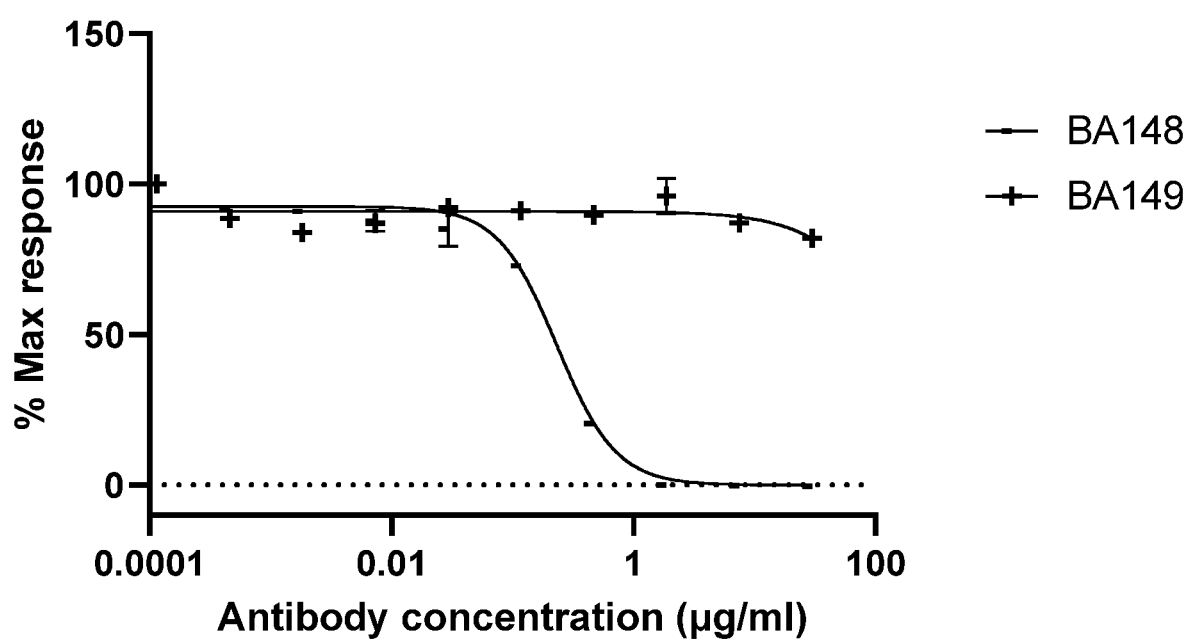
Figure 24A:
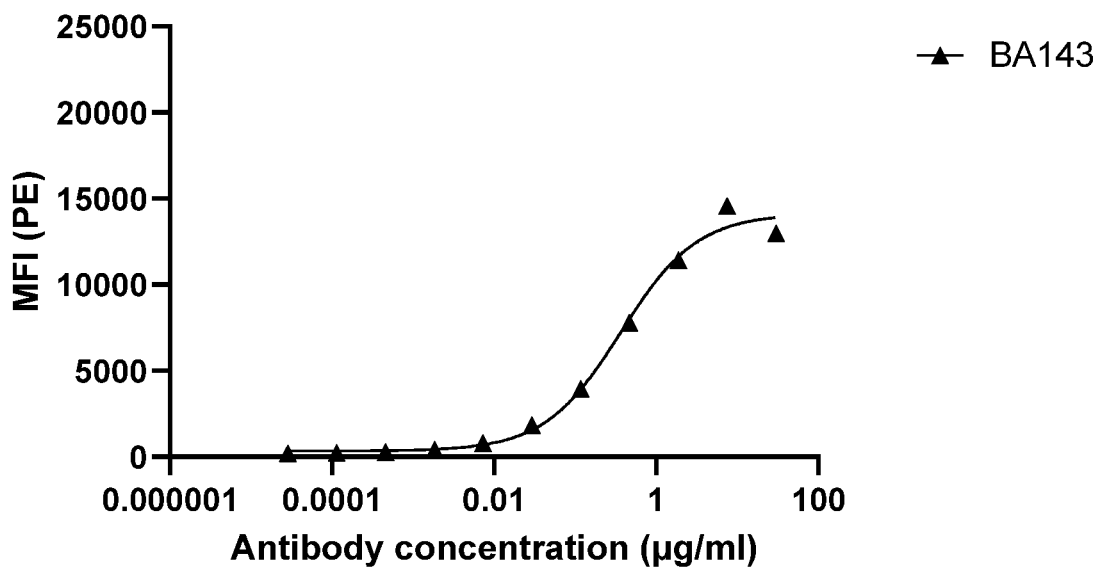
Figure 24B:
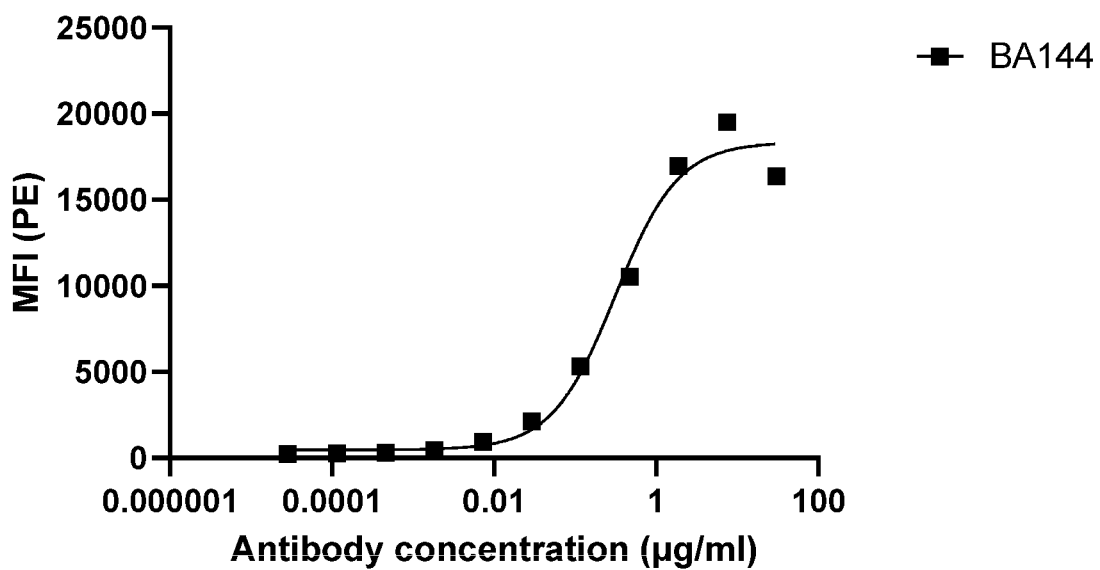
Figure 24C:
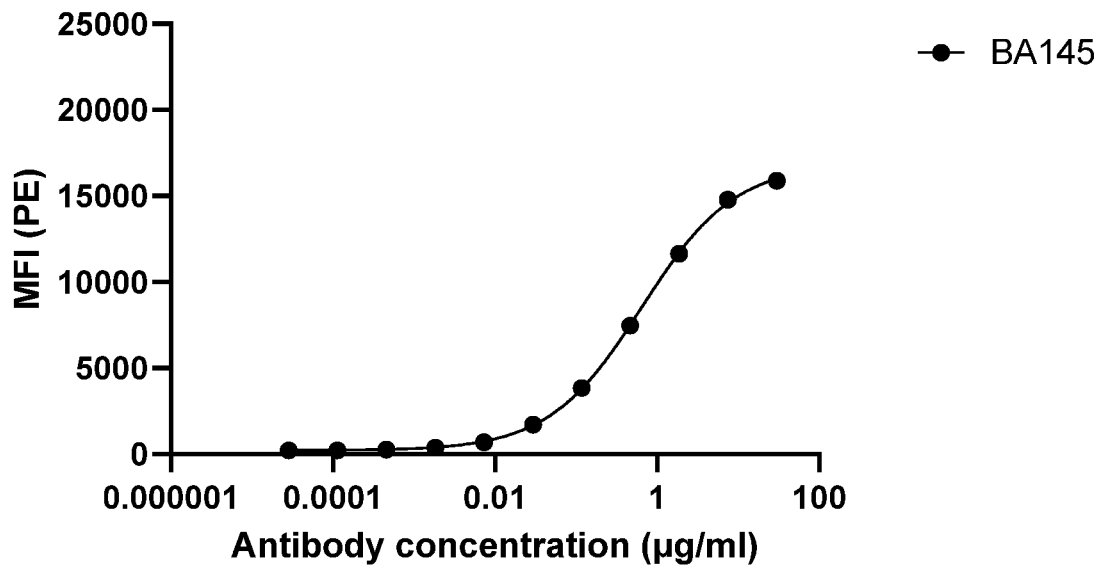
Figure 24D:
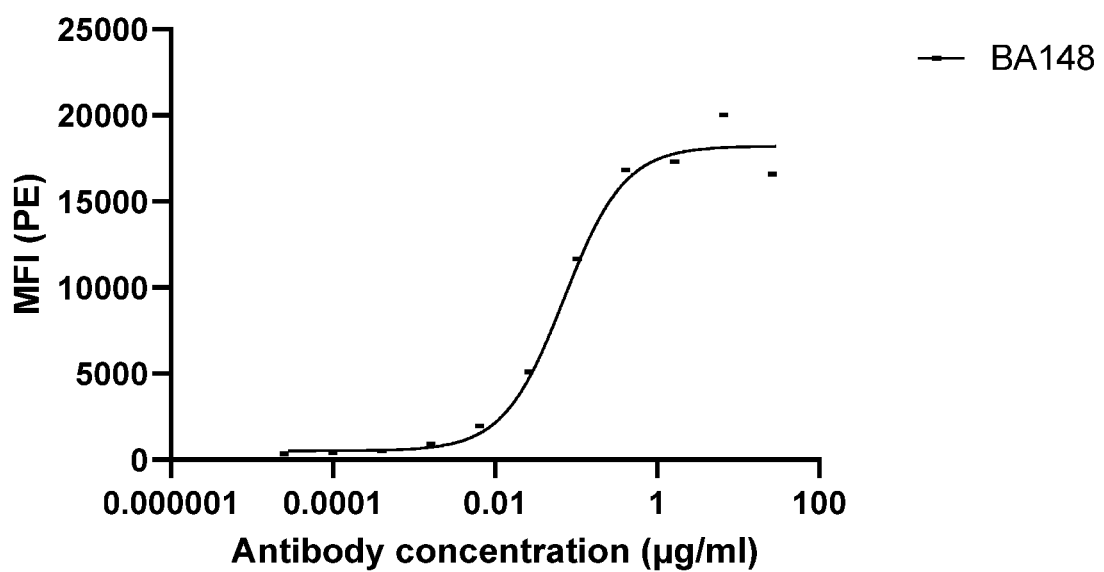
Figure 25A:
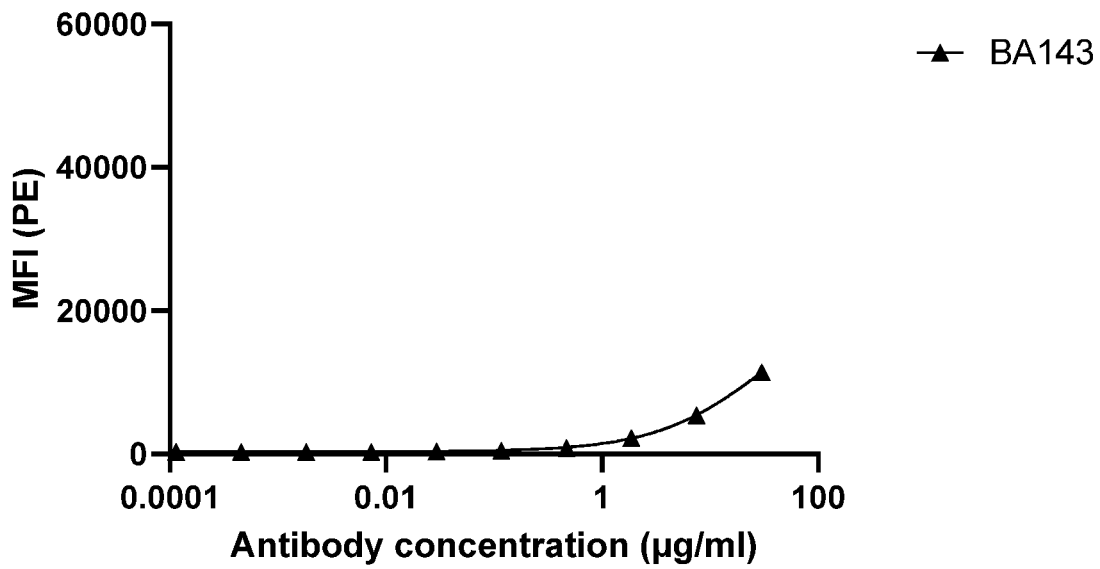
Figure 25B:
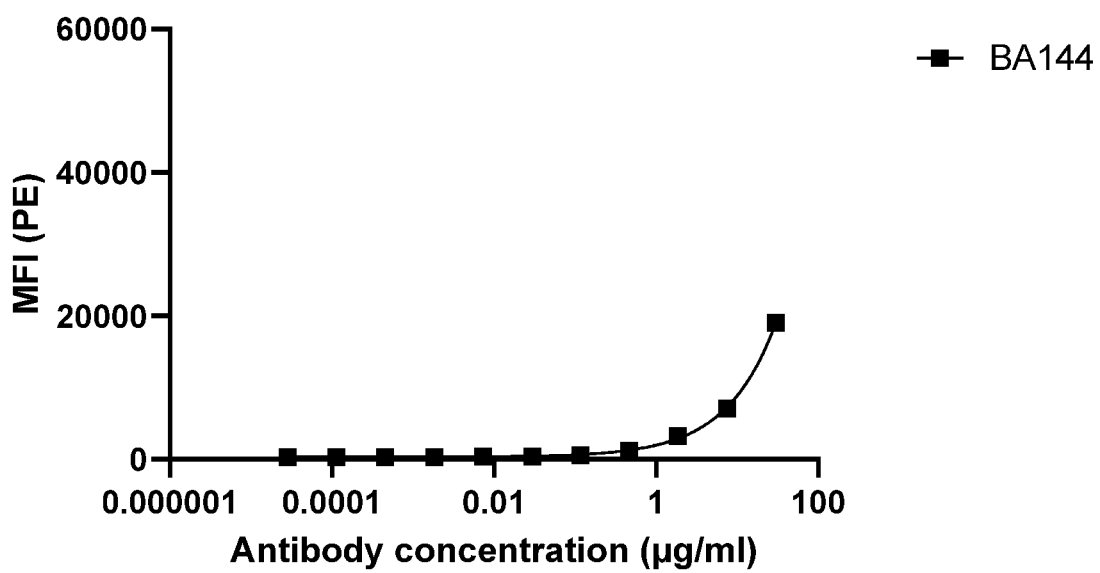
Figure 25C:
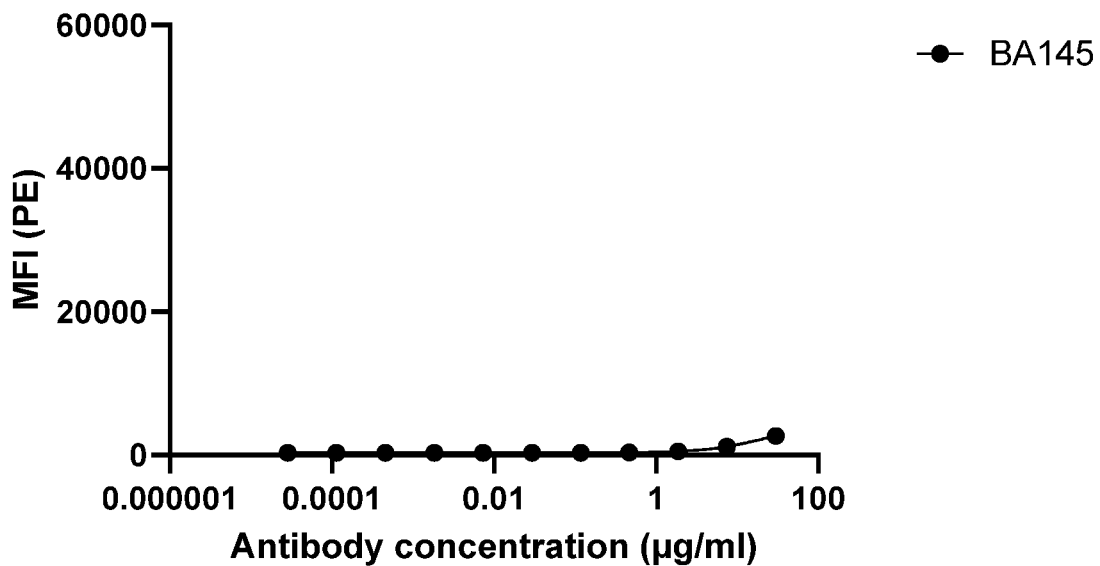
Figure 25D:
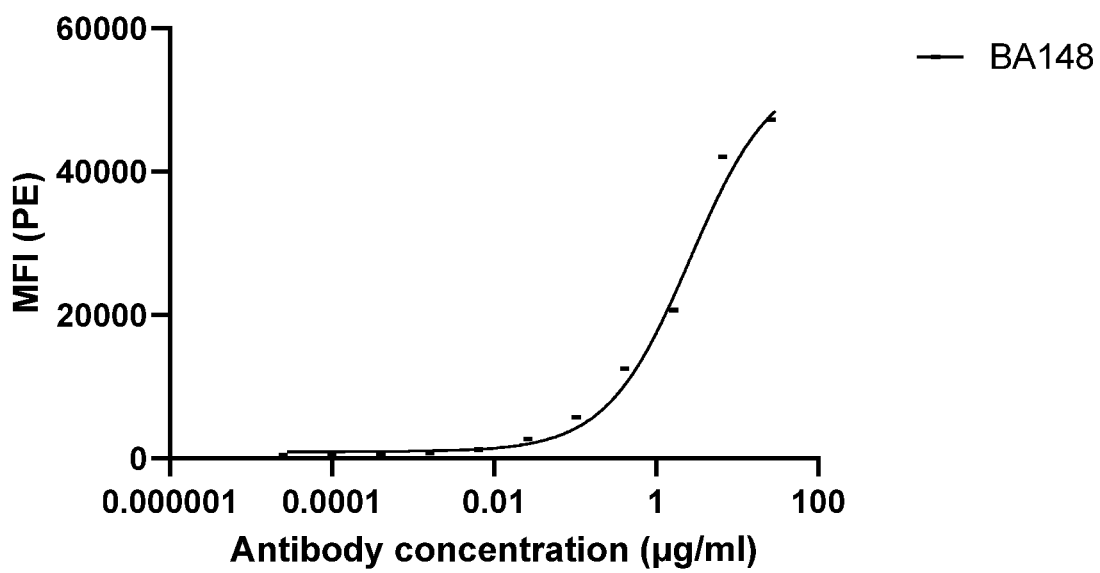

As shown in FIG. 23, BA148 blocked cynomolgus TIGIT-CHO binding to CD155. Mean IC50 values were calculated for each antibody and are reported in Table 52. The area under the curve (AUC) was calculated for a representative experiment and is reported in Table 53.

TABLE 52

IC50 values for anti-TIGIT antibodies blocking cynomolgus TIGIT-CHO binding to human CD155.

| Antibody | IC50 (Geomean), ng/mL |
| --- | --- |
| BA148 | 243.1 |

*Calculated from 3 experiments.

TABLE 53

AUC values for a representative experiment showing anti-TIGIT antibodies blocking cynomolgus TIGIT-CHO binding to human CD155.

| Antibody | Area under the curve (AUC) | Standard error |
| --- | --- | --- |
| BA148 | 359.9 | 3.18 |
| BA149 | 543.4 | 3.59 |

8.9 Example 9: Anti-Human TIGIT and Anti-Human CD96 Antibodies Bind to Cells Expressing FcγRIIIa Variants V/V and F/F The capacity of anti-TIGIT and anti-CD96 antibodies to bind to human FcγRIIIa (variant V/V and variant F/F) on the surface of various cell types was tested in vitro by flow cytometry.

Binding to Human FcγRIIIa-Expressing CHO Cells

The ability of anti-TIGIT and anti-CD96 antibodies to bind to human FcγRIIIa expressed on the surface of CHO cells was assessed. Briefly, CHO cells were transfected with a vector encoding human FcγRIIIa (human FcγRIIIa-CHO) variant V/V or variant F/F, and clones stably expressing FcγRIIIa variant V/V or variant F/F were selected. Stable cell lines were cultured in Power CHO-2 medium containing 4 mM L-Glutamine, 100 U/mL 1× HT-Supplement, and 2.5 µg/mL Puromycin.

For the antibody binding assay, a frozen aliquot of human FcγRIIIa-CHO cells (variant V/V or variant F/F) was thawed at 37° C. and then transferred to a tube containing DPBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of $2×10^5$ cells per well in 50 pt. In a separate microplate, a 2× concentrated intermediate stock of each antibody was prepared. Antibodies were serially diluted 1-to-4 in FACS buffer. A total of 11 working dilutions ranging from 60 µg/mL to 0.000057 µg/mL were prepared. Fifty microlitres of each dilution were then transferred to the microplate containing human FcγRIIIa-CHO (variant V/V or variant F/F) cells. The cells were then incubated for 45 minutes at 4° C. For antibody staining, the cells were washed twice with cold FACS Buffer and re-suspended in FACS Buffer containing R-Phycoerythrin (PE) AffiniPure F(ab')$_2$ Fragment Goat Anti-Human IgG, Fcγ fragment specific (Jackson, Cat #109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs. SSC-A. Mean fluorescence intensity (MFI) values for PE were calculated, and the data were plotted by GraphPad Prism software. The software was used to determine the concentration of antibody resulting in 50% of maximal binding (Effective Concentration 50, [EC50]) by curve fitting using a four-parameter logistic equation.

As shown in FIGS. 24A-24D, BA143, BA144, BA145, and BA148 bound to variant V/V of human FcγRIIIa-expressing CHO cells in a dose-dependent manner. Mean EC50 values were calculated for each antibody and are reported in Table 54. The area under the curve (AUC) was calculated for a representative experiment and is reported in Table 55.

As shown in FIGS. 25A-25E, BA143, BA144, and BA148 bound to variant F/F of human FcγRIIIa-expressing CHO cells in a dose-dependent manner. EC50 values were calculated for each antibody and are reported in Table 56. The area under the curve (AUC) was calculated and is reported in Table 57.

TABLE 54

EC50 values for anti-TIGIT and anti-CD96 antibodies binding to human FcγRIIIa (V/V) CHO cells.*

| Antibody | EC50, ng/mL |
| --- | --- |
| BA143 | 191.5 |
| BA144 | 271.7 |
| BA145 | 329.1 |
| BA148 | 45.5 |

*Calculated from 2 experiments.

TABLE 55

AUC values for a representative experiment showing anti-TIGIT and anti-CD96 antibodies binding to human FcγRIIIa (V/V) CHO cells.

| Antibody | Area under the curve (AUC) |
| --- | --- |
| BA143 | 28879 |
| BA144 | 38938 |
| BA145 | 29559 |
| BA148 | 50127 |

TABLE 56

EC50 values for anti-TIGIT and anti-CD96 antibodies binding to human FcγRIIIa (F/F) CHO cells.

| Antibody | EC50, ng/mL |
| --- | --- |
| BA143 | Not fit |
| BA144 | Not fit |
| BA145 | Not fit |
| BA148 | 2.62 |

*Calculated from 1 experiment.

TABLE 57

AUC values for an experiment showing anti-TIGIT and anti-CD96 antibodies binding to human FcγRIIIa (F/F) CHO cells

| Antibody | Area under the curve (AUC) |
| --- | --- |
| BA143 | 10043 |
| BA144 | 14171 |
| BA145 | 3333 |
| BA148 | 66622 |

8.10 Example 10: Binding of Anti-TIGITxCD96 Multispecific Molecules to Primary Human T Cells In this example, the ability of anti-TIGITxCD96 multispecific molecule BA127, as well as the anti-CD96 monospecific control antibody BA143, the anti-TIGIT monospecific antibody BA148, or the bispecific isotype control antibody BA128, to bind to activated human T cells was tested. For activated T cells, a frozen aliquot of human PBMCs from four different healthy donors were retrieved from liquid nitrogen and immediately thawed in 37° C. water until floating ice was observed. Cells were then transferred to 10 mL of pre-warmed R10 media. 20 μL was removed and added to 380 μL viability dye to count cells and check viability using a Muse apparatus. Samples were centrifuged at 1200 rpm for five minutes and then suspended to a final concentration of $1 \times 10^6$ cells/mL with R10 media. Cells were stimulated with immunoCult CD3/CD28 T cell activator at 25 ul per $1 \times 10^6$ cells and 100 μL of stimulated cells were pipetted into each well of a 96-well round-bottom tissue culture plate and incubated at 37° C. in 5% $CO_2$ for four days.

A dose range of the multispecific molecule or antibody was placed in a 96-well round bottom plate. First, 200 μL of 50 μg/mL of each antibody was prepared in buffer. The multispecific molecule and antibodies were then serially diluted 1-to-10 by pipetting 20 μL of the previous dilution into 180 μL of sample buffer. A total of 8 dilutions ranging from 50 μg/mL to 0.000005 μg/mL were prepared. After four days, the sample plates were centrifuged for two minutes at 2000 rpm, and supernatants were discarded. Samples were blocked with FcγR Block prepared in FACs buffer at 5 μL per 100 μL test for 10 minutes. Sample plates were then centrifuged for two minutes at 2000 rpm, and the supernatant was discarded. The cells were then re-suspended in 100 μL of anti-TIGITxCD96 multispecific molecule or a relevant isotype control at the concentrations shown in FIGS. 26A-26F. Sample plates were incubated for 30 minutes at 4° C. Cells were washed by addition of cold sample buffer and centrifuged for two minutes at 2000 rpm, and the supernatant was discarded. This wash was repeated once.

Cells were then resuspended in a cocktail of fluorescently labeled antibodies. A cocktail of fluorescently labeled antibodies sufficient for all samples was prepared in FACs buffer. 100 μL of antibody per well was then added to a round-bottom 96-well plate. The sample plate was incubated for 20 minutes on ice. Cells were washed by addition of cold sample buffer, centrifuged for two minutes at 2000 rpm, and supernatants discarded. This wash was repeated once. A final cocktail of PE-labeled secondary anti-human IgG antibody was prepared in 11 mL of FACs buffer. 100 μL of secondary antibody was added per well to a round-bottom 96-well plate. The sample plate was incubated for 5 minutes on ice. Cells were washed by addition of cold sample buffer, centrifuged for two minutes at 2000 rpm, and the supernatants were discarded. This wash was repeated once.

Antibody binding was measured by flow cytometry using a BD LSR Fortessa Flow Cytometer. Unstained control cells were used to gate on the lymphocyte population using a plot of forward scatter-area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 100,000 events were recorded for each sample. Samples were analyzed by sequentially gating on the following populations: FSC-A vs. SSC-A, FSC-H vs. FSC-A, SSC-A vs. LIVE/DEAD, CD4 vs. CD8, and SSC vs. CD25. Mean fluorescence intensity (MFI) was calculated.

Figures 26A, 26B, 26C:
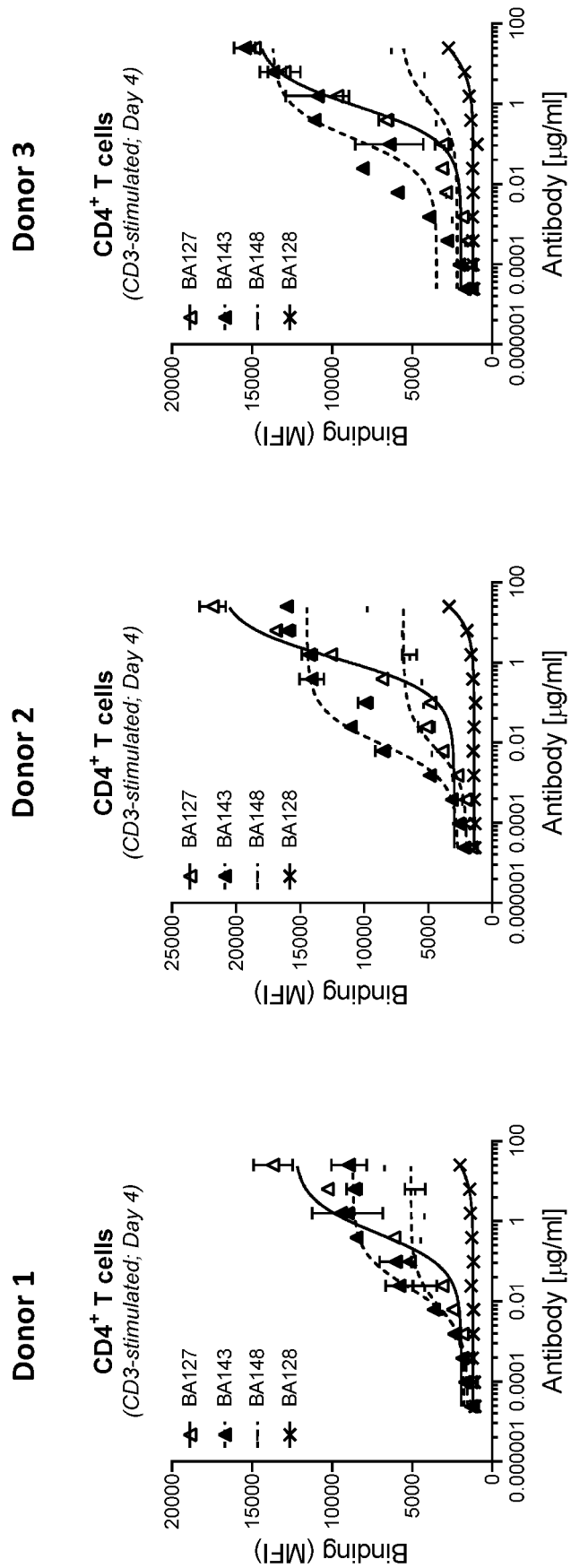
Figures 26D, 26E, 26F:
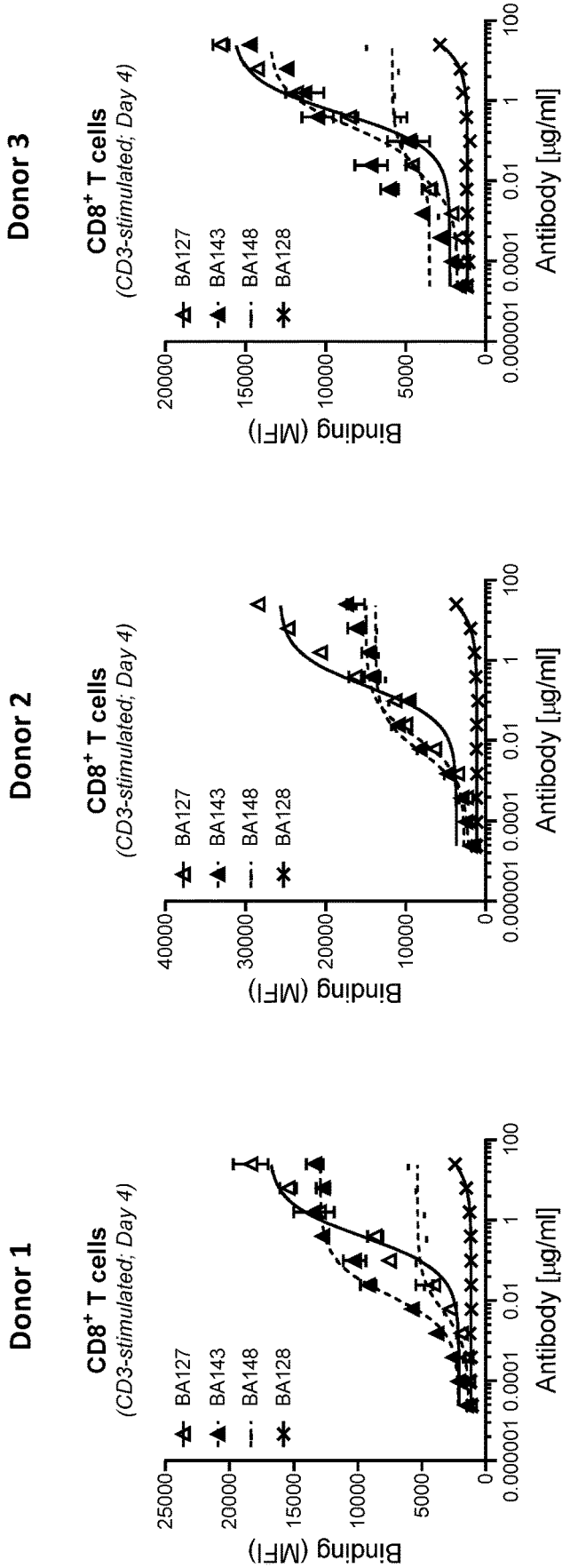
Figures 27A, 27B, 27C:
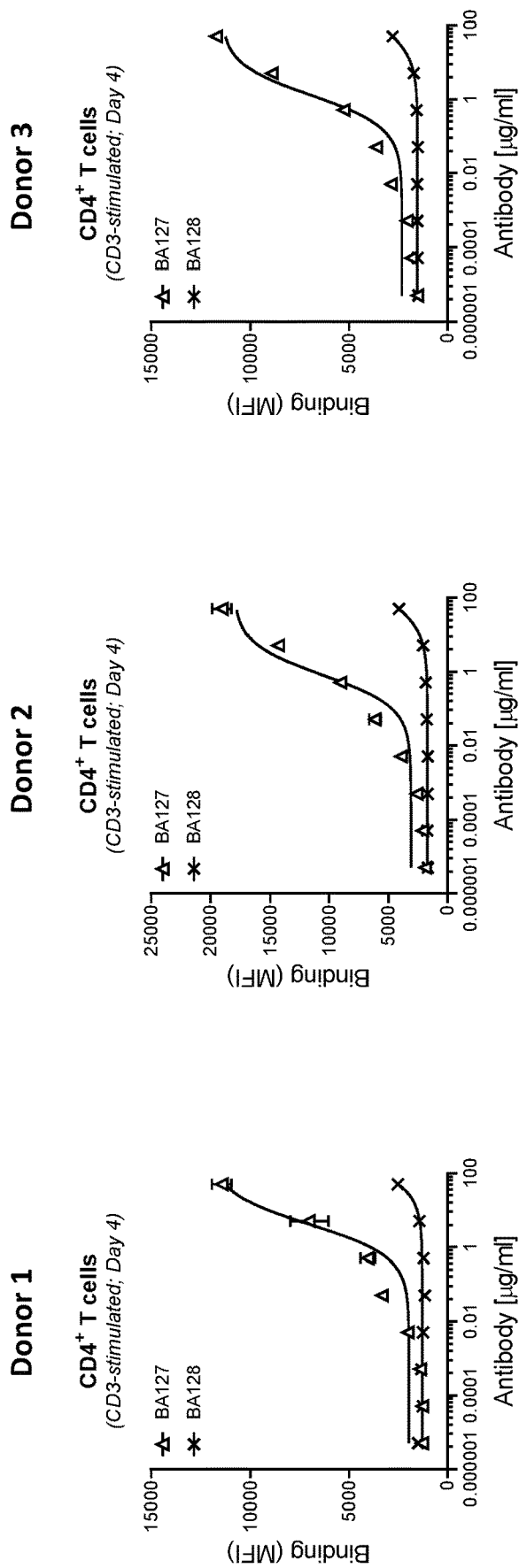
FIG. 27A-FIG. 27F are a series of graphs showing the ability of BA127 or BA128 to bind to activated human T cells in three different donors. Binding to CD4+ T cells (FIG. 27A, FIG. 27B, and FIG. 27C) and CD8+ T cells (FIG. 27D, FIG. 27E, and FIG. 27F), as assessed by median fluorescence intensity (MFI), was plotted against the concentrations of the respective antibody incubated with the cells.
Figures 27D, 27E, 27F:
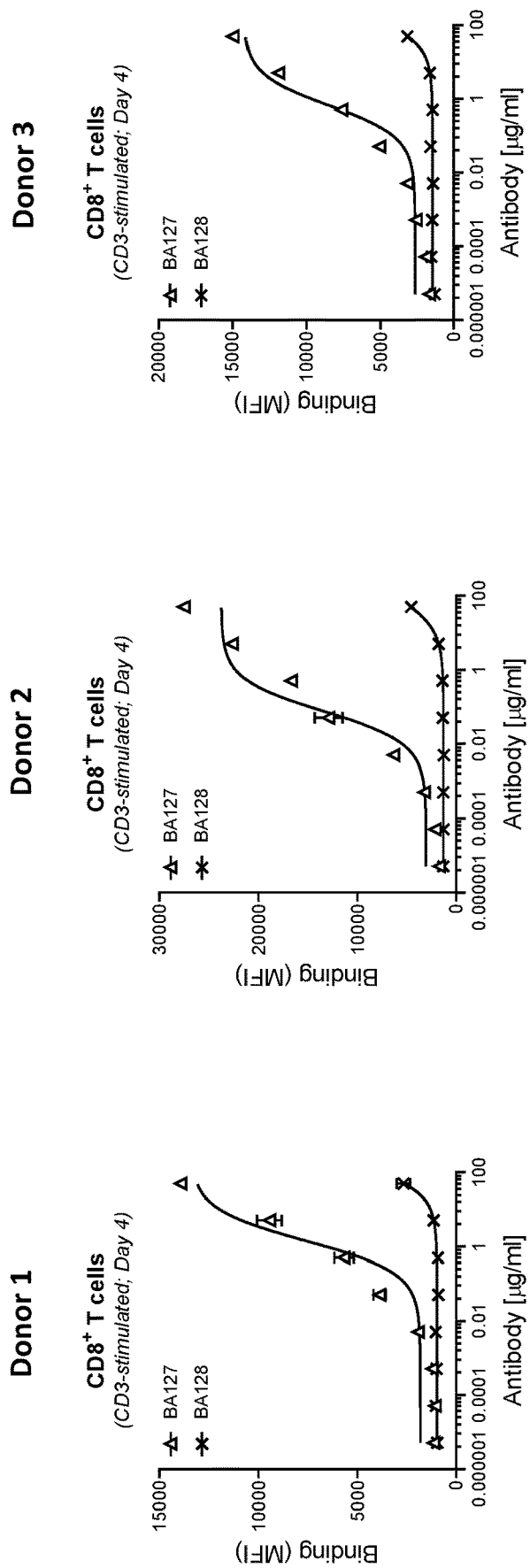

As shown in FIGS. 26A-26F, TIGITxCD96 multispecific molecule BA127 demonstrated potent binding to activated primary human CD4+ T cells (FIGS. 26A, 26B and 26C) and activated primary human CD8+ T cells (FIGS. 26D, 256 and 26F) across three independent donors. Notably, BA127 demonstrated superior maximal binding to activated CD4+ (FIGS. 26A and 26B) and CD8+(FIGS. 26D and 26E) T cells from donors 1 and 2 compared to corresponding anti-CD96 monospecific control antibody BA143 and the anti-TIGIT monospecific antibody BA148. BA127 showed comparable binding to activated CD4+ and CD8+ T cells from donor 3 as compared to BA143 (FIGS. 26C and 26F).

8.11 Example 11: Binding of Anti-TIGITxCD96 Multispecific Molecules to Primary Human T Cells In this experiment the ability of anti-TIGITxCD96 multispecific molecule BA127 to bind to activated human T cells was tested. For activated T cells, a frozen aliquot of human PBMCs from four different healthy donors were retrieved from liquid nitrogen and immediately thawed in 37° C. water until floating ice was observed. Cells were then transferred to 10 mL of pre-warmed R10 media. 20 pt was removed and added to 380 μL viability dye to count cells and check viability using a Muse apparatus. Samples were centrifuged at 1200 rpm for five minutes and then suspended to a final concentration of $1 \times 10^6$ cells/mL with R10 media. Cells were stimulated with immunoCult CD3/CD28 T cell activator at 25 ul per $1 \times 10^6$ cells and 100 μL, of stimulated cells were pipetted into each well of a 96-well round-bottom tissue culture plate and incubated at 37° C. in 5% $CO_2$ for four days.

A dose range of multispecific molecule or antibody (BA127 or the bispecific isotype control antibody BA128) was placed in a 96-well round bottom plate. First, 200 μL of 25 μg/mL of each antibody was prepared in buffer. The multispecific molecule and antibody were then serially diluted 1-to-4 by pipetting 50 ρt of the previous dilution into 150 ρt of sample buffer. A total of 8 dilutions ranging from 50 μg/mL to 0.000005 μg/mL were prepared. After four days, the sample plates were centrifuged for two minutes at 2000 rpm, and supernatants were discarded. Samples were blocked with FcγR Block prepared in FACs buffer at 5 μL per 100 μL test for 10 minutes. Sample plates were then centrifuged for two minutes at 2000 rpm, and the supernatant was discarded. The cells were then re-suspended in 100 μL of anti-TIGITxCD96 multispecific molecule (BA127) or a relevant isotype control (BA128) at the concentrations shown in FIGS. 27A-27F. Sample plates were incubated for 30 minutes at 4° C. Cells were washed by addition of cold sample buffer and centrifuged for two minutes at 2000 rpm, and the supernatant was discarded. This wash was repeated once.

Cells were then resuspended in a cocktail of fluorescently labeled antibodies. A cocktail of fluorescently labeled antibodies sufficient for all samples was prepared in FACs buffer. 100 μL of antibody per well was then added to a round-bottom 96-well plate. The sample plate was incubated for 20 minutes on ice. Cells were washed by addition of cold sample buffer, centrifuged for two minutes at 2000 rpm, and supernatants discarded. This wash was repeated once. A final cocktail of PE-labeled secondary anti-human IgG antibody was prepared in 11 mL of FACs buffer. 100 μl of secondary antibody was added per well to a round-bottom 96-well plate. The sample plate was incubated for 5 minutes on ice. Cells were washed by addition of cold sample buffer, centrifuged for two minutes at 2000 rpm, and the supernatants were discarded. This wash was repeated once.

Antibody binding was measured by flow cytometry using a BD LSR Fortessa Flow Cytometer. Unstained control cells were used to gate on the lymphocyte population using a plot of forward scatter-area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 100,000 events were recorded for each sample. Samples were analyzed by sequentially gating on the following populations: FSC-A vs. SSC-A, FSC-H vs. FSC-A, SSC-A vs. LIVE/DEAD, CD4 vs. CD8, and SSC vs. CD25. Mean fluorescence intensity (MFI) was calculated.

As shown in FIGS. 27A-27F, TIGITxCD96 multispecific molecule, BA127 bound to activated primary human CD4+ T cells (FIGS. 27A, 27B, and 27C) and activated primary human CD8+ T cells (FIGS. 27D, 27E, and 27F) from three independent donors in a dose-dependent manner.

8.12 Example 12: SEA-Stimulation Assay

In this example, the capacity of anti-TIGITxCD96 multispecific molecules, as compared to control multispecific molecules to promote secretion of the cytokine interleukin-2 (IL-2) by PBMCs stimulated with SEA was tested.

A dose range of each of anti-TIGITxCD96 multispecific molecules BA123, BA125, and BA127, isotype control multispecific molecule BA128, and anti-CD96xisotype control multispecific molecules BA129, BA130, and BA131 was prepared at 5x concentrated intermediate stock in 1.2 mL bullet tubes. First, a 250 μg/ml intermediate stock was prepared in R10 media and antibodies were serially diluted 1 to 10 by serial dilution for a total of 8 dilutions. 20 μL of antibody was added per well to a round-bottom 96-well plate for a final concentration ranging from 50 μg/mL to 0.000005 μg/mL.

Frozen aliquots of human PBMCs were retrieved from liquid nitrogen and immediately thawed in 37° C. water until floating ice was observed. Cells were transferred to 10 mL of pre-warmed R10 media and immediately centrifuged at 1500 rpm for five minutes. The supernatant was discarded, and cells were resuspended in fresh R10 media. To count cells and check viability, 20 μL, of sample was removed and added to 380 μl of viability dye, mixed, and read using a Muse apparatus.

Cells resuspended to an intermediate concentration. An intermediate stock concentration of SEA was made by adding 10 μl of 10 μg/mL SEA to 90 μL R10 to make an intermediate concentration of 1 μg/mL. Cells were first stimulated with SEA peptide and 80 μL cells and SEA mixture were added into corresponding wells and incubated in tissue culture incubator at 37° C. and 5% CO2 within a humidified chamber for four days. A total of 100,000 cells/well and final concentration of 1 ng/mL of SEA were used.

After four days of incubation, plates were removed from the incubator. The plates were then centrifuged for two minutes at 2000 rpm. 5 μL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10x AlphaLISA Immunoassay Buffer to 22.5 mL water. Human IL-2 analyte was used to prepare a standard dilution. A mixture of 1.6x AlphaLISA anti-IL-2 acceptor beads and biotinylated anti-IL-2 antibody was prepared in assay buffer. 8 μL was added to each well and incubated in darkness at room temperature. AlphaLISA plates were briefly centrifuged at 2000 rpm. A 2.3x Streptavidin Donor Bead intermediate stock was prepared in assay buffer. 10 μL was added to each well and incubated in darkness at room temperature. AlphaLISA plates were briefly centrifuged at 2000 rpm. Relative light units (RLU) were measured using the AlphaScreen protocol on an EnVision Plate Reader. Results were plotted in GraphPad Prism and curves were fit using non-linear regression.

Figure 28A:
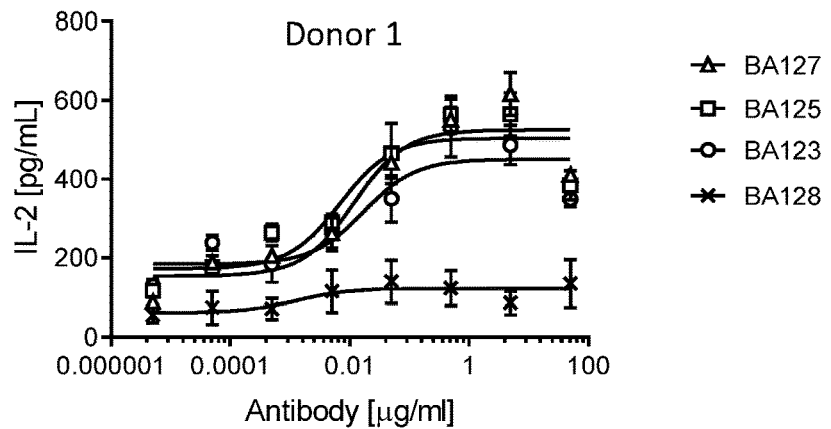
FIG. 28A-FIG. 28C are a series of graphs showing the ability of BA123, BA125, BA127, BA128, BA129, BA130, and BA131 multispecific molecules to promote IL-2 secretion by SEA-stimulated PBMCs from a single donor over a range of multispecific molecule concentrations. Each panel represents an independent experiment using the same donor.
Figure 28B:
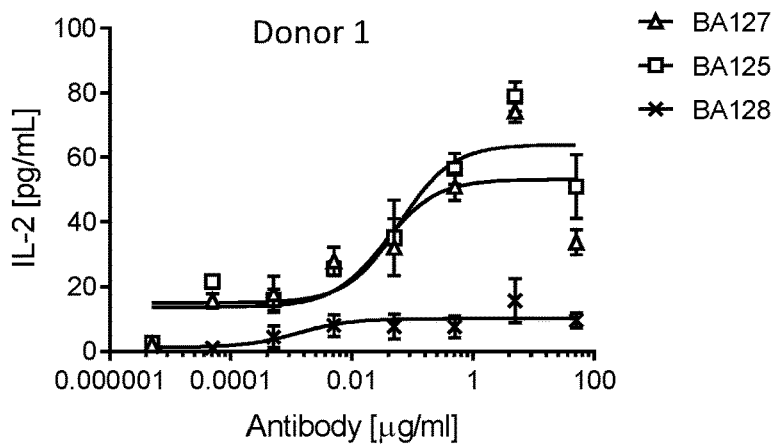
Figure 28C:
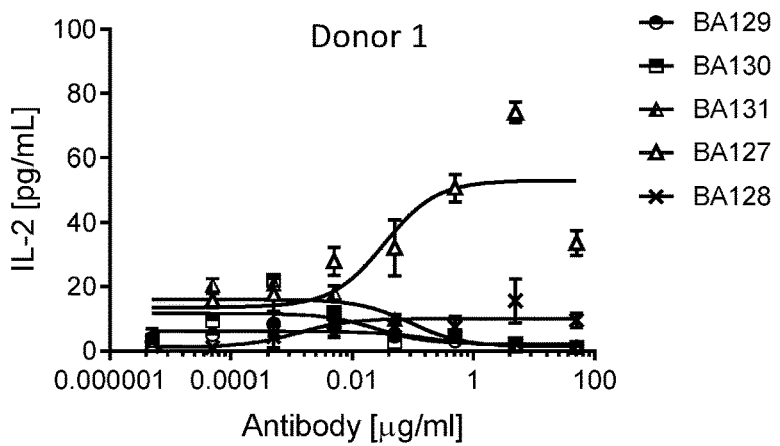

As shown in FIGS. 28A-28C, anti-TIGITxCD96 multispecific molecules, BA123, BA125 and BA127 (FIG. 28A) and BA125 and BA127 (FIG. 28B) potently enhanced T cell responsiveness as determined by interleukin-2 (IL-2) cytokine secretion as compared to isotype control, BA128. Further, BA127 demonstrated superior functional activity compared to CD96 only binding multispecific molecules, BA129, BA130, and BA131 or isotype control antibody, BA128 (FIG. 28C).

8.13 Example 13: SEA-Stimulation Assay

A dose range of each of anti-TIGITxCD96 multispecific molecule BA127, isotype control multispecific molecule BA128, anti-CD96 monospecific antibody control BA143, and anti-TIGIT monospecific antibody control BA148 was prepared at 5x concentrated intermediate stock in 1.2 mL bullet tubes. First, a 250 μg/ml intermediate stock was prepared in R10 media and antibodies were serially diluted 1 to 10 by serial dilution for a total of 8 dilutions. 20 μL of antibody was added per well to a round-bottom 96-well plate for a final concentration ranging from 50 μg/mL to 0.000005 μg/mL.

Frozen aliquots of human PBMCs were retrieved from liquid nitrogen and immediately thawed in 37° C. water until floating ice was observed. Cells were transferred to 10 mL of pre-warmed R10 media and immediately centrifuged at 1500 rpm for five minutes. The supernatant was discarded, and cells were resuspended in fresh R10 media. To count cells and check viability, 20 μL, of sample was removed and added to 380 μL of viability dye, mixed, and read using a Muse apparatus.

Cells resuspended to an intermediate concentration. An intermediate stock concentration of SEA was made by adding 10 μL of 10 μg/mL SEA to 90 μL R10 to make an intermediate concentration of 1 μg/mL. Cells were first stimulated with SEA peptide and 80 μL cells and SEA mixture were added into corresponding wells and incubated in tissue culture incubator at 37° C. and 5% CO2 within a humidified chamber for four days. A total of 100,000 cells/well and final concentration of 1 ng/mL of SEA were used.

After four days of incubation, plates were removed from the incubator. The plates were then centrifuged for two minutes at 2000 rpm. 5 μL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 μL was added to each well and incubated in darkness at room temperature. AlphaLISA plates were briefly centrifuged at 2000 rpm. A 2.3× Streptavidin Donor Bead intermediate stock was prepared in assay buffer. 10 μL was added to each well and incubated in darkness at room temperature. AlphaLISA plates were briefly centrifuged at 2000 rpm. Relative light units (RLU) were measured using the AlphaScreen protocol on an EnVision Plate Reader. Results were plotted in GraphPad Prism and curves were fit using non-linear regression.

Figure 29:
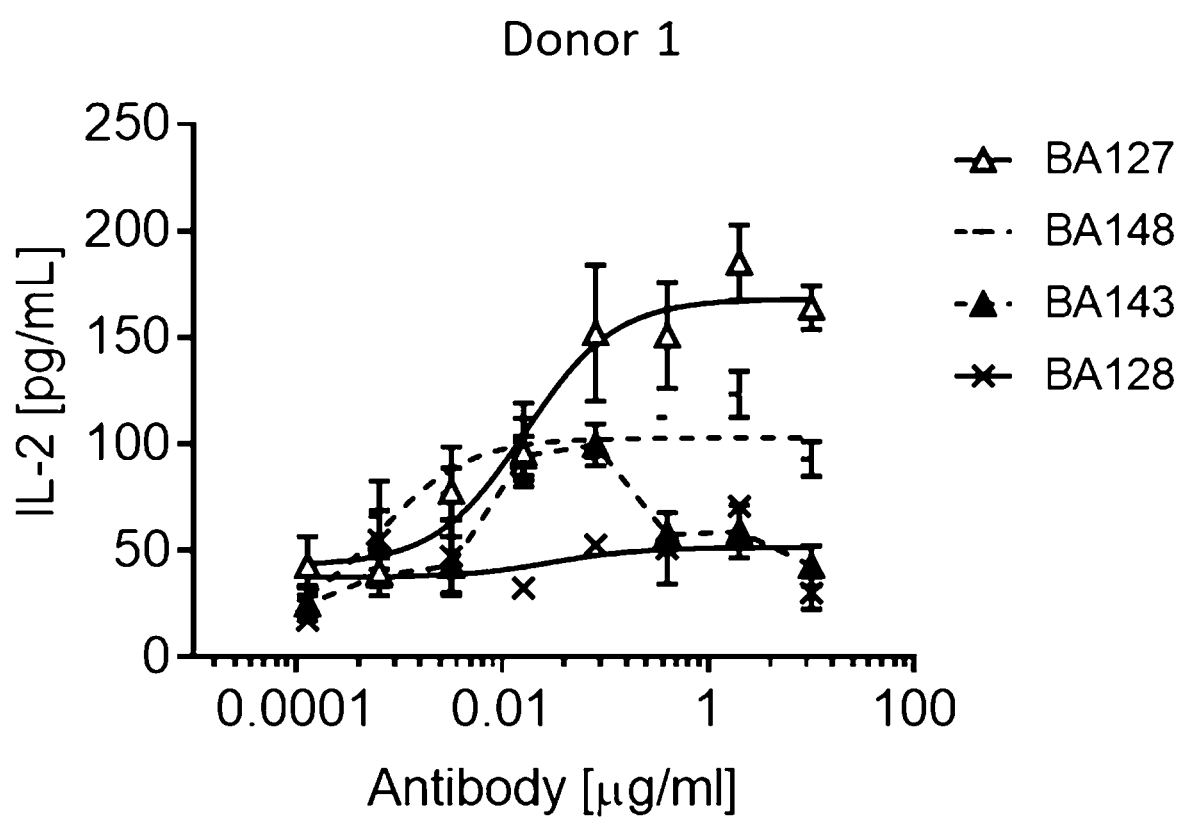
FIG. 29 is a graph showing the ability of BA127 and BA128 multispecific molecules and BA143 and BA148 antibodies to promote IL-2 secretion by SEA-stimulated PBMCs from a single donor over a range of multispecific molecules concentrations.

As shown in FIG. 29, the TIGIT×CD96 multispecific molecule BA127 potently enhanced T cell responsiveness as determined by interleukin-2 (IL-2) cytokine secretion as compared to isotype control, BA128. Further, BA127 demonstrated superior functional activity compared to monospecific anti-TIGIT antibody BA148 or monospecific anti-CD96 antibody BA143.

8.14 Example 14: SEA-Stimulation Assay

A dose range of each of anti-TIGIT×CD96 multispecific molecule BA127 and isotype control multispecific molecule BA128 was prepared at 5× concentrated intermediate stock in 1.2 mL bullet tubes. For donors 1 and 2, a 250 μg/ml intermediate stock was prepared in R10 media and antibodies were serially diluted 1 to 10 by serial dilution for a total of 8 dilutions. 20 μL of antibody was added per well to a round-bottom 96-well plate for a final concentration ranging from 50 μg/mL to 0.000005 μg/mL.

For donors 3, 4, 5, and 6, a 10 μg/mL intermediate stock was prepared in R10 media and antibodies were serially diluted 1 to 5 by serial dilution. A total of 8 dilutions ranging from 10 μg/mL to 0.000128 μg/mL were prepared in R10 media. 20 μL of antibody was added per well to a round-bottom 96-well plate.

Frozen aliquots of human PBMCs were retrieved from liquid nitrogen and immediately thawed in 37° C. water until floating ice was observed. Cells were transferred to 10 mL of pre-warmed R10 media and immediately centrifuged at 1500 rpm for five minutes. The supernatant was discarded, and cells were resuspended in fresh R10 media. To count cells and check viability, 20 μt of sample was removed and added to 380 μL of viability dye, mixed, and read using a Muse apparatus.

Cells resuspended to an intermediate concentration. An intermediate stock concentration of SEA was made by adding 10 μL of 10 μg/mL SEA to 90 μL R10 to make an intermediate concentration of 1 μg/mL. Cells were first stimulated with SEA peptide and 80 μL cells and SEA mixture were added into corresponding wells and incubated in tissue culture incubator at 37° C. and 5% CO2 within a humidified chamber for four days. A total of 100,000 cells/well and final concentration of 1 ng/mL of SEA were used.

After four days of incubation, plates were removed from the incubator. The plates were then centrifuged for two minutes at 2000 rpm. 5 μt of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 μL was added to each well and incubated in darkness at room temperature. AlphaLISA plates were briefly centrifuged at 2000 rpm. A 2.3× Streptavidin Donor Bead intermediate stock was prepared in assay buffer. 10 μL was added to each well and incubated in darkness at room temperature. AlphaLISA plates were briefly centrifuged at 2000 rpm. Relative light units (RLU) were measured using the AlphaScreen protocol on an EnVision Plate Reader. Results were plotted in GraphPad Prism and curves were fit using non-linear regression.

Figure 30A:
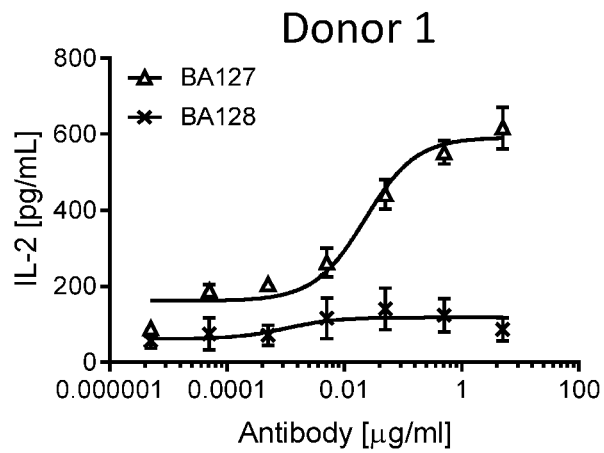
FIG. 30A-FIG. 30F are a series of graphs showing the ability of BA127 and BA128 to promote IL-2 secretion by SEA-stimulated PBMCs from six different donors over a range of antibody concentrations.
Figure 30B:
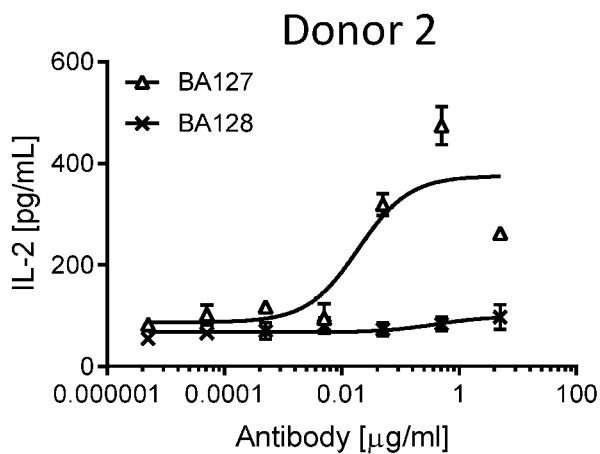
Figure 30C:
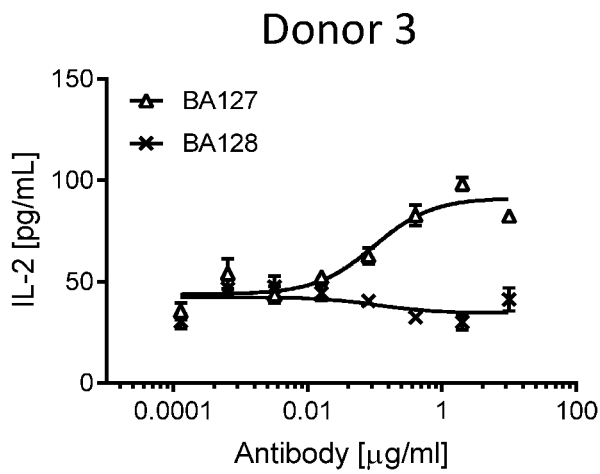
Figure 30D:
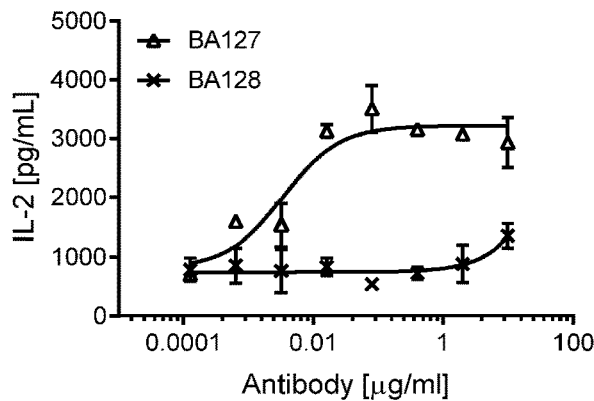
Figure 30E:
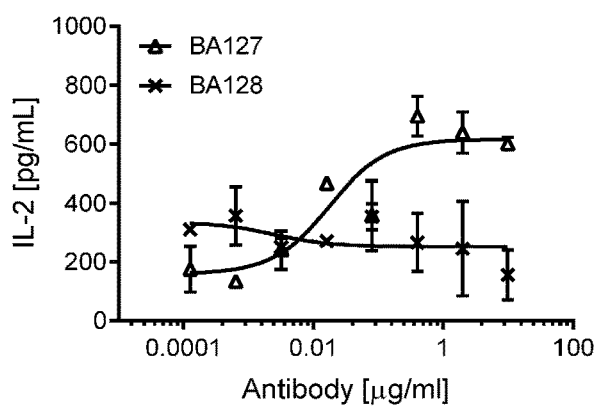
Figure 30F:
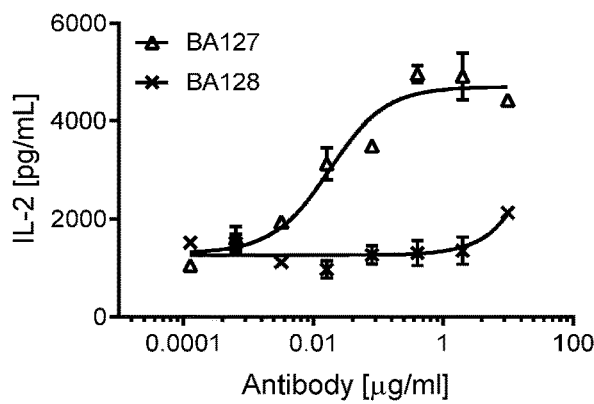

As shown in FIGS. 30A-309F, TIGIT×CD96 multispecific molecule, BA127 potently enhanced T cell responsiveness as determined by interleukin-2 (IL-2) secretion in SEA-stimulated PBMCs from six separate donors in a dose-dependent manner as compared to isotype control BA128. EC10, EC50, and EC90 values for each donor in FIG. 30 are listed in Table 58.

TABLE 58

| EC10, EC50, and EC90 values. | | | |
|---|---|---|---|
| Donor | EC10 | EC50 | EC90 |
| 1 | 0.002519 | 0.02267 | 0.204 |
| 2 | 0.002114 | 0.01908 | 0.1713 |
| 3 | 0.0183 | 0.09746 | 0.8771 |
| 4 | 0.0003820 | 0.003438 | 0.03094 |
| 5 | 0.001937 | 0.01743 | 0.1569 |
| 6 | 0.001954 | 0.01758 | 0.1583 |
| Mean | 0.0045 | 0.0296 | 0.2664 |

8.15 Example 15: TIGIT Blocking Reporter Assay

This example demonstrates the capacity of anti-TIGIT×CD96 multispecific molecules to block TIGIT/CD155 inhibitory signaling.

A TIGIT blocking reporter assay was performed according to the manufacturer's protocol (Promega). First, Jurkat effector T cells engineered to express human TIGIT with a luciferase reporter driven by a native promoter that can respond to both TCR activation and CD226 co-stimulation were retrieved from liquid nitrogen and immediately thawed in 37° C. water until floating ice was observed. Cells were then transferred to 12 mL of pre-warmed (37° C.) assay buffer (90% RPMI 1640/10% FBS) in a conical tube. The cell suspension was gently mixed and transferred to a sterile reservoir and 80 µL of cell suspension transferred to the inner 60 wells of a 96-well, white, flat-bottom assay plate. 120 µL of prewarmed (37° C.) assay buffer was added to each of the outside wells of the assay plates. Cells were then incubated for 16-20 hours in a 37° C., 5% CO2 incubator.

Dose ranges of anti-TIGITxCD96 multispecific molecules BA125 and BA127, isotype control multispecific molecule BA128, anti-TIGITxisotype control multispecific molecule BA133, anti-CD96 monospecific antibody control BA143, anti-CD96xisotype control multispecific molecule BA131, monospecific isotype control BA146, anti-TIGIT reference antibody 1, anti-TIGIT reference antibody 2, and anti-TIGIT reference antibody 3, were prepared at 6× concentrated intermediate stock in 1.2 mL bullet tubes. First, a 50 µg/mL intermediate stock was prepared in assay buffer and antibodies were serially diluted 1 to 2.5 by serial dilution. A total of 10 dilutions ranging from 50 µg/mL to 0.0131 µg/mL (FIGS. 31A and 31B) or 40 µg/mL to 0.0262 µg/mL (FIG. 31C) were prepared in assay buffer. 20 µL of antibody was added per well to the pre-plated TIGIT effector cells.

CHO-K1 cells engineered to express human CD155 with an engineered cell-surface protein (CD155 aAPC/CHO-K1 cells) designed to activate the TCR complex in an antigen-independent manner were retrieved from liquid nitrogen and immediately thawed in 37° C. water until floating ice was observed. Cells were then transferred to a 15 mL conical tube containing 3 mL of assay buffer. The cell suspension was gently mixed and transferred to a sterile reservoir and 20 µL of cell suspension was transferred to the pre-plated TIGIT effector cells and antibody mixture. The final assay volume was 120 µL.

Cells were then incubated for 6 hours in a 37° C., 5% CO2 incubator. After incubation, assay plates were removed from the incubator and allowed to equilibrate to ambient temperature for 10 minutes. 120 µl of Bio-Glo™ reagent was then added to the pre-plated cell and multispecific molecule or antibody mixture and incubated for 5 minutes at room temperature. Relative light units (RLU) were measured using a luminescence EnVision Plate Reader. Results were plotted in GraphPad Prism and curves were fit using non-linear regression.

As shown in FIGS. 31A, 31B, and 31C, anti-TIGITx CD96 multispecific molecules BA125 and BA127 potently enhanced luciferase gene expression, a surrogate for T cell receptor (TCR) activation and CD226 co-stimulatory pathway activation in a dose dependent manner as a result of TIGIT-CD155 ligand blockade. As expected, anti-TIGITx isotype control multispecific molecule BA133, but not anti-CD96 monospecific antibody control BA143, also enhanced luciferase gene expression. In comparison to reference anti-TIGITxisotype control multispecific molecules, BA125 and BA127, demonstrated comparable ability to enhance reporter activity.

8.16 Example 16: Anti-TIGITxCD96 Multispecific Molecules Elicit IL-2 Secretion in T-Cell Stimulation Assay In this example, the ability of the anti-TIGITxCD96 multispecific molecule BA127 to elicit IL-2 cytokine secretion in primary healthy donor human PBMCs stimulated with a sub-optimal concentration of the SEA superantigen was assessed.

A dose range of BA127, reference anti-TIGIT monoclonal reference antibody 1 or isotype control multispecific molecule BA128, was prepared at 5× concentrated intermediate stock in 1.2 mL bullet tubes. First, a 50 µg/mL intermediate stock was prepared in R10 media and antibodies were serially diluted 1 to 5 by serial dilution for a total of 8 dilutions. 20 µL of antibody was added per well to a round-bottom 96-well plate for a final concentration ranging from 10 µg/mL to 0.000128 µg/mL.

Frozen aliquots of human PBMCs were retrieved from liquid nitrogen and immediately thawed in 37° C. water until floating ice was observed. Cells were transferred to 10 mL of pre-warmed R10 media and immediately centrifuged at 1500 rpm for five minutes. The supernatant was discarded, and cells were resuspended in fresh R10 media. To count cells and check viability, 20 µL of sample was removed and added to 380 µL of viability dye, mixed, and read using a Muse apparatus.

Cells were resuspended to an intermediate concentration. An intermediate stock concentration of SEA was made by adding 10 µl of 10 µg/mL SEA to 90 µL R10 to make an intermediate concentration of 1 µg/mL. Cells were first stimulated with SEA peptide and 80 µL cells and SEA mixture were added into corresponding wells and incubated in tissue culture incubator at 37° C. and 5% CO2 within a humidified chamber for four days. A total of 100,000 cells/well and final concentration of 1 ng/mL of SEA were used.

After four days of incubation, plates were removed from the incubator. The plates were then centrifuged for two minutes at 2000 rpm. 5 µL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 µL was added to each well and incubated in darkness at room temperature. AlphaLISA plates were briefly centrifuged at 2000 rpm. A 2.3× Streptavidin Donor Bead intermediate stock was prepared in assay buffer. 10 µL was added to each well and incubated in darkness at room temperature. AlphaLISA plates were briefly centrifuged at 2000 rpm. Relative light units (RLU) were measured using the AlphaScreen protocol on an EnVision Plate Reader. Results were plotted in GraphPad Prism and curves were fit using non-linear regression.

As shown in FIGS. 32A and 32B, the anti-TIGITxCD96 multispecific molecule BA127 resulted in higher levels of IL-2 cytokine secretion as compared to a Reference anti-TIGIT antibody, and an isotype control antibody in two donors over a range of concentrations.

8.17 Example 17: Anti-TIGITxCD96 Multispecific Molecules Inhibited Tumor Growth in a Preclinical Mouse Tumor Model This example demonstrated that blockade with anti-TIGITxCD96 multispecific molecules promotes superior tumor control compared to corresponding monospecific antibodies and combinations of monospecific antibodies in a mouse model.

Mouse surrogate anti-TIGIT and anti-CD96 monospecific antibodies and anti-TIGITxCD96 multispecific molecules were tested in a mouse colorectal carcinoma model. Specifically, Balb/c mice (Jackson Labs #000651) 6-8 weeks of age were first acclimated for two weeks and were shaved and tagged. CT26 mouse colorectal carcinoma cells (ATCC® CRL-2638™) were expanded in tissue culture in RPMI medium supplemented with 10% heat-inactivated FBS and normocin for 1 week. The mice were injected subcutaneously with 1×10⁵ CT26 cells suspended in 100 of PBS. The implanted tumor cells were allowed to establish for 9-10 days to reach the size of approximately 50 mm³. The mice were then randomized and treated with 200 μg of anti-TIGIT mIgG$_2$a surrogate antibody (Clone: 10A7), anti-CD96 mIgG$_2$a surrogate antibody (Clone: 6A6), a combination of anti-TIGIT and anti-CD96 surrogate mAbs, anti-TIGIT×CD96 mIgG$_2$a surrogate multispecific molecule, anti-TIGIT×CD96 mIgG$_2$a.N297A surrogate multispecific molecule, an isotype control monospecific antibody (mIgG$_2$a), or an isotype control multispecific molecule (mIgG$_2$a), twice a week via intraperitoneal administration for 2 weeks. The tumor volumes were measured biweekly by caliper and were calculated as 0.5×length×width².

As shown in FIGS. 33A-33E, anti-TIGIT×CD96 surrogate multispecific molecule mIgG$_2$a led to a complete response in 13 out of 15 mice. By contrast, anti-TIGIT×CD96 surrogate multispecific mIgG$_2$a-N297A had no effect on controlling tumor growth. Anti-TIGIT×CD96 mIgG$_2$a multispecific molecule showed superior tumor control compared single agent therapy with anti-TIGIT mAb or anti-CD96 mAb or the combination of anti-TIGIT and CD96 mAbs. This result corroborated the in vitro observation that anti-TIGIT×CD96 multispecific molecules depend on FcγR co-engagement to enhance immune effector function and are functionally superior to monospecific antibodies or combination of monospecific antibodies.

8.18 Example 18: FcγR Co-Engagement is Critical for Anti-Tumor Immunity

This example demonstrated the ability of anti-TIGIT×CD96 multispecific molecules to inhibit tumor growth in a preclinical mouse tumor model.

The mouse surrogate anti-TIGIT and anti-CD96 monospecific antibodies and anti-TIGIT×CD96 multispecific molecules were tested in a mouse colorectal carcinoma model. Specifically, Balb/c mice (Jackson Labs #000651) 6-8 weeks of age were first acclimated for two weeks and were shaved and tagged. CT26 mouse colorectal carcinoma cells (ATCC® CRL-2638™) were expanded in tissue culture in RPMI medium supplemented with 10% heat-inactivated FBS and normocin for 1 week. The mice were injected subcutaneously with 1×10⁵ CT26 cells suspended in 100 of PBS. The implanted tumor cells were allowed to establish for 9-10 days to reach the size of approximately 50 mm³. The mice were then randomized and treated with 200 μg of anti-TIGIT mIgG$_2$a surrogate antibody (Clone: 10A7), anti-CD96 mIgG$_2$a surrogate antibody (Clone: 6A6), combination of anti-TIGIT and anti-CD96 surrogate monospecific antibodies, anti-TIGIT×CD96 mIgG$_2$a surrogate antibody, anti-TIGIT×CD96 bispecific mIgG$_2$a.N297A surrogate multispecific molecule, an isotype control antibody (mIgG$_2$a), or an isotype control multispecific (mIgG$_2$a) twice a week via intraperitoneal administration for 2 weeks. The tumor volumes were measured biweekly by caliper and were calculated as 0.5×length×width².

As shown in FIGS. 34A-34E, anti-TIGIT×CD96 surrogate multispecific molecule mIgG$_2$a led to a complete response in 13 out of 15 mice. By contrast, anti-TIGIT×CD96 surrogate multispecific molecule mIgG$_2$a-N297A had no effect on controlling tumor growth. Anti-TIGIT×CD96 mIgG$_2$a multispecific molecule showed superior tumor control compared to single agent therapy with anti-TIGIT monospecific antibody or anti-CD96 monospecific antibody or the combination of anti-TIGIT and CD96 monospecific antibodies. This result corroborated the in vitro observation that anti-TIGIT×CD96 multispecific molecules depend on FcγR co-engagement to enhance immune effector function and are functionally superior to mAbs or combination of mAbs.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

SEQUENCE LISTING

```
Sequence total quantity: 114
SEQ ID NO: 1            moltype = AA  length = 448
FEATURE                 Location/Qualifiers
REGION                  1..448
                        note = Synthetic peptide
source                  1..448
                        mol_type = protein
                        organism = synthetic construct
SEQUENCE: 1
QVQLVQSGAE VKKPGASVKV SCKASGYTFT SYGISWVRQA PGQGLEWMGW ISAYNANTNY  60
AQKLQGRVTM TTDTSTSTAY MELRSLRSDD TAVYYCARSA GVLGGMDVWG RGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKRVEPK SCDKTHTCPP CPAPELLGGP 240
DVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSREEM 360
TKNQVSLSCA VKGFYPSDIA VEWESNGQPE NNYKTTPPVL DSDGSFFLVS KLTVDKSRWQ 420
QGNVFSCSVM HEALHNHYTQ KSLSLSPG                                   448
```

```
SEQ ID NO: 2              moltype = AA   length = 213
FEATURE                   Location/Qualifiers
REGION                    1..213
                          note = Synthetic peptide
source                    1..213
                          mol_type = protein
                          organism = synthetic construct
SEQUENCE: 2
EIVMTQSPAT LSVSPGERAT LSCRASQSVN AYLAWYQQKP GQAPRLLIYG ASTRATGIPA   60
RFSGSGSGTE FTLTISSLQS EDFAVYYCQQ YNNWPSFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 3              moltype = AA   length = 448
FEATURE                   Location/Qualifiers
REGION                    1..448
                          note = Synthetic peptide
source                    1..448
                          mol_type = protein
                          organism = synthetic construct
SEQUENCE: 3
QVQLVQSGAE VKKPGASVKV SCKASGYTFT NYAVHWVRQA PGQRLEWMGW INTGNANTKY   60
SQKFQGRVTI TRDTSASTAY MELSSLRSED TAVYYCARSL GVYYGMDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPG                                     448

SEQ ID NO: 4              moltype = AA   length = 214
FEATURE                   Location/Qualifiers
REGION                    1..214
                          note = Synthetic peptide
source                    1..214
                          mol_type = protein
                          organism = synthetic construct
SEQUENCE: 4
DIQMTQSPSS LSASVGDRVT ITCRASQSVS TFLNWYQQKP GKAPKLLIYA ASSLQSGVPS   60
RFSGSGSGTD FTLTISSLQP EDFATYYCLQ TYSIPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 5              moltype = AA   length = 448
FEATURE                   Location/Qualifiers
REGION                    1..448
                          note = Synthetic peptide
source                    1..448
                          mol_type = protein
                          organism = synthetic construct
SEQUENCE: 5
QVQLVQSGAE VKKPGASVKV SCKASGYTFT TYALHWVRQA PGQRLEWMGW INTGSGDTKY   60
SQKFQGRVTI TRDTSASTAY MELSSLRSED TAVYYCARSL GVYYGMDVWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPG                                     448

SEQ ID NO: 6              moltype = AA   length = 215
FEATURE                   Location/Qualifiers
REGION                    1..215
                          note = Synthetic peptide
source                    1..215
                          mol_type = protein
                          organism = synthetic construct
SEQUENCE: 6
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPKITFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 7              moltype = AA   length = 451
FEATURE                   Location/Qualifiers
REGION                    1..451
                          note = Synthetic peptide
source                    1..451
                          mol_type = protein
```

```
                         organism = synthetic construct
SEQUENCE: 7
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPLPEEKT ISKAKGQPRE PQVYTLPPSR   360
EEMTKNQVSL WCLVKGFYPS DIAVEWESNG QPENNYKTTP PVLDSDGSFF LYSKLTVDKS   420
RWQQGNVFSC SVMHEALHNH YTQKSLSLSP G                                 451

SEQ ID NO: 8           moltype = AA  length = 216
FEATURE                Location/Qualifiers
REGION                 1..216
                       note = Synthetic peptide
source                 1..216
                       mol_type = protein
                       organism = synthetic construct
SEQUENCE: 8
QSALTQPRSV SGSPGQSVTI SCTGTSPDVG SHAYRSWYQQ HPGKAPKLMI YEVSYRPSGV    60
SNRFSGSKSG NTASLTISGL QAEDEADYYC SSYPPSSATV FGAGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 9           moltype = AA  length = 215
FEATURE                Location/Qualifiers
REGION                 1..215
                       note = Synthetic peptide
source                 1..215
                       mol_type = protein
                       organism = synthetic construct
SEQUENCE: 9
QSALTQPRSV SGSPGQSVTI SCTGTSPDVG SHAYRSWYQQ HPGKAPKLMI YEVSYRPSGV    60
SNRFSGSKSG NTASLTISGL QAEDEADYYC SSYPPSSATV FGAGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTEC                             215

SEQ ID NO: 10          moltype = AA  length = 5
FEATURE                Location/Qualifiers
REGION                 1..5
                       note = Synthetic peptide
source                 1..5
                       mol_type = protein
                       organism = synthetic construct
SEQUENCE: 10
SYGIS                                                                5

SEQ ID NO: 11          moltype = AA  length = 17
FEATURE                Location/Qualifiers
REGION                 1..17
                       note = Synthetic peptide
source                 1..17
                       mol_type = protein
                       organism = synthetic construct
SEQUENCE: 11
WISAYNANTN YAQKLQG                                                  17

SEQ ID NO: 12          moltype = AA  length = 10
FEATURE                Location/Qualifiers
REGION                 1..10
                       note = Synthetic peptide
source                 1..10
                       mol_type = protein
                       organism = synthetic construct
SEQUENCE: 12
SAGVLGGMDV                                                          10

SEQ ID NO: 13          moltype = AA  length = 11
FEATURE                Location/Qualifiers
REGION                 1..11
                       note = Synthetic peptide
source                 1..11
                       mol_type = protein
                       organism = synthetic construct
SEQUENCE: 13
RASQSVNAYL A                                                        11

SEQ ID NO: 14          moltype = AA  length = 7
FEATURE                Location/Qualifiers
```

```
REGION                    1..7
                          note = Synthetic peptide
source                    1..7
                          mol_type = protein
                          organism = synthetic construct
SEQUENCE: 14
GASTRAT                                                                    7

SEQ ID NO: 15             moltype = AA   length = 8
FEATURE                   Location/Qualifiers
REGION                    1..8
                          note = Synthetic peptide
source                    1..8
                          mol_type = protein
                          organism = synthetic construct
SEQUENCE: 15
QQYNNWPS                                                                   8

SEQ ID NO: 16             moltype = AA   length = 5
FEATURE                   Location/Qualifiers
REGION                    1..5
                          note = Synthetic peptide
source                    1..5
                          mol_type = protein
                          organism = synthetic construct
SEQUENCE: 16
NYAVH                                                                      5

SEQ ID NO: 17             moltype = AA   length = 17
FEATURE                   Location/Qualifiers
REGION                    1..17
                          note = Synthetic peptide
source                    1..17
                          mol_type = protein
                          organism = synthetic construct
SEQUENCE: 17
WINTGNANTK YSQKFQG                                                        17

SEQ ID NO: 18             moltype = AA   length = 10
FEATURE                   Location/Qualifiers
REGION                    1..10
                          note = Synthetic peptide
source                    1..10
                          mol_type = protein
                          organism = synthetic construct
SEQUENCE: 18
SLGVYYGMDV                                                                10

SEQ ID NO: 19             moltype = AA   length = 11
FEATURE                   Location/Qualifiers
REGION                    1..11
                          note = Synthetic peptide
source                    1..11
                          mol_type = protein
                          organism = synthetic construct
SEQUENCE: 19
RASQSVSTFL N                                                              11

SEQ ID NO: 20             moltype = AA   length = 7
FEATURE                   Location/Qualifiers
REGION                    1..7
                          note = Synthetic peptide
source                    1..7
                          mol_type = protein
                          organism = synthetic construct
SEQUENCE: 20
AASSLQS                                                                    7

SEQ ID NO: 21             moltype = AA   length = 9
FEATURE                   Location/Qualifiers
REGION                    1..9
                          note = Synthetic peptide
source                    1..9
                          mol_type = protein
                          organism = synthetic construct
SEQUENCE: 21
LQTYSIPYT                                                                  9

SEQ ID NO: 22             moltype = AA   length = 5
```

```
FEATURE             Location/Qualifiers
REGION              1..5
                    note = Synthetic peptide
source              1..5
                    mol_type = protein
                    organism = synthetic construct
SEQUENCE: 22
TYALH                                                                          5

SEQ ID NO: 23       moltype = AA  length = 17
FEATURE             Location/Qualifiers
REGION              1..17
                    note = Synthetic peptide
source              1..17
                    mol_type = protein
                    organism = synthetic construct
SEQUENCE: 23
WINTGSGDTK YSQKFQG                                                            17

SEQ ID NO: 24       moltype = AA  length = 10
FEATURE             Location/Qualifiers
REGION              1..10
                    note = Synthetic peptide
source              1..10
                    mol_type = protein
                    organism = synthetic construct
SEQUENCE: 24
SLGVYYGMDV                                                                    10

SEQ ID NO: 25       moltype = AA  length = 11
FEATURE             Location/Qualifiers
REGION              1..11
                    note = Synthetic peptide
source              1..11
                    mol_type = protein
                    organism = synthetic construct
SEQUENCE: 25
RASQSISSYL N                                                                  11

SEQ ID NO: 26       moltype = AA  length = 7
FEATURE             Location/Qualifiers
REGION              1..7
                    note = Synthetic peptide
source              1..7
                    mol_type = protein
                    organism = synthetic construct
SEQUENCE: 26
AASSLQS                                                                        7

SEQ ID NO: 27       moltype = AA  length = 10
FEATURE             Location/Qualifiers
REGION              1..10
                    note = Synthetic peptide
source              1..10
                    mol_type = protein
                    organism = synthetic construct
SEQUENCE: 27
QQSYSTPKIT                                                                    10

SEQ ID NO: 28       moltype = AA  length = 5
FEATURE             Location/Qualifiers
REGION              1..5
                    note = Synthetic peptide
source              1..5
                    mol_type = protein
                    organism = synthetic construct
SEQUENCE: 28
SYGIS                                                                          5

SEQ ID NO: 29       moltype = AA  length = 17
FEATURE             Location/Qualifiers
REGION              1..17
                    note = Synthetic peptide
source              1..17
                    mol_type = protein
                    organism = synthetic construct
SEQUENCE: 29
GITPFFNRVD VAEKFQG                                                            17
```

| | | |
|---|---|---|
| SEQ ID NO: 30 | moltype = AA   length = 13 | |
| FEATURE | Location/Qualifiers | |
| REGION | 1..13 | |
| | note = Synthetic peptide | |
| source | 1..13 | |
| | mol_type = protein | |
| | organism = synthetic construct | |
| SEQUENCE: 30 | | |
| DLRRGGVGDA FDI | | 13 |
| | | |
| SEQ ID NO: 31 | moltype = AA   length = 14 | |
| FEATURE | Location/Qualifiers | |
| REGION | 1..14 | |
| | note = Synthetic peptide | |
| source | 1..14 | |
| | mol_type = protein | |
| | organism = synthetic construct | |
| SEQUENCE: 31 | | |
| TGTSPDVGSH AYRS | | 14 |
| | | |
| SEQ ID NO: 32 | moltype = AA   length = 7 | |
| FEATURE | Location/Qualifiers | |
| REGION | 1..7 | |
| | note = Synthetic peptide | |
| source | 1..7 | |
| | mol_type = protein | |
| | organism = synthetic construct | |
| SEQUENCE: 32 | | |
| EVSYRPS | | 7 |
| | | |
| SEQ ID NO: 33 | moltype = AA   length = 10 | |
| FEATURE | Location/Qualifiers | |
| REGION | 1..10 | |
| | note = Synthetic peptide | |
| source | 1..10 | |
| | mol_type = protein | |
| | organism = synthetic construct | |
| SEQUENCE: 33 | | |
| SSYPPSSATV | | 10 |
| | | |
| SEQ ID NO: 34 | moltype = AA   length = 119 | |
| FEATURE | Location/Qualifiers | |
| REGION | 1..119 | |
| | note = Synthetic peptide | |
| source | 1..119 | |
| | mol_type = protein | |
| | organism = synthetic construct | |
| SEQUENCE: 34 | | |
| QVQLVQSGAE VKKPGASVKV SCKASGYTFT SYGISWVRQA PGQGLEWMGW ISAYNANTNY | | 60 |
| AQKLQGRVTM TTDTSTSTAY MELRSLRSDD TAVYYCARSA GVLGGMDVWG RGTLVTVSS | | 119 |
| | | |
| SEQ ID NO: 35 | moltype = AA   length = 106 | |
| FEATURE | Location/Qualifiers | |
| REGION | 1..106 | |
| | note = Synthetic peptide | |
| source | 1..106 | |
| | mol_type = protein | |
| | organism = synthetic construct | |
| SEQUENCE: 35 | | |
| EIVMTQSPAT LSVSPGERAT LSCRASQSVN AYLAWYQQKP GQAPRLLIYG ASTRATGIPA | | 60 |
| RFSGSGSGTE FTLTISSLQS EDFAVYYCQQ YNNWPSFGQG TKLEIK | | 106 |
| | | |
| SEQ ID NO: 36 | moltype = AA   length = 119 | |
| FEATURE | Location/Qualifiers | |
| REGION | 1..119 | |
| | note = Synthetic peptide | |
| source | 1..119 | |
| | mol_type = protein | |
| | organism = synthetic construct | |
| SEQUENCE: 36 | | |
| QVQLVQSGAE VKKPGASVKV SCKASGYTFT NYAVHWVRQA PGQRLEWMGW INTGNANTKY | | 60 |
| SQKFQGRVTI TRDTSASTAY MELSSLRSED TAVYYCARSL GVYYGMDVWG QGTTVTVSS | | 119 |
| | | |
| SEQ ID NO: 37 | moltype = AA   length = 107 | |
| FEATURE | Location/Qualifiers | |
| REGION | 1..107 | |
| | note = Synthetic peptide | |
| source | 1..107 | |
| | mol_type = protein | |

```
                              organism   = synthetic construct
SEQUENCE: 37
DIQMTQSPSS LSASVGDRVT ITCRASQSVS TFLNWYQQKP GKAPKLLIYA ASSLQSGVPS    60
RFSGSGSGTD FTLTISSLQP EDFATYYCLQ TYSIPYTFGQ GTKLEIK                 107

SEQ ID NO: 38             moltype = AA   length = 119
FEATURE                   Location/Qualifiers
REGION                    1..119
                          note = Synthetic peptide
source                    1..119
                          mol_type = protein
                          organism = synthetic construct
SEQUENCE: 38
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSS    119

SEQ ID NO: 39             moltype = AA   length = 108
FEATURE                   Location/Qualifiers
REGION                    1..108
                          note = Synthetic peptide
source                    1..108
                          mol_type = protein
                          organism = synthetic construct
SEQUENCE: 39
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPKITFG QGTKLEIK                108

SEQ ID NO: 40             moltype = AA   length = 122
FEATURE                   Location/Qualifiers
REGION                    1..122
                          note = Synthetic peptide
source                    1..122
                          mol_type = protein
                          organism = synthetic construct
SEQUENCE: 40
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SS                                                                 122

SEQ ID NO: 41             moltype = AA   length = 110
FEATURE                   Location/Qualifiers
REGION                    1..110
                          note = Synthetic peptide
source                    1..110
                          mol_type = protein
                          organism = synthetic construct
SEQUENCE: 41
QSALTQPRSV SGSPGQSVTI SCTGTSPDVG SHAYRSWYQQ HPGKAPKLMI YEVSYRPSGV    60
SNRFSGSKSG NTASLTISGL QAEDEADYYC SSYPPSSATV FGAGTKLTVL             110

SEQ ID NO: 42             moltype = AA   length = 107
FEATURE                   Location/Qualifiers
REGION                    1..107
                          note = Synthetic peptide
source                    1..107
                          mol_type = protein
                          organism = synthetic construct
SEQUENCE: 42
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 43             moltype = AA   length = 106
FEATURE                   Location/Qualifiers
REGION                    1..106
                          note = Synthetic peptide
source                    1..106
                          mol_type = protein
                          organism = synthetic construct
SEQUENCE: 43
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                 106

SEQ ID NO: 44             moltype = AA   length = 105
FEATURE                   Location/Qualifiers
REGION                    1..105
                          note = Synthetic peptide
source                    1..105
                          mol_type = protein
                          organism = synthetic construct
```

```
SEQUENCE: 44
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTEC                  105

SEQ ID NO: 45           moltype = AA  length = 449
FEATURE                 Location/Qualifiers
REGION                  1..449
                        note = Synthetic peptide
source                  1..449
                        mol_type = protein
                        organism = synthetic construct
SEQUENCE: 45
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 46           moltype = AA  length = 449
FEATURE                 Location/Qualifiers
REGION                  1..449
                        note = Synthetic peptide
source                  1..449
                        mol_type = protein
                        organism = synthetic construct
SEQUENCE: 46
QVQLVQSGAE VKKPGASVKV SCKASGYTFT NYAVHWVRQA PGQRLEWMGW INTGNANTKY    60
SQKFQGRVTI TRDTSASTAY MELSSLRSED TAVYYCARSL GVYYGMDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 47           moltype = AA  length = 449
FEATURE                 Location/Qualifiers
REGION                  1..449
                        note = Synthetic peptide
source                  1..449
                        mol_type = protein
                        organism = synthetic construct
SEQUENCE: 47
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 48           moltype = AA  length = 452
FEATURE                 Location/Qualifiers
REGION                  1..452
                        note = Synthetic peptide
source                  1..452
                        mol_type = protein
                        organism = synthetic construct
SEQUENCE: 48
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPLPEEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 49           moltype = AA  length = 329
FEATURE                 Location/Qualifiers
REGION                  1..329
                        note = Synthetic peptide
source                  1..329
                        mol_type = protein
                        organism = synthetic construct
```

```
SEQUENCE: 49
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLSC AVKGFYPSDI AVEWESNGQP ENNYKTTPPV LDSDGSFFLV SKLTVDKSRW    300
QQGNVFSCSV MHEALHNHYT QKSLSLSPG                                      329

SEQ ID NO: 50           moltype = AA   length = 329
FEATURE                 Location/Qualifiers
REGION                  1..329
                        note = Synthetic peptide
source                  1..329
                        mol_type = protein
                        organism = synthetic construct
SEQUENCE: 50
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLSC AVKGFYPSDI AVEWESNGQP ENNYKTTPPV LDSDGSFFLV SKLTVDKSRW    300
QQGNVFSCSV MHEALHNHYT QKSLSLSPG                                      329

SEQ ID NO: 51           moltype = AA   length = 329
FEATURE                 Location/Qualifiers
REGION                  1..329
                        note = Synthetic peptide
source                  1..329
                        mol_type = protein
                        organism = synthetic construct
SEQUENCE: 51
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPEEKTIS KAKGQPREPQ VYTLPPSREE    240
MTKNQVSLSC AVKGFYPSDI AVEWESNGQP ENNYKTTPPV LDSDGSFFLV SKLTVDKSRW    300
QQGNVFSCSV MHEALHNHYT QKSLSLSPG                                      329

SEQ ID NO: 52           moltype = AA   length = 329
FEATURE                 Location/Qualifiers
REGION                  1..329
                        note = Synthetic peptide
source                  1..329
                        mol_type = protein
                        organism = synthetic construct
SEQUENCE: 52
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPLPEEKTIS KAKGQPREPQ VYTLPPSREE    240
MTKNQVSLSC AVKGFYPSDI AVEWESNGQP ENNYKTTPPV LDSDGSFFLV SKLTVDKSRW    300
QQGNVFSCSV MHEALHNHYT QKSLSLSPG                                      329

SEQ ID NO: 53           moltype = AA   length = 329
FEATURE                 Location/Qualifiers
REGION                  1..329
                        note = Synthetic peptide
source                  1..329
                        mol_type = protein
                        organism = synthetic construct
SEQUENCE: 53
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLWC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 54           moltype = AA   length = 329
FEATURE                 Location/Qualifiers
REGION                  1..329
                        note = Synthetic peptide
source                  1..329
                        mol_type = protein
                        organism = synthetic construct
SEQUENCE: 54
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PDVFLFPPKP KDTLMISRTP EVTCVVVDVS HEDPEVKFNW YVDGVEVHNA KTKPREEQYN    180
```

```
STYRVVSVLT VLHQDWLNGK EYKCKVSNKA LPAPIEKTIS KAKGQPREPQ VYTLPPSREE     240
MTKNQVSLWC LVKGFYPSDI AVEWESNGQP ENNYKTTPPV LDSDGSFFLY SKLTVDKSRW     300
QQGNVFSCSV MHEALHNHYT QKSLSLSPG                                     329

SEQ ID NO: 55            moltype = AA   length = 329
FEATURE                  Location/Qualifiers
REGION                   1..329
                         note = Synthetic peptide
source                   1..329
                         mol_type = protein
                         organism = synthetic construct
SEQUENCE: 55
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPEEKTIS KAKGQPREPQ VYTLPPSREE    240
MTKNQVSLWC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 56            moltype = AA   length = 329
FEATURE                  Location/Qualifiers
REGION                   1..329
                         note = Synthetic peptide
source                   1..329
                         mol_type = protein
                         organism = synthetic construct
SEQUENCE: 56
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPLPEEKTIS KAKGQPREPQ VYTLPPSREE    240
MTKNQVSLWC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 57            moltype = AA   length = 329
FEATURE                  Location/Qualifiers
REGION                   1..329
                         note = Synthetic peptide
source                   1..329
                         mol_type = protein
                         organism = synthetic construct
SEQUENCE: 57
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 58            moltype = AA   length = 329
FEATURE                  Location/Qualifiers
REGION                   1..329
                         note = Synthetic peptide
source                   1..329
                         mol_type = protein
                         organism = synthetic construct
SEQUENCE: 58
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 59            moltype = AA   length = 329
FEATURE                  Location/Qualifiers
REGION                   1..329
                         note = Synthetic peptide
source                   1..329
                         mol_type = protein
                         organism = synthetic construct
SEQUENCE: 59
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PDVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPEEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329
```

```
SEQ ID NO: 60              moltype = AA   length = 329
FEATURE                    Location/Qualifiers
REGION                     1..329
                           note = Synthetic peptide
source                     1..329
                           mol_type = protein
                           organism = synthetic construct
SEQUENCE: 60
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PDVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPLPEEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 61              moltype = AA   length = 498
FEATURE                    Location/Qualifiers
source                     1..498
                           mol_type = protein
                           organism = Homo sapiens
SEQUENCE: 61
VWEKTVNTEE NVYATLGSDV NLTCQTQTVG FFVQMQWSKV TNKIDLIAVY HPQYGFYCAY   60
GRPCESLVTF TETPENGSKW TLHLRNMSCS VSGRYECMLV LYPEGIQTKI YNLLIQTHVT  120
ADEWNSNHTI EIEINQTLEI PCFQNSSSKI SSEFTYAWSV ENSSTDSWVL LSKGIKEDNG  180
TQETLISQNH LISNSTLLKD RVKLGTDYRL HLSPVQIFDD GRKFSCHIRV GPNKILRSST  240
TVKVFAKPEI PVIVENNSTD VLVERRFTCL LKNVFPKANI TWFIDGSFLH DEKEGIYITN  300
EERKGKDGFL ELKSVLTRVH SNKPAQSDNL TIWCMALSPV PGNKVWNISS EKITFLLGSE  360
ISSSTDPPLSV TESTLDTQPS PASSVSPARY PATSSVTLVD VSALRPNTTP QPSNSSMTTR  420
GFNYPWTSSG TDTKKSVSRI PSETYSSSPS GAGSTLHDNV FTSTARAFSE VPTTANGSTK  480
TNHVHITGIV VNKPKDGM                                               498

SEQ ID NO: 62              moltype = AA   length = 482
FEATURE                    Location/Qualifiers
source                     1..482
                           mol_type = protein
                           organism = Homo sapiens
SEQUENCE: 62
VWEKTVNTEE NVYATLGSDV NLTCQTQTVG FFVQMQWSKV TNKIDLIAVY HPQYGFYCAY   60
GRPCESLVTF TETPENGSKW TLHLRNMSCS VSGRYECMLV LYPEGIQTKI YNLLIQTHVT  120
ADEWNSNHTI EIEINQTLEI PCFQNSSSKI SSEFTYAWSV EDNGTQETLI SQNHLISNST  180
LLKDRVKLGT DYRLHLSPVQ IFDDGRKFSC HIRVGPNKIL RSSTTVKVFA KPEIPVIVEN  240
NSTDVLVERR FTCLLKNVFP KANITWFIDG SFLHDEKEGI YITNEERKGK DGFLELKSVL  300
TRVHSNKPAQ SDNLTIWCMA LSPVPGNKVW NISSEKITFL LGSEISSTDP PLSVTESTLD  360
TQPSPASSVS PARYPATSSV TLVDVSALRP NTTPQPSNSS MTTRGFNYPW TSSGTDTKKS  420
VSRIPSETYS SSPSGAGSTL HDNVFTSTAR AFSEVPTTAN GSTKTNHVHI TGIVVNKPKD  480
GM                                                                482

SEQ ID NO: 63              moltype = AA   length = 514
FEATURE                    Location/Qualifiers
source                     1..514
                           mol_type = protein
                           organism = Homo sapiens
SEQUENCE: 63
VWEKTVNTEE NVYATLGSDV NLTCQTQTVG FFVQMQWSKV TNKIDLIAVY HPQYGFYCAY   60
GRPCESLVTF TETPENGSKW TLHLRNMSSS VSGRYECMLV LYPEGIQTKI YNLLIQTHVT  120
ADEWNSNHTI EIEINQTLEI PCFQNSSSKI SSEFTYAWSV EDNGTQETLI SQNHLISNST  180
LLKDRVKLGT DYRLHLSPVQ IFDDGRKFSC HIRVGPNKIL RSSTTVKVFA KPEIPVIVEN  240
NSTDVLVERR FTCLLKNVFP KANITWFIDG SFLHDEKEGI YITNEERKGK DGFLELKSVL  300
TRVHSNKPAQ SDNLTIWCMA LSPVPGNKVW NISSEKITFL LGSEISSTDP PLSVTESTLD  360
TQPSPASSVS PARYPATSSV TLVDVSALRP NTTPQPSNSS MTTRGFNYPW TSSGTDTKKS  420
VSRIPSETYS SSPSGAGSTL HDNVFTSTAR AFSEVPTTAN GSTKTNHVHI TGIVVNKPKD  480
GMENLYFQGL EHHHHHHHHH HGGSGGLPET GGDR                              514

SEQ ID NO: 64              moltype = AA   length = 119
FEATURE                    Location/Qualifiers
source                     1..119
                           mol_type = protein
                           organism = Homo sapiens
SEQUENCE: 64
VWEKTVNTEE NVYATLGSDV NLTCQTQTVG FFVQMQWSKV TNKIDLIAVY HPQYGFYCAY   60
GRPCESLVTF TETPENGSKW TLHLRNMSCS VSGRYECMLV LYPEGIQTKI YNLLIQTHV   119

SEQ ID NO: 65              moltype = AA   length = 119
FEATURE                    Location/Qualifiers
source                     1..119
                           mol_type = protein
                           organism = Homo sapiens
SEQUENCE: 65
VWEKTVNTEE NVYATLGSDV NLTCQTQTVG FFVQMQWSKV TNKIDLIAVY HPQYGFYCAY   60
```

```
GRPCESLVTF TETPENGSKW TLHLRNMSSS VSGRYECMLV LYPEGIQTKI YNLLIQTHV    119

SEQ ID NO: 66           moltype = AA  length = 499
FEATURE                 Location/Qualifiers
source                  1..499
                        mol_type = protein
                        organism = Macaca fascicularis
SEQUENCE: 66
VWGKPFNTEE NIYATLGSDV NLTCQTQAKG FLVQMWSKV TDKADLIALY HPQYGFHCAY    60
GSPCESLVTF TQTPENGSKW TLHLRNMSSS VSGRYECMLT LYPEGMQTKI YNLLIQTHVT   120
PDEWKSNHTI EIEINQTLEI PCFQNSSSEI SSEFTYAWLV VKNSSTDSWV LLSKGKRYDN   180
GTQQTLISQD HLISSSTLLK DRVKVGIDYR LHLSPVQIFD DGRKFSCHIR VGPDKILRSS   240
TTIKVFAKPE IPMIVENNST DVLVERTFTC LLKNVFPKAN IIWFIDGSFL HDEKEGIYIT   300
NEERKGKDGF LELKSVLTRV HSDKPAQSDN LTIWCMALSP VPGNKVWNIS SEKITFLLGS   360
EMSTTDLPPS VTESTLDTQP SPASSVSPTR YPATSSVTLA DVSALRPNTT PQSSSSSVTT   420
QDFNYPWTSS GTDAKKSFSQ IPSETYSSSP SGAGSTLHDN VFTSTTRALS EVPTTANGST   480
KTNHVHITGI VVSKPKDGM                                                499

SEQ ID NO: 67           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 67
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                      448

SEQ ID NO: 68           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 68
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPEEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                      448

SEQ ID NO: 69           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 69
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PLPEEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                      448

SEQ ID NO: 70           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 70
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
```

```
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLWCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 71           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 71
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 72           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 72
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPEEKTISK AKGQPREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 73           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 73
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PLPEEKTISK AKGQPREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 74           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 74
QVQLVQSGAE VKKPGASVKV SCKASGYTFT SYGISWVRQA PGQGLEWMGW ISAYNANTNY    60
AQKLQGRVTM TTDTSTSTAY MELRSLRSDD TAVYYCARSA GVLGGMDVWG RGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 75           moltype = AA  length = 448
FEATURE                 Location/Qualifiers
REGION                  1..448
                        note = Synthetic peptide
```

```
source                      1..448
                            mol_type = protein
                            organism = synthetic construct
SEQUENCE: 75
QVQLVQSGAE VKKPGASVKV SCKASGYTFT SYGISWVRQA PGQGLEWMGW ISAYNANTNY   60
AQKLQGRVTM TTDTSTSTAY MELRSLRSDD TAVYYCARSA GVLGGMDVWG RGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 76               moltype = AA  length = 448
FEATURE                     Location/Qualifiers
REGION                      1..448
                            note = Synthetic peptide
source                      1..448
                            mol_type = protein
                            organism = synthetic construct
SEQUENCE: 76
QVQLVQSGAE VKKPGASVKV SCKASGYTFT SYGISWVRQA PGQGLEWMGW ISAYNANTNY   60
AQKLQGRVTM TTDTSTSTAY MELRSLRSDD TAVYYCARSA GVLGGMDVWG RGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 77               moltype = AA  length = 448
FEATURE                     Location/Qualifiers
REGION                      1..448
                            note = Synthetic peptide
source                      1..448
                            mol_type = protein
                            organism = synthetic construct
SEQUENCE: 77
QVQLVQSGAE VKKPGASVKV SCKASGYTFT SYGISWVRQA PGQGLEWMGW ISAYNANTNY   60
AQKLQGRVTM TTDTSTSTAY MELRSLRSDD TAVYYCARSA GVLGGMDVWG RGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PLPEEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 78               moltype = AA  length = 448
FEATURE                     Location/Qualifiers
REGION                      1..448
                            note = Synthetic peptide
source                      1..448
                            mol_type = protein
                            organism = synthetic construct
SEQUENCE: 78
QVQLVQSGAE VKKPGASVKV SCKASGYTFT NYAVHWVRQA PGQRLEWMGW INTGNANTKY   60
SQKFQGRVTI TRDTSASTAY MELSSLRSED TAVYYCARSL GVYYGMDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPG                                    448

SEQ ID NO: 79               moltype = AA  length = 448
FEATURE                     Location/Qualifiers
REGION                      1..448
                            note = Synthetic peptide
source                      1..448
                            mol_type = protein
                            organism = synthetic construct
SEQUENCE: 79
QVQLVQSGAE VKKPGASVKV SCKASGYTFT NYAVHWVRQA PGQRLEWMGW INTGNANTKY   60
SQKFQGRVTI TRDTSASTAY MELSSLRSED TAVYYCARSL GVYYGMDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSREEM  360
TKNQVSLSCA VKGFYPSDIA VEWESNGQPE NNYKTTPPVL DSDGSFFLVS KLTVDKSRWQ  420
```

```
QGNVFSCSVM HEALHNHYTQ KSLSLSPG                                              448

SEQ ID NO: 80            moltype = AA  length = 448
FEATURE                  Location/Qualifiers
REGION                   1..448
                         note = Synthetic peptide
source                   1..448
                         mol_type = protein
                         organism = synthetic construct
SEQUENCE: 80
QVQLVQSGAE VKKPGASVKV SCKASGYTFT NYAVHWVRQA PGQRLEWMGW INTGNANTKY            60
SQKFQGRVTI TRDTSASTAY MELSSLRSED TAVYYCARSL GVYYGMDVWG QGTTVTVSSA           120
STKGPSVFPL APSSKSTSGG TAALGCLVKD YFPEPVTVSW NSGALTSGVH TFPAVLQSSG           180
LYSLSSVVTV PSSSLGTQTY ICNVNHKPSN TKVDKRVEPK SCDKTHTCPP CPAPELLGGP           240
DVFLFPPKPK DTLMISRTPE VTCVVVDVSH EDPEVKFNWY VDGVEVHNAK TKPREEQYNS           300
TYRVVSVLTV LHQDWLNGKE YKCKVSNKAL PLPEEKTISK AKGQPREPQV YTLPPSREEM           360
TKNQVSLSCA VKGFYPSDIA VEWESNGQPE NNYKTTPPVL DSDGSFFLVS KLTVDKSRWQ           420
QGNVFSCSVM HEALHNHYTQ KSLSLSPG                                              448

SEQ ID NO: 81            moltype = AA  length = 448
FEATURE                  Location/Qualifiers
REGION                   1..448
                         note = Synthetic peptide
source                   1..448
                         mol_type = protein
                         organism = synthetic construct
SEQUENCE: 81
QVQLVQSGAE VKKPGASVKV SCKASGYTFT NYAVHWVRQA PGQRLEWMGW INTGNANTKY            60
SQKFQGRVTI TRDTSASTAY MELSSLRSED TAVYYCARSL GVYYGMDVWG QGTTVTVSSA           120
STKGPSVFPL APSSKSTSGG TAALGCLVKD YFPEPVTVSW NSGALTSGVH TFPAVLQSSG           180
LYSLSSVVTV PSSSLGTQTY ICNVNHKPSN TKVDKRVEPK SCDKTHTCPP CPAPELLGGP           240
SVFLFPPKPK DTLMISRTPE VTCVVVDVSH EDPEVKFNWY VDGVEVHNAK TKPREEQYNS           300
TYRVVSVLTV LHQDWLNGKE YKCKVSNKAL PAPIEKTISK AKGQPREPQV YTLPPSREEM           360
TKNQVSLWCL VKGFYPSDIA VEWESNGQPE NNYKTTPPVL DSDGSFFLYS KLTVDKSRWQ           420
QGNVFSCSVM HEALHNHYTQ KSLSLSPG                                              448

SEQ ID NO: 82            moltype = AA  length = 448
FEATURE                  Location/Qualifiers
REGION                   1..448
                         note = Synthetic peptide
source                   1..448
                         mol_type = protein
                         organism = synthetic construct
SEQUENCE: 82
QVQLVQSGAE VKKPGASVKV SCKASGYTFT NYAVHWVRQA PGQRLEWMGW INTGNANTKY            60
SQKFQGRVTI TRDTSASTAY MELSSLRSED TAVYYCARSL GVYYGMDVWG QGTTVTVSSA           120
STKGPSVFPL APSSKSTSGG TAALGCLVKD YFPEPVTVSW NSGALTSGVH TFPAVLQSSG           180
LYSLSSVVTV PSSSLGTQTY ICNVNHKPSN TKVDKRVEPK SCDKTHTCPP CPAPELLGGP           240
DVFLFPPKPK DTLMISRTPE VTCVVVDVSH EDPEVKFNWY VDGVEVHNAK TKPREEQYNS           300
TYRVVSVLTV LHQDWLNGKE YKCKVSNKAL PAPIEKTISK AKGQPREPQV YTLPPSREEM           360
TKNQVSLWCL VKGFYPSDIA VEWESNGQPE NNYKTTPPVL DSDGSFFLYS KLTVDKSRWQ           420
QGNVFSCSVM HEALHNHYTQ KSLSLSPG                                              448

SEQ ID NO: 83            moltype = AA  length = 448
FEATURE                  Location/Qualifiers
REGION                   1..448
                         note = Synthetic peptide
source                   1..448
                         mol_type = protein
                         organism = synthetic construct
SEQUENCE: 83
QVQLVQSGAE VKKPGASVKV SCKASGYTFT NYAVHWVRQA PGQRLEWMGW INTGNANTKY            60
SQKFQGRVTI TRDTSASTAY MELSSLRSED TAVYYCARSL GVYYGMDVWG QGTTVTVSSA           120
STKGPSVFPL APSSKSTSGG TAALGCLVKD YFPEPVTVSW NSGALTSGVH TFPAVLQSSG           180
LYSLSSVVTV PSSSLGTQTY ICNVNHKPSN TKVDKRVEPK SCDKTHTCPP CPAPELLGGP           240
DVFLFPPKPK DTLMISRTPE VTCVVVDVSH EDPEVKFNWY VDGVEVHNAK TKPREEQYNS           300
TYRVVSVLTV LHQDWLNGKE YKCKVSNKAL PAPEEKTISK AKGQPREPQV YTLPPSREEM           360
TKNQVSLWCL VKGFYPSDIA VEWESNGQPE NNYKTTPPVL DSDGSFFLYS KLTVDKSRWQ           420
QGNVFSCSVM HEALHNHYTQ KSLSLSPG                                              448

SEQ ID NO: 84            moltype = AA  length = 448
FEATURE                  Location/Qualifiers
REGION                   1..448
                         note = Synthetic peptide
source                   1..448
                         mol_type = protein
                         organism = synthetic construct
SEQUENCE: 84
QVQLVQSGAE VKKPGASVKV SCKASGYTFT NYAVHWVRQA PGQRLEWMGW INTGNANTKY            60
```

```
SQKFQGRVTI TRDTSASTAY MELSSLRSED TAVYYCARSL GVYYGMDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PLPEEKTISK AKGQPREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 85           moltype = AA   length = 448
FEATURE                 Location/Qualifiers
REGION                  1..448
                        note = Synthetic peptide
source                  1..448
                        mol_type = protein
                        organism = synthetic construct
SEQUENCE: 85
QVQLVQSGAE VKKPGASVKV SCKASGYTFT NYAVHWVRQA PGQRLEWMGW INTGNANTKY    60
SQKFQGRVTI TRDTSASTAY MELSSLRSED TAVYYCARSL GVYYGMDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 86           moltype = AA   length = 448
FEATURE                 Location/Qualifiers
REGION                  1..448
                        note = Synthetic peptide
source                  1..448
                        mol_type = protein
                        organism = synthetic construct
SEQUENCE: 86
QVQLVQSGAE VKKPGASVKV SCKASGYTFT NYAVHWVRQA PGQRLEWMGW INTGNANTKY    60
SQKFQGRVTI TRDTSASTAY MELSSLRSED TAVYYCARSL GVYYGMDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 87           moltype = AA   length = 448
FEATURE                 Location/Qualifiers
REGION                  1..448
                        note = Synthetic peptide
source                  1..448
                        mol_type = protein
                        organism = synthetic construct
SEQUENCE: 87
QVQLVQSGAE VKKPGASVKV SCKASGYTFT NYAVHWVRQA PGQRLEWMGW INTGNANTKY    60
SQKFQGRVTI TRDTSASTAY MELSSLRSED TAVYYCARSL GVYYGMDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPEEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 88           moltype = AA   length = 448
FEATURE                 Location/Qualifiers
REGION                  1..448
                        note = Synthetic peptide
source                  1..448
                        mol_type = protein
                        organism = synthetic construct
SEQUENCE: 88
QVQLVQSGAE VKKPGASVKV SCKASGYTFT NYAVHWVRQA PGQRLEWMGW INTGNANTKY    60
SQKFQGRVTI TRDTSASTAY MELSSLRSED TAVYYCARSL GVYYGMDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PLPEEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 89           moltype = AA   length = 448
FEATURE                 Location/Qualifiers
REGION                  1..448
```

```
                           note = Synthetic peptide
source                     1..448
                           mol_type = protein
                           organism = synthetic construct
SEQUENCE: 89
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                     448

SEQ ID NO: 90              moltype = AA   length = 448
FEATURE                    Location/Qualifiers
REGION                     1..448
                           note = Synthetic peptide
source                     1..448
                           mol_type = protein
                           organism = synthetic construct
SEQUENCE: 90
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPEEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                     448

SEQ ID NO: 91              moltype = AA   length = 448
FEATURE                    Location/Qualifiers
REGION                     1..448
                           note = Synthetic peptide
source                     1..448
                           mol_type = protein
                           organism = synthetic construct
SEQUENCE: 91
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PLPEEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                     448

SEQ ID NO: 92              moltype = AA   length = 448
FEATURE                    Location/Qualifiers
REGION                     1..448
                           note = Synthetic peptide
source                     1..448
                           mol_type = protein
                           organism = synthetic construct
SEQUENCE: 92
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 93              moltype = AA   length = 448
FEATURE                    Location/Qualifiers
REGION                     1..448
                           note = Synthetic peptide
source                     1..448
                           mol_type = protein
                           organism = synthetic construct
SEQUENCE: 93
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
```

```
TKNQVSLWCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 94           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 94
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
DVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPEEKTISK AKGQPREPQV YTLPPSREEM    360
TKNQVSLWCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 95           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 95
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
DVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PLPEEKTISK AKGQPREPQV YTLPPSREEM    360
TKNQVSLWCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 96           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 96
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 97           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 97
QVQLVQSGAE VKKPGASVKV SCKASGYTFT TYALHWVRQA PGQRLEWMGW INTGSGDTKY    60
SQKFQGRVTI TRDTSASTAY MELSSLRSED TAVYYCARSL GVYYGMDVWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
DVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 98           moltype = AA  length = 448
FEATURE                 Location/Qualifiers
REGION                  1..448
                        note = Synthetic peptide
source                  1..448
                        mol_type = protein
                        organism = synthetic construct
SEQUENCE: 98
```

```
QVQLVQSGAE VKKPGASVKV SCKASGYTFT TYALHWVRQA PGQRLEWMGW INTGSGDTKY     60
SQKFQGRVTI TRDTSASTAY MELSSLRSED TAVYYCARSL GVYYGMDVWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
DVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPEEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 99           moltype = AA   length = 448
FEATURE                 Location/Qualifiers
REGION                  1..448
                        note = Synthetic peptide
source                  1..448
                        mol_type = protein
                        organism = synthetic construct
SEQUENCE: 99
QVQLVQSGAE VKKPGASVKV SCKASGYTFT TYALHWVRQA PGQRLEWMGW INTGSGDTKY     60
SQKFQGRVTI TRDTSASTAY MELSSLRSED TAVYYCARSL GVYYGMDVWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPELLGGP    240
DVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PLPEEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 100          moltype = AA   length = 451
FEATURE                 Location/Qualifiers
REGION                  1..451
                        note = Synthetic peptide
source                  1..451
                        mol_type = protein
                        organism = synthetic construct
SEQUENCE: 100
EVQLVQSGAE VKKPGSSVKV SCKASGYTFA SYGISWVRQA PGQGLEWMGG ITPFFNRVDV     60
AEKFQGRVTI TADKSTSTAY IELSSLRSED TAVYYCARDL RRGGVGDAFD IWGRGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL WCLVKGFYPS DIAVEWESNG QPENNYKTTP PVLDSDGSFF LYSKLTVDKS    420
RWQQGNVFSC SVMHEALHNH YTQKSLSLSP G                                  451

SEQ ID NO: 101          moltype = AA   length = 451
FEATURE                 Location/Qualifiers
REGION                  1..451
                        note = Synthetic peptide
source                  1..451
                        mol_type = protein
                        organism = synthetic construct
SEQUENCE: 101
EVQLVQSGAE VKKPGSSVKV SCKASGYTFA SYGISWVRQA PGQGLEWMGG ITPFFNRVDV     60
AEKFQGRVTI TADKSTSTAY IELSSLRSED TAVYYCARDL RRGGVGDAFD IWGRGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPDVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL WCLVKGFYPS DIAVEWESNG QPENNYKTTP PVLDSDGSFF LYSKLTVDKS    420
RWQQGNVFSC SVMHEALHNH YTQKSLSLSP G                                  451

SEQ ID NO: 102          moltype = AA   length = 451
FEATURE                 Location/Qualifiers
REGION                  1..451
                        note = Synthetic peptide
source                  1..451
                        mol_type = protein
                        organism = synthetic construct
SEQUENCE: 102
EVQLVQSGAE VKKPGSSVKV SCKASGYTFA SYGISWVRQA PGQGLEWMGG ITPFFNRVDV     60
AEKFQGRVTI TADKSTSTAY IELSSLRSED TAVYYCARDL RRGGVGDAFD IWGRGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPDVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPEEKT ISKAKGQPRE PQVYTLPPSR    360
EEMTKNQVSL WCLVKGFYPS DIAVEWESNG QPENNYKTTP PVLDSDGSFF LYSKLTVDKS    420
RWQQGNVFSC SVMHEALHNH YTQKSLSLSP G                                  451

SEQ ID NO: 103          moltype = AA   length = 451
FEATURE                 Location/Qualifiers
```

```
REGION                       1..451
                             note = Synthetic peptide
source                       1..451
                             mol_type = protein
                             organism = synthetic construct
SEQUENCE: 103
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL SCAVKGFYPS DIAVEWESNG QPENNYKTTP PVLDSDGSFF LVSKLTVDKS   420
RWQQGNVFSC SVMHEALHNH YTQKSLSLSP G                                 451

SEQ ID NO: 104               moltype = AA  length = 451
FEATURE                      Location/Qualifiers
REGION                       1..451
                             note = Synthetic peptide
source                       1..451
                             mol_type = protein
                             organism = synthetic construct
SEQUENCE: 104
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL SCAVKGFYPS DIAVEWESNG QPENNYKTTP PVLDSDGSFF LVSKLTVDKS   420
RWQQGNVFSC SVMHEALHNH YTQKSLSLSP G                                 451

SEQ ID NO: 105               moltype = AA  length = 451
FEATURE                      Location/Qualifiers
REGION                       1..451
                             note = Synthetic peptide
source                       1..451
                             mol_type = protein
                             organism = synthetic construct
SEQUENCE: 105
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPEEKT ISKAKGQPRE PQVYTLPPSR   360
EEMTKNQVSL SCAVKGFYPS DIAVEWESNG QPENNYKTTP PVLDSDGSFF LVSKLTVDKS   420
RWQQGNVFSC SVMHEALHNH YTQKSLSLSP G                                 451

SEQ ID NO: 106               moltype = AA  length = 451
FEATURE                      Location/Qualifiers
REGION                       1..451
                             note = Synthetic peptide
source                       1..451
                             mol_type = protein
                             organism = synthetic construct
SEQUENCE: 106
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPLPEEKT ISKAKGQPRE PQVYTLPPSR   360
EEMTKNQVSL SCAVKGFYPS DIAVEWESNG QPENNYKTTP PVLDSDGSFF LVSKLTVDKS   420
RWQQGNVFSC SVMHEALHNH YTQKSLSLSP G                                 451

SEQ ID NO: 107               moltype = AA  length = 451
FEATURE                      Location/Qualifiers
REGION                       1..451
                             note = Synthetic peptide
source                       1..451
                             mol_type = protein
                             organism = synthetic construct
SEQUENCE: 107
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
```

```
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                 451

SEQ ID NO: 108           moltype = AA   length = 451
FEATURE                  Location/Qualifiers
REGION                   1..451
                         note = Synthetic peptide
source                   1..451
                         mol_type = protein
                         organism = synthetic construct
SEQUENCE: 108
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                 451

SEQ ID NO: 109           moltype = AA   length = 451
FEATURE                  Location/Qualifiers
REGION                   1..451
                         note = Synthetic peptide
source                   1..451
                         mol_type = protein
                         organism = synthetic construct
SEQUENCE: 109
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPEEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                 451

SEQ ID NO: 110           moltype = AA   length = 451
FEATURE                  Location/Qualifiers
REGION                   1..451
                         note = Synthetic peptide
source                   1..451
                         mol_type = protein
                         organism = synthetic construct
SEQUENCE: 110
EVQLVQSGAE VKKPGSSVKV SCKASGYTFA SYGISWVRQA PGQGLEWMGG ITPFFNRVDV    60
AEKFQGRVTI TADKSTSTAY IELSSLRSED TAVYYCARDL RRGGVGDAFD IWGRGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPLPEEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                 451

SEQ ID NO: 111           moltype = AA   length = 514
FEATURE                  Location/Qualifiers
source                   1..514
                         mol_type = protein
                         organism = Macaca fascicularis
SEQUENCE: 111
VWGKPFNTEE NIYATLGSDV NLTCQTQAKG FLVQMQWSKV TDKADLIALY HPQYGFHCAY    60
GSPCESLVTF TQTPENGSKW TLHLRNMSSS VSGRYECMLT LYPEGMQTKI YNLLIQTHVT   120
PDEWKSNHTI EIEINQTLEI PCFQNSSSEI SSEFTYAWLV EDNGTQQTLI SQDHLISSST   180
LLKDRVKVGI DYRLHLSPVQ IFDDGRKFSC HIRVGPDKIL RSSTTIKVFA KPEIPMIVEN   240
NSTDVLVERT FTCLLKNVFP KANIIWFIDG SFLHDEKEGI YITNEERKGK DGFLELKSVL   300
TRVHSDKPAQ SDNLTIWCMA LSPVPGNKVW NISSEKITFL LGSEMSTTDL PPSVTESTLD   360
TQPSPASSVS PTRYPATSSV TLADVSALRP NTTPQSSSSS VTTQDFNYPW TSSGTDAKKS   420
FSQIPSETYS SSPSGAGSTL HDNVFTSTTR ALSEVPTTAN GSTKTNHVHI TGIVVSKPKD   480
GMENLYFQGL EHHHHHHHHH HGGSGGLPET GGDR                               514

SEQ ID NO: 112           moltype = AA   length = 119
FEATURE                  Location/Qualifiers
source                   1..119
                         mol_type = protein
                         organism = Macaca fascicularis
SEQUENCE: 112
VWGKPFNTEE NIYATLGSDV NLTCQTQAKG FLVQMQWSKV TDKADLIALY HPQYGFHCAY    60
GSPCESLVTF TQTPENGSKW TLHLRNMSSS VSGRYECMLT LYPEGMQTKI YNLLIQTHV    119
```

```
SEQ ID NO: 113          moltype = AA  length = 150
FEATURE                 Location/Qualifiers
source                  1..150
                        mol_type = protein
                        organism = Homo sapiens
SEQUENCE: 113
MMTGTIETTG NISAEKGGSI ILQCHLSSTT AQVTQVNWEQ QDQLLAICNA DLGWHISPSF    60
KDRVAPGPGL GLTLQSLTVN DTGEYFCIYH TYPDGTYTGR IFLEVLESSV AEHGARFQEN   120
LYFQGLEHHH HHHHHHGGS GGLPETGGDR                                    150

SEQ ID NO: 114          moltype = AA  length = 151
FEATURE                 Location/Qualifiers
source                  1..151
                        mol_type = protein
                        organism = Macaca fascicularis
SEQUENCE: 114
MMTGTIETTG NISAKKGGSV ILQCHLSSTM AQVTQVNWEQ HDHSLLAIRN AELGWHIYPA    60
FKDRVAPGPG LGLTLQSLTM NDTGEYFCTY HTYPDGTYRG RIFLEVLESS VAEHSARFQE   120
NLYFQGLEHH HHHHHHHGG SGGLPETGGD R                                  151
```

What is claimed:

1. A multispecific molecule comprising:
(a) a first antigen-binding region that specifically binds to human CD96, the first antigen-binding region comprising a first heavy chain variable region (VH) comprising CDRs CDRH1, CDRH2, and CDRH3, and a first light chain variable region (VL) comprising CDRs CDRL1, CDRL2, and CDRL3; wherein the first VH comprises the CDRH1, CDRH2, and CDRH3 amino acid sequences of the VH amino acid sequence of SEQ ID NO: 38; and the first VL comprises the CDRL1, CDRL2, and CDRL3 amino acid sequences of the VL amino acid sequence of SEQ ID NO: 39; and
(b) a second antigen-binding region that specifically binds to human TIGIT, the second antigen-binding region comprising a second VH comprising CDRs CDRH1, CDRH2, and CDRH3, and a second VL comprising CDRs CDRL I, CDRL2, and CDRL3; wherein the second VH comprises the CDRH1, CDRH2, and CDRH3 amino acid sequences of the VH amino acid sequence of SEQ ID NO: 40; and/or the second VL comprises the CDRL1, CDRL2, and CDRL3 amino acid sequences of the VL amino acid sequence of SEQ ID NO: 41.

2. A multispecific molecule comprising:
(a) a first antigen-binding region that specifically binds to human CD96, comprising a first VH comprising CDRs CDRH1, CDRH2, and CDRH3, and a first VL comprising CDRs CDRL1, CDRL2, and CDRL3, wherein the CDRH1, CDRH2, CDRH3, CDRL1, CDRL2, and CDRL3 of the first antigen-binding region comprise the amino acid sequences of SEQ ID NOs: 22, 23, 24, 25, 26, and 27, respectively; and
(b) a second antigen-binding region that specifically binds to human TIGIT, comprising a second VH comprising CDRs CDRH1, CDRH2, and CDRH3, and a second VL comprising CDRs CDRL1, CDRL2, and CDRL3, wherein the CDRH1, CDRH2, CDRH3, CDRL1, CDRL2, and CDRL3 of the second antigen-binding region comprise the amino acid sequences of SEQ ID NOs: 28, 29, 30, 31, 32, and 33, respectively.

3. The multispecific molecule of claim 2, wherein:
(a) the first VH comprises an amino acid sequence at least 95% identical to SEQ ID NO: 38;
(b) the first VH comprises the amino acid sequence of SEQ ID NO: 38;
(c) the first VL comprises an amino acid sequence at least 95% identical to SEQ ID NO: 39;
(d) the first VL comprises the amino acid sequence of SEQ ID NO: 39;
(e) the first VH and first VL comprise the amino acid sequences of SEQ ID NOs: 38 and 39, respectively;
(f) the second VH comprises an amino acid sequence at least 95% identical to SEQ ID NO: 40;
(g) the second VH comprises the amino acid sequence of SEQ ID NO: 40;
(h) the second VL comprises an amino acid sequence at least 95% identical to SEQ ID NO: 41;
(i) the second VL comprises the amino acid sequence of SEQ ID NO: 41; and/or
(j) the second VH and second VL comprise the amino acid sequences of SEQ ID NOs: 40 and 41, respectively.

4. The multispecific molecule of claim 2, wherein the first antigen-binding region and/or the second antigen-binding region comprises a heavy chain constant region selected from the group consisting of human $IgG_1$, $IgG_2$, $IgG_3$, $IgG_4$, $IgA_1$, and $IgA_2$.

5. The multispecific molecule of claim 2, wherein:
(a) the first antigen-binding region comprises a first human IgG heavy chain constant region comprising aspartate, serine, alanine, and valine at amino acid positions 239, 366, 368, and 407, respectively, and the second antigen-binding region comprises a second human IgG heavy chain constant region comprising aspartate, leucine, glutamate, and tryptophan at amino acid positions 239, 330, 332, and 366, respectively; and/or
(b) the first antigen-binding region comprises a first human IgG heavy chain constant region comprising aspartate, leucine, glutamate, and tryptophan at amino acid positions 239, 330, 332, and 366, respectively, and the second antigen-binding region comprises a second human IgG heavy chain constant region comprising aspartate, serine, alanine, and valine at amino acid positions 239, 366, 368, and 407, respectively,
wherein the amino acid positions are numbered according to the EU numbering system.

6. The multispecific molecule of claim 5, wherein:
(a) the first antigen-binding region comprises a first heavy chain constant region comprising the amino acid sequence of SEQ ID NO: 50, and the second antigen-binding region comprises a second heavy chain constant region comprising the amino acid sequence of SEQ ID NO: 56; and/or
(b) the first antigen-binding region comprises a first heavy chain constant region comprising the amino acid sequence of SEQ ID NO: 56, and the second antigen-binding region comprises a second heavy chain constant region comprising the amino acid sequence of SEQ ID NO: 50.

7. The multispecific molecule of claim 2, wherein the first antigen-binding region comprises a first heavy chain comprising the amino acid sequence of SEQ ID NO: 5, and/or the second antigen-binding region comprises a second heavy chain comprising the amino acid sequence of SEQ ID NO: 7.

8. The multispecific molecule of claim 2, wherein the first antigen-binding region and/or the second antigen-binding region comprises a human kappa light chain constant region or a human lambda light chain constant region.

9. The multispecific molecule of claim 2, wherein the first antigen-binding region comprises a first light chain comprising the amino acid sequence of SEQ ID NO: 6, and/or the second antigen-binding region comprises a second light chain comprising the amino acid sequence of SEQ ID NO: 9.

10. The multispecific molecule of claim 2, wherein:
(a) the first VH comprises the amino acid sequence of SEQ ID NO: 38, and the first VL comprises the amino acid sequence of SEQ ID NO: 39; and
(b) the second VH comprises the amino acid sequence of SEQ ID NO: 40, and the second VL comprises the amino acid sequence of SEQ ID NO: 41.

11. The multispecific molecule of claim 10, wherein:
(a) the first antigen-binding region comprises a first heavy chain comprising an amino acid sequence at least 95% identical to SEQ ID NO: 5;
(b) the second antigen-binding region comprises a second heavy chain comprising an amino acid sequence at least 95% identical to SEQ ID NO: 7;
(c) the first antigen-binding region comprises a first light chain comprising an amino acid sequence at least 95% identical to SEQ ID NO: 6; and/or
(d) the second antigen-binding region comprises a second light chain comprising an amino acid sequence at least 95% identical to SEQ ID NO: 9.

12. The multispecific molecule of claim 2 wherein:
(a) the first antigen-binding region comprises a first VH comprising an amino acid sequence at least 95% identical to SEQ ID NO:38;
(b) the first antigen-binding region comprises a first VL comprising an amino acid sequence at least 95% identical to SEQ ID NO:39;
(c) the second antigen-binding region comprises a second VH comprising an amino acid sequence at least 95% identical to SEQ ID NO:40; and/or (d) the second antigen-binding region comprises a first VL comprising an amino acid sequence at least 95% identical to SEQ ID NO:41.

13. The multispecific molecule of claim 10, wherein the first antigen-binding region and/or the second antigen-binding region comprises a heavy chain constant region selected from the group consisting of human IgG$_1$, IgG$_2$, IgG$_3$, IgG$_4$, IgA$_1$, and IgA$_2$.

14. The multispecific molecule of claim 13, wherein:
(a) the first antigen-binding region comprises a first human IgG heavy chain constant region comprising aspartate, serine, alanine, and valine at amino acid positions 239, 366, 368, and 407, respectively, and the second antigen-binding region comprises a second human IgG heavy chain constant region comprising aspartate, leucine, glutamate, and tryptophan at amino acid positions 239, 330, 332, and 366, respectively; and/or
(b) the first antigen-binding region comprises a first human IgG heavy chain constant region constant region comprising aspartate, leucine, glutamate, and tryptophan at amino acid positions 239, 330, 332, and 366, respectively, and the second antigen-binding region comprises a second human IgG heavy chain constant region comprising aspartate, serine, alanine, and valine at amino acid positions 239, 366, 368, and 407, respectively,
wherein the amino acid positions are numbered according to the EU numbering system.

15. The multispecific molecule of claim 14, wherein:
(a) the first antigen-binding region comprises a first heavy chain constant region comprising the amino acid sequence of SEQ ID NO: 50, and the second antigen-binding region comprises a second heavy chain constant region comprising the amino acid sequence of SEQ ID NO: 56; and/or
(b) the first antigen-binding region comprises a first heavy chain constant region comprising the amino acid sequence of SEQ ID NO: 56, and the second antigen-binding region comprises a second heavy chain constant region comprising the amino acid sequence of SEQ ID NO: 50.

16. The multispecific molecule of claim 10, wherein the first antigen-binding region comprises a first heavy chain comprising the amino acid sequence of SEQ ID NO: 5, and/or the second antigen-binding region comprises a second heavy chain comprising the amino acid sequence of SEQ ID NO: 7.

17. The multispecific molecule of claim 10, wherein the first antigen-binding region and/or the second antigen-binding region comprises a human kappa light chain constant region or a human lambda light chain constant region.

18. The multispecific molecule of claim 10, wherein the first antigen-binding region comprises a first light chain comprising the amino acid sequence of SEQ ID NO: 6, and/or the second antigen-binding region comprises a second light chain comprising the amino acid sequence of SEQ ID NO: 9.

19. A multispecific molecule comprising:
(a) a first antigen-binding region that specifically binds to human CD96, the first antigen-binding region comprising a first heavy chain comprising the amino acid sequence of SEQ ID NO: 5, and a first light chain comprising the amino acid sequence of SEQ ID NO: 6; and
(b) a second antigen-binding region that specifically binds to human TIGIT, the second antigen-binding region comprising a second heavy chain comprising the amino acid sequence of SEQ ID NO: 7, and a second light chain comprising the amino acid sequence of SEQ ID NO: 9.

20. An antibody that specifically binds to human TIGIT, the antibody comprising: a VH comprising the CDRH1, CDRH2, and CDRH3 amino acid sequences of the VH amino acid sequence of SEQ ID NO: 40; and a VL comprising the CDRL1, CDRL2, and CDRL3 amino acid sequences of the VL amino acid sequence of SEQ ID NO: 41.

21. The antibody of claim 20, comprising the CDRH1, CDRH2, CDRH3, CDRL1, CDRL2, and CDRL3 amino acid sequences of SEQ ID NOs: 28, 29, 30, 31, 32, and 33, respectively.

22. The antibody of claim 20, comprising the VH and VL amino acid sequences of SEQ ID NOs: 40 and 41, respectively.

23. The antibody of claim 20, wherein the antibody comprises a heavy chain constant region selected from the group consisting of human $IgG_1$, $IgG_2$, $IgG_3$, $IgG_4$, $IgA_1$, and $IgA_2$.

24. The antibody of claim 23, wherein the heavy chain constant region comprises the amino acid sequence of any one of SEQ ID NO: 49-60.

25. The antibody of claim 20, the antibody comprising a heavy chain comprising the amino acid sequence of SEQ ID NO: 7, and a light chain comprising the amino acid sequence of SEQ ID NO: 9.

26. A multispecific molecule comprising:
(a) a first antigen-binding region that specifically binds to human CD96, the first antigen-binding region comprising a first VH comprising CDRs CDRH1, CDRH2, and CDRH3, and a first VL comprising CDRs CDRL1, CDRL2, and CDRL3, wherein the first VH comprises the CDRH1, CDRH2, and CDRH3 amino acid sequences of the VH amino acid sequence of SEQ ID NO: 38; and the first VL comprises the CDRL1, CDRL2, and CDRL3 amino acid sequences of the VL amino acid sequence of SEQ ID NO: 39; and
(b) a second antigen-binding region that specifically binds to human TIGIT.

27. The multispecific molecule of claim 26, wherein the CDRH1, CDRH2, CDRH3, CDRL1, CDRL2, and CDRL3 of the first antigen-binding region comprise the amino acid sequences of SEQ ID NOs: 22, 23, 24, 25, 26, and 27, respectively.

28. The multispecific molecule of claim 27, wherein the first VH and first VL comprise the amino acid sequences of SEQ ID NOs: 38 and 39, respectively.

29. The multispecific molecule of claim 27, wherein the first antigen-binding region and/or the second antigen-binding region comprises a heavy chain constant region selected from the group consisting of human $IgG_1$, $IgG_2$, $IgG_3$, $IgG_4$, $IgA_1$, and $IgA_2$.

30. The multispecific molecule of claim 29, wherein the heavy chain constant region comprises the amino acid sequence of any one of SEQ ID NO: 49-60.

31. The multispecific molecule of claim 27, the first antigen-binding region comprises a heavy chain comprising the amino acid sequence of SEQ ID NO: 5, and a light chain comprising the amino acid sequence of SEQ ID NO: 6.

32. A multispecific molecule comprising:
(a) a first antigen-binding region that specifically binds to human CD96; and
(b) a second antigen-binding region that specifically binds to human TIGIT, the second antigen-binding region comprising a VH comprising CDRs CDRH1, CDRH2, and CDRH3 and a VL comprising CDRs CDRL1, CDRL2, and CDRL3, wherein the VH comprises the CDRH1, CDRH2, and CDRH3 amino acid sequences of the VH amino acid sequence of SEQ ID NO: 40; and the VL comprises the CDRL1, CDRL2, and CDRL3 amino acid sequences of the VL amino acid sequence of SEQ ID NO: 41.

33. The multispecific molecule of claim 32, wherein the CDRH1, CDRH2, CDRH3, CDRL1, CDRL2, and CDRL3 of the second antigen-binding region comprise the amino acid sequences of SEQ ID NOs: 28, 29, 30, 31, 32, and 33, respectively.

34. The multispecific molecule of claim 32, wherein the VH and VL of the second antigen-binding region comprise the amino acid sequences of SEQ ID NOs: 40 and 41, respectively.

35. The multispecific molecule of claim 32, wherein the first antigen-binding region and/or the second antigen-binding region comprises a heavy chain constant region selected from the group consisting of human $IgG_1$, $IgG_2$, $IgG_3$, $IgG_4$, $IgA_1$, and $IgA_2$.

36. The multispecific molecule of claim 35, wherein the heavy chain constant region comprises the amino acid sequence of any one of SEQ ID NO: 49-60.

37. The multispecific molecule of claim 32, wherein the second antigen-binding region comprises a heavy chain comprising the amino acid sequence of SEQ ID NO: 7, and a light chain comprising the amino acid sequence of SEQ ID NO: 9.

* * * * *

UNITED STATES PATENT AND TRADEMARK OFFICE
CERTIFICATE OF CORRECTION

PATENT NO. : 11,718,669 B2
APPLICATION NO. : 17/818840
DATED : August 8, 2023
INVENTOR(S) : Dhan Sidhartha Chand et al.

It is certified that error appears in the above-identified patent and that said Letters Patent is hereby corrected as shown below:

In the Specification

At Column 11, subset (i), Line number 2, delete "of" before the word "disclosed";

At Column 72, Line 27, revise "molecule" to "molecules";

At Column 78, Line 4, delete "a comprising";

At Column 78, Line 7, delete "a comprising";

At Column 134, Line number 25, delete "containing";

At Column 151, section 8, Line number 1, delete "6" and replace with "8";

At Column 190, Line 39, revise to read, "FIGs. 30A-30F";

At Column 190, Line 45, revise to read, "FIGs. 30A-30F";

In the Claims

At Column 238, Claim number 14(b), Line number 8, delete "constant region"; and

At Column 240, Claim number 31, Line number 4, insert --wherein-- after "claim 27,".

Signed and Sealed this
Twenty-third Day of April, 2024

*Katherine Kelly Vidal*

Katherine Kelly Vidal
*Director of the United States Patent and Trademark Office*